US008912394B2

(12) United States Patent
Century et al.

(10) Patent No.: US 8,912,394 B2
(45) Date of Patent: Dec. 16, 2014

(54) TRANSCRIPTIONAL REGULATION OF PLANT DISEASE TOLERANCE

(75) Inventors: Karen S. Century, Albany, CA (US);
Emily L. Queen, San Bruno, CA (US);
T. Lynne Reuber, San Mateo, CA (US);
Oliver Ratcliffe, Oakland, CA (US);
Roger D. Canales, San Francisco, CA (US); Neal I. Gutterson, Oakland, CA (US)

(73) Assignee: Mendel Biotechnology Inc., Hayward, CA (US)

( * ) Notice: Subject to any disclaimer, the term of this patent is extended or adjusted under 35 U.S.C. 154(b) by 1348 days.

(21) Appl. No.: 10/903,236

(22) Filed: Jul. 30, 2004

(65) Prior Publication Data

US 2005/0155117 A1 Jul. 14, 2005

Related U.S. Application Data

(63) Continuation-in-part of application No. 10/666,642, filed on Sep. 18, 2003, now Pat. No. 7,196,245, and a continuation-in-part of application No. 10/714,887, filed on Nov. 13, 2003, now abandoned, which is a continuation-in-part of application No. 10/374,780, filed on Feb. 25, 2003, now Pat. No. 7,511,190, which is a continuation-in-part of application No. 09/837,944, filed on Apr. 18, 2001, now abandoned, and a continuation-in-part of application No. 10/171,468, filed on Jun. 14, 2002, now abandoned, application No. 10/903,236, which is a continuation-in-part of application No. 10/456,882, filed on Jun. 6, 2003, now abandoned, which is a continuation-in-part of application No. 10/171,468, filed on Jun. 14, 2002, now abandoned, and a continuation-in-part of application No. 09/934,455, filed on Aug. 22, 2001, now abandoned, application No. 10/903,236, which is a continuation-in-part of application No. 10/225,068, filed on Aug. 9, 2002, now Pat. No. 7,193,129, which is a continuation-in-part of application No. 09/837,944, filed on Apr. 18, 2001, now abandoned, and a continuation-in-part of application No. 10/171,468, filed on Jun. 14, 2002, now abandoned, application No. 10/903,236, which is a continuation-in-part of application No. 10/225,066, filed on Aug. 9, 2002, now Pat. No. 7,238,860, and a continuation-in-part of application No. 10/374,780, filed on Feb. 25, 2003, now Pat. No. 7,511,190.

(60) Provisional application No. 60/411,837, filed on Sep. 18, 2002, provisional application No. 60/465,809, filed on Apr. 24, 2003, provisional application No. 60/310,847, filed on Aug. 9, 2001.

(51) Int. Cl.
C12N 15/82 (2006.01)
A01H 5/00 (2006.01)
A01H 5/10 (2006.01)

(52) U.S. Cl.
CPC ........ *C12N 15/8273* (2013.01); *C12N 15/8282* (2013.01)
USPC ........................................... 800/279; 800/301

(58) Field of Classification Search
None
See application file for complete search history.

(56) References Cited

U.S. PATENT DOCUMENTS

| 5,892,009 | A | 4/1999 | Thomashow et al. |
| 5,981,729 | A | 11/1999 | Chun et al. |
| 5,994,622 | A | 11/1999 | Jofuku et al. |
| 6,093,874 | A | 7/2000 | Jofuku et al. |
| 6,248,937 | B1 | 6/2001 | Finkelstein et al. |
| 6,329,567 | B1 | 12/2001 | Jofuku et al. |
| 6,417,428 | B1 | 7/2002 | Thomashow et al. |
| 6,846,669 | B1 | 1/2005 | Jofuku et al. |
| 2002/0138882 | A1 | 9/2002 | Cahoon et al. |
| 2003/0135888 | A1 | 7/2003 | Zhu et al. |
| 2003/0226170 | A1 | 12/2003 | Lammers et al. |
| 2003/0233670 | A1 | 12/2003 | Edgerton et al. |
| 2003/0233680 | A1 | 12/2003 | Thomashow et al. |
| 2004/0010815 | A1 | 1/2004 | Lange et al. |
| 2004/0016025 | A1 | 1/2004 | Budworth et al. |
| 2004/0019927 | A1 | 1/2004 | Sherman et al. |
| 2004/0031072 | A1 | 2/2004 | La Rosa et al. |
| 2004/0034888 | A1 | 2/2004 | Liu et al. |
| 2004/0091874 | A1 | 5/2004 | Yamazaki et al. |
| 2004/0123343 | A1 | 6/2004 | La Rosa et al. |
| 2004/0143098 | A1 | 7/2004 | Pages et al. |

(Continued)

FOREIGN PATENT DOCUMENTS

| EP | 1033405 | 9/2000 |
| JP | 2003344404 | 3/2003 |

(Continued)

OTHER PUBLICATIONS

Liu et al, 1999, Eur. J. Biochem. 262:247-257.*

(Continued)

*Primary Examiner* — Anne Kubelik
*Assistant Examiner* — Jeffrey Bolland

(57) ABSTRACT

The invention relates to plant transcription factor polypeptides, polynucleotides that encode them, homologs from a variety of plant species, and methods of using the polynucleotides and polypeptides to produce transgenic plants having advantageous properties, including disease stress and abiotic stress tolerance, as compared to wild-type or control plants. The invention also pertains to expression systems that may be used to regulate these transcription factor polynucleotides, providing constitutive, transient, inducible and tissue-specific regulation.

16 Claims, 19 Drawing Sheets

Figure 1:
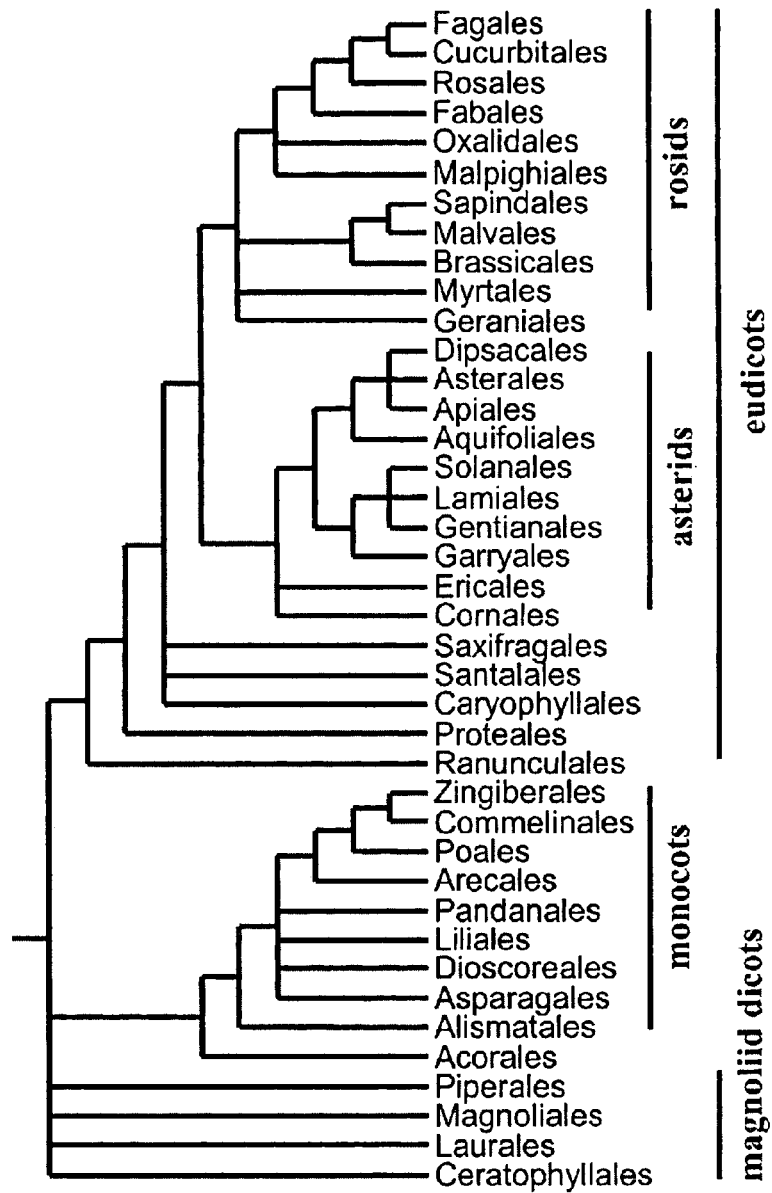

(2 of 19 Drawing Sheet(s) Filed in Color)

(56) References Cited

U.S. PATENT DOCUMENTS

| | | | |
|---|---|---|---|
| 2004/0172684 | A1 | 9/2004 | Kovalic et al. |
| 2004/0214272 | A1 | 10/2004 | La Rosa et al. |
| 2004/0216190 | A1 | 10/2004 | Kovalic et al. |
| 2005/0009187 | A1 | 1/2005 | Shinozaki et al. |
| 2005/0070697 | A1 | 3/2005 | Hu et al. |

FOREIGN PATENT DOCUMENTS

| | | |
|---|---|---|
| KR | 1020040050633 | 6/2004 |
| WO | WO 96/32007 | 10/1996 |
| WO | WO 97/47183 | 12/1997 |
| WO | WO98/07842 | 2/1998 |
| WO | WO99/41974 | 8/1999 |
| WO | WO99/55840 | 11/1999 |
| WO | WO00/32761 | 6/2000 |
| WO | WO00/46383 | 8/2000 |
| WO | WO-02/15675 | 2/2002 |
| WO | WO 02/079245 | 10/2002 |
| WO | WO03/008540 | 1/2003 |
| WO | WO-03/014327 | 2/2003 |
| WO | WO03/048319 | 6/2003 |
| WO | WO 03/081978 | 10/2003 |
| WO | WO 03/097790 | 11/2003 |
| WO | WO-2004/031349 | 4/2004 |
| WO | WO 2004/035798 | 4/2004 |
| WO | WO2004029222 | 4/2004 |
| WO | WO 2005/001050 | 1/2005 |

OTHER PUBLICATIONS

Park et al, 2001, Plant Cell 13:1035-1046.*
Gu et al, 2002, Plant Cell 14:817-831.*
Gu et a1, 2000, Plant Cell 12:771-785.*
Tournier et al, 2003, FEBS Lett. 550:149-154.*
Shin et al, 2002, Mol. Plant Microbe Interact. 15:983-989.*
Berrocal-Lobo et al, 2002, Plant J. 29:23-32.*
Lazar et al, 1988, Mol. Cell. Biol. 8:1247-1252.*
Hill et al, 1998, Biochem. Biophys. Res. Comm. 244:573-577.*
Guo et al, 2004, Proc. Natl. Acad. Sci. USA 101: 9205-9210.*
Osborne et al, 1999, GenBank Accession No. AAB70439.*
Supplemental Content only from Oñate-Sánchez et al (2002, Plant Physiol. 128:1313-1322).*
Nieva et al, 2000, In "Plant Tolerance to Abiotic stresses in Agriculture: Role of genetic engineering", Kluwer Academic Pub, pp. 157-180.*
Lee, J.H. et al. (Oct. 1, 1995). "Derepression of the activity of the genetically engineered heat shock factor causes constitutive synthesis of heat shock proteins and increased thermotolerance in transgenic *Arabidopsis*," Plant Journal, 8(4):603-612.
Dubouzet, J.G. et al. (Feb. 2003). "OsDREB genes in rice, *Oryza sativa* L., encode transcription activators that function in drought-, high-salt- and cold-responsive gene expression," Plant Journal 33(4):751-763.
Database EMBL (Aug. 24, 2003). "*Arabidopsis thaliana* mRNA for putative ethylene responsive element binding protein," XP002382624 retrieved online from EBI accession No. EM_PRO:AJ580377.
Yanagisawa Shuichi et al. (May 18, 2004). "Metabolic engineering with Dof1 transcription factor in plants: Improved nitrogen assimilation and growth under low-nitrogen conditions," Proceedings of the National Academy of Sciences of the United States of America, 101(20):7833-7838.
U.S. Appl. No. 09/601,802, Aug. 5, 1999, Thomashow et al.
AA556800 NCBI acc. No. AA556800 (gi: 3365814) (Aug. 14, 1997); Allona,I., et al. "642 Loblolly pine C *Pinus taeda* cDNA done 6C11C, mRNA sequence"; source: *Pinus taeda* (loblolly pine); Title: "Analysis of xylem formation in pine by cDNA sequencing" (Proc. Natl. Acad. Sci. U.S.A. 95 (16), 9693-9698 (1998)).
AAAA01000537 NCBI acc. No. AAAA01000537 (gi: 19924846) (Apr. 4, 2002); Yu,J., et al. "*Oryza sativa* (indica cultivar-group) scaffold000537, whole genome shotgun sequence"; source: *Oryza sativa* (indica cultivar-group); Title: "The Genomes of *Oryza sativa*: A History of Duplications" (PLoS Biol. 3 (2), E38 (2005)).
AAAA01000764 NCBI acc. No. AAAA01000764 (gi: 19925073) (Apr. 4, 2002); Yu,J., et al. "*Oryza sativa* (indica cultivar-group) scaffold000764, whole genome shotgun sequence"; source: *Oryza sativa* (indica cultivar-group); Title: "The Genomes of *Oryza sativa*: A History of Duplications" (PLoS Biol. 3 (2), E38 (2005)).
AAAA01001138 NCBI acc. No. AAAA01001138 (gi: 19925447) (Apr. 4, 2002); Yu,J., et al. "*Oryza sativa* (indica cultivar-group) scaffold001138, whole genome shotgun sequence"; source: *Oryza sativa* (indica cultivar-group); Title: "The Genomes of *Oryza sativa*: A History of Duplications" (PLoS Biol. 3 (2), E38 (2005)).
AAAA01001242 NCBI acc. No. AAAA01001242 (gi: 19925551) (Apr. 4, 2002); Yu,J., et al. "*Oryza sativa* (indica cultivar-group) scaffold001242, whole genome shotgun sequence"; source: *Oryza sativa* (indica cultivar-group); Title: "The Genomes of *Oryza sativa*: A History of Duplications" (PLoS Biol. 3 (2), E38 (2005)).
AAAA01002144 NCBI acc. No. AAAA01002144 (gi: 19926453) (Apr. 4, 2002); Yu,J., et al. "*Oryza sativa* (indica cultivar-group) scaffold002144, whole genome shotgun sequence"; source: *Oryza sativa* (indica cultivar-group); Title: "The Genomes of *Oryza sativa*: A History of Duplications" (PLoS Biol. 3 (2), E38 (2005)).
AAAA01002491 NCBI acc. No. AAAA01002491 (gi: 19926800) (Apr. 4, 2002); Yu,J., et al. "*Oryza sativa* (indica cultivar-group) scaffold002491, whole genome shotgun sequence"; source: *Oryza sativa* (indica cultivar-group); Title: "The Genomes of *Oryza sativa*: A History of Duplications" (PLoS Biol. 3 (2), E38 (2005)).
AAAA01002646 NCBI acc. No. AAAA01002646 (gi: 19926955) (Apr. 4, 2002); Yu,J., et al. "*Oryza sativa* (indica cultivar-group) scaffold002646, whole genome shotgun sequence"; source: *Oryza sativa* (indica cultivar-group); Title: "The Genomes of *Oryza sativa*: A History of Duplications" (PLoS Biol. 3 (2), E38 (2005)).
AAAA01003158 NCBI acc. No. AAAA01003158 (gi: 19927467) (Apr. 4, 2002); Yu,J., et al. "*Oryza sativa* (indica cultivar-group) scaffold003158, whole genome shotgun sequence"; source: *Oryza sativa* (indica cultivar-group); Title: "The Genomes of *Oryza sativa*: A History of Duplications" (PLoS Biol. 3 (2), E38 (2005)).
AAAA01004215 NCBI acc. No. AAAA01004215 (gi: 19928525) (Apr. 4, 2002); Yu,J., et al. "*Oryza sativa* (indica cultivar-group) scaffold004215, whole genome shotgun sequence"; source: *Oryza sativa* (indica cultivar-group); Title: "The Genomes of *Oryza sativa*: A History of Duplications" (PLoS Biol. 3 (2), E38 (2005)).
AAAA01005323 NCBI acc. No. AAAA01005323 (gi: 19929633) (Apr. 4, 2002); Yu,J., et al. "*Oryza sativa* (indica cultivar-group) scaffold005323, whole genome shotgun sequence"; source: *Oryza sativa* (indica cultivar-group); Title: "The Genomes of *Oryza sativa*: A History of Duplications" (PLoS Biol. 3 (2), E38 (2005)).
AAAA01008298 NCBI acc. No. AAAA01006298 (gi: 19930608) (Apr. 4, 2002); Yu,J., et al. "*Oryza sativa* (indica cultivar-group) scaffold006298, whole genome shotgun sequence"; source: *Oryza sativa* (indica cultivar-group); Title: "The Genomes of *Oryza sativa*: A History of Duplications" (PLoS Biol. 3 (2), E38 (2005)).
AAAA01008724 NCBI acc. No. AAAA01008724 (gi: 19933034) (Apr. 4, 2002); Yu,J., et al. "*Oryza sativa* (indica cultivar-group) scaffold008724, whole genome shotgun sequence"; source: *Oryza sativa* (indica cultivar-group); Title: "The Genomes of *Oryza sativa*: A History of Duplications" (PLoS Biol. 3 (2), E38 (2005)).
AAAA01010631 NCBI acc. No. AAAA01010631 (gi: 19936489) (Apr. 4, 2002); Yu,J., et al. "*Oryza sativa* (indica cultivar-group) scaffold010631, whole genome shotgun sequence"; source: *Oryza sativa* (indica cultivar-group); Title: "The Genomes of *Oryza sativa*: A History of Duplications" (PLoS Biol. 3 (2), E38 (2005)).
AAAA01012531 NCBI acc. No. AAAA01012531 (gi: 19939938) (Apr. 4, 2002); Yu,J., et al. "*Oryza sativa* (indica cultivar-group) scaffold012531, whole genome shotgun sequence"; source: *Oryza sativa* (indica cultivar-group); Title: "The Genomes of *Oryza sativa*: A History of Duplications" (PLoS Biol. 3 (2), E38 (2005)).
AAAA01035494 NCBI acc. No. AAAA01035494 (gi: 19975076) (Apr. 4, 2002); Yu,J., et al. "*Oryza sativa* (indica cultivar-group) scaffold035494, whole genome shotgun sequence"; source: *Oryza sativa* (indica cultivar-group); Title: "The Genomes of *Oryza sativa*: A History of Duplications" (PLoS Biol. 3 (2), E38 (2005)).

(56) References Cited

OTHER PUBLICATIONS

AB016264 NCBI acc. No. AB016264 (gi: 8809570) (Jun. 28, 2000); Kitajima,S., et al. "*Nicotiana sylvestris* nserf2 gene for ethylene-responsive element binding factor, complete cds"; source: *Nicotiana sylvestris* (wood tobacco); Title: Characterization of gene expression of NsERFs, transcription factors of basic PR genes from *Nicotiana*.
AB035270 NCBI acc. No. AB035270 (gi: 6478844) (Nov. 30, 1999); Ashida,Y., et al. "*Matricaria chamomilla* McEREBP1 mRNA for ethylene-responsive element binding protein1 homolog, partial cds"; source: *Matricaria chamomilla*.
AB036883 NCBI acc. No. AB036883 (gi: 10567105) (Oct. 3, 2000); Ohta,M., et al. "*Oryza sativa* mRNA for osERF3, complete cds"; source: *Oryza sativa*; Title: "A nobel repression domain of class II ERF transcriptional repressors" (Unpublished (2000)).
AB037183 NCBI acc. No. AB037183 (gi: 9309341) (Jul. 20, 2000); Ohta,M., et al. "*Oryza sativa* osERF3 mRNA for ethylene responsive element binding factor3, complete cds"; source: *Oryza sativa*; Title: "Novel transcriptional repression in plants" (Unpublished (2000)).
AC025907 NCBI acc. No. AC025907 (gi: 7249444) (Mar. 16, 2000); Llaca.V., et al. "*Oryza sativa* chromosome 10 clone nbxb0094K20, \*\*\* Sequencing in Progress \*\*\*, 2 ordered pieces"; source: *Oryza sativa*; Title: "Rice Chromosome 10" (Unpublished).
AC079890 NCBI acc. No. AC079890 (gi: 10179366) (Sep. 16, 2000); Buell,R., et al. "*Oryza sativa* chromosome 10 clone OSJNBb0089A17, \*\*\* Sequencing in Progress \*\*\*, 12 unordered pieces"; source: *Oryza sativa*; Title: "*Oryza sativa* ssp. japonica cv. Nipponbare OSJNBb0089A17 BAC genomic sequence" (Unpublished).
AC084763 NCBI acc. No. AC084763 (gi: 11178087) (Nov. 15, 2000); Buell,R., et al. "*Oryza sativa* chromosome 10 clone OSJNBa0027P10, \*\*\* Sequencing in Progress \*\*\*, 9 unordered pieces"; source: *Oryza sativa*; Title: "*Oryza sativa* ssp. japonica cv. Nipponbare OSJNBa0027P10 BAC genomic sequence" (Unpublished).
AC092263 NCBI acc. No. AC092263 (gi: 14578167) (Jun. 30, 2001); Buell,R., et al. "*Oryza sativa* chromosome 3 clone OSJNBa0033P04, \*\*\* Sequencing in Progress \*\*\*, 15 unordered pieces"; source: *Oryza sativa*; Title: "*Oryza sativa* ssp. japonica cv. Nipponbare OSJNBa0033P04 BAC genomic sequence" (Unpublished).
AC105318 NCBI acc. No. AC105318 (gi: 17998701) (Dec. 30, 2001); Chow,T.-Y., et al. "*Oryza sativa* chromosome 5 clone OJ1058F05, \*\*\* Sequencing in Progress \*\*\*, 3 ordered pieces"; source: *Oryza sativa*; Title: "*Oryza sativa* BAC OJ1058F05 genomic sequence" (Unpublished).
AC105734 NCBI acc. No. AC105734 (gi: 18092960) (Jan. 9, 2002); Wing, R.A., et al. "*Oryza sativa* chromosome 3 clone OSJNBa0050N02, \*\*\* Sequencing in Progress \*\*\*, 11 ordered pieces"; source: *Oryza sativa*; Title: "Rice Genomic Sequence" (Unpublished).
AC137635 NCBI acc. No. AC137635 (gi: 25697839) (Nov. 27, 2002); McCombie,W.R., et al. "*Oryza sativa* (japonica cultivar-group) chromosome 3 clone OSJNBa0038D20, \*\*\* Sequencing in Progress \*\*\*, 2 ordered pieces"; source: *Oryza sativa*(japonica cultivar-group); Title: "Rice genomic sequence" (Unpublished).
AF057373 NCBI acc. No. AF057373 (gi: 3695033) (Oct. 6, 1998); Horvath,D.M., et al. "*Nicotiana tabacum* ethylene response element binding protein 1 (EREBP1) mRNA, EREBP1-2 allele, partial cds"; source: *Nicotiana tabacum* (common tobacco); (Mol. Plant Microbe Interact. 11 (9), 895-905 (1998)).
AF204784 NCBI acc. No. AF204784 (gi: 12231293) (Jan. 16, 2001); Giovannoni,J.J., et al. "*Lycopersicon esculentum* ripening regulated protein DDTFR10/A (DDTFR10/A) mRNA, partial cds"; source: *Solanum lycopersicum* (*Lycopersicon esculentum*); (Theor. Appl Genet. 98 (6/7), 1005-1013 (1999)).
AF211527 NCBI acc. No. AF211527 (gi: 12003375) (Jan. 2, 2001); Durrant, W.E., et al. "*Nicotiana tabacum* Avr9/Cf-0 rapidly elicited protein 1 (ACRE1) mRNA, complete cds"; source: *Nicotiana tabacum* (common tobacco).
AF245119 NCBI acc. No. AF245119 (gi: 7528275) (Apr. 9, 2000); Scharte,J., et al. "*Mesembryanthemum crystallinum* AP2-related transcription factor (CDBP) mRNA, complete cds"; source: *Mesembryanthemum crystallinum* (common iceplant).
AF357211 NCBI acc. No. AF357211 (gi: 21304711) (Jun. 1, 2002); Mazarei,M., et al. "*Glycine max* ethylene-responsive element binding protein 1 (EREBP1) mRNA, complete cds"; source: *Glycine max* (soybean); (Mol. Plant Microbe Interact. 15 (6), 577-586 (2002)).
AF494201 NCBI acc. No. AF494201 (gi: 23452023) (Oct. 2, 2002); Zhang,H., et al. "*Lycopersicon esculentum* transcription factor TSRF1 (TSRF1) mRNA, complete cds"; source: *Lycopersicon esculentum* (tomato); title: "A tomato transicription factor regulating expression of stress responsive genes" (Unpublished).
AF502085 NCBI acc. No. AF502085 (gi: 25992125) (Dec. 2, 2002); Cheng, X.G., et al. "*Lycopersicon esculentum* ethylene responsive element binding protein (EREB) mRNA, complete cds"; source: *Solanum lycopersicum* (*Lycopersicon esculentum*); Title: "Direct Submission" (Submitted (Apr. 13, 2002).
AI442716 NCBI acc. No. AI442716 (gi: 4298124) (Feb. 19, 1999); Shoemaker,R., et al. "sa85d10.y1 Gm-c1004 *Glycine max* cDNA clone Genome Systems Clone ID: Gm-c1004-6092 5 similar to TR:O04680 O04680 PTI4. ;, mRNA sequence"; source: *Glycine max* (soybean).
AI483501 NCBI acc. No. AI483501 (gi: 4387425) (Mar. 9, 1999); Alcala,J., et al. "EST249322 tomato ovary, TAMU *Solanum lycopersicum* cDNA clone cLED24G10, mRNA sequence"; source: *Solanum lycopersicum* (*Lycopersicon esculentum*); Title: "Generation of ESTs from tomato carpel tissue" (Unpublished (1999)).
AI483510 NCBI acc. No. AI483510 (gi: 4387434) (Mar. 9, 1999); Alcala,J., et al. "EST249359 tomato ovary, TAMU *Solanum lycoperslcum* cDNA clone cLED25A22, mRNA sequence"; source: *Solanum lycoperslcum* (Unpublished (1999)).
AI483636 NCBI acc. No. AI483636 (gi: 4387560) (Mar. 9, 1999); Alcala,J., et al. "EST249507 tomato ovary, TAMU *Solanum lycopersicum* cDNA clone cLED25J16, mRNA sequence"; source: *Solanum lycopersicum* (*Lycopersicon esculentum*); Title: "Generation of ESTs from tomato carpel tissue" (Unpublished (1999)).
AI483741 NCBI acc. No. AI483741 (gi: 4387665) (Mar. 9, 1999); Alcala,J., et al. "EST249612 tomato ovary, TAMU *Solanum lycopersicum* cDNA clone cLED2F21, mRNA sequence"; source: *Solanum lycopersicum* (*Lycopersicon esculentum*); Title: "Generation of ESTs from tomato carpel tissue" (Unpublished (1999)).
AI484961 NCBI acc. No. AI484961 (gi: 4380332) (Mar. 9, 1999); Alcala,J., et al. "EST243224 tomato ovary, TAMU *Solanum lycopersicum* cDNA clone cLED2F21, mRNA sequence"; source: *Solanum lycopersicum* (*Lycopersicon esculentum*); Title: "Generation of ESTs from tomato carpel tissue" (Unpublished (1999)).
AI485175 NCBI acc. No. AI485175 (gi: 4380546) (Mar. 9, 1999); Alcala,J., et al. "EST243479 tomato ovary, TAMU *Solanum lycopersicum* cDNA clone cLED6D8, mRNA sequence"; source: *Solanum lycopersicum* (*Lycopersicon esculentum*); Title: "Generation of ESTs from tomato carpel tissue" (Unpublished (1999)).
AI485460 NCBI acc. No. AI485460 (gi: 4380831) (Mar. 9, 1999); Alcala,J., et al. "EST243781 tomato ovary, TAMU *Solanum lycopersicum* cDNA clone cLED4J9, mRNA sequence"; source: *Solanum lycopersicum* (*Lycopersicon esculentum*); Title: "Generation of ESTs from tomato carpal tissue" (Unpublished (1999)).
AI485634 NCBI acc. No. AI485634 (gi: 4381005) (Mar. 9, 1999); Alcala,J., et al. "EST243955 tomato ovary, TAMU *Solanum lycopersicum* cDNA clone cLED6J8, mRNA sequence"; source: *Solanum lycopersicum* (*Lycopersicon esculentum*); Title: "Generation of ESTs from tomato carpal tissue" (Unpublished (1999)).
AI486689 NCBI acc. No. AI486689 (gi: 4382060) (Mar. 9, 1999); Alcala,J., et al. "EST245011 tomato ovary, TAMU *Solanum lycopersicum* cDNA clone cLED11H4, mRNA sequence"; source: *Solanum lycopersicum* (*Lycopersicon esculentum* ); Title: "Generation of ESTs from tomato carpel tissue" (Unpublished (1999)).
AI486798 NCBI acc. No. AI486798 (gi: 4382169) (Mar. 9, 1999); Alcala,J., et al. "EST245120 tomato ovary, TAMU *Solanum lycopersicum* cDNA clone cLED11D21, mRNA sequence"; source: *Solanum lycopersicum* (*Lycopersicon esculentum*); Title: "Generation of ESTs from tomato carpel tissue" (Unpublished (1999)).
AI486929 NCBI acc. No. AI486929 (gi: 4382300) (Mar. 9, 1999); Alcala,J., et al. "EST245251 tomato ovary, TAMU *Solanum lycopersicum* cDNA clone cLED6L21, mRNA sequence"; source:

(56) References Cited

OTHER PUBLICATIONS

*Solanum lycopersicum (Lycopersicon esculentum)*; Title: "Generation of ESTs from tomato carpel tissue" (Unpublished (1999)).
AI487698 NCBI acc. No. AI487698 (gi: 4383069) (Mar. 9, 1999); Alcala,J., et al. "EST246020 tomato ovary, TAMU *Solanum lycopersicum* cDNA clone cLED14C15, mRNA sequence"; source: *Solanum lycopersicum (Lycopersicon esculentum)*; Title: "Generation of ESTs from tomato carpel tissue" (Unpublished (1999)).
AI489199 NCBI acc. No. AI489199 (gi: 4384570) (Mar. 9, 1999); Alcala,J., et al. "EST247538 tomato ovary, TAMU *Solanum lycopersicum* cDNA clone cLED17M16, mRNA sequence"; source: *Solanum lycopersicum (Lycopersicon esculentum)*; Title: "Generation of ESTs from tomato carpel tissue" (Unpublished (1999)).
AI490296 NCBI acc. No. AI490296 (gi: 4385606) (Mar. 9, 1999); Alcala,J., et al. "EST248622 tomato ovary, TAMU *Solanum lycopersicum* cDNA clone cLED24JB, mRNA sequence"; source: *Solanum lycopersicum (Lycopersicon esculentum)*; Title: "Generation of ESTs from tomato carpel tissue" (Unpublished (1999)).
AI495036 NCBI acc. No. AI495036 (gi: 4396039) (Mar. 11, 1999); Shoemaker,R., et al. "sa90a09.y1 Gm-c1004 *Glycine max* cDNA clone Genome Systems Clone ID: Gm-c1004-6545 5' similar to TR:O22167 O22167 EREBP Isolog. ;, mRNA sequence"; source: *Glycine max* (soybean).
AI771213 NCBI acc. No. AI771213 (gi: 5269350) (Jun. 29, 1999); Alcala,J., et al. "EST252409 tomato ovary, TAMU *Solanum lycopersicum* cDNA clone cLED29K9, mRNA sequence"; source: *Solanum lycopersicum (Lycopersicon esculentum)*; Title: "Generation of ESTs from tomato carpal tissue" (Unpublished (1999)).
AI771245 NCBI acc. No. AI771245 (gi: 5269202) (Jun. 29, 1999); Alcala,J., et al. "EST252261 tomato ovary, TAMU *Solanum lycopersicum* cDNA clone cLED28N15, mRNA sequence"; source: *Solanum lycopersicum (Lysopersicon esculentum)*; Title: "Generation of ESTs from tomator carpel tissue" (Unpublished (1999)).
AI771755 NCBI acc. No. AI771755 (gi: 5269796) (Jun. 29, 1999); Alcala,J., et al. "EST252855 tomato ovary, TAMU *Solanum lycopersicum* cDNA clone cLED35M15, mRNA sequence"; source: *Solanum lycopersicum (Lycopersicon esculentum)*; Title: "Generation of ESTs from tomato carpel tissue" (Unpublished (1999)).
AI771795 NCBI acc. No. AI771795 (gi: 5269836) (Jun. 29, 1999); Alcala,J., et al. "EST252895 tomato ovary, TAMU *Solanum lycopersicum* cDNA clone cLED3BA15, mRNA sequence"; source: *Solanum lycopersicum (Lycopersicon esculentum)*; Title: "Generation of ESTs from tomato carpel tissue" (Unpublished (1999)).
AI771834 NCBI acc. No. AI771834 (gi: 5269875) (Jun. 29, 1999); Alcala,J., et al, "EST252934 tomato ovary, TAMU *Solanum lycopersicum* cDNA clone cLED3811, mRNA sequence"; source: *Solanum lycopersicum (Lycopersicon esculentum)*; Title: "Generation of ESTs from tomato carpel tissue" (Unpublished (1999)).
AI776626 NCBI acc. No. AI776626 (gi: 5274667) (Jun. 29, 1999); D'Ascenzo, M. et al. "EST253720 tomato resistant, Cornell *Solanum lycopersicum* cDNA clone cLER312, mRNA sequence"; source: *Solanum lycopersicum (Lycopersicon esculentum)*; Title: "Generation of ESTs from *Pseudomonas* resistant tomato" (Unpublished (1999)).
AI775562 NCBI acc. No. AI775562 (gi: 5273603) (Jun. 29, 1999); D'Ascenzo, M. et al. "EST256662 tomato resistant, Cornell *Solanum lycopersicum* cDNA clone cLER15L16, mRNA sequence"; source: *Solanum lycopersicum (Lycopersicon esculentum)*.
AI776626 NCBI acc. No. AI776626 (gi: 5274667) (Jun. 29, 1999); D'Ascenzo, M. et al. "EST257726 tomato resistant, Cornell *Solanum lycopersicum* cDNA clone cLER19A14, mRNA sequence"; source: *Solanum lycopersicum (Lycopersicon esculentum)*.
AI778498 NCBI acc. No. AI778498 (gi: 5276539) (Jun. 29, 1999); D'Ascenzo, M. et al. "EST259377 tomato susceptible, Cornell *Solanum lycopersicum* cDNA clone cLESSD19, mRNA sequence"; source: *Solanum lycopersicum (Lycopersicon esculentum)*.
AI778693 NCBI acc. No. AI778693 (gi: 5276734) (Jun. 29, 1999); D'Ascenzo, M. et al. "EST259572 tomato susceptible, Cornell *Solanum lycopersicum* cDNA clone cLES619, mRNA sequence"; source: *Solanum lycopersicum (Lycopersicon esculentum)*.

AI779791 NCBI acc. No. AI779791 (gi: 5277832) (Jun. 29, 1999); D'Ascenzo, M. et al. "EST260670 tomato susceptible, Cornell *Solanum lycopersicum* cDNA clone cLES9K15, mRNA sequence"; source: *Solanum lycopersicum (Lycopersicon esculentum)*.
AI780258 NCBI acc. No. AI780258 (gi: 5278299) (Jun. 29, 1999); D'Ascenzo, M. et al. "EST261137 tomato susceptible, Cornell *Solanum lycopersicum* cDNA clone cLES11B13, mRNA sequence"; source: *Solanum lycopersicum (Lycopersicon esculentum)*.
AI782381 NCBI acc. No. AI782381 (gi: 5280422) (Jun. 29, 1999); D'Ascenzo, M., et al. "EST263260 tomato susceptible, Cornell *Solanum lycopersicum* cDNA done cLES18P16, mRNA sequence"; source: *Solanum lycopersicum (Lycopersicon esculentum)*.
AI794657 NCBI acc. No. AI794657 (gi: 5342373) (Jul. 2, 1999); Shoemaker,R., et al. "sb67b03.y1 Gm-c1019 *Glycine max* cDNA clone Genome Systems Clone ID: Gm-c1019-6 5' similar to TR:Q40478 Q40478 EREBP-4. ;, mRNA sequence"; source: *Glycine max* (soybean).
AI855585 NCBI acc. No. AI855585 (gi: 5509027) (Jul. 16, 1999); Shoemaker,R., et al. "sc28b12.y1 Gm-c1014 *Glycine max* cDNA done Genome Systems Clone ID: Gm-c1014-408 5' similar to TR:O81365 O81365 AP2 Domain Containing Protein :, mRNA sequence"; source: *Glycine max* (soybean).
AI894515 NCBI acc. No. AI894515 (gi: 5600417) (Jul. 27, 1999); Alcala,J., et al. "EST263958 tomato callus, TAMU *Solanum lycopersicum* cDNA clone cLEC4M24, mRNA sequence"; source: *Solanum lycopersicum (Lycopersicon esculentum)*; Title: "Generation of ESTs from tomato callus tissue" (Unpublished (1999)).
AI894873 NCBI acc. No. AI894873 (gi: 5600775) (Jul. 27, 1999); Alcala,J., et al. "EST264316 tomato callus, TAMU *Solanum lycopersicum* cDNA clone cLEC6K7, mRNA sequence"; source: *Solanum lycopersicum (Lycopersicon esculentum)*; Title: "Generation of ESTs from tomato callus tissue" (Unpublished (1999)).
AI895391 NCBI acc. No. AI895391 (gi: 5601293) (Jul. 27, 1999); Alcala,J., et al. "EST264834 tomato callus, TAMU *Solanum lycopersicum* cDNA clone cLEC7L3, mRNA sequence"; source: *Solanum lycopersicum (Lycopersicon esculentum)*; Title: "Generation of ESTs from tomato callus tissue" (Unpublished (1999)).
AI895742 NCBI acc. No. AI895742 (gi: 5601644) (Jul. 27, 1999); Alcala,J., et al. "EST265185 tomato callus, TAMU *Solanum lycopersicum* cDNA clone cLEC10A3, mRNA sequence"; source: *Solanum lycopersicum (Lycopersicon esculentum)*; Title "Generation of ESTs from tomato callus tissue" (Unpublished (1999)).
AI896308 NCBI acc. No. AI896308 (gi: 5602210) (Jul. 27, 1999); Alcala,J., et al. "EST265751 tomato callus, TAMU *Solanum lycopersicum* cDNA clone cLEC14N19, mRNA sequence"; source: *Solanum lycopersicum (Lycopersicon esculentum)*; Title: "Generation of ESTs from tomato callus tissue" (Unpublished (1999)).
AI897787 NCBI acc. No. AI897787 (gi: 5603689) (Jul. 27, 1999); Alcala,J., et al. "EST267230 tomato ovary, TAMU *Solanum lycopersicum* cDNA clone cLED30N5, mRNA sequence"; source: *Solanum lycopersicum (Lycopersicon esculentum)*; Title: "Generation of ESTs from tomato carpel tissue" (Unpublished (1999)).
AI897797 NCBI acc. No. AI897797 (gi: 5603699) (Jul. 27, 1999); Alcala,J., et al. "EST267240 tomato ovary, TAMU *Solanum lycopersicum* cDNA clone cLED30P1, mRNA sequence"; source: *Solanum lycopersicum (LYcopersicon esculentum)*; Title: "Generation of ESTs from tomato carpel tissue" (Unpublished (1999)).
AI897834 NCBI acc. No. AI897834 (gi: 5603736) (Jul. 27, 1999); Alcala,J., "EST267277 tomato ovary, TAMU *Solanum lycopersicum* cDNA clone cLED30F18, mRNA sequence"; source: *Solanum lycopersicum (Lycopersicon esculentum)*; Title: "Generation of ESTs from tomato carpal tissue" (Unpublished (1999)).
AI899000 NCBI acc. No. AI899000 (gi: 5604902) (Jul. 27, 1999); Alcala,J., et al. "EST268443 tomato ovary, TAMU *Solanum lycopersicum* cDNA clone cLED36J9, mRNA sequence"; *Solanum lycopersicum (Lycopersicon esculentum)*; Title: "Generation of ESTs from tomato carpel tissue" (Unpublished (1999)).
AI899889 NCBI acc. No. AI899889 (gi: 5605791) (Jul. 27, 1999); Shoemaker,R., et al. "sb94g05.y1 Gm-c1017 *Glycine max* cDNA clone Genome Systems clone ID: Gm-c1017-2237 5' similar to TRQ40478 Q40478 EREBP-4. :, mRNA sequence"; source: *Glycine max* (soybean).

(56) References Cited

OTHER PUBLICATIONS

AI965917 NCBI acc. No. AI965917 (gi: 5760554) (Aug. 23, 1999); Shoemaker,R., et al. "sc79f12.y1 Gm-c1018 *Glycine max* cDNA clone Genome Systems Clone ID: Gm-c1018-1128 5' similar to TR:O80341 O80341 Ethylene Responsive Element Binding Factor 5. ;, mRNA sequence"; source: *Glycine max.*
AI966369 NCBI acc. No. AI966369 (gi: 5761006) (Aug. 23, 1999); Shoemaker, R., et al. "sc37h09.y1 Gm-c1014 *Glycine max* cDNA clone Genome Systems Clone ID: Gm-c1014-1338 5' similar to TR:O81365 O81365 AP2 Domain Containing Protein ;, mRNA sequence"; source: *Glycine max* (soybean).
AI966559 NCBI acc. No. AI966559 (gi: 5761196) (Aug. 23, 1999); Shoemaker,R., et al. "sc52a04.y1 Gm-c1015 *Glycine max* cDNA clone Genome Systems Clone ID: Gm-c1015-1159 5' similar to TR:O23591 O23591 EREBP-4 Homolog. ;, mRNA sequence"; source: *Glycine max* (soybean).
AI967551 NCBI acc. No. AI967551 (gi: 5762854) (Aug. 24, 1999); Poulsen,C., et al. "Ljimpest05-400-d11 Ljimp Lambda HybriZap two-hybrid library *Lotus japonicus* cDNA clone LP400-05-d11 5' similar to ethylene response factor 1, mRNA sequence"; source: *Lotus japonicus.*
AI973653 NCBI acc. No. AI973653 (gi: 5770479) (Aug. 25, 1999); Shoemaker,R., et al. "sd07h05.y1 Gm-c1020 *Glycine max* cDNA clone Genome Systems Clone ID: Gm-c1020-1042 5' similar to TR:O22167 O22167 EREBP Isolog. ;, mRNA sequence"; source: *Glycine max* (soybean).
AJ503278 NCBI acc. No. AJ503278 (gi: 22084206) (Aug. 1, 2002); Manthey,K., et al. "*Medicago truncatula* EST, clone mtgmadc120032c02"; source: *Medicago truncatula.*
AL387092 NCBI acc. No. AL367092 (gi: 9666845) (Aug. 3, 2000); Journet,E.P., et al. "MtBA12B12F1 MtBA *Medicago truncatula* cDNA clone MtBA12B12 T3, mRNA sequence"; source: *Medicago truncatula* (barrel medic); Title: "*Medicago truncatula* ESTs from nitrogen-starved roots" (Unpublished (2000)).
AL374803 NCBI acc. No. AL374803 (gi: 9674555) (Aug. 3, 2000); Journet,E.P., et al. "MtBB09D02F1 MtBB *Medicago truncatula* cDNA clone MtBB09D02 T3, mRNA sequence"; source: *Medicago truncatula* (barrel medic); Title: "*Medicago truncatula* ESTs from *Sinorhizobium meliloti*-induced root nodules" (Unpublished (2000)).
AL378570 NCBI acc. No. AL378570 (gi: 9678322) (Aug. 3, 2000); Journet,E.P., et al. "MtBB39B01F1 MtBB *Medicago truncatula* cDNA clone MtBB39B01 T3, mRNA sequence"; source: *Medicago truncatula* (barrel medic); Title: "*Medicago truncatula* ESTs from *Sinorhizobium meliloti*-induced root nodules" (Unpublished (2000)).
AL378571 NCBI acc. No. AL378571 (gi: 9678323) (Aug. 3, 2000); Journet,E.P., et al. "MtBB39B01R1 MtBB *Medicago truncatula* cDNA clone MtBB39B01 T7, mRNA sequence"; source: *Medicago truncatula* (barrel medic); Title: "*Medicago truncatula* ESTs from *Sinorhizobium meliloti*-induced root nodules" (Unpublished (2000)).
AL381730 NCBI acc. No. AL381730 (gi: 9681481) (Aug. 3, 2000); Journet,E.P., et al. "MtBC02F03F3 MtBC *Medicago truncatula* cDNA clone MtBC02F03 T3, mRNA sequence"; source: *Medicago truncatula* (barrel medic); Title: "*Medicago truncatula* ESTs from endomycorrhizal roots"(Unpublished (2000)).
AL387924 NCBI acc. No. AL387924 (gi: 9687675) (Aug. 3, 2000); Journet,E.P., et al. "MtBC45F03F1 MtBC *Medicago truncatula* cDNA clone MtBC45F03 T3, mRNA sequence"; source: *Medicago truncatula* (barrel medic); Title: "*Medicago truncatula* ESTs from endomycorrhizal roots" (Unpublished (2000)).
AL388234 NCBI acc. No. AL388234 (gi: 9687985) (Aug. 3, 2000); Journet,E.P., et al. "MtBC47D08F1 MtBC *Medicago truncatula* cDNA clone MtBC47D08 T3, mRNA sequence"; source: *Medicago truncatula* (barrel medic); Title: "*Medicago truncatula* ESTs from endomcorrhizal roots" (Unpublished (2000)).
AL750652 NCBI acc. No. AL750652 (gi: 21491890) (Jun. 20, 2002); Frigerio,J., et al. "AL750652 RN *Pinus pinaster* cDNA clone RN05H01 similar to Ethylene Responsive Element Binding Factor, mRNA sequence"; source: *Pinus pinaster.*
AP003237 NCBI acc. No. AP003237 (gi: 13027267) (Feb. 21, 2001); Sasaki,T., et al. *Oryza sativa* chromosome 1 clone P0046E05, * Sequencing in Progress *; source: *Oryza sativa*; Title: "*Oryza sativa* nipponbare(GA3) genomic DNA, chromosome 1, PAC clone:P0046E05".
AP003249 NCBI acc. No. AP003249 (gi: 13027279) (Feb. 21, 2001); Sasaki,T., et al. "*Oryza sativa* chromosome 1 clone P0435B05, * Sequencing in Progress *"; source: *Oryza sativa*; Title: "*Oryza sativa* nipponbare(GA3) genomic DNA, chromosome 1, PAC clone: P0435B05"(Published Only in DataBase (2001).
AP003286 NCBI acc. No. AP003286 (gi: 13027316) (Feb. 21, 2001); Sasaki,T., et al. "*Oryza sativa* chromosome 1 clone P0677H08, *Sequencing in Progress *"; source: *Oryza sativa*; title: "*Oryza sativa* nipponbare(GA3) genomic DNA, chromosome 1, PAC clone:P0677H08" (Published Only in DataBase (2001).
AP003294 NCBI acc. No. AP003294 (gi: 13027324) (Feb. 21, 2001); Sasaki,T., et al. "*Oryza sativa* chromosome 1 clone P0694A04, * Sequencing in Progress *"; source: *Oryza sativa*; Title: "*Oryza sativa* nipponbare(GA3) genomic DNA, chromosome 1, PAC clone:P0694A04" (Published Only in DataBase (2001).
AP003820 NCBI acc. No. AP003820 (gi: 14595160) (Jul. 3, 2001); Sasaki,T., et al. "*Oryza sativa* chromosome 7 clone OJ1235_H07, * Sequencing in Progress *"; source: *Oryza sativa*; Title: "*Oryza sativa* nipponbare(GA3) genomic DNA, chromosome 7, BAC clone:OJ1235_H07" (Published Only in Database (2001).
AP003891 NCBI acc. No. AP003891 (gi: 14646849) (Jul. 9, 2001); Sasaki,T., et al. "*Oryza sativa* chromosome 8 clone OJ1314_F06, * Sequencing in Progress *"; source: *Oryza sativa*; Title: "*Oryza sativa* nipponbare(GA3) genomic DNA, chromosome 8, BAC clone:OJ1314_OJ1314_F06" (Published Only in Database (2001).
AP004623 NCBI acc. No. AP004623 (gi: 18157388) (Jan. 15, 2002); Sasaki,T., et al. "*Oryza sativa* chromosome 8 clone P0705A05, * Sequencing in Progress *"; source: *Oryza sativa*; Title: "*Oryza sativa* nipponbare (GA3) genomic DNA, chromosome 8, PAC clone:P0705A05" (Published Only in Database (2002)).
AP005006 NCBI acc. No. AP005006 (gi: 19773546) (Mar. 27, 2002); Sasaki,T., et al. "*Oryza sativa* (japonica cultivar-group) chromosome 2 clone P0519E06, * Sequencing in Progress *"; source: *Oryza sativa* (japonica cultivar-group).
AP006162 NCBI acc. No. AP006162 (gi: 27884274) (Jan. 23, 2003); Sasaki,T., et al. "*Oryza sativa* (japonica cultivar-group) chromosomes 9 clone B1331F11, * Sequencing in Progress *"; source: *Oryza sativa* (japnica cultivar-group).
AU083457 NCBI acc. No. AU083457 (gi: 7273913) (Mar. 21, 2000); Sasaki,T., et al. "AU083457 Rice panicle at flowering stage *Oryza sativa* (japonica cultivar-group) cDNA clone E4394, mRNA sequence"; source: *Oryza sativa* (japonica cultivar-group).
AU083511 NCBI acc. No. AU083511 (gi: 7273967) (Mar. 21, 2000); Sasaki,T., et al. "AU083511 Rice cDNA from young root *Oryza sativa* (japonica cuitivar-group) cDNA clone R10838, mRNA sequence"; source: *Oryza sativa* (japonica cultivar-group).
AU173832 NCBI acc. No. AU173832 (gi: 13165035) (Feb. 28, 2001); Sasaki,T., et al. "AU173832 Rice cDNA from young root *Oryza sativa* (japonica cultivar-group) cDNA done R10061, mRNA sequence"; source: *Oryza sativa* (japonica cultivar-group); Title: "Rice cDNA from young root (2001)" (Unpublished (2001)).
AU181580 NCBI acc. No. AU181580 (gi: 13806594) (Apr. 26, 2001); Sasaki,T., et al. "AU181580 Rice callus (2001) *Oryza sativa* (japnica cultivar-group) cDNA clone C50458, mRNA sequence"; source: *Oryza sativa* (japonica cultivar-group); Title: "Rice cDNA from callus (2001)" (Unpublished (2001)).
AV407462 NCBI acc. No. AV407462 (gi: 7720316) (May 8, 2000); Asamizu,E., et al. "AV407462 *Lotus japonicus* young plants (two-week old) *Lotus japonicus* cDNA clone MWL024d04_r 5', mRNA sequence"; source: *Lotus japonicus*; (DNA Res. 7 (2), 127-130 (2000)).
AV417624 NCBI acc. No. AV417624 (gi: 7746802) (May 9, 2000); Asamizu,E., et al. "AV417624 *Lotus japonicus* young plants (two-week old) *Lotus japonicus* cDNA clone MWM146e09_r 5', mRNA sequence"; source: *Lotus japonicus*;(DNA Res. 7 (2), 127-130 (2000)).

(56) References Cited

OTHER PUBLICATIONS

AV421566 NCBI acc. No. AV421566 (gi: 7775366) (May 12, 2000); Asamizu,E., et al. "AV421566 *Lotus japonicus* young plants (two-week old) *Lotus japonicus* cDNA done MWM196a01_r 5&apos:, mRNA sequence"; source: *Lotus japonicus*; (DNA Res. 7 (2), 127-130 (2000)).

AV422393 NCBI acc. No. AV422393 (gi: 7777209) (May 12, 2000); Asamizu, E., et al. "AV422393 *Lotus japonicus* young plants (two-week old) *Lotus japonicus* cDNA clone MWM012d12_r 5', mRNA sequence"; source: *Lotus japonicus*; (DNA Res. 7 (2), 127-130 (2000)).

AV422603 NCBI acc. No. AV422603 (gi: 7777670) (May 12, 2000); Asamizu,E., et al. "AV422603 *Lotus japonicus* young plants (two-week old) *Lotus japonicus* cDNA clone MWM015a04_r 5&apos:, mRNA sequence"; source: *Lotus japonicus*; (DNA Res. 7 (2), 127-130 (2000)).

AV423260 NCBI acc. No. AV423260 (gi: 7778996) (May 12, 2000); Asamizu,E., et al. "AV423260 *Lotus japonicus* young plants (two-week old) *Lotus japonicus* cDNA clone MWM024b09_r 5', mRNA sequence"; source: *Lotus japonicus*; (DNA Res. 7 (2), 127-130 (2000)).

AV425560 NCBI acc. No. AV425560 (gi: 7783624) (May 12, 2000); Asamizu,E., et al. "AV425560 *Lotus japonicus* young plants (two-week old) *Lotus japonicus* cDNA clone MWM055f07_r 5', mRNA sequence"; source: *Lotus japonicus*; (DNA Res. 7 (2), 127-130 (2000)).

AV425829 NCBI acc. No. AV425829 (gi: 7784155) (May 12, 2000); Asamizu,E., et al. "AV425829 *Lotus japonicus* young plants (two-week old) *Lotus japonicus* cDNA done MWM059g11_r 5', mRNA sequence"; source: *Lotus japonicus*; (DNA Res. 7 (2), 127-130 (2000)).

AV426605 NCBI acc. No. AV426605 (gi: 7785709) (May 12, 2000); Asamizu,E., et al. "AV426605 *Lotus japonicus* young plants (two-week old) *Lotus japonicus* cDNA clone MWM070e11_r 5', mRNA sequence"; source: *Lotus japonicus*; (DNA Res. 7 (2), 127-130 (2000)).

AV428124 NCBI acc. No. AV428124 (gi: 7788764) (May 12, 2000); Asamizu,E., et al. "AV428124 *Lotus japonicus* young plants (two-week old) *Lotus japonicus* cDNA clone MWM092d01_r 5&apos:, mRNA sequence"; source: *Lotus japonicus*;(DNA Res. 7 (2), 127-130 (2000)).

AW030009 NCBI acc. No. AW030009 (gi: 5888765) (Sep. 15, 1999); Alcala,J., et al. "EST273264 tomato callus, TAMU *Solanum lycopersicum* cDNA clone cLEC11J16, mRNA sequence"; source: *Solanum lycopersicum* (*Lycopersicon esculentum*); Title: "Generation of ESTs from tomato callus tissue" (Unpublished (1999)).

AW030386 NCBI acc. No. AW030386 (gi: 5889142) (Sep. 15, 1999); Alcala,J., et al. "EST273641 tomato callus, TAMU *Solanum lycopersicum* cDNA clone cLEC20I12, mRNA sequence"; source: *Solanum lycopersicum* (*Lycopersicon esculentum*(; Title: "Generation of ESTs from tomato callus tissue" (Unpublished (1999)).

AW031184 NCBI acc. No. AW031184 (gi: 5890024) (Sep. 15, 1999); Alcala,J., et al. "EST274722 tomato callus, TAMU *Solanum lycopersicum* cDNA clone cLEC18K13, mRNA sequence"; source: *Solanum lycopersicum* (*Lycopersicon esculentum*); Title: "Generation of ESTs from tomato callus tissue" (Unpublished (1999)).

AW032555 NCBI acc. No. AW032555 (gi: 5891311) (Sep. 15, 1999); Alcala,J., et al. "EST276114 tomato callus, TAMU *Solanum lycopersicum* cDNA clone cLECBC12, mRNA sequence"; source: *Solanum lycopersicum* (*Lycopersicon esculentum*); Title: "Generation of ESTs from tomato callus tissue" (Unpublished (1999)).

AW032633 NCBI acc. No. AW032633 (gi: 5891389) (Sep. 15, 1999); Alcala,J., et al. "EST276192 tomato callus, TAMU *Solanum lycopersicum* cDNA clone cLEC20L6, mRNA sequence"; source: *Solanum lycopersicum* (*Lycopersicon esculentum*); Title: "Generation of ESTs from tomato callus tissue" (Unpublished (1999)).

AW033743 NCBI acc. No. AW033743 (gi: 5892499) (Sep. 15, 1999); Alcala,J., et al. "EST277314 tomato callus, TAMU *Solanum lycopersicum* cDNA clone cLEC29G11 similar to AP2 domain-containing protein, putative, mRNA sequence"; source: *Solanum lycopersicum* (*Lycopersicon esculentum*).

AW034216 NCBI acc. No. AW034216 (gi: 5892972) (Sep. 15, 1999); Alcala,J., et al. "EST277787 tomato callus, TAMU *Solanum lycopersicum* cDNA clone cLEC32P18 similar to Pti4, mRNA sequence"; source: *Solanum lycopersicum* (*Lycopersicon esculentum*).

AW034241 NCBI acc. No. AW034241 (gi: 5892997) (Sep. 15, 1999 ; Alcala,J., et al. "EST277812 tomato callus, TAMU *Solanum lycopersicum* cDNA clone cLEC33C21 similar to DNA binding protein homolog, putative, mRNA sequence"; source: *Solanum lycopersicum* (*Lycopersicon esculentum*).

AW035648 NCBI acc. No. AW035648 (gi: 5894404) (Sep. 15, 1999); Alcala,J., et al. "EST281480 tomato callus, TAMU *Solanum lycopersicum* cDNA clone cLEC34P21 similar to EREBP-3 homolog, putative, mRNA sequence"; source: *Solanum lycopersicum* (*Lycopersicon esculentum*).

AW040234 NCBI acc. No. AW040234 (gi: 5898988) (Sep. 15, 1999); D'Ascenzo, M. et al. "EST282740 tomato mixed elicitor, BTI *Solanum lycopersicum* cDNA clone cLET19L2, mRNA sequence"; source: *Solanum lycopersicum* (*Lycopersicon esculentum*).

AW101483 NCBI acc. No. AW101483 (gi: 6072036) (Oct. 19, 1999); Shoemakerr,R., et al. "sd78g09.y1 Gm-c1009 *Glycine max* cDNA clone Genome Systems Clone ID: Gm-c1009-569 5' similar to TR:O23107 O23107 AP2 Domain Containing Protein RAP2.5 [1];, mRNA sequence"; source: *Glycine*.

AW156366 NCBI acc. No. AW156366 (gi: 6227767) (Nov. 4, 1999); Shoemaker,R., et al. "se25b08.y1 Gm-c1015 *Glycine max* cDNA clone Genome Systems Clone ID: Gm-c1015-2224 5' similar to TR:O23108 O23108 RAP2.6 ;, mRNA sequence"; source: *Glycine max* (soybean).

AW164527 NCBI acc. No. AW164527 (gi: 6341778) (Nov. 10, 1999); Shoemaker,R., et al. "se75a02.y1 Gm-c1023 *Glycine max* cDNA clone Genome Systems Clone ID: Gm-c1023-483 5' similar to TR:P93589 P93589 DNA Binding Protein Homolog. ;, mRNA sequence"; source: *Glycine max* (soybean).

AW185126 NCBI acc. No. AW185126 (gi: 6454443) (Nov. 19, 1999); Shoemaker,R., et al. "se87b08.y1 Gm-c1023 *Glycine max* cDNA clone Genome Systems Clone ID: Gm-c1023-1648 5' similar to TR:O23108 O23108 RAP2.6 ;, mRNA sequence"; source: *Glycine max* (soybean).

AW185128 NCBI acc. No. AW185128 (gi: 6454445) (Nov. 19, 1999); Shoemaker,R., et al. "se87b10.y1 Gm-c1023 *Glycine max* cDNA clone Genome Systems Clone ID: Gm-c1023-1652 5' similar to TR:O80341 Ethylene Responsive Element Binding Factor 5. ;, mRNA sequence".

AW186005 NCBI acc. No. AW186005 (gi: 6455322) (Nov. 19, 1999); Shoemaker,R., et al. "se62d09.y1 Gm-c1019 *Glycine max* cDNA clone Genome Systems Clone ID: Gm-c1019-1578 5' similar to TR:O23107 O23107 AP2 Domain Containing Protein RAP2.5 [1];, mRNA sequence".

AW200919 NCBI acc. No. AW200919 (gi: 6481648) (Nov. 30, 1999); Shoemaker,R., et al. "se95c12.y1 Gm-c1027 *Glycine max* cDNA clone Genome Systems Clone ID: Gm-c1027-527 5' similar to TR:O80341 O80341 Ethylene Responsive Element Binding Factor 5. ;, mRNA sequence".

AW219198 NCBI acc. No. AQ219198 (gi: 6530072) (Dec. 6, 1999); Van Der Hoeven,R.S., et al. "EST301680 tomato root during/after fruit set, Cornekk University *Solanum lycopersicum* cDNA clone cLEX3G6, mRNA sequence"; source: *Solanum lycopersicum* (*Lycopersicon esculentum*).

AW220395 NCBI acc. No. AW220395 (gi: 6531269) (Dec. 6, 1999); Van Der Hoeven,R.S., et al. "EST302878 tomato root during/after fruit set, Cornell University *Solanum lycopersicum* cDNA clone cLEX10F20, mRNA sequence"; source: *Solanum lycopersicum* (*Lycopersicon esculentum*).

AW221854 NCBI acc. No. AW221854 (gi: 6533538) (Dec. 7, 1999); Alcala,J., et al. "EST298665 tomato fruit red ripe, TAMU *Solanum lycopersicum* cDNA clone cLEN4I21, mRNA sequence"; source: *Solanum lycopersicum*.

(56) References Cited

OTHER PUBLICATIONS

AW233956 NCBI acc. No. AW233956 (gi: 6566281) (Dec. 13, 1999); Shoemaker,R., et al. "sf32e02.y1 Gm-c1028 *Glycine max* cDNA clone Genome Systems Clone ID: Gm-c1028-1683 5' similar to TR:O80337 O80337 Ethylene Responsive Element Binding Factor 1. ;, mRNA sequence".

AW234175 NCBI acc. No. AW234175 (gi: 6568532) (Dec. 13, 1999); Shoemaker,R., et al. "sf22b03.y1 Gm-c1028 *Glycine max* cDNA clone Genome Systems Clone ID: Gm-c1028-678 5 similar to TR:O81365 O81365 AP2 Domain Containing Protein ;, mRNA sequence"; source: *Glycine max.*

AW256448 NCBI acc. No. AW256448 (gi: 6604705) (Dec. 20, 1999); Vandenbosch,K., et al. "EST304585 KV2 *Medicago truncatula* cDNA clone KV2-4N11, mRNA sequence"; source: *Medicago truncatula* (barrel medic); Title: "ESTs from roots of *Medicago truncatula* after Rhizobium inoculation" (Unpublished (1999)).

AW267756 NCBI acc. No. AW267756 (gi: 6654712) (Jan. 3, 2000); Fedorova,M., et al. "EST305884 DSIR *Medicago truncatula* cDNA done pDSIR-7O1, mRNA sequence"; source: *Medicago truncatula* (barrel medic); Title: "ESTs from roots of *Medicago truncatula* after inoculation with *Phytophthora medicaginis*".

AW267820 NCBI acc. No. AW267820 (gi: 6654776) (Jan. 3, 2000); Fedorova,M., et al. "EST305948 DSIR *Medicago truncatula* cDNA clone pDSIR-8M17, mRNA sequence"; source: *Medicago truncatula* (barrel medic); Title: "ESTs from roots of *Medicago truncatula* after inoculation with *Phytophthora medicaginis*".

AW267914 NCBI acc. No. AW267914 (gi: 6654934) (Jan. 3, 2000); Fedorova,M., et al. "EST306256 DSIR *Medicago truncatula* cDNA clone pDSIR-8D12, mRNA sequence"; source: *Medicago truncatula* (barrel medic); Title: "ESTs from roots of *Medicago truncatula* after inoculation with *Phytophthora medicaginis*".

AW278190 NCBI acc. No. AW278190 (gi: 6666731) (Jan. 4, 2000); Shoemaker, R., et al. "sf40f11.y1 Gm-c1009 *Glycine max* cDNA clone Genome Systems Clone ID: Gm-c1009-2493 5' similar to TR:Q40476 Q40476 ERF1. ;, mRNA sequence"; source: *Glycine max* (soybean); Title: "Public Soybean EST Project".

AW308784 NCBI acc. No. AW308784 (gi: 8724385) (Jan. 21, 2000); Shoemaker,R., et al. "sf71h01.y1 Gm-c1013 *Glycine max* cDNA clone Genome Systems Clone ID: Gm-c1013-5066 5' similar to TR:P93822 P93822 F19P19.18. ;, mRNA sequence"; source: *Glycine max* (soybean).

AW329209 NCBI acc. No. AW329209 (gi: 7675608) (Jan. 28, 2000); Harrison,M.J., et al. "N200421e rootphos(−) *Medicago truncatula* cDNA clone MHRP-17E1, mRNA sequence"; source: *Medicago truncatula* (barrel medic); Title: "ESTs from phosphate starved roots" (Unpublished (1999)).

AW348322 NCBI acc. No. AW348322 (gi: 6846032) (Feb. 1, 2000); Vodkin,L., et al. "GM210001B23F6 Gm-r1021 *Glycine max* cDNA clone Gm-r1021-276 3', mRNA sequence"; source: *Glycine max* (soybean); Title: "A Functional Genomics Program for Soybean (NSF 9872565)" (Unpublished (1999)).

AW349516 NCBI acc. No. AW349516 (gi: 6847226) (Feb. 1, 2000); Vodkin,L., et al. "GM210007B10A12 Gm-r1021 *Glycine max* cDNA clone Gm-r1021-2351 3&apos:, mRNA sequence"; source: *Glycine max* (soybean); Title: "A Functional Genomics Program for Soybean (NSF 9872565)" (Unpublished (1999)).

AW349638 NCBI acc. No. AW349638 (gi: 6847348) (Feb. 1, 2000); Vodkin,L., et al. "GM210005B21A4 Gm-r1021 *Glycine max* cDNA clone Gm-r1021-1568 3', mRNA sequence"; source: *Glycine max* (soybean); Title: "A Functional Genomics Program for Soybean (NSF 9872565)" (Unpublished (1999)).

AW396250 NCBI acc. No. AW396250 (gi: 6914720) (Feb. 7, 2000); Shoemakerr,R., et al. "sh26c01.y1 Gm-c1016 *Glycine max* cDNA clone Genome Systems Clone ID: Gm-c1016-5881 5' similar to TR:O80341 O80341 Ethylene Responsive Element Binding Factor 5. ;, mRNA sequence".

AW396612 NCBI acc. No. AW396612 (gi: 6915151) (Feb. 7, 2000); Shoemaker,R., et al. "sg80c07.y1 Gm-c1026 *Glycine max* cDNA clone Genome Systems Clone ID: Gm-c1026-37 5' similar to TR:O80339 O80339 Ethylene Responsive Element Binding Factor 3. ;, mRNA sequence".

AW441715 NCBI acc. No. AW441715 (gi: 6976966) (Feb. 14, 2000); Alcala,J., et al. "EST311111 tomato fruit red ripe, TAMU *Solanum lycopersicum* cDNA done cLEN18A16 5', mRNA sequence"; source: *Solanum lycopersicum* (*Lycopersicon esculentum*); Title: "Generation of ESTs from tomato fruit tissue" (Unpublished (1999).

AW441775 NCBI acc. No. AW441775 (gi: 6977026) (Feb. 14, 2000); Alcala,J., et al. "EST311171 tomato fruit red ripe, TAMU *Solanum lycopersicum* cDNA clone cLEN18018 5', mRNA sequence"; source: *Solanum lycopersicum* (*Lycopersicon esculentum*); Title: "Generation of ESTs from tomato fruit tissue" (Unpublished (1999).

AW507860 NCBI acc. No. AW507860 (gi: 7145938) (Mar. 3, 2000); Shoemaker,R., et al. "si45h05.y1 Gm-r1030 *Glycine max* cDNA clone Genome Systems Clone ID: Gm-r1030-1906 5' similar to TR:Q40478 Q40478 EREBP-4. ;, mRNA sequence"; source: *Glycine max* (soybean).

AW507898 NCBI acc. No. AW507898 (gi: 7145976) (Mar. 3, 2000); Shoemaker,R., et al. "s146f03.y1 Gm-r1030 *Glycine max* cDNA clone Genome Systems Clone ID: Gm-r1030-1974 5' similar to TR:Q9ZNR2 Q9ZNR2 Ethylene Response Factor 1. ;, mRNA sequence"; source: *Glycine max* (soybean).

AW559315 NCBI acc. No. AW559315 (gi: 7204741) (Mar. 7, 2000); Fedorova,M., et al. "EST306358 DSIR *Medicago truncatula* cDNA clone pDSIR-25I5, mRNA sequence"; source: *Medicago truncatula* (barrel medic); Title: "ESTs from roots of *Medicago truncatula* after inoculation with *Phytophthora medicaginis*".

AW559374 NCBI acc. No. AW559374 (gi: 7204800) (Mar. 7, 2000); Fedorova,M., et al. "EST314422 DSIR *Medicago truncatula* cDNA clone pDSIR-7J9, mRNA sequence"; source: *Medicago truncatula* (barrel medic); Title: "ESTs from roots of *Medicago truncatula* after inoculation with *Phytophthora medicaginis*".

AW559641 NCBI acc. No. AW559641 (gi: 7205131) (Mar. 7, 2000); Fedorova,M., et al. "EST314753 DSIR *Medicago truncatula* cDNA clone pDSIR-24137, mRNA sequence"; source: *Medicago truncatula* (barrel medic); Title: "ESTs from roots of *Medicago truncatula* after inoculation with *Phytophthora medicaginis*".

AW560134 NCBI acc. No. AW560134 (gi: 7205560) (Mar. 7, 2000); Fedorova,M., et al. "EST315182 DSIR *Medicago truncatula* cDNA clone pDSIR-26O23, mRNA sequence"; source: *Medicago truncatula* (barrel medic); Title: "ESTs from roots of *Medicago truncatula* after inoculation with *Phytophthora medicaginis*".

AW560135 NCBI acc. No. AW560135 (gi: 7205561) (Mar. 7, 2000); Fedorova,M., et al. "EST315183 DSIR *Medicago truncatula* cDNA clone pDSIR-26O23, mRNA sequence"; source: *Medicago truncatula* (barrel medic): Title "ESTs from roots of *Medicago truncatula* after inoculation with *Phytophthora medicaginis*".

AW560196 NCBI acc. No. AW560196 (gi: 7205622) (Mar. 7, 2000); Fedorova,M., et al. "EST315244 DSIR *Medicago truncatula* cDNA clone pDSIR-26K12, mRNA sequence"; source: *Medicago truncatula* (barrel medic); Title: "ESTs from roots of *Medicago truncatula* after inoculation with *Phytophthora medicaginis*".

AW560968 NCBI acc. No. AW560968 (gi: 7206394) (Mar. 7, 2000); Fedorova,M., et al. "EST316016 DSIR *Medicago truncatula* cDNA clone pDSIR-30N21, mRNA sequence"; source: *Medicago truncatula* (barrel medic); Title: "ESTs from roots of *Medicago truncatula* after inoculation with *Phytophthora medicaginis*".

AW568194 NCBI acc. No. AW568194 (gi: 7232842) (Mar. 13, 2000); Shoemaker,R., et al. "si57g03.y1 Gm-r1030 *Glycine max* cDNA clone Genome Systems Clone ID: Gm-r1030-3053 5' similar to TR:O23107 O23107 AP2 Domain Containing Protein RAP2.5. [1];, mRNA sequence".

AW574073 NCBI acc. No. AW574073 (gi: 7238806) (Mar. 13, 2000); Fedorova,M., et al. "EST316664 GVN *Medicago truncatula* cDNA clone pGVN-51E4, mRNA sequence"; source: *Medicago truncatula* (barrel medic); Title: "ESTs from one month old nitrogen-fixing root nodules of *Medicago truncatula*" (Unpublished (2000)).

(56) References Cited

OTHER PUBLICATIONS

AW574222 NCBI acc. No. AW574222 (gi: 7238955) (Mar. 13, 2000); Fedorova,M., et al. "EST316813 GVN *Medicago truncatula* cDNA clone pGVN-52B10, mRNA sequence"; source: *Medicago truncatula* (barrel medic); Title: "ESTs from one month old nitrogen-fixing root nodules of *Medicago truncatula*" (Unpublished (2000)).

AW598384 NCBI acc. No. AW596384 (gi: 7283781) (Mar. 22, 2000); Shoemaker,R., et al. "sj02f12.y1 Gm-c1032 *Glycine max* cDNA clone Genome Systems Clone ID: Gm-c1032-744 5apos; similar to TR:Q40478 Q40478 EREBP-4. ;, mRNA sequence"; source: *Glycine max* (soybean).

AW618112 NCBI acc. No. AW618112 (gi: 7324339) (Mar. 24, 2000); Alcala,J., et al. "EST314162 *L. pennellii* trichome, Cornell University *Solanum pennellii* cDNA clone cLPT12K17 5&apos:, mRNA sequence"; source: *Solanum pennellii* (*Lycopersicon pennellii*).

AW618245 NCBI acc. No. AW618245 (gi: 7324479) (Mar. 24, 2000); Alcala,J., et al. "EST314295 *L. pennellii* trichome, Cornell University *Solanum pennellii* cDNA clone cLPT15H2O 5', mRNA sequence"; source: *Solanum pennellii* (*Lycopersicon pennellii*).

AW620490 NCBI acc. No. AW620490 (gi: 7326692) (Mar. 24, 2000); Shoemaker,R., et al. "sj05h02.y1.Gm-c1032 *Glycine max* cDNA clone Genome Systems Clone ID: Gm-c1032-1036 5' similar to TR:O80387 O80387 Ethylene Responsive Element Binding Factor. ;, mRNA sequence".

AW622531 NCBI acc. No. AW622531 (gi: 7334178) (Mar. 28, 2000); Van Der Hoeven,R.S., et al. "EST313331 tomato root during/after fruit set, Cornell University *Solanum lycopersicum* cDNA clone cLEX15D17 5', mRNA sequence"; source: *Solanum lycopersicum* (*Lycopersicon esculentum*).

AW647824 NCBI acc. No. AW647824 (gi: 7409062) (Apr. 4, 2000); Alcala,J., "EST326278 tomato germinating seedings, TAMU *Solanum lycopersicum* cDNA clone cLEI2M8 5', mRNA sequence"; source: *Solanum lycopersicum* (*Lycopersicon esculentum*).

AW685799 NCBI acc. No. AW685799 (gi: 7560535) (Apr. 14, 2000); Watson,B.S., et al. "NF030D09NR1F1000 Nodulated root *Medicago truncatula* cDNA clone NF030D09NR 5', mRNA sequence"; source: *Medicago truncatula* (barrel medic).

AW686013 NCBI acc. No. AW686013 (gi: 11930899) (Apr. 14, 2000); Watson,B.S., et al. "NF033D04NR1F1000 Nodulated root *Medicago truncatula* cDNA clone NF033D04NR 5', mRNA seequence"; source: *Medicago truncatula* (barrel medic).

AW686992 NCBI acc. No. AW686992 (gi: 11930183) (Apr. 14, 2000); Watson,B.S., et al. "NF004G07RT1F1055 Developing root *Medicago truncatula* cDNA clone NF004G07RT 5', mRNA sequence"; source: *Medicago truncatula* (barrel medic).

AW706554 NCBI acc. No. AW706554 (gi: 7590810) (Apr. 18, 2000); Shoemaker,R., et al. sj58h12.y1 Gm-c1033 *Glycine max* cDNA clone Genome Systems Clone ID: Gm-c1033-1536 5' similar to TR:Q9ZR85 Q9ZR85 Ethylene-Responsive Element Binding Protein Homolog. ;, mRNA.

AW737966 NCBI acc. No. AW737966 (gi: 7646911) (Apr. 25, 2000); Van Der Hoeven,R.S., et al. "EST339393 tomato flower buds, anthesis, Cornell University *Solanum lycopersicum* cDNA clone cTOD4F22 5&apos:, mRNA sequence"; source: *Solanum lycopersicum* (*Lycopersicon esculentum*).

AW759181 NCBI acc. No. AW759181 (gi: 7691047) (May 4, 2000); Shoemaker,R., et al. "sI38a09.y1 Gm-c1027 *Glycine max* cDNA done Genome Systems Clone ID: Gm-c1027-3569 5' similar to TR:O80387 O80387 Ethylene Responsive Element Binding Factor. ;, mRNA sequence".

AW760204 NCBI acc. No. AW760204 (gi: 7692089) (May 4, 2000); Shoemaker,R., et al. "s159d04.y1 Gm-c1027 *Glycine max* cDNA clone Genome Systems Clone ID: Gm-c1027-5600 5' similar to TR:O23143 O23143 Putative CKC2. ;, mRNA sequence"; source: *Glycine max* (soybean).

AW774176 NCBI acc. No. AW774176 (gi: 7718021) (May 8, 2000); Vandenbosch,K., et al. "EST333259 KV3 *Medicago truncatula* cDNA clone pKV3-21J17, mRNA sequence"; source: *Medicago truncatula* (barrel medic); Title: "ESTs from roots of *Medicago truncatula* after Rhizoblum inoculation" (Unpublished (1999)).

AW776668 NCBI acc. No. AW776668 (gi: 7766481) (May 9, 2000); Federova,M., et al. "EST335733 DSIL *Medicago truncatula* cDNA clone pDSIL-13B14, mRNA sequence"; source: *Medicago truncatula* (barrel medic); Title: "ESTs from leaves of *Medicago truncatula* after inoculation with *Colletotrichum trifolii*" (Unpublished (2000)).

AW781602 NCBI acc. No. AW781602 (gi: 7796205) (May 12, 2000); Shoemaker,R., et al. "sI82d06.y1 Gm-c1037 *Glycine max* cDNA clone Genome Systems Clone ID: Gm-c1037-516 5' similar to TR:Q40478 Q40478 EREBP-4. ;, mRNA sequence"; source: *Glycine max* (soybean).

AW782252 NCBI acc. No. AW782252 (gi: 7796858) (May 12, 2000); Shoemaker,R., et al. "sm03d11.y1 Gm-c1027 *Glycine max* cDNA clone Genome Systems Clone ID: Gm-c1027-7822 5' similar to TR:P93007 P93007 Cadmium-Induced Protein Isolog. ;, mRNA sequence"; source: *Glycine max*.

AW840600 NCBI acc. No. AW840600 (gi: 7934583) (May 18, 2000); Anderson,J.V., et al. "00058 leafy spurge Lambda HybriZAP 2.1 two-hybrid vector cDNA Library *Euphorbia esula* cDNA clone 16G 5' similar to DNA-binding Protein/AP2-Domain Containing Protein, mRNA sequence"; source: *Euphorbia esula* (leafy spurge).

AW840611 NCBI acc. No. AW840611 (gi: 7934594) (May 18, 2000); Anderson,J.V., et al. "00057 leafy spurge Lambda HybriZAP 2.1 two-hybrid vector cDNA Library *Euphorbia esula* cDNA clone 1G 5' similar to DNA-binding Protein/Ethylene Responsive Factor, mRNA sequence"; source: *Euphorbia esula* (leafy spurge).

AW930351 NCBI acc. No. AW930351 (gi: 8105848) (May 30, 2000); Alcala,J., et al. "EST340904 tomato fruit mature green, TAMU *Solanum lycopersicum* cDNA clone cLEF43H15 5', mRNA sequence"; source:. *Solanum lycopersicum* (*Lycopersicon esculentum*); Title: "Generation of ESTs from tomato fruit tissue".

AW931292 NCBI acc. No. AW931292 (gi: 8106693) (May 30, 2000); Alcala,J., et al. "EST357135 tomato fruit mature green, TAMU *Solanum lycopersicum* cDNA clone cLEF44J15 5', mRNA sequence"; source: *Solanum lycopersicum* (*Lycopersicon esculentum*); Title: "Generation of ESTs from tomato fruit tissue".

AW933517 NCBI acc. No. AW933517 (gi: 8108834) (May 30, 2000); Alcala,J., et al. "EST359276 tomato fruit mature green, TAMU *Solanum lycopersicum* cDNA clone cLEF54C10 5', mRNA sequence"; source: *Solanum lycopersicum* (*Lycopersicon esculentum* ); Title: "Generation of ESTs from tomato fruit tissue".

AW980654 NCBI acc. No. AW980654 (gi: 8172193) (Jun. 2, 2000); Fedorova,M., et al. "EST391807 GVN *Medicago truncatula* cDNA clone pGVN-55D7, mRNA sequence"; source: *Medicago truncatula* (barrel medic); Title: "ESTs from one month old nitrogen-fixing root nodules of *Medicago truncatula*" (Unpublished (2000)).

AW980969 NCBI acc. No. AW980969 (gi: 8172507) (Jun. 2, 2000); Fedorova,M., et al. "EST392114 GVN *Medicago truncatula* cDNA clone pGVN-60O17, mRNA sequence"; source: *Medicago truncatula* (barrel medic); Title: "ESTs from one month old nitrogen-fixing root nodules of *Medicago truncatula*" (Unpublished (2000)).

AW981151 NCBI acc. No. AW981151 (gi: 8172743) (Jun. 2, 2000); Federova,M., et al. "EST392345 DSIL *Medicago truncatula* cDNA clone pDSIL-12I11, mRNA sequence"; source: *Medicago truncatula* (barrel medic); Title: "ESTs from leaves of *Medicago truncatula* after inoculation with *Colletotrichum trifolii*" (Unpublished (2000)).

AX033191 NCBI acc. No. AX033191 (gi: 10280046) (Sep. 22, 2000); Memelink,J., et al. "Sequence 2 from Patent WO0046383"; source: *Catharanthus roseus* (Madagascar periwinkle); Title: "Method of modulating metabolite biosynthesis in recombinant cells" (Patent: WO 0046383-A Aug. 10, 2000; Univ Leiden (NL).

AX033192 NCBI acc. No. AX033192 (gi: 10280047) (Sep. 22, 2000); Memelink,J., et al. "Sequence 3 from Patent WO0046383"; source: *Catharanthus roseus* (Madagascar periwinkle); Title: "Method of modulating metabolite biosynthesis in recombinant cells" (Patent: WO 0046383-A Aug. 10, 2000; Univ Leiden (NL).

AX573798 NCBI acc. No. AX573798 (gi: 27551457) (Jan. 9, 2003); Pages,M., et al. "Sequence 15 from Patent WO02079245"; source: *Oryza sativa*; Title "Method for improving plant tolerance to environmental stress" (Patent: WO 02079245-A Oct. 10, 2002; Consejo Superior Investigaciones Cientificas.

(56) References Cited

OTHER PUBLICATIONS

AY192370 NCBI acc. No. AY192370 (gi: 28274833) (Feb. 9, 2003); Tournier.B., et al. "*Lycopersicon esculentum* ethylene response factor 4 (ERF4) mRNA, complete cds"; source: *Lycopersicon esculentum* (tomato).
BE057468 NCBI acc. No. BE057468 (gi: 8401834) (Jun. 9, 2000); Shoemaker,R., et al. "sm58e08.y1 Gm-c1028 *Glycine max* cDNA done Genome Systems Clone ID: Gm-c1028-8127 5' similar to TR:O23105 O23105 AP2 Domain Containing Protein RAP2.3. ;, mRNA sequence"; source: *Glycine max* (soybean).
BE191029 NCBI acc. No. BE191029 (gi: 8669922) (Jun. 22, 2000); Shoemaker,R., et al. sn83h08.y1 Gm-c1038 *Glycine max* cDNA clone Genome Systems Clone ID: GM-c1038-1240 5' similar to TR:Q9ZR85 Q9ZR85 Ethylene-Responsive Element Binding Protein Homolog. ;, mRNA.
BE203165 NCBI acc. No. BE203165 (gi: 8746436) (Jun. 27, 2000); Vandenbosch,K., et al. "EST403187 KV1 *Medicago truncatula* cDNA clone pKV1-4L15, mRNA sequence"; source: *Medicago truncatula* (barrel medic); Title: ESTs from roots of *Medicago truncatula* 24 hours after inoculation with *Sinorhizobium*.
BE203296 NCBI acc. No. BE203296 (gi: 8746567) (Jun. 27, 2000); Vandenbosch,K., et al. "EST403318 KV1 *Medicago truncatula* cDNA clone pKV1-5G15, mRNA sequence"; source: *Medicago truncatula* (barrel medic); Title: ESTs from roots of *Medicago truncatula* 24 hours after inoculation with *Sinorhizobium*.
BE318516 NCBI acc. No. BE318516 (gi: 11960607) (Jul. 14, 2000); Torres-Jerez,I., et al."NF071G07LF1F1053 Developing leaf *Medicago truncatula* cDNA clone NF071G07LF 5', mRNA sequence"; source: *Medicago truncatula* (barrel medic).
BE325359 NCBI acc. No. BE325359 (gi: 11935917) (Jul. 14. 2000); He,X.-Z., et al. "NF087B110ST1F1077 Developing stem *Medicago truncatula* cDNA clone NF087B10ST 5', mRNA sequence"; source: *Medicago truncatula* (barrel medic); Title: Expressed Sequence Tags from the Samuel Roberts Noble Foundation.
BE326131 NCBI acc. No. BE326131 (gi: 11934119) (Jul. 14, 2000); He,X.-Z., et al. "NF085C08ST1F1055 Developing stem *Medicago truncatula* cDNA clone NF085C08ST 5', mRNA sequence"; source: *Medicago truncatula* (barrel medic); Title: Expressed Sequence Tages from the Samuel Roberts Noble Foundation.
BE330726 NCBI acc. No. BE330726 (gi: 9204502) (Jul. 14, 2000); Shoemaker,R., et al. "so84a08.y1 Gm-c1041 *Glycine max* cDNA clone Genome Systems Clone ID: Gm-c1041-15 5' similar to TR:O81365 O81365 AP2 Domain Containing Protein ;, mRNA sequence"; source: *Glycine max* (soybean).
BE331593 NCBI acc. No. BE331593 (gi: 9205369) (Jul. 14, 2000); Shoemaker,R., et al. "sp16c03.y1 Gm-c1042 *Glycine max* cDNA clone Genome Systems Clone ID: Gm-c1042-701 5' similar to TR:Q40478 Q40478 EREBP-4. ;, mRNA sequence"; source: *Glycine max* (soybean).
BE357795 NCBI acc. No. BE357795 (gi: 9299352) (Jul. 20, 2000); Cordonnier-Pratt,M.-M., et al. "DG1_22_A02.b1_A002 Dark Grown 1 (DG1) *Sorghum bicolor* cDNA, mRNA sequence"; source: *Sorghum bicolor* (sorghum); Title: "An EST database from Sorghum: dark-grown seedlings" (Unpublished (2000)).
BE365169 NCBI acc. No. BE365169 (gi: 9306726) (Jul. 20, 2000); Cordonnier-Pratt,M.-M., et al."PI1_25_F08.b1_A002 Pathogen Induced 1 (PI1) *Sorghum bicolor* cDNA, mRNA sequence"; source: *Sorghum bicolor* (sorghum); Title "An EST database from Sorghum: pathogen-induced plants" (Unpublished (2000)).
BE427520 NCBI acc. No. BE427520 (gi: 9425363) (Jul. 24, 2000); Anderson,O.A., et al. "PSR7136 ITEC PSR Wheat Pericarp/Testa Library *Triticum aestivum* cDNA clone PSR7136, mRNA sequence"; source: *Triticum aestivum* (bread wheat).
BE429439 NCBI acc. No. BE429439 (gi: 9427282) (Jul. 24, 2000); Anderson,O.A., et al. "TAS000.B08R990618 ITEC TAS Wheat cDNA Library *Triticum aestivum* cDNA clone TAS000.B08, mRNA sequence"; source: *Triticum aestivum* (bread wheat).
BE432465 NCBI acc. No. BE432465 (gi: 9430308) (Jul. 24, 2000); Alcala,J., at al. "EST398994 tomato breaker fruit, TIGR *Solanum lycopersicum* cDNA clone cLEG8I18, mRNA sequence"; source: *Solanum lycopersicum* (*Lycopersicon esculentum*).
BE433462 NCBI acc. No. BE433462 (gi: 9431305) (Jul. 24, 2000); Alcala,J., et al. "EST399991 tomato breaker fruit, TIGR *Sofanum lycopersicum* cDNA clone cLEG14M13, mRNA sequence"; source: *Solanum lycopersicum* (Lycopersicon esculentum).
BE435827 NCBI acc. No. BE435827 (gi: 9433670) (Jul. 24, 2000); Alcala,J., at al. "EST406905 tomato breaker fruit, TIGR *Solanum lycopersicum* cDNA clone cLEG2909, mRNA sequence"; source: *Solanum lycopersicum* (*Lycopersicon esculentum*).
BE436333 NCBI acc. No. BE436333 (gi: 9434176) (Jul. 24, 2000); Alcala,J., et al. "EST407411 tomato breaker fruit, TIGR *Solanum lycopersicum* cDNA done cLEG32E7, mRNA sequence"; source: *Solanum lycopersicum* (*Lycopersicon esculentum*).
BE436391 NCBI acc. No. BE436391 (gi: 9434234) (Jul. 24, 2000); Alcala,J., et al. "EST407469 tomato breaker fruit, TIGR *Solanum lycopersicum* cDNA done cLEG32A16, mRNA sequence"; source: *Solanum lycopersicum* (*Lycopersicon esculentum*).
BE436556 NCBI acc. No. 8E436556 (gi: 9434399) (Jul. 24, 2000); Alcala,J., et al. "EST407634 tomato breaker fruit, TIGR *Solanum lycopersicum* cDNA clone cLEG3313, mRNA sequence"; source: *Solanum lycopersicum* (*Lycopersicon esculentum*).
BE449392 NCBI acc. No. BE449392 (gi: 9454895) (Jul. 26, 2000); Van Der Hoeven,R.S., et al. "EST356151 L. Hirsutum trichome, Cornell University *Solanum habrochaites* cDNA clone cLHT31K6, mRNA sequence"; source: *Solanum habrochaites* (*Lycopersicon hirsutum*).
BE459781 NCBI acc. No. BE459781 (gi: 9504083) (Jul. 27, 2000); Alcala,J., et al. "EST415073 tomato developing/immature green fruit *Solanum lycopersicum* cDNA clone cLEM8C19, mRNA sequence"; source: *Solanum lycopersicum* (*Lycopersicon esculentum*).
BE461852 NCBI acc. No. BE461852 (gi: 9506154) (Jul. 27, 2000); Alcala,J., et al. "EST413271 tomato breaker fruit, TIGR *Solanum lycopersicum* cDNA clone cLEG40017, mRNA sequence"; source: *Solanum lycopersicum* (*Lycopersicon esculentum*).
BE474049 NCBI acc. No. BE474049 (gi: 9564540) (Jul. 28, 2000); Shoemaker,R., et al. "sp58d12.y1 Gm-c1044 *Glycine max* cDNA clone Genome Systems Clone ID: Gm-c1044-144 5' similar to TR:081365 O81365 AP2 Domain Containing Protein ;, mRNA sequence"; source: *Glycine max* (soybean).
BE494041 NCBI acc. No. BE494041 (gi: 9660634) (Aug. 2, 2000); Anderson,O.D., et al."WHE1277_B09_D17ZS *Secale cereale* anther cDNA library *Secale cereale* cDNA clone WHE1277_B09_D17, mRNA sequence"; source: *Secale cereale* (rye).
BE554898 NCBI acc. No. BE554898 (gi: 9819385) (Aug. 15, 2000); Shoemaker,R., et al. "sp82c07.y1 Gm-c1045 *Glycine max* cDNA clone Genome Systems Clone ID: Gm-c1045-133 5' similar to TR:Q40478 Q40478 EREBP-4. ;, mRNA sequence"; source: *Glycine max* (soybean).
BE555398 NCBI acc. No. BE555398 (gi: 9819822) (Aug. 15, 2000); Shoemaker,R., et al. sp88c01.y1 Gm-c1045 *Glycine max* cDNA clone Genome Systems Clone ID: Gm-c1045-697 5' similar to TR:Q9ZR85 Q9ZR85 Ethylene-Responsive Element Binding Protein Homolog. ;, mRNA.
BE599413 NCBI acc. No. BE599413 (gi: 9854486) (Aug. 18, 2000); Cordonnier-Pratt,M.-M., et al. "PI1$_{13}$_87_A002 Pathogen induced 1 (PI1) *Sorghum bicolor* cDNA, mRNA sequence"; source: *Sorghum bicolor* (sorghum); Title: "An EST database from Sorghum: pathogen-dincued plants" (Unpublished (2000)).
BE610114 NCBI acc. No. BE610114 (gi: 9901146) (Aug. 24, 2000); Shoemaker,R., et al. "sp80h02.y1 Gm-c1044 *Glycine max* cDNA clone Genome Systems Clone ID: Gm-c1044-2284 5' similar to TR:Q40478 Q40478 EREBP-4. ;, mRNA sequence"; source: *Glycine max* (soybean).
BE801560 NCBI acc. No. BE801560 (gi: 10232672) (Sep. 20, 2000); Shoemaker,R., et al. "sr16a08.y1 Gm-c1050 *Glycine max* cDNA clone Genome Systems Clone ID: Gm-c1050-495 5' similar to TR:O80387 O80387 Ethylene Responsive Element Binding Factor. ;, mRNA sequence".

(56) References Cited

OTHER PUBLICATIONS

BE804368 NCBI acc. No. BE804368 (gi: 10235480) (Sep. 20, 2000); Shoemaker,R., et al. "sr78h05.y1 Gm-c1052 *Glycine max* cDNA clone Genome Systems Clone ID: Gm-c1050 5' similar to TR:Q40478 Q40478 EREBP-4. ;, mRNA sequence"; source: *Glycine max* (soybean).
BE805304 NCBI acc. No. BE805304 (gi: 10236416) (Sep. 20, 2000); Shoemaker,R., et al. "ss40h06.y1 Gm-c1061 *Glycine max* cDNA clone Genome Systems Clone ID: Gm-c1061-1236 5' similar to TR:Q40478 Q40478 EREBP-4. ;, mRNA sequence"; source: *Glycine max* (soybean).
BE820195 NCBI acc. No. BE820195 (gi: 10252429) (Sep. 21, 2000); Vodkin,L., et al. "GM700006A11012 Gm-r1070 *Glycine max* cDNA clone Gm-r1070-2231 3', mRNA sequence"; source: *Glycine max* (soybean); Title: "A Functional Genomics Program for Soybean (NSF 9872565)" (Unpublished (1999)).
BE941508 NCBI acc. No. BE941508 (gi: 10519339) (Oct. 3, 2000); Cote,F., et al."EST421159 MGHG *Medicago truncatula* cDNA clone pMGHG-4M14, mRNA sequence"; source: *Medicago truncatula* (barrel medic).
BE941864 NCBI acc. No. BE941864 (gi: 10519623) (Oct. 3, 2000); Cote,F., et al. "EST421443 MGHG *Medicago truncatula* cDNA clone pMGHG-6D2, mRNA sequence"; source: *Medicago truncatula* (barrel medic).
BE942996 NCBI acc. No. BE942996 (gi: 10520755) (Oct. 3, 2000); Cote,F., et al. "EST422575 MGHG *Medicago truncatula* cDNA clone pMGHG-1481, mRNA sequence"; source: *Medicago truncatula* (barrel medic).
BE997398 NCBI acc. No. BE997398 (gi: 10697674) (Oct. 6, 2000); Fedorova,M., et al. "EST429121 GVSN *Medicago truncatula* cDNA clone pGVSN-1C3, mRNA sequence"; source: *Medicago truncatula* (barrel medic); Title: "ESTs from senescent nodules of *Medicago truncatula*" (Unpublished (2000)).
BE997780 NCBI acc. No. BE997780 (gi: 10698056) (Oct. 6, 2000); Fedorova,M., et al. "EST429503 GVSN *Medicago truncatula* cDNA clone pGVSN-4M3, mRNA sequence"; source: *Medicago truncatula* (barrel medic); Title: "ESTs from senescent nodules of *Medicago truncatula*" (Unpublished (2000)).
BE997834 NCBI acc. No. BE997834 (gi: 10698110) (Oct. 6, 2000); Fedorova,M., et al. "EST429557 GVSN *Medicago truncatula* cDNA clone pGVSN-8G17, mRNA sequence"; source: *Medicago truncatula* (barrel medic); Title: "ESTs from senescent nodules of *Medicago truncatula*" (Unpublished (2000)).
8E999493 NCBI acc. No. 8E999493 (gi: 10699769) (Oct. 6, 2000); Fedorova,M., et al. "EST431216 GVSN *Medicago truncatula* cDNA clone pGVSN-16L15, mRNA sequence"; source: *Medicago truncatula* (barrel medic); Title: "ESTs from senescent nodules of *Medicago truncatula*" (Unpublished (2000)).
BF006068 NCBI acc. No. BF006068 (gi: 10706343) (Oct. 6, 2000); Fedorova,M., et al. "EST434566 DSLC *Medicago truncatula* cDNA clone pDSLC-39F7, mRNA sequence"; source: *Medicago truncatula* (barrel medic); Title: "ESTs from *Medicago truncatula* leaves and cotyledons" (Unpublished (2000)).
BF006539 NCBI acc. No. BF006539 (gi: 10706814) (Oct. 6, 2000); Fedorova,M., et al. "EST435037 DSLC *Medicago truncatute* cDNA clone pDSLC-41L18, mRNA sequence"; source: *Medicago truncatula* (barrel medic); Title: "ESTs from *Medicago truncatula* leaves and cotyledons" (Unpublished (2000)).
BF008875 NCBI acc. No. BF008875 (gi: 10709151) (Oct. 6, 2000); Shoemaker,R., et al. "ss70e04.y1 Gm-c1062 *Glycine max* cDNA clone Genome Systems Clone ID: Gm-c1062-1783 5' similar to TR:O81365 O81365 AP2 Domain Containing Protein ;, mRNA sequence"; source: *Glycine max* (soybean).
BF009446 NCBI acc. No. BF009446 (gi; 10709722) (Oct. 6, 2000); Shoemaker,R., et al. "ss78g12.y1 Gm-c1064 *Glycine max* cDNA clone Genome Systems Clone ID: Gm-c1064-287 5' similar to TR:Q9ZR85 Q9ZR85 Ethylene-Responsive Element Binding Protein Homolog. ;, mRNA sequence".
BF068784 NCBI acc. No. BF068784 (gi: 10845722) (Oct. 17, 2000); Shoemaker,R., et al. "st02e12.y1 Gm-c1065 *Glycine max* cDNA clone Genome Systems Clone ID: Gm-c1065-167 5' similar to TR:P93589 P93589 DNA Binding Protein Homolog. ;, mRNA sequence"; source: *Glycine max* (soybean).
BF070873 NCBI acc. No. BF070873 (gi: 10843956) (Oct. 17, 2000); Shoemaker,R., et al. "st38c09.y1 Gm-c1067 *Glycine max* cDNA clone Genome Systems Clone ID: Gm-c1067-1266 5' similar to TR:O23143 O23143 Putative CKC2. ;, mRNA sequence"; source: *Glycine max* (soybean).
BF096818 NCBI acc. No. BF096818 (gi: 10902528) (Oct. 19, 2000); Van Der Hoeven,R.S., et al. "EST360845 tomato nutrient deficient roots *Solanum lycopersicum* cDNA clone cLEW17I10 5' sequence, mRNA sequence"; source: *Solanum lycopersicum* (*Lycopersicon esculentum*).
BF112878 NCBI acc. No. BF112878 (gi: 10942568) (Oct. 20, 2000); Alcala,J., et al. "EST440468 tomato breaker fruit *Solanum lycopersicum* cDNA clone cLEG42N7 5 sequence, mRNA sequence"; source: *Solanum lycopersicum* (*Lycopersicon esculentum*).
BF113172 NCBI acc. No. BF113172 (gi: 10942862) (Oct. 20, 2000); Alcala,J., et al. "EST440762 tomato breaker fruit *Solanum lycopersicum* cDNA clone cLEG43D8 5' sequence, mRNA sequence"; source: *Solanum lycopersicum* (*Lycopersicon esculentum*).
BF263411 NCBI acc. No. BF263411 (gi: 13260800) (Nov. 17, 2000); Wing,R., et al. "HV__CEa0006K20f *Hordeum vulgare* seedling green leaf EST library HVcDNA0004 (Blumeria challenged) *Hordeum vulgare* subsp. *vulgare* cDNA clone HV__CEa0006K20f, mRNA sequence"; source: *Hordeum vulgare* subsp. *vulgare*.
BF275458 NCBI acc. No. BF275458 (gi: 11206528) (Nov. 17, 2000); Wing,R.A., et al. "GA__Eb0024816f *Gossypium arboreum* 7-10 dpa fiber library *Gossypium arboreum* cDNA clone GA__Eb0024B16f, mRNA sequence"; source: *Gossypium arboreum*.
BF275652 NCBI acc. No. BF275652 (gi: 11206722) (Nov. 17, 2000); Wing,R.A., et al. "GA__Eb0024J23f *Gossypium arboreum* 7-10 dpa fiber library *Gossypium arboreum* cDNA clone GA__Eb0024J23f, mRNA sequence"; source: *Gossypium arboreum*.
BF277659 NCBI acc. No. BF277659 (gi: 11208729) (Nov. 17, 2000); Wing,R.A., at al. "GA__Eb0031C19f *Gossypium arboreum* 7-10 dpa fiber library *Gossypium arboreum* cDNA clone GA__Eb0031C19f, MRNA sequence"; source: *Gossypium arboreum*.
BF324075 NCBI acc. No. BF324075 (gi: 11273699) (Nov. 21, 2000); Shoemaker,R., et al. "su22c11.y1 Gm-c1068 *Glycine max* cDNA clone Genome Systems Clone ID: Gm-c1068-117 5' similar to TR:P93589 P93589 DNA Binding Protein Homolog. ;, mRNA sequence"; source: *Glycine max* (soybean).
BF518896 NCBI acc. No. BF518896 (gi: 11607651) (Dec. 8, 2000); Fedorova,M., et al. "EST456428 DSIL *Medicago truncatula* cDNA clone pDSIL-19G12, mRNA sequence"; source: *Medicago truncatula* (barrel medic); Title: "ESTs from leaves of *Medicago truncatula* after inoculation with *Colletobichum trifolii*" (Unpublished (2000)).
BF520727 NCBI acc. No. BF520727 (gi: 11609410) (Dec. 8, 2000); Fedorova,M., et al. "EST458200 DSIL *Medicago truncatula* cDNA clone pDSIL-39A6, mRNA sequence"; source: *Medicago truncatula* (barrel medic); Title: "ESTs from leaves of *Medicago truncatula* after inoculation with *Colletotrichum trifolii*" (Unpublished (2000)).
BF596417 NCBI acc. No. BF596417 (gi: 11688741) (Dec. 12, 2000); Shoemaker,R., et al. "su51a06.y1 Gm-c1069 *Glycine max* cDNA clone Genome Systems Clone ID: Gm-c1069-396 5' similar to TRO81365 O81365 AP2 Domain Containing Protein ;, mRNA sequence"; source: *Glycine max*.
BF617601 NCBI acc. No. BF617601 (gi: 13109111) (Dec. 18, 2000); Wing,R., et al. "HVSMEc0018D19f *Hordeum vulgare* seedling shoot EST library HVcDNA0003 (Etiolated and unstressed) *Hordeum vulgare* subsp. *vulgare* cDNA clone HVSMEc0018D19f, mRNA sequence"; source: *Hordeum vulgare* subsp. *vulgare*.
BF618047 NCBI acc. No. BF618047 (gi: 13106669) (Dec. 18, 2000); Wing,R., et al. "HVSMEc0003G22f *Hordeum vulgare* seedling shoot EST library HVcDNA0003 (Etiolated and unstressed) *Hordeum vulgare* subsp. *vulgare* cDNA clone HVSMEc0003G22f, mRNA sequence"; source: *Hordeum vulgare* subsp. *vulgare*.

(56) References Cited

OTHER PUBLICATIONS

BF621655 NCBI acc. No. BF621655 (gi: 13083645) (Dec. 18, 2000); Wing,R., et al. "HVSMEa0011L23f *Hordeum vulgare* seedling shoot EST library HVcDNA0001 (Cold stress) *Hordeum vulgare* subsp. *vulgare* cDNA clone HVSMEa0011L23f, mRNA sequence"; source: *Hordeum vulgare* subsp. *vulgare*.

BF624177 NCBI acc. No. BF624177 (gi: 13083964) (Dec. 18, 2000); Wing,R., et al. "HVSMEa0012F20f *Hordeum vulgare* seedling shoot EST library HVcDNA0001 (Cold stress) *Hordeum vulgare* subsp. *vulgare* cDNA clone HVSMEa0012F20f, mRNA sequence"; source: *Hordeum vulgare* subsp. *vulgare*.

BF634482 NCBI acc. No. BF634482 (gi: 11898640) (Dec. 19, 2000); Torres-Jerez,I., et al. "NF074A12DT1F1088 Drough *Medicago truncatula* cDNA clone NF074A12DT 5', mRNA sequence"; source: *Medicago truncatula* (barrel medic).

BF637755 NCBI acc. No. BF637755 (gi: 11901913) (Dec. 19, 2000); Liu,J., et al. "NF041803PL1F1027 Phosphate starved leaf *Medicago truncatula* cDNA clone NF041803PL 5', mRNA sequence"; source: *Medicago truncatula* (barrel medic); Title: Expressed Sequence Tags from the Samuel Roberts Noble Foundation.

BF637999 NCBI acc. No. BF637999 (gi: 11902157) (Dec. 19, 2000); Liu,J., et al. "NF028F04PL1F1041 Phosphate starved leaf *Medicago truncatula* cDNA clone NF028F04PL 5&apos:, mRNA sequence"; source: *Medicago truncatula* (barrel medic); Title: Expressed Sequence Tags from the Samuel Roberts Noble Foundation.

BF643225 NCBI acc. No. BF643225 (gi: 11908350) (Dec. 20, 2000); Torres-Jerez,I., et al."NF001G02EC1F1017 Elicited cell culture *Medicago truncatula* cDNA clone NF001G02EC 5', mRNA sequence"; source: *Medicago truncatula* (barrel medic).

BF644716 NCBI acc. No. BF644716 (gi: 11909845) (Dec. 20, 2000); Torres-Jerez,I., et al. "NF019F07EC1F1062 Ellicited cell culture *Medicago truncatula* cDNA clone NF019F07EC 5', mRNA sequence"; source: *Medicago truncatula* (barrel medic).

BF645474 NCBI acc. No. BF645474 (gi: 11910603) (Dec. 20, 2000); Torres-Jerez,I., et al. "NF019D04EC1F1041 Elicited cell culture *Medicago truncatula* cDNA done NF019D04EC 5', mRNA sequence"; source: *Medicago truncatula* (barrel medic).

BF645999 NCBI acc. No. BF645999 (gi: 11911128) (Dec. 20, 2000); Torres-Jerez,I., et al. "NF043808EC1F1064 Elicited cell culture *Medicago truncatula* cDNA clone NF043B08EC 5', mRNA sequence"; source: *Medicago truncatula* (barrel medic).

BF646324 NCBI acc. No. BF646324 (gi: 11911454) (Dec. 20, 2000); Torres-Jerez,I., et al. "NF074E05EC1F1038 Elicited cell culture *Medicago truncatula* cDNA clone NF074E05EC 5', mRNA sequence"; source: *Medicago truncatula* (barrel medic).

BF647222 NCBI acc. No. BF647222 (gi: 11912352) (Dec. 20, 2000); Torres-Jerez,I., et al. "NF033B03EC1F1028 Elicited cell culture *Medicago truncatula* cDNA clone NF033B03EC 5', mRNA sequence"; source: *Medicago truncatula* (barrel medic).

BF648210 NCBI acc. No. BF648210 (gi: 11913340) (Dec. 20, 2000); Torres-Jerez,I., et al. "NF045C04EC1F1033 Elicited cell culture *Medicago truncatula* cDNA clone NF045C04EC 5', mRNA sequence"; source: *Medicago truncatula* (barrel medic).

BF647376 NCBI acc. No. BF647376 (gi: 11912506) (Dec. 20, 2000); Torres-Jerez,I., et al. "NF033B02EC1F1016 Elicited cell culture *Medicago truncatula* cDNA clone NF033B02EC 5', mRNA sequence"; source: *Medicago trunculata* (barrel medic).

BF648225 NCBI acc. No. BF648225 (gi: 11913355) (Dec. 20, 2000); Torres-Jerez,I., et al. "NF045D10EC1F1089 Elicited cell culture *Medicago truncatula* cDNA done NF045D10EC 5', mRNA sequence"; source: *Medicago truncatula* (barrel medic).

BF648429 NCBI acc. No. BF648429 (gi: 11913559) (Dec. 20, 2000); Torres-Jerez,I., et al. "NF045H02EC1F1027 Elicited cell culture *Medicago truncatula* cDNA clone NF045H02EC 5', mRNA sequence"; source: *Medicago truncatula* (barrel medic).

BF649047 NCBI acc. No. BF649047 (gi: 11914093) (Dec. 20, 2000); Torres-Jerez,I., et al. "NF053B11EC1F1091 Elicited cell culture *Medicago truncatula* cDNA clone NF053811EC 5%apos;, mRNA sequence"; source: *Medicago truncatula* (barrel medic).

BF649327 NCBI acc. No. BF649327 (gi: 11914457) (Dec. 20, 2000); Torres-Jerez,I., et al. "NF056E12EC1F1097 Elicited cell culture *Medicago truncatula* cDNA clone NF056E12EC 5', mRNA sequence"; source: *Medicago truncatula* (barrel medic).

BF649790 NCBI acc. No. BF649790 (gi: 11914920) (Dec. 20, 2000); Torres-Jerez,I., et al. "NF084C07EC1F1052 Elicited cell culture *Medicago truncatula* cDNA clone NF084C07EC 5', mRNA sequence"; source: *Medicago truncatula* (barrel medic).

BF649879 NCBI acc. No. BF649879 (gi: 11915009) (Dec. 20, 2000); Torres-Jerez,I., et al. "NF086A05EC1F1035 Elicited cell culture *Medicago truncatula* cDNA clone NF086A05EC 5', mRNA sequence"; source: *Medicago truncatula* (barrel medic).

BF650089 NCBI acc. No. BF650089 (gi: 11915219) (Dec. 20, 2000); Torres-Jerez,I., et al. "NF088B12EC1F1095 Elicited cell culture *Medicago truncatula* cDNA done NF088B12EC 5', mRNA sequence"; source: *Medicago truncatula* (barrel medic).

BF650178 NCBI acc. No. BF650178 (gi: 11915308) (Dec. 20, 2000); Torres-Jerez,I., et al. "NF085H09EC1F1078 Elicited cell culture *Medicago truncatula* cDNA clone NF085H09EC 5&apos:, mRNA sequence"; source: *Medicago truncatula* (barrel medic).

BF650547 NCBI acc. No. BF650547 (gi: 11915677) (Dec. 20, 2000); Torres-Jerez,I., et al. "NF097H02EC1F1026 Elicited cell culture *Medicago truncatula* cDNA clone NF097H02EC 5&apos:, mRNA sequence"; source: *Medicago truncatula* (barrel medic).

BF650930 NCBI acc. No. BF650930 (gi: 11916060) (Dec. 20, 2000); Torres-Jerez,I., et al. "NF098F10EC1F1089 Elicited cell culture *Medicago truncatula* cDNA done NF098F10EC 5', mRNA sequence"; source: *Medicago truncatula* (barrel medic).

BF651153 NCBI acc. No. BF651153 (gi: 11916283) (Dec. 20, 2000); Torres-Jerez,I., et al."NF102B10EC1F1079 Elicited cell culture *Medicago truncatula* cDNA clone NF102810EC 5', mRNA sequence"; source: *Medicago truncatula* (barrel medic).

BF729336 NCBI acc. No. BF729336 (gi: 12047197) (Jan. 8, 2001); Walbot,V., et al. "1000076A12.x1 1000—Unigene I from Maize Genome Project *Zea mays* cDNA, mRNA sequence"; source: *Zea mays*; Title: "Maize ESTs from various cDNA libraries sequenced at Stanford University" (Unpublished (1999)).

BG046680 NCBI acc. No. BG046680 (gi: 12495682) (Jan. 25, 2001); Shoemaker,R., et al. "saa58c10.y1 Gm-c1060 *Glycine soja* cDNA clone Genome Systems Clone ID: Gm-c1060-884 5' similar to TR:Q40478 Q40478 EREBP-4. ;, mRNA sequence"; source: *Glycine soja*.

BG103305 NCBI acc. No. BG103305 (gi: 12618124) (Jan. 30, 2001); Cordonnier-Pratt.M.-M., et al."RH1Z2__18__D08.b1__A003 Rhizome2 (RH1Z2) *Sorghum propinquum* cDNA, mRNA sequence"; source: *Sorghum propinquum*; Title: "An EST database from Sorghum: *Sorghum propinquum* rhizomes" (Unpublished (2000)).

BG128566 NCBI acc. No. BG128566 (gi: 12628754) (Jan. 31, 2001); Van Der Hoeven,R., et al. "EST474212 tomato shoot/meristem *Solanum lycopersicum* cDNA clone cTOF21K4 5' sequence, mRNA sequence"; source: *Solanum lycopersicum* (*Lycopersicon esculentum*).

BG129573 NCBI acc. No. BG129573 (gi: 12629761) (Jan. 31, 2001); Van Der Hoeven,R., et al. "EST475219 tomato shoot/meristem *Solanum lycopersicum* cDNA clone cTOF25A11 5' sequence, mRNA sequence"; source: *Solanum lycopersicum* (*Lycopersicon esculentum*).

BG155935 NCBI acc. No. BG155935 (gi: 12689599) (Feb. 6, 2001); Shoemaker,R., et al. "saa66d04.y1 Gm-c1060 *Glycine soja* cDNA clone Genome Systems Clone ID: Gm-c1060-1688 5' similar to TR:Q40478 Q40478 EREBP-4. ;, mRNA sequence"; source: *Glycine soja*.

BG239157 NCBI acc. No. BG239157 (gi: 12774230) (Feb. 13, 2001); Shoemaker,R., et al. sab66d01.y1 Unknown Library Type *Glycine max* cDNA clone Genome Systems Clone ID: Gm-c1043-4369 5' similar to TR:Q9ZR85 Q9ZR85 Ethylene-Responsive Element Binding Protein Homolog. ;, mRNA.

(56) References Cited

OTHER PUBLICATIONS

BG368839 NCBI acc. No. BG368839 (gi: 13257940) (Mar. 8, 2001); Wing,R., et al. "HVSMEi0020012f *Hordeum vulgare* 20 DAP spike EST library HVcDNA0010 (20 DAP) *Hordeum vulgare* subsp. *vulgare* cDNA clone HVSMEi0020O1212f, mRNA sequence"; source: *Hordeum vulgare* subsp. *vulgare*.

BG381764 NCBI acc. No. BG381764 (gi: 13306236) (Mar. 12, 2001); Anderson,J.V., et al. "00735 leafy spurge Lambda HybriZAP 2.1 two-hybrid vector cDNA Library *Euphorbia esula* cDNA clone 5AC 5' similar to ethylene-responsive element binding factor, mRNA sequence"; source: *Euphorbia esula* (leafy spurge).

BG411150 NCBI acc. No. BG411150 (gi: 13316703) (Mar. 13, 2001); Reid,S.P., et al. "EM1_26_C09.b1_A002 Embryo 1 (EM1) *Sorghum bicolor* cDNA, mRNA sequence"; source: *Sorghum bicolor* (sorghum); Title: "An EST database from *Sorghum*: developing embryos" (Unpublished (2000)).

BG417325 NCBI acc. No. 83417325 (gi: 13322972) (Mar. 13, 2001); Wing,R., et al. "HVSMEk0017108f *Hordeum vulgare* testa/pericarp EST library HVcDNA0013 (normal) *Hordeum vulgare* subsp. *vulgare* cDNA clone HVSMEk0017108f, mRNA sequence"; source: *Hordeum vulgare* subsp. *vulgare*.

BG444654 NCBI acc. No. BG444654 (gi: 13354306) (Mar. 15, 2001); Wing,R.A., et al. "GA_Ea002561 if *Gossyplum arboreum* 7-10 dpa fiber library *Gossypium arboreum* cDNA clone GA_Ea00251311f, mRNA sequence"; source: *Gossyplum arboreum*.

BG447769 NCBI acc. No. B3447769 (gi: 13366548) (Mar. 16, 2001); Torres-Jerez,I., et al. "NF093H08EC1F1076 Elicited cell culture *Medicago truncatula* cDNA clone NF093H08EC 5', mRNA sequence"; source: *Medicago truncatula* (barrel medic).

BG448225 NCBI acc. No. BG448225 (gi: 13367006) (Mar. 16, 2001); Torres-Jerez,I., et al. "NF107H09EC1F1078 Elicited cell culture *Medicago truncatula* cDNA done NF107H09EC 5', mRNA sequence"; source: *Medicago truncatula* (barrel medic).

BG448686 NCBI acc. No. BG448686 (gi: 13367383) (Mar. 16, 2001); Watson,B.S., et al. "NF023A03NR1F1000 Nodulated root *Medicago truncatula* cDNA clone NF023A03NR 5', mRNA sequence"; source: *Medicago truncatula* (barrel medic).

BG449954 NCBI acc. No. BG449954 (gi: 13368736) (Mar. 16, 2001); Torres-Jerez,I., et al. "NF013A1ODT1F1081 Drought *Medicago truncatula* cDNA clone NF013A10DT 5', mRNA sequence"; source: *Medicago truncatula* (barrel medic).

BG450588 NCBI acc. No. BG450588 (gi: 13369358) (Mar. 16, 2001); Torres-Jerez,I., et al. "NF031F10DT1F1091 Drought *Medicago truncatula* cDNA clone NF031F10DT 5', mRNA sequence"; source: *Medicago truncatula* (barrel medic).

BG451892 NCBI acc. No.BG451892 (gi: 13370674) (Mar. 16, 2001); Torres-Jerez,I., et al. "NF101E12DT1F1088 Drought *Medicago truncatula* cDNA done NF101E12DT 5&apos, mRNA sequence"; source: *Medicago truncatula* (barrel medic).

BG455325 NCBI acc. No. BG455325 (gi: 13378650) (Mar. 19, 2001); Liu,J., et al. "NF046F09PL1F1077 Phosphate starved leaf *Medicago truncatula* cDNA done NF046F09PL 5', mRNA sequence"; source: *Medicago truncatula* (barrel medic).

BG457772 NCBI acc. No. BG457772 (gi: 13381097) (Mar. 19, 2001); Liu,J., et al. "NF033D11PL1F1091 Phosphate starved leaf *Medicago truncatula* cDNA clone NF033D11PL 5', mRNA sequence"; source: *Medicago truncatula* (barrel medic).

BG459073 NCBI acc. No. BG359073 (gi: 13382398) (Mar. 19, 2001); Anderson,J.V., et al. "00846 leafy spurge Lambda HybriZAP 2.1 two-hybrid vector cDNA Library *Euphorbia esula* cDNA clone 18AF 5' similar to putative Ckc2 [*Arabidopsis thaliana*], accession# CAA05084, mRNA sequence"; source: *Euphorbia esula* .

BG507541 NCBI acc. No. BG507541 (gi: 13477813) (Mar. 28, 2001); Shoemaker,R., et al. "sac60g11.y1 Gm-c1062 *Glycine max* cDNA clone Genome Systems Clone ID: Gm-c1062-4534 5' similar to TR:O81365 O81365 AP2 Domain Containing Protein ;, mRNA sequence"; source: *Glycine max*.

BG507761 NCBI acc. No. BG507761 (gi: 13478178) (Mar. 28, 2001); Shoemaker,R., et al. "sac89a05.y1 Gm-c1073 *Glycine max* cDNA clone Genome Systems Clone ID: Gm-c1073-33 5' similar to TR:P93393 P93393 S25-XP1 DNA Binding Protein, ;, mRNA sequence"; source: *Glycine max* (soybean).

BG508757 NCBI acc. No. BG508757 (gi: 12479414) (Mar. 28, 2001); Shoemaker,R., et al. "sac90a05.y1 Gm-c1073 *Glycine max* cDNA clone Genome Systems Clone ID: Gm-c1073-34 5' similar to TR:P93392 P93392 S25-XP1 DNA Binding Protein. ;, mRNA sequence"; source: *Glycine max* (soybean).

BG510218 NCBI acc. No. BG510218 (gi: 13480875) (Mar. 28, 2001); Shoemaker,R., et al. "sac64a08.y1 Gm-c1072 *Glycine max* cDNA clone Genome Systems Clone ID: Gm-c1072-16 5' similar to TR:O80387 O80387 Ethylene Responsive Element Binding Factr. ;, mRNA sequence".

BG518375 NCBI acc. No. BG518375 (gi: 13516099) (Apr. 2, 2001); Walbot,V., et al. "947066G11.y1 947—2 week shoot from Barkan lab *Zea mays* cDNA, mRNA sequence"; source: *Zea mays*; Title: "Maize ESTs from various cDNA libraries sequenced at Stanford University" (Unpublished (1999)).

BG581520 NCBI acc. No. BG581520 (gi: 13596584) (Apr. 11, 2001); Fedorova,M., et al. "EST483254 GVN *Medicago truncatula* cDNA clone pGVN-65I3 5' end, mRNA sequence"; source: *Medicago truncatula* (barrel medic); Title: ESTs from one month old nitrogen-fixing root nodules of *Medicago truncatula*.

BG581532 NCBI acc. No. BG581532 (gi: 13596596) (Apr. 11 2001); Fedorova,M., et al. "EST483266 GVN *Medicago truncatula* cDNA clone pGVN-69O23 5' end, mRNA sequence"; source: *Medicago truncatula* (barrel medic); Title: ESTs from one month old nitrogen-fixing root nodules of *Medicago truncatula*.

BG582281 NCBI acc. No. BG582281 (gi: 13597345) (Apr. 11, 2001); Fedorova,M., et al. "EST484022 GVN *Medicago truncatula* cDNA clone pGVN-69O23 5' end, mRNA sequence"; source: *Medicago truncatula* (barrel medic); Title: ESTs from one month old nitrogen-fixing root nodules of *Medicago truncatula*.

BG582759 NCBI acc. No. BG582759 (gi: 13597823) (Apr. 11, 2001); Fedorova,M., et al. "EST484505 GVN *Medicago truncatula* cDNA clone pGVN-70J21 5' end, mRNA sequence"; source: *Medicago truncatula* (barrel medic); Title: ESTs from one month old nitrogen-fixing root nodules of *Medicago truncatula*.

BG582854 NCBI acc. No. 60582854 (gi: 13597918) (Apr. 11, 2001); Fedorova,M., et al. "EST484600 GVN *Medicago truncatula* cDNA clone pGVN-70L24 5' end, mRNA sequence"; source: *Medicago truncatula* (barrel medic); Title: ESTs from one month old nitrogen-fixing root nodules of *Medicago truncatula*.

BG582869 NCBI acc. No. BG582869 (gi: 13597933) (Apr. 11, 2001); Fedorova,M., et al. "EST484615 GVN *Medicago truncatula* cDNA clone pGVN-70P6 5' end, mRNA sequence"; source: *Medicago truncatula* (barrel medic); Title: ESTs from one month old nitrogen-fixing root nodules of *Medicago truncatula*.

BG583042 NCBI acc. No. BG583042 (gi: 13598098) (Apr. 11, 2001); Fedorova,M., et al. "EST484784 GVN *Medicago truncatula* cDNA clone pGVN-71O4 5' end, mRNA sequence"; source: *Medicago truncatula* (barrel medic); Title: ESTs from one month old nitrogen-fixing root nodules of *Medicago truncatula*.

BG583111 NCBI acc. No. BG583111 (gi: 13598175) (Apr. 11, 2001); Fedorova,M., et al. "EST484861 GVN *Medicago truncatula* cDNA clone pGVN-71N15 5' end, mRNA sequence"; source: *Medicago truncatula* (barrel medic); Title: ESTs from one month old nitrogen-fixing root nodules of *Medicago truncatula*.

BG583265 NCBI acc. No. BG583265 (gi: 13598329) (Apr. 11, 2001); Fedorova,M., et al. "EST485016 GVN *Medicago truncatula* cDNA clone pGVN-72M9 5' end, mRNA sequence"; source: *Medicago truncatula* (barrel medic); Title: ESTs from one month old nitrogen-fixing root nodules of *Medicago truncatula*.

BG583402 NCBI acc. No. BG583402 (gi: 13598466) (Apr. 11, 2001); Fedorova,M., et al. "EST485154 GVN *Medicago truncatula* cDNA clone pGVN-73K11 5' end, mRNA sequence"; source: *Medicago truncatula* (barrel medic); Title: ESTs from one month old nitrogen-fixing root nodules of *Medicago truncatula*.

BG583604 NCBI acc. No. BG583604 (gi: 13598668) (Apr. 11, 2001); Fedorova,M., et al. "EST485356 GVN *Medicago truncatula* cDNA done pGVN-73L16 5' end, mRNA sequence"; source: *Medicago truncatula* (barrel medic); Title: ESTs from one month old nitrogen-fixing root nodules of *Medicago truncatula*.

(56) References Cited

OTHER PUBLICATIONS

BG583826 NCBI acc. No. BG583626 (gi: 13598690) (Apr. 11, 2001); Fedorova,M., et al. "EST485378 GVN *Medicago truncatula* cDNA clone pGVN-73P18 5' end, mRNA sequence"; source: *Medicago truncatula* (barrel medic); Title: ESTs from one month old nitrogen-fixing root nodules of *Medicago truncatula*.
BG583711 NCBI acc. No. BG583711 (gi: 13598775) (Apr. 11, 2001); Federova,M., et al. "EST485464 GVN *Medicago truncatula* cDNA clone pGVN-74C14 5' end, mRNA sequence"; source: *Medicago truncatula* (barrel medic); Title: ESTs from one month old nitrogen-fixing root nodules of *Medicago truncatula*.
BG583745 NCBI acc. No. BG583745 (gi: 13598809) (Apr. 11, 2001); Fedorova,M., et al. "EST485500 GVN *Medicago truncatula* cDNA clone pGVN-74I24 5' end, mRNA sequence"; source: *Medicago truncatula* (barrel medic); Title: ESTs from one month old nitrogen-fixing root nodules of *Medicago truncatula*.
BG583761 NCBI acc. No. BG583761 (gi: 13598825) (Apr. 11, 2001); Fedorova,M., et al. "EST485516 GVN *Medicago truncatula* cDNA clone pGVN-74M12 5' end, mRNA sequence"; source: *Medicago truncatula* (barrel medic); Title: ESTs from one month old nitrogen-fixing root nodules of *Medicago truncatula*.
BG587841 NCBI acc. No. BG587841 (gi: 13602905) (Apr. 11, 2001); Harrison,M.J., et al. "EST489616 KV3 *Medicago truncatula* cDNA clone pKV3-13E10 5' end, mRNA sequence"; source: *Medicago truncatula* (barrel medic); Title: ESTs from roots of *Medicago truncatula* after colonization with *Glomus versiforme*.
BG591632 NCBI acc. No. BG591632 (gi: 13609772) (Apr. 12, 2001); Zhang,P., et al. "EST499474 *P. infestans*-challenged leaf *Solanum tuberosum* cDNA clone BPLI9N11 5' sequence, mRNA sequence"; source: *Solanum tuberosum* (potato).
BG592132 NCBI acc. No. BG592132 (gi: 13610272) (Apr. 12, 2001); Zhang,P., et al:"EST499974 *P. infestans*-challenged leaf *Solanum tuberosum* cDNA clone BPLI11I10 5' sequence, mRNA sequence"; source: *Solanum tuberosum* (potato).
BG596455 NCBI acc. No. BG596455 (gi: 13614595) (Apr. 12, 2001); Van Der Hoeven,R., et al. "EST495133 cSTS *Solanum tuberosum* cDNA clone cSTS14A18 5' sequence, mRNA sequence"; source: *Solanum tuberosum* (potato); Title "Generations of ESTs from sprouting potato eyes" (Unpublished (2000)).
BG600086 NCBI acc. No. BG600086 (gi: 13617222) (Apr. 12, 2001); Van Der Hoeven,R., et al. "EST504981 cSTS *Solanum tuberosum* cDNA clone cSTS27A2 5' sequence, mRNA sequence"; source: *Solanum tuberosum* (potato); Title: "Generations of ESTs from sprouting potato eyes" (Unpublished (2000)).
BG606428 NCBI acc. No. BG606428 (gi: 13656411) (Apr. 17, 2001); Anderson,O.D., et al."WHE2956_B01_C02ZS Wheat dormant embryo cDNA library *Triticum aestivum* cDNA clone VVHE2956_B01_C02, mRNA sequence"; source: *Triticum aestivum* (bread wheat).
BG642691 NCBI acc. No. BG642691 (gi: 13777572) (Apr. 24, 2001); Van Der Hoeven,R., et al. "EST510885.tomato shoot/ meristem *Solanum lycopersicum* cDNA clone cT0F25K14 5%apos; sequence, mRNA sequence"; source: *Solanum lycopersicum* (*Lycopersicon esculentum*).
BG643340 NCBI acc. No. BG643340 (gi: 13778565) (Apr. 24, 2001); Van Der Hoeven,R., et al. "EST511534 tomato shool/ meristem *Solanum lycopersicum* cDNA clone cTOF27E22 5' sequence, mRNA sequence"; source: *Solanum lycopersicum* (*Lycopersicon esculentum*).
BG644911 NCBI acc. No. BG644911 (gi: 13780023) (Apr. 24, 2001); Vandenbosch,K., et al. "EST506530 KV3 *Medicago truncatula* cDNA clone pKV3-38P9 5%apos; end, mRNA sequence"; source: *Medicago truncatula* (barrel medic); Title: ESTs from roots of *Medicago truncatula* 72 h after Rhizobium inoculation.
BG645028 NCBI acc. No. BG645028 (gi: 13780140) (Apr. 24, 2001); Vandenbosch,K., et al. "EST506647 KV3 *Medicago truncatula* cDNA clone pKV3-39C23 5 end, mRNA sequence"; source: *Medicago truncatula* (barrel medic); Title: ESTs from roots of *Medicago truncatula* 72 h after Rhizobium inoculation.

BG646470 NCBI acc. No. BG646470 (gi: 13781582) (Apr. 24, 2001); Hahn,M.G., et al. "EST508089 HOGA *Medicago truncatula* cDNA clone pHOGA-9M7 5' end, mRNA sequence"; source: *Medicago truncatula* (barrel medic).
BG646567 NCBI acc. No. BG646567 (gi: 13781679) (Apr. 24, 2001); Hahn,M.G., et al. "EST508186 HOGA *Medicago truncatula* cDNA clone pHOGA-9M7 5' end, mRNA sequence"; source: *Medicago truncatula* (barrel medic).
BG646774 NCBI acc. No. BG646774 (gi: 13781886) (Apr. 24, 2001); Hahn,M.G., et al. "EST508393 HOGA *Medicago truncatula* cDNA clone pHOGA-9D12 5' end, mRNA sequence"; source: *Medicago truncatula* (barrel medic).
BG647592 NCBI acc. No. BG647592 (gi: 13782704) (Apr. 24, 2001 ; Hahn,M.G., et al. "EST509211 HOGA *Medicago truncatula* cDNA clone pHOGA-17G24 5' end, mRNA sequence"; source: *Medicago truncatula* (barrel medic).
BG647771 NCBI acc. No. BG647771 (gi: 13782883) (Apr. 24, 2001); Hahn,M.G., et al. "EST509390 HOGA *Medicago truncatula* cDNA clone pHOGA-17J8 5' end, mRNA sequence"; source: *Medicago truncatula* (barrel medic).
BG647799 NCBI acc. No. BG647799 (gi: 13782911) (Apr. 24, 2001); Hahn,M.G., et al. "EST509418 HOGA *Medicago truncatula* cDNA clone pHOGA-17N20 5' end, mRNA sequence"; source: *Medicago truncatula* (barrel medic).
BG647917 NCBI acc. No. BG647917 (gi: 13783029) (Apr. 24, 2001); Hahn,M.G., et al. "EST509536 HOGA *Medicago truncatula* cDNA clone pHOGA-18C12 5' end, mRNA sequence"; source: *Medicago truncatula* (barrel medic).
BG648548 NCBI acc. No. BG648548 (gi: 13783660) (Apr. 24, 2001); Hahn,M.G., et al. "EST510167 HOGA *Medicago truncatula* cDNA clone pHOGA-2311 5' end, mRNA sequence"; source: *Medicago truncatula* (barrel medic).
BG652103 NCBI acc. No. BG652103 (gi: 13789512) (Apr. 25, 2001); Shoemaker,R., et al. "sad74b10.y1 Gm-c1051 *Glycine max* cDNA clone Genome Systems Clone ID: Gm-c1051-5851 5' similar to TR:P93822 P93822 F 19P19.18. ;, mRNA sequence"; source: *Glycine max* (soybean).
BG652103 NCBI acc. No. BG652103 (gi: 13789512) (Apr. 25, 2001); Shoemaker., et al. "sad74b10.y1 Gm-c1051 *Glycine max* cDNA clone Genome Systems Clone ID: Gm-c1051-5851 5' similar to TR:Q40477 Q40477 EREBP-3. ;, mRNA sequence"; source: *Glycine max* (soybean).
BG726262 NCBI acc. No. BG726262 (gi: 14011340) (May 9, 2001); Shoemaker,R., et al. sae13f10.y1 Gm-c1067 *Glycine max* cDNA clone Genome Systems Clone ID: Gm-c1067-2947 5' similar to TR:Q9SJX3 Q9SJX3 Ethylene Response Factor-Like AP2 Domain Transcription Factor.
BG789540 NCBI acc. No. BG789540 (gi: 14125102) (May 16, 2001); Shoemaker,R., et al. sae65811.y1 Gm-c1084 *Glycine max* cDNA clone Genome Systems Clone ID: Gm-c1064-3093 5' similar to TR:Q9ZR85 Q9ZR85 Ethylene-Responsive Element Binding Protein Homolog. ;, mRNA.
BG790680 NCBI acc. No. BG790680 (gi: 14126242) (May 16, 2001); Shoemaker,R., et al. "sae75d09.y1.Gm-c1064 *Glycine max* cDNA clone Genome Systems Clone ID: Gm-c1064-4025 5 similar to TR:P93822 P93822 F 19P19.18. ;, mRNA sequence"; source: *Glycine max* (soybean).
BG790996 NCBI acc. No. BG790998 (gi: 14126558) (May 16, 2001); Shoemaker,R., et al. sae72tr12.y1 Gm-c1064 *Glycine max* cDNA clone Genome Systems Clone ID: Gm-c1064-3840 5' similar to TR:Q9ZR85 Q9ZR85 Ethylene-Responsive Element Binding Protein Homolog. ;, mRNA.
BG886550 NCBI acc. No. BG886550 (gi: 14263636) (May 30, 2001); Van Der Hoeven,R., et al. "EST512401 cSTD *Solanum tuberosum* cDNA clone cSTD1K11 5' sequence similar to similar to *Prunus armenlaca* AP2 domain containing protein, mRNA sequence"; source: *Solanum tuberosum* (potato).
BG888738 NCBI acc. No. BG888738 (gi: 14265824) (May 30, 2001);Van Der Hoeven,R., et al. "EST514589 cSTD *Solanum tuberosum* cDNA clone cSTD11I12 5' sequence, mRNA sequence"; source: *Solanum tuberosum* (potato); Title: "Generations of ESTs from dormant potato tubers" (Unpublished (2001)).

(56) References Cited

OTHER PUBLICATIONS

BG890347 NCBI acc. No. BG890347 (gi: 14267448) (May 30, 2001); Van Der Hoeven,R., et al. "EST516198 cSTD *Solanum tuberosum* cDNA clone cSTD18G1 5' sequence, mRNA sequence"; source: *Solanum tuberosum* (potato); Title: "Generations of ESTs from dormant potato tubers" (Unpublished (2001)).

BH454277 NCBI acc. No. BH454277 (gi: 17639988) (Dec. 12, 2001); Ayele,M., et al. "BOGSI45TR BOGS *Brassica oleracea* genomic clone BOGSI45, genomic survey sequence"; source: *Brassica oleracea*.

BH460596 NCBI acc. No. BH460596 (gi: 17650341) (Dec. 13, 2001); Ayele,M., et al. "BOGWG8OTR BOGW *Brassica oleracea* genomic clone BOGWG80, genomic survey sequence"; source: *Brassica oleracea*.

BH517030 NCBI acc. No. BH517030 (gi: 17725120) (Dec. 13, 2001); Ayele,M., et al. "BOHRB76TF BOHR *Brassica oleracea* genomic clone BOHRB76, genomic survey sequence"; source: *Brassica oleracea*.

BH519444 NCBI acc. No. BH519444 (gi: 17727529) (Dec. 13, 2001); Ayele,M., et al. "BOGKI41TF BOGK *Brassica oleracea* genomic clone BOGKI41, genomic survey sequence"; source: *Brassica oleracea*.

BH603154 NCBI acc. No. BH603154 (gi: 17855600) (Dec. 15, 2001); Ayele,M., et al. "BOGDP09TF BOGD *Brassica oleracea* genomic clone BOGDP09, genomic survey sequence"; source: *Brassica oleracea*.

BH672011 NCBI acc. No. BH672011 (gi: 18737461) (Feb. 19, 2002); Ayele,M., et al. "BOHYF95TR BO_2_3_KB *Brassica oleracea* genomic clone BOHYF95, genomic survey sequence"; source: *Brassica oleracea*.

BH683728 NCBI acc. No. BH683728 (gi: 18754171) (Feb. 19, 2002); Ayele,M., et al. "BOHTE23TR BO_2_3_KB *Brassica oleracea* genomic clone BOHTE23, genomic survey sequence"; source: *Brassica oleracea*.

BH715240 NCBI acc. No. BH715240 (gi: 18809815) (Feb. 20, 2002); Ayele,M., et al. "BOHVQ41TR BO_2_3_KB *Brassica oleracea* genomic clone BOHVQ41, genomic survey sequence"; source: *Brassica oleracea*.

BH777081 NCBI acc. No. BH777081 (gi: 19779485) (Mar. 28, 2002); Budiman,M.A., et al. "fzmb013f019h09f0fzmb filtered library *Zea mays* genomic clone fzmb013f019h09 5', genomic survey sequence"; source: *Zea mays*; Title: "Gene Thresher methylation filtered genomic sequences from maize" (Unpublished (2002)).

BI263133 NCBI acc. No. BI263133 (gi: 14864047) (Jul. 18, 2001); Liu,J., et al. "NF085D03PL1F1030 Phosphate starved leaf *Medicago truncatula* cDNA clone NF085D03PL 5', mRNA sequence"; source: *Medicago truncatula* (barrel medic); Title: Expressed Sequence Tags from the Samuel Roberts Noble Foundation.

BI265074 NCBI acc. No. BI265074 (gi: 14867921) (Jul. 18, 2001); Korth,K., et al. "NF078F08IN1F1075 insect herbivory *Medicago truncatula* cDNA clone NF078F08IN 5', mRNA sequence"; source: *Medicago truncatula* (barrel medic); Title: Expressed Sequence Tags from the Samuel Roberts Noble Foundation.

BI265685 NCBI acc. No. BI265685 (gi: 14869141) (Jul. 18, 2001); Korth,K., et al. "NF083007IN1F1062 insect herbivory *Medicago truncatula* cDNA clone NF083D07IN 5', mRNA sequence"; source: *Medicago truncatula* (barrel medic); Title: Expressed Sequence Tags from the Samuel Roberts Noble Foundation.

BI266358 NCBI acc. No. BI266358 (gi: 14870395) (Jul. 18, 2001); Korth,K., et al. "NF084D12IN1F1102 insect herbivory *Medicago truncatula* cDNA clone NF084012IN 5', mRNA sequence"; source: *Medicago truncatula* (barrel medic); Title: Expressed Sequence Tags from the Samuel Roberts Noble Foundation.

BI271853 NCBI acc. No. BI271853 (gi: 14880681) (Jul. 18, 2001); Torres-Jerez,I., et al. "NF013E04FL1F1034 Developing flower *Medicago truncatula* cDNA clone NF013E04FL 5', mRNA sequence"; source: *Medicago truncatula* (barrel medic); Title: Expressed Sequence Tags from the Samuel Roberts Noble Foundation.

BI305323 NCBI acc. No. BI305323 (gi: 14980645) (Jul. 20, 2001); Reddy,A.R., et al. "NRS2R_1_N04 Drought stress (root) *Oryza sativa* (indica cultivar-group) cDNA clone NRS2R_1_N04 3', mRNA sequence"; source: *Oryza sativa* (indica cultivar-group).

BI305776 NCBI acc. No. BI305776 (gi: 14981085) (Jul. 20, 2001); Reddy,A.R., et al. "NL_1_L02 Drought stress (leaf) *Oryza sativa* (indica cultivar-group) cDNA clone NL_1_L02 3&apos:, mRNA sequence"; source: *Oryza sativa* (indica cultivar-group).

BI308635 NCBI acc. No. BI308635 (gi: 14982962) (Jul. 20, 2001); Grusak,M.A., et al. "EST530045 GPOD *Medicago truncatula* cDNA clone pGPOD-7M22 5' end, mRNA sequence"; source: *Medicago truncatula* (barrel medic); Title: "ESTs from developing reproductive tissues of *Medicago truncatula*" (Unpublished (2001)).

BI308895 NCBI acc. No. BI308895 (gi: 14983222) (Jul. 20, 2001); Grusak,M.A., et al. "EST530305 GPOD *Medicago truncatula* cDNA clone pGPOD-10E21 5' end, mRNA sequence"; source: *Medicago truncatula* (barrel medic); Title: "ESTs from developing reproductive tissues of *Medicago truncatula*" (Unpublished (2001)).

BI310543 NCBI acc. No. BI310543 (gi: 14984870) (Jul. 20, 2001); Grusak,M.A., et al. "EST5312293 GESD *Medicago truncatula* cDNA clone pGESD8I18 5' end, mRNA sequence": source: *Medicago truncatula* (barrel medic); Title: "ESTs from developing reproductive tissues of *Medicago truncatula*" (Unpublished (2001)).

BI311856 NCBI acc. No. BI311856 (gi: 14986183) (Jul. 20, 2001); Grusak,M.A., et al. "EST5313606 GESD *Medicago truncatula* cDNA clone pGESD15N15 5' end, mRNA sequence"; source: *Medicago truncatula* (barrel medic); Title: "ESTs from developing reproductive tissues of *Medicago truncatula*" (Unpublished (2001)).

BI321594 NCBI acc. No. BI321594 (gi: 15000780) (Jul. 23, 2001); Shoemaker,R., et al. "saf15b09.y3 Gm-c1076 *Glycine max* cDNA clone Genome Systems Clone ID: Gm-c1076-834 5' similar to TR:Q9ZR85 Q9ZR85 Ethylene-Responsive Element Binding Protein Homolog. ;, mRNA sequence".

BI418604 NCBI acc. No. BI418604 (gi: 15189627) (Aug. 15, 2001); Colebatch,G., at al. "LJNEST43f5r *Lotus japonicus* nodule library 5 and 7 week-old *Lotus japonicus* cDNA 5', mRNA sequence"; source: *Lotus japonicus*; Title: "*Lotus japonicus* root nodule ESTs: tools for functional genomics" (Unpublished (2000)).

BI420305 NCBI acc. No. BI420305 (gi: 15191328) (Aug. 15, 2001); Colebatch,G., et al. "LjNEST55d6r *Lotus japonicus* nodule library 5 and 7 week-old *Lotus japonicus* cDNA 5', mRNA sequence"; source: *Lotus japonicus*; Title:."*Lotus japonicus* root nodule ESTs: tools for functional genomics" (Unpublished (2000)).

BI421270 NCBI acc. No. BI421270 (gi: 15194638) (Aug. 16, 2001); Alcala,J., et al. "EST531936 tomato callus, TAMU *Solanum lycopersicum* cDNA clone cLEC66M2 5' end, mRNA sequence"; source: *Solanum lycopersicum* (*Lycoperslcon esculentum*); Title: "Generation of ESTs from tomato callus tissue".

BI421507 NCBI acc. No. BI421507 (gi: 15195085) (Aug. 16, 2001); Alcala,J., et al. "EST532173 tomato callus, TAMU *Solanum lycopersicum* cDNA clone cLEC67G17 5' end, mRNA sequence"; source: *Solanum lycopersicum* (*Lycopersicon esculentum*); Title: "Generation of ESTs from tomato callus tissue".

BI421558 NCBI acc. No. BI421558 (gi: 15195182) (Aug. 16, 2001); Alcala,J., et al. "EST532224 tomato callus, TAMU *Solanum lycopersicum* cDNA clone cLEC67A22 5' end, mRNA sequence"; source: *Solanum lycopersicum* (*Lycopersicon esculentum*); Title: "Generation of ESTs from tomato callus tissue".

BI421895 NCBI acc. No. BI421895 (gi: 15195839) (Aug. 16, 2001); Alcala,J., et al. "EST532561 tomato callus, TAMU *Solanum lycopersicum* cDNA clone cLEC68E16 5' end, mRNA sequence"; source: *Solanum lycopersicum* (*Lycopersicon esculentum*); Title: "Generation of ESTs from tomato callus tissue".

BI422101 NCBI acc. No. BI422101 (gi: 15196219) (Aug. 16, 2001); Alcala,J., et al. "EST532767 tomato callus, TAMU *Solanum lycopersicum* cDNA clone cLEC69A23 5' end, mRNA sequence"; source: *Solanum lycopersicum* (*Lycopersicon esculentum*); Title: "Generation of ESTs from tomato callus tissue".

BI424734 NCBI acc. No. BI424734 (gi: 15201177) (Aug. 16, 2001); Shoemaker,R., et al. "sah48a08.y2 Gm-c1036 *Glycine max* cDNA clone Genome Systems Clone ID: Gm-c1036-4623 5' similar to TR:O81365 O81365 AP2 Domain Containing Protein ;, mRNA sequence"; source: *Glycine max*.

(56) References Cited

OTHER PUBLICATIONS

BI427468 NCBI acc. No. BI427468 (gi: 15204700) (Aug. 16, 2001); Shoemaker,R., et al. "sah80f02.y1 Gm-c1050 *Glycine max* cDNA clone Genome Systems Clone ID: Gm-c1050-2547 5' similar to SW:ERF5_ARATH O80341 Ethylene Responsive Element Binding Factor 5', mRNA sequence".

BI436183 NCBI acc. No. BI436183 (gi: 15260873) (Aug. 21, 2001); Van Der Hoeven,R., et al. "EST538944 cSTE *Solanum tuberosum* cDNA clone cSTE21L16 5 sequence, mRNA sequence"; source: *Solanum tuberosum* (potato); Title: "Generation of ESTs from in vitro grown microtubers" (Unpublished (2001)).

BI436295 NCBI acc. No. BI436295 (gi: 15260985) (Aug. 21, 2001); Van Der Hoeven,R., et al. "EST539056 cSTE *Solanum tuberosum* cDNA clone cSTE22021 5' sequence, mRNA sequence"; source: *Solanum tuberosum* (potato); Title: "Generation of ESTs from in vitro grown microtubers" (Unpublished (2001)).

BI468669 NCBI acc. No. BI468669 (gi: 15284778) (Aug. 24, 2001); Shoemaker,R., et al. "sai01h08.y1 Gm-c1050 *Glycine max* cDNA clone Genome Systems Clone ID: Gm-c1050-4575 5' similar to TR:Q40478 Q40478 EREBP-4. ;, mRNA sequence"; source: *Glycine max* (soybean).

BI469284 NCBI acc. No. BI469284 (gi: 15285393) (Aug. 24, 2001); Shoemaker,R., et al. "sai09h04.y1 Gm-c1053 *Glycine max* cDNA clone Genome Systems Clone ID: Gm-c1053-3031 5' similar to TR:O23143 O23143 Putative CKC2. ;, mRNA sequence"; source: *Glycine max* (soybean).

BI784879 NCBI acc. No. BI784879 (gi: 15812604) (Oct. 1, 2001); Shoemaker,R., et al. "saf94g11.y3 Gm-c1079 *Glycine max* cDNA clone Genome Systems Clone ID: Gm-c1079-1845 5' similar to TR:Q40478 Q40478 EREBP-4. ;, mRNA sequence"; source: *Glycine max* (soybean).

BI786168 NCBI acc. No. BI786168 (gi: 15813893) (Oct. 1, 2001); Shoemaker,R., et al. "sai33g03.y1 Gm-c1065 *Glycine max* cDNA clone Genome Systems Clone ID: Gm-c1065-5285 5' similar to TR:O80387 O80387 Ethylene Responsive Element Binding Factor. ;, mRNA sequence"; source: *Glycine max*.

BI787734 NCBI acc. No. BI787734 (gi: 15815459) (Oct. 1, 2001); Shoemaker,R., et al. "sag75b04.y1 Gm-c1084 *Glycine max* cDNA clone Genome Systems Clone ID: Gm-c1084-55 5' similar to TR:Q9ZNR2 Q9ZNR2 Ethylene Response Factor 1. ;, mRNA sequence"; source: *Glycine max* (soybean).

BI893228 NCBI acc. No. BI893228 (gi: 16105488) (Oct. 12, 2001); Shoemaker,R., et al. "sa163b03.y1 Gm-c1068 *Glycine max* cDNA clone Genome Systems Clone ID: Gm-c1068-3149 5' similar to TR:O80387 O80387 Ethylene Responsive Element Binding Factor. ;, mRNA sequence".

BI921995 NCBI acc. No. BI921995 (gi: 16218023) (Oct. 17, 2001); Alcala,J., et al. "EST541898 tomato callus *Solanum lycopersicum* cDNA clone cLEC75P13 5' end, mRNA sequence"; source: *Solanum lycopersicum* (*Lycopersicon esculentum*); Title: "Generation of ESTs from tomato callus tissue (2001)" (Unpublished (2001)).

BI968964 NCBI acc. No. BI968964 (gi: 16343369) (Oct. 23, 2001); Vodkin,L., et al. "GM830006B21G05 Gm-r1083 *Glycine* max cDNA clone Gm-r1083-2242 3', mRNA sequence"; source: *Glycine max* (soybean); Title: "A Functional Genomics Program for Soybean (NSF 9872565)" (Unpublished (1999)).

BI973708 NCBI acc. No. BI973708 (gi: 18348113) (Oct. 23, 2001); Shoemaker,R., et al. "sai91o09.y1 Gm-c1065 *Glycine max* cDNA clone Genome Systems Clone ID: Gm-c1065-8393 5' similar to TR:O9ZNR2 O9ZNR2 Ethylene Response Factor 1. ;, mRNA sequence"; source: *Glycine max*.

BI973872 NCBI acc. No. BI973872 (gi: 16348277) (Oct. 23, 2001); Shoemaker,R., at al. "sai93h12.y1 Gm-c1065 *Glycine max* cDNA clone Genome Systems Clone ID: Gm-c1065-8807 5' similar to SW:ERFI_ARATH O80337 Ethylene Responsive Element Binding Factor 1 ;, mRNA sequence".

BM062245 NCBI acc. No. BM062245 (gi: 22782363) (Sep. 11, 2002);Lee,S., et al. "KS01040C11 KS01 *Capsicum annuum* cDNA, mRNA sequence"; source: *Capsicum annuum*.

BM075553 NCBI acc. No. BM075553 (gi: 16922376) (Nov. 13, 2001); Wen.T.J., et al. "MEST357-A11.73 ISUM5-RN *Zea mays* cDNA clone MEST357-A11 3', mRNA sequence"; source: *Zea mays*.

BM093669 NCBI acc. No. BM093669 (gi: 17022635) (Nov. 20, 2001); Shoemaker,R., at al. "saj12f09.y1 Gm-c1066 *Glycine max* cDNA clone Genome Systems Clone ID: Gm-c1066-2585 5' similar to TR:Q92NR2 Q9ZNR2 Ethylene Response Factor 1. ;, mRNA sequence"; source: *Glycine max*.

BM094577 NCBI acc. No. BM094577 (gi: 17023543) (Nov. 20, 2001); Shoemaker,R., et al. "saj17g07.y1 Gm-c1066 *Glycine max* cDNA clone Genome Systems Clone ID: Gm-c1066-3014 5' similar to TR:O80387 O80387 Ethylene Responsive Element Binding Factor. ;, mRNA sequence".

BM110901 NCBI acc. No. BM110901 (gi: 17073001) (Nov. 26, 2001); Van Der Hoeven,R, et al. "EST558437 potato roots *Solanum tuberosum* cDNA clone cPRO9J5 5' end, mRNA sequence"; source: *Solanum tuberosum* (potato); Title: "Generation of ESTs from potato roots" (Unpublished (2001)).

BM110909 NCBI acc. No. BM110909 (gi: 17073016) (Nov. 26, 2001); Van Der Hoeven,R., et al. "EST558445 potato roots *Solanum tuberosum* cDNA clone cPRO9L5 5%apos; end, mRNA sequence"; source: *Solanum tuberosum* (potato); Title: "Generation of ESTs from potato roots" (Unpublished (2001)).

BM110921 NCBI acc. No. BM110921 (gi: 17073038) (Nov. 26, 2001); Van Der Hoeven,R., at al. "EST558457 potato roots *Solanum tuberosum* cDNA clone cPRO9N5 5' end, mRNA sequence"; source: *Solanum tuberosum* (potato); Title: "Generation of ESTs from potato roots" (Unpublished (2001)).

BM143375 NCBI acc. No. BM143375 (gi: 17153433) (Nov. 29, 2001); Shoemaker,R., et al. "saj43b11.y1 Gm-c1072 *Glycine max* cDNA clone Soybean Clone ID: Gm-c1072-2374 5%apos; similar to TR:Q40478 Q40478 EREBP-4. ;, mRNA sequence "; source: *Glycine max* (soybean).

BM178361 NCBI acc. No. BM178361 (gi: 17401579) (Dec. 6, 2001); Shoemaker,R., et al. "saj72a10.y1 Gm-c1072 *Glycine max* cDNA clone Soybean Clone ID: Gm-c1072-5035 5' similar to TR:Q9ZNR2 Q9ZNR2 Ethylene Response Factor 1. ;, mRNA sequence"; source: *Glycine max* (soybean).

BM178875 NCBI acc. No. BM178875 (gi: 17402093) (Dec. 6, 2001); Shoemaker,R., et al. "saj60f01.y1 Gm-c1072 *Glycine max* cDNA clone Soybean Clone ID: Gm-c1072-4105 5' similar to TR:P93822 P93822 F 19P19.18. ;, mRNA sequence"; source: *Glycine max* (soybean); Title: Public Soybean EST.

BM268956 NCBI acc. No. BM268956 (gi: 17931996) (Dec. 18, 2001); Wen,T.J., et al. "MEST402-H11.univ ISUM5-RN *Zea mays* cDNA clone MEST402-H11 3', mRNA sequence"; source: *Zea mays*.

BM271048 NCBI acc. No. BM271048 (gi: 17964311) (Dec. 20, 2001); Shoemaker,R., et al. "sak04f02.y1 Gm-c1074 *Glycine max* cDNA clone Soybean Clone ID: Gm-c1074-5236 5%apos; similar to TR:Q40478 Q40478 EREBP-4. ;, mRNA sequence"; source: *Glycine max* (soybean).

BM332316 NCBI acc. No. BM332316 (gi: 18162477) (Jan. 16, 2002); Wen,T.J., et al. "MEST167-B07.T3 ISUM5-RN *Zea mays* cDNA clone MEST167-B07 3', mRNA sequence"; source: *Zea mays*.

BM332461 NCBI acc. No. BM332461 (gi: 18162622) (Jan. 16, 2002); Wen,T.J., et al. "MEST169-C11.T3 ISUM5-RN *Zea mays* cDNA done MEST169-C11 3', mRNA sequence"; source: *Zea mays*.

BM348130 NCBI acc. No. BM348130 (gi: 18172742) (Jan. 16, 2002); Wen,T.J., et al. "MEST286-H07.T3 ISUM5-RN *Zea mays* cDNA clone MEST286-H07 3', mRNA sequence"; source: *Zea mays*.

BM348921 NCBI acc. No. BM348921 (gi: 18173533) (Jan. 16, 2002); Wen,T.J., et al. "MEST303-H12.T3 ISUM5-RN *Zea mays* cDNA clone MEST303-H12 3', mRNA sequence"; source: *Zea mays*.

BM403974 NCBI acc. No. BM403974 (gi: 18255379) (Jan. 22, 2002); Restrepo,S., et al. "EST578301 *P. infestans*-challenged potato leaf, compatible reaction *Solanum tuberosum* cDNA clone PPCCR61 5' end, mRNA sequence"; source: *Solanum tuberosum* (potato).

(56) References Cited

OTHER PUBLICATIONS

BM409157 NCBI acc. No. BM409157 (gi: 18260787) (Jan. 22, 2002); Alcala,J., et al. "EST583484 tomato breaker fruit *Solanum lycopersicum* cDNA clone cLEG47M16 5' end, mRNA sequence"; source: *Solanum lycopersicum* (*Lycopersicon esculentum*).

BM411708 NCBI acc. No. BM411708 (gi: 18263338) (Jan. 22, 2002); Alcala,J., et al. "EST586035 tomato breaker fruit *Solanum lycopersicum* cDNA clone cLEG57L21 5' end, mRNA sequence"; source: *Solanum lycopersicum* (*Lycopersicon esculentum*).

BM412823 NCBI acc. No. BM412823 (gi: 18264453) (Jan. 22, 2002); Alcala,J., at al. "EST587150 tomato breaker fruit *Solanum lycopersicum* cDNA clone cLEG61C12 5' end, mRNA sequence"; source: *Solanum lycopersicum* (*Lycopersicon esculentum*).

BM412928 NCBI acc. No. BM412928 (gi: 18264558) (Jan. 22, 2002); Alcala,J., et al. "EST587255 tomato breaker fruit *Solanum lycopersicum* cDNA clone cLEG61N3 5' end, mRNA sequence"; source: *Solanum lycopersicum* (*Lycopersicon esculentum*).

BM436925 NCBI acc. No. BM436925 (gi: 18458647) (Jan. 31, 2002); Cramer,G.R., et al. "VVA011E03__53345 An expressed sequence tag database for abiotic stressed leaves of *Vitis vinifera* var. Chardonnay *Vitis vinifera* cDNA clone VVA011E03 5, mRNA sequence"; source: *Vitis vinifera*.

BM437083 NCBI acc. No. BM437083 (gi: 18458805) (Jan. 31, 2002); Cramer,G.R., et al. "VVA014A06__53661 An expressed sequence tag database for abiotic stressed leaves of *Vitis vinifera* var. Chardonnay *Vitis vinifera* cDNA clone VVA014A08 5, mRNA sequence"; source: *Vitis vinifera*.

BM437580 NCBI acc. No. BM437580 (gi: 18459302) (Jan. 31, 2002); Cramer,G.R., et al. "VVA021G02__54655 An expressed sequence tag database for abiotic stressed leaves of *Vitis vinifera* var. Chardonnay *Vitis vinifera* cDNA clone VVA021G02 5, mRNA sequence"; source: *Vitis vinifera*.

BM535956 NCBI acc. No. BM535956 (gi: 18814998) (Feb. 20, 2002); Alcala,J., et al. "EST588978 tomato breaker fruit *Solanum lycopersicum* cDNA clone cLEG70J23 5%apos; end, mRNA sequence"; source: *Solanum lycopersicum* (*Lycopersicon esculentum*).

BM536165 NCBI acc. No. BM536165 (gi: 18815366) (Feb. 20, 2002); Alcala,J., et al. "EST589187 tomato breaker fruit *Solanum lycopersicum* cDNA clone cLEG71N23 5' end, mRNA sequence"; source: *Solanum lycopersicum* (*Lycopersicon esculentum*).

BM779603 NCBI acc. No. BM779603 (gi: 19109483) (Mar. 4, 2002); Vandenbosch,K., et al. "EST590179 KV2 *Medicago truncatula* cDNA clone pKV2-52D13, mRNA sequence"; source: *Medicago truncatula* (barrel medic); Title: "ESTs from roots of *Medicago truncatula* 48 hr after inoculation with *Sinorhizobium meliloti*".

BM779692 NCBI acc. No. BM779692 (gi: 19109604) (Mar. 4, 2002); Vandenbosch,K., at al. "EST590268 KV2 *Medicago truncatula* cDNA clone pKV2-52D24, mRNA sequence"; source: *Medicago truncatula* (barrel medic); Title: "ESTs from roots of *Medicago truncatula* 48 hr after inoculation with *Sinorhizobium meliloti*".

BM886268 NCBI acc. No. BM886268 (gi: 19270021) (Mar. 8, 2002); Shoemaker,R., et al. "sam14e12.y1 Gm-c1068 *Glycine max* cDNA clone Soybean Clone ID: Gm-c1068-4824 5%apos; similar to TR:O80387 O80387 Ethylene Responsive Element Binding Factor. ;, mRNA sequence"; source: *Glycine max*.

BM891538 NCBI acc. No. BM891538 (gi: 19346658) (Mar. 11, 2002); Shoemaker,R., et al. "sam28e11.y1 Gm-c1068 *Glycine max* cDNA clone Soybean Clone ID: Gm-c1068-5998 5' similar to TR:O80387 O80387 Ethylene Responsive Element Binding Factor. ;, mRNA sequence"; source: *Glycine max*.

BM954448 NCBI acc. No. BM954448 (gi: 19453038) (Mar. 14, 2002); Shoemaker,R., et al. "san03e10.y1 Gm-c1084 *Glycine max* cDNA clone Soybean Clone ID: Gm-c1084-2900 5' similar to SW:ERF5__ARATH O80341 Ethylene Responsive Element Binding Factor 5 ;, mRNA sequence".

BP174381 NCBI acc. No. BP174381 (gi: 29056877) (Mar. 18, 2003); Ujino-Ihara,T., et al. "BP174381 *Cryptomeria japonica* inner bark *Cryptomeria japonica* cDNA clone CC1389R 3', mRNA sequence"; source: *Cryptomeria japonica* (Japanese cedar).

BQ045702 NCBI acc. No. BQ045702 (gi: 19819688) (Mar. 29, 2002); Zhang,P., et al. "EST594820 *P. infestans*-challenged potato leaf, incompatible reaction *Solanum tuberosum* cDNA clone BPLI12L1 5' end, mRNA sequence"; source: *Solanum tuberosum* (potato).

BQ047502 NCBI acc. No. BQ047502 (gi: 19821488) (Mar. 29, 2002); Zhang, P., et al. "EST596620 *P. infestans*-challenged potato leaf, incompatible reaction *Solanum tuberosum* cDNA clone BPLI17L16 5' end, mRNA sequence"; source: *Solanum tuberosum* (potato).

BQ080756 NCBI acc. No. BQ080756 (gi: 19936180) (Apr. 4, 2002); Shoemaker,R., et al. "san37g07.y1 Gm-c1084 *Glycine max* cDNA clone Soybean Clone ID: Gm-c1084-6086 5' similar to TR:Q9SJX3 Q9SJX3 Ethylene Reponse Factor-Like AP2 Domain Transcription Factor. ;, mRNA sequence".

BQ081056 NCBI acc. No. BQ081056 (gi: 19938893) (Apr. 4, 2002); Shoemaker,R., et al. "san18g09.y1 Gm-c1084 *Glycine max* cDNA clone Soybean Clone ID: Gm-c1084-4529 5' similar to TR:P93822 P93822 F19P19.18. ;, mRNA sequence"; source: *Glycine max* (soybean).

BQ081073 NCBI acc. No. BQ081073 (gi: 19936936) (Apr. 4, 2002); Shoemaker,R., et al. "san19a08.y1 Gm-c1084 *Glycine max* cDNA clone Soybean Clone ID: Gm-c1084-4240 5%apos; similar to TR:P93822 P93822 F19P19.18. ;, mRNA sequence"; source: *Glycine max* (soybean).

BQ081329 NCBI acc. No. BQ081329 (gi: 19937535) (Apr. 4, 2002); Shoemaker,R., et al. "san23a04.y1 Gm-c1084 *Glycine max* cDNA clone Soybean Clone ID: Gm-c1084-4616 5' similar to TR:Q9ZNR2 Q9ZNR2 Ethylene Response Factor 1. ;, mRNA sequence"; source: *Glycine max* (soybean).

BQ122054 NCBI acc. No. BQ122054 (gi: 20174016) (Apr. 17, 2002); Buell,C.R., at al. "EST607630 mixed potato tissues *Solanum tuberosum* cDNA clone STMFC37 3' end, mRNA sequence"; source: *Solanum tuberosum* (potato); Title: "Generation of a set of potato cDNA clones for microarray analyses" (Unpublished (2002)).

BQ138491 NCBI acc. No. BQ138491 (gi: 20274617) (Apr. 23, 2002); Watson,B.S., et al. "NF003G09PH1F1070 Phoma-infected *Medicago truncatula* cDNA clone NF003G09PH 5%apos;, mRNA sequence"; source: *Medicago truncatula* (barrel medic).

BQ165291 NCBI acc. No. BQ165291 (gi: 20307557) (Apr. 25, 2002); Vandenbosch,K., et al. "EST611160 KVKC *Medicago truncatula* cDNA clone pKVKC-7F4, mRNA sequence"; source: *Medicago truncatula* (barrel medic); Title: The *Medicago truncatula* 'kiloclone' set; ESTs selected and re-arrayed from various.

BQ452871 NCBI acc. No. BQ452871 (gi: 21255983) (May 29, 2002); Shoemaker,R., et al. "sao92e10.y1 Gm-c1081 *Glycine max* cDNA clone Soybean Clone ID: Gm-c1081-3284 5', similar to SW:ERFI__ARATH O80337 Ethylene Responsive Element Binding Factor 1 ;, mRNA sequence".

BQ469024 NCBI acc. No. BQ469024 (gi: 21276806) (May 30, 2002); Zhang,H., et al. "HM03C08r HM *Hordeum vulgare* subsp. *vulgare* cDNA clone HM03C08 5-PRIME, mRNA sequence"; source: *Hordeum vulgare* subsp. *vulgare*; Title: "Large-scale analysis of the barley transcdriptome based on expressed sequence tags".

BQ514194 NCBI acc. No. BQ514194 (gi: 21373063) (Jun. 10, 2002); Buell,C.R., et al. "EST621609 Generation of a set of potato cDNA clones for microarray analyses mixed potato tissues *Solanum tuberosum* cDNA clone STMIK39 5' end, mRNA sequence"; source: *Solanum tuberosum* (potato).

BQ514195 NCBI acc. No. BQ514195 (gi: 21373064) (Jun. 10, 2002); Buell,C.R., et al. "EST621610 Generation of a set of potato cDNA clones for mlcroarray analyses mixed potato tissues *Solanum tuberosum* cDNA clone STMIK39 3' end, mRNA sequence"; source: *Solanum tuberosum* (potato).

BQ517082 NCBI acc. No. BQ517082 (gi: 21375951) (Jun. 10, 2002); Buell,C.R., et al. "EST624497 Generation of a set of potato cDNA clones for microarray analyses mixed potato tissues *Solanum tuberosum* cDNA clone STMJB52 5' end, mRNA sequence"; source: *Solanum tuberosum* (potato).

(56) References Cited

OTHER PUBLICATIONS

BQ517083 NCBI acc. No. BQ517083 (gi: 21375952) (Jun. 10, 2002); Buell,C.R., et al. "EST624498 Generation of a set of potato cDNA clones for microarray analyses mixed potato tissues *Solanum tuberosum* cDNA clone STMJB52 3' end, mRNA sequence"; source: *Solanum tuberosum* (potato).

BQ592225 NCBI acc. No. BQ592225 (gi: 26121808) (Dec. 6, 2002); Herwig,R., et al. "E012698-024-021-H24-SP6 MPIZ-ADIS-024-developing root *Beta vulgaris* cDNA clone 024-021-H24 5-PRIME, mRNA sequence"; source: *Beta vulgaris*.

BQ623351 NCBI acc. No. BQ623351 (gi: 21650520) (Jul. 1, 2002); Bausher,M., et al. "USDA-FP_00442 Ridge pineapple sweet orange entire seedling *Citrus sinensis* cDNA clone USDA-FP_00442 5', mRNA sequence"; source: *Citrus sinensis*.

BQ628375 NCBI acc. No. BQ628375 (gi: 21676024) (Jul. 2, 2002); Shoemaker,R., et al. "sap46b10.y1 Gm-c1087 *Glycine max* cDNA clone Soybean Clone ID: Gm-c1087-3547 5' similar to SW:ERF5_ARATH O80341 Ethylene Responsive Element Binding Factor 5 ;, mRNA sequence".

BQ630661 NCBI acc. No. BQ630661 (gi: 21678310) (Jul. 2, 2002); Shoemaker,R., et al. "sap29e09.y1 Gm-c1082 *Glycine max* cDNA clone Soybean Clone ID: Gm-c1082-4050 5' similar to TR:Q40478 Q40478 EREBP-4. ;, mRNA sequence"; source: *Glycine max* (soybean).

BQ743147 NCBI acc. No. BQ743147 (gi: 21889934) (Jul. 17, 2002); Shoemaker,R., et al. "saq60901.y1 Gm-c1076 *Glycine max* cDNA clone Soybean Clone ID: Gm-c1076-4154 5' similar to SW:ERF1_ARATH O80337 Ethylene Responsive Element Binding Factor 1 ;, mRNA sequence".

BQ762577 NCBI acc. No. BQ762577 (gi: 21971049) (Jul. 26, 2002); Hedley,P., et al. "EBro02_SQ004_H12_R root, 3 week, hydroponic grown, low nitrogen, cv Optic, EBro02 *Hordeum vulgare* subsp. *vulgare* cDNA clone EBro02_SQ004_H12 5', mRNA sequence"; source: *Hordeum vulgare* subsp. *vulgare*.

BQ785400 NCBI acc. No. BQ785400 (gi: 21993872) (Jul. 26, 2002); Shoemaker,R., et al. "saq77c02.y1 Gm-c1078 *Glycine max* cDNA clone Soybean Clone ID: Gm-c1076-5859 5' similar to TR:Q9ZNR2 Q9ZNR2 Ethylene Response Factor 1. ;, mRNA sequence"; source: *Glycine max* (soybean).

BQ786714 NCBI acc. No. BQ786714 (gi: 21995186) (Jul. 26, 2002); Shoemaker,R., et al. "saq72c10.y1 Gm-c1076 *Glycine max* cDNA clone Soybean Clone ID: Gm-c1076-5132 5' similar to SW:ERF5_ARATH O80341 Ethylene Responsive Element Binding Factor 5 ;, mRNA sequence".

BQ991410 NCBI acc. No. BQ991410 (gi: 22410945) (Aug. 21, 2002); Kozik,A., et al. "QGF22M18.yg.ab1 QG_EFGHJ lettuce serriola *Lactuca serriola* cDNA clone QGF22M18, mRNA sequence"; source: *Lactuca serriola*; Title: Lettuce and Sunflower ESTs from the Compositae Genome Project.

BU547894 NCBI acc. No. BU547894 (gi: 22930755) (Sep. 16, 2002); Vodkin,L., et al. "GM880014B10B09 Gm-r1088 *Glycine max* cDNA clone Gm-r1088-5081 3', mRNA sequence"; source: *Glycine max* (soybean); Title: "A Functional Genomics Program for Soybean (NSF 9872565) (2002)" (Unpublished (2002)).

BU763420 NCBI acc. No. BU763420 (gi: 23730658) (Oct. 10, 2002); Shoemaker,R., et al. "sas42d05.y1 Gm-c1080 *Glycine max* cDNA clone Soybean Clone ID: Gm-c1080-6322 5%apos; similar to TR:Q40478 Q40478 EREBP-4. ;, mRNA sequence"; source: *Glycine max* (soybean).

BU765444 NCBI acc. No. BU765444 (gi: 23734437) (Oct. 10, 2002); Shoemaker,R., et al. sas18g12.y1 Gm-c1080 *Glycine max* cDNA clone Soybean Clone ID: Gm-c1080-4176 5 similar to SW:ERF5_ARATH O80341 Ethylene Responsive Element Binding Factor 5 :, mRNA sequence.

BU765819 NCBI acc. No. BU765819 (gi: 23735106) (Oct. 10, 2002); Shoemaker,R., et al. "sas20d07.y1 Gm-c1080 *Glycine max* cDNA clone Soybean Clone ID: Gm-c1080-4382 5' similar to SW:ERF5_ARATH O80341 Ethylene Responsive Element Binding Factor 5 ;, mRNA sequence".

BU765920 NCBI acc. No. BU765920 (gi: 23735288) (Oct. 10, 2002); Shoemaker,R., et al. "sar82b04.y1 Gm-c1074 *Glycine max* max cDNA clone Soybean Clone ID: Gm-c1074-8887 5' similar to TR:Q40478 Q40478 EREBP-4. ;, mRNA sequence"; source: *Glycine max* (soybean).

BU765924 NCBI acc. No. 8U765924 (gi: 23735295) (Oct. 10, 2002); Shoemaker,R., et al. "sar82c04.y1.Gm-c1074 *Glycine max* cDNA clone Soybean Clone ID: Gm-c1074-8935 5' similar to TR:Q40478 Q40478 EREBP-4. ;, mRNA sequence", source: *Glycine max* (soybean).

BU814218 NCBI acc. No. BU814218 (gi: 23971351) (Oct. 15, 2002); Unneberg,P., et al. "N026E12 Populus bark cDNA library *Populus tremula* x *Populus tremuloides* cDNA 5 prime, mRNA sequence"; source: *Populus tremula* x *Populus tremuloides*.

BU823955 NCBI acc. No. BU823955 (gi: 23993933) (Oct. 15, 2002); Unneberg,P., et al. "UB58DPE07 *Populus tremula* cambium cDNA library *Populus tremula* cDNA 5 prime, mRNA sequence"; source: *Populus tremula*; Title: "The poplar tree transcriptome: Analysis of expressed sequence tags from multiple libraries" (Unpublished (2002)).

BU830292 NCBI acc. No. BU830292 (gi: 24007304) (Oct. 15, 2002); Unneberg,P., et al. "T006E02 Populus apical shoot cDNA library *Populus tremula* x *Populus tremuloides* cDNA 5 prime, mRNA sequence"; source: *Populus tremula* x *Populus tremuloides*.

BU832225 NCBI acc. No. BU832225 (gi: 24011454) (Oct. 15, 2002); Unneberg,P., et al. "T031A05 Populus apical shoot cDNA library *Populus tremula* x *Populus tremuloides* cDNA 5 prime, mRNA sequence"; source: *Populus tremula* x *Populus tremuloides*.

BU837816 NCBI acc. No. BU837816 (gi: 24020612) (Oct. 16, 2002); Unneberg,P., et al. "T106A05 Populus apical shoot cDNA library *Populus tremula* x *Populus tremuloides* cDNA 5 prime, mRNA sequence"; source: *Populus tremula* x *Populus tremuloides*.

BU871861 NCBI acc. No. BU871861 (gi: 24063385) (Oct. 16, 2002); Unneberg,P., et al. "Q35D06 Populus flower cDNA library *Populus trichocarpa* cDNA 5 prime, mRNA sequence"; source: *Populus trichocarpa* (*Populus balsamifera* subsp. *trichocarpa*).

BU874000 NCBI acc. No. BU874000 (gi: 24065524) (Oct. 16, 2002); Unneberg,P., et al. "Q63C02 Populus flower cDNA library *Populus trichocarpa* cDNA 5 prime, mRNA sequence"; source: *Populus trichocarpa* (*Populus balsamifera* subsp. *trichocarpa*).

BU884339 NCBI acc. No. BU884339 (gi: 24075856) (Oct. 17, 2002); Unneberg,P., et al. "R009C12 Populus root cDNA library *Populus tremula* x *Populus tremuloides* cDNA 5 prime, mRNA sequence"; source: *Populus tremula* x *Populus tremuloides*.

BU884448 NCBI acc. No. BU884448 (gi: 24075965) (Oct. 17, 2002); Unneberg,P., et al. "R010G08 Populus root cDNA library *Populus tremula* x *Populus tremuloides* cDNA 5 prime, mRNA sequence"; source: *Populus tremula* x *Populus tremuloides*.

BU887519 NCBI acc. No. BU887519 (gi: 24080231) (Oct. 17, 2002); Unneberg,P., et al. "R062F03 Populus root cDNA library *Populus tremula* x *Populus tremuloides* cDNA 5 prime, mRNA sequence"; source: *Populus tremula* x *Populus tremuloides*.

BZ020356 NCBI acc. No. BZ020356 (gi: 23580089) (Oct. 8, 2002); Delehaunty,K.; at al. "oegO4a10.g1 B.oleracea002 *Brassica oleracea* genomic, genomic survey sequence"; source: *Brassica oleracea*; Title: "Whole genome shotgun reads from *Brassica Oleracea*" (Unpublished (2002)).

BZ332067 NCBI acc. No. BZ332067 (gi: 24720629) (Nov. 6, 2002); Rabinowicz,P.D., et al. "hx25b08.b1 WGS-SbicolorF (JM107 adapted methyl filtered) *Sorghum bicolor* genomic clone hx25b08 5', genomic survey sequence"; source: *Sorghum bicolor* (*sorghum*).

BZ337899 NCBI acc. No. BZ337899 (gi: 24733043) (Nov. 6, 2002); Rabinowicz,P.D., et al. "ia91f11.b1 WGS-SbicolorF (JM107 adapted methyl filtered) *Sorghum bicolor* genomic clone ia91f11 5', genomic survey sequence"; source: *Sorghum bicolor* (*sorghum*).

BZ359367 NCBI acc. No. BZ359367 (gi: 25059121) (Nov. 18, 2002); Rabinowicz, P.D., et al. "id72f11.b1 WGS-ZmaysF (JM107 adapted methyl filtered) *Zea mays* genomic clone Id72f11 5', genomic survey sequence"; source: *Zea mays*; Title: "Genomic shotgun sequences from *Zea mays* (methyl-filtered)".

(56) References Cited

OTHER PUBLICATIONS

BZ401507 NCBI acc. No. BZ401507 (gi: 26026577) (Dec. 4, 2002); Whitelaw, C.A., et al. "OGABH91TC ZM_0.7_KB *Zea mays* genomic clone ZMMBMa0022B11, genomic survey sequence"; source: *Zea mays*; Title: "Consortium for Maize Genomics" (Unpublished (2002)).

BZ401512 NCBI acc. No. BZ401512 (gi: 26026582) (Dec. 4, 2002); Whitelaw, C.A., et al. "OGABH91TM ZM_0.7_1.5_KB *Zea mays* genomic clone ZMMBMa0022811, genomic survey sequence"; source: *Zea mays*; Title: "Consortium for Maize Genomics" (Unpublished (2002)).

BZ489256 NCBI acc. No. BZ489258 (gi: 26995806) (Dec. 16, 2002); Ayele,M., et al. "BOOAW09TF BO_1.6_2_KB_tot *Brassica oleracea* genomic clone BOOAW09, genomic survey sequence"; source: *Brassica oleracea*.

BZ489264 NCBI acc. No. BZ489264 (gi: 26995814) (Dec. 16, 2002); Ayele,M., et al. "BOOAW09TR BO_1.6_2_KB_tot *Brassica oleracea* genomic clone BOOAW09, Ayele,M survey sequence"; source: *Brassica oleracea*.

BZ536116 NCBI acc. No. BZ536116 (gi: 27083627) (Dec. 16, 2002); Whitelaw,C.A., et al. "OGAGZ06TC ZM2_0.7_1.5_KB *Zea mays* genomic clone ZMMBMa0059A12, genomic survey sequence"; source: *Zea mays*; Title: "Consortium for Maize Genomics" (Unpublished (2002)).

BZ646476 NCBI acc. No. BZ646476 (gi: 28108680) (Jan. 29, 2003); Whitelaw,C.A., et al. "OGAMK11TC ZM_0.7_1.5_KB *Zea mays* genomic clone ZMMBMa0094B21, genomic survey sequence"; source: *Zea mays*; Title: "Consortium for Maize Genomics" (Unpublished (2002)).

CA019696 NCBI acc. No. CA019696 (gi: 24297040) (Oct. 23, 2002); Zhang,H., et al. "HV12M24r HV *Hordeum vulgare* subsp. *vulgare* cDNA clone HV12M24 5-PRIME, mRNA sequence"; source: *Hordeum vulgare* subsp. *vulgare*; Title: "Large-scale analysis of the barley transcriptome based on expressed sequence tags".

CA514062 NCBI acc. No. CA514062 (gi: 25014619) (Nov. 15, 2002); Lee,S., et al. "KS09016D12 KS09 *Capsicum annuum* cDNA, mRNA sequence"; source: *Capsicum annuum*.

CA522916 NCBI acc. No. CA522916 (gi: 25036961) (Nov. 15, 2002); Lee,S., et al. "KS12015D10 KS12 *Capsicum annuum* cDNA, mRNA sequence"; source: *Capsicum annuum*.

CA723694 NCBI acc. No. CA723694 (gi: 25445487) (Nov. 26, 2002); Tingey,S.V., et al. "wdr1f.pk003.I5 wdr1f *Triticum aestivum* cDNA clone wdr1f.pk003.I5 5' end, mRNA sequence"; source: *Triticum aestivum* (bread wheat); Title: "Dupont Wheat cDNA Sequence" (Unpublished (2002)).

CA783253 NCBI acc. No. CA783253 (gi: 26045764) (Dec. 4, 2002); Shoemaker,R., et al. "sat21f08.y1 Gm-c1036 *Glycine max* cDNA clone Soybean Clone Id: Gm-c1036-14464 5' similar to TR:Q40478 Q40478 EREBP-4. ;, mRNA sequence"; source: *Glycine max* (soybean).

CA783313 NCBI acc. No. CA783313 (gi: 26045880) (Dec. 4, 2002); Shoemaker, R., et al. "sat22e09.y1Gm-c1036 *Glycine max* cDNA clone Soybean Clone ID: Gm-c1036-14441 5' similar to TR:Q40478 Q40478 EREBP-4. ;, mRNA sequence"; source: *Glycine max* (soybean).

CA799724 NCBI acc. No. CA799724 (gi: 26056810) (Dec. 5, 2002); Shoemaker,R., et al. "sat61h01.y1 Gm-c1056 *Glycine soja* cDNA clone Soybean Clone ID: Gm-c1056-6098 5' similar to TR:Q40478 Q40478 EREBP-4. ;, mRNA sequence"; source: *Glycane soja*.

CA801993 NCBI acc. No. CA801993 (gi: 26059079) (Dec. 5, 2002); Shoemaker,R., et al. "sau28c10.y1 Gm-c1062 *Glycine max* cDNA clone Soybean Clone ID: Gm-c1062-9356 5' similar to TR:040478 Q40478 EREBP-4. ;, mRNA sequence"; source: *Glycine max* (soybean).

CA918826 NCBI acc. No. CA918826 (gi: 27405756) (Dec. 27, 2002); Vandenbosch,K., et al. "EST636544 MTUS *Medicago truncatula* cDNA clone MTUS-3F12, mRNA sequence"; source: *Medicago truncatula* (barrel medic).

CA926476 NCBI acc. No. CA926476 (gi: 27414955) (Dec. 30, 2002); Ranjan,P., et al. "MTU6CR.P15.E02 Aspen root cDNA Library *Populus tremuloides* cDNA, mRNA sequence"; source: *Populus tremuloides* (quaking aspen); Title: "Expressed sequence tags from Aspen" (Unpublished (2003)).

CB001513 NCBI acc. No. CB001513 (gi: 27578818) (Jan. 10, 2003); Cramer,G.R., et al. "VVB004H10_124488. An expressed sequence tag database for abiotic stressed leaves of *Vitis vinifera* var. Chardonnay *Vitis vinifera* cDNA clone VVB004H10 5, mRNA sequence"; source: *Vitis vinifera*.

CB002777 NCBI acc. No. CB002777 (gi: 27580082) (Jan. 10, 2003); Cramer,G.R., et al. "VVB020G03_132412 An exprseed sequence tag database for abiotic stressed leaves of *Vitis vinifera* var. Chardonnay *Vitis vinifera* cDNA clone VVB020G03 5, mRNA sequence"; source: *Vitis vinifera*.

CB003172 NCBI acc. No. CB003172 (gi: 27580477) (Jan. 10, 2003); Cramer,G.R., et al. "VVB027C01_133202 An expressed sequence tag database for abiotic stressed leaves of *Vitis vinifera* var. Chardonnay *Vitis vinifera* cDNA clone VVB027C01 5, mRNA sequence"; source: *Vitis vinifera*.

C8003334 NCBI acc. No. C8003334 (gi: 27580639) (Jan. 10, 2003); Cramer,G.R., et al. "VVB029A07_133526 An expressed sequence tag database for abiotic stressed leaves of *Vitis vinifera* var. Chardonnay *Vitis vinifera* VVB029A07 5, mRNA sequence"; source: *Vitis vinifera*.

CB003997 NCBI acc. No. CB003997 (gi: 27581302) (Jan. 10, 2003): Cramer,G.R., et al. "VVB034F08_134852 An expressed sequence tag database for abiotic stressed leaves of *Vitis vinifera* var. Chardonnay *Vitis vinifera* cDNA clone VVB034F08 5, mRNA sequence"; source: *Vitis vinifera*.

CB007463 NCBI acc. No. CB007463 (gi: 27584768) (Jan. 10, 2003); Cushman,J.C., et al. "VVC045F10_141982 An expressed sequence tag database for abiotic stressed berries of *Vitis vinifera* var. Chardonnay *Vitis vinifera* cDNA clone VVC045F10 5, mRNA sequence"; source: *Vitis vinifera*.

CB288719 NCBI acc. No. CB288719 (gi: 28602460) (Feb. 27, 2003); Hou,H.S., et al. "V-B-18C10 VAN-Baker-1 *Vitis aestivalis* cDNA clone V-B-18C10 5', mRNA sequence"; source: *Vitis aestivalis*; Title: "Expressed sequence tags of young leaf tissues of a disease-resistant *Vitis aestivalis* var. Norton" (Unpublished (2003)).

CB288872 NCBI acc. No. C8288872 (gi: 28602813) (Feb. 27, 2003); Hou,H.S., et al. "V-B-110A09 VAN-Baker-1 *Vitis aestivalis* cDNA clone V-B-110A09 5', mRNA sequence"; source: *Vitis aestivalis*; Title: "Expressed sequence tags of young leaf tissues of a disease-resistant *Vitis aestivalis* var. Norton" (Unpublished (2003)).

CB289287 NCBI acc. No. CB289287 (gi: 28603028) (Feb. 27, 2003); Hou, H.S., et al. "V-B-115B12 VAN-Baker-1 *Vitis aestivalis* cDNA clone V-B-115B12 5%apos;, mRNA sequence"; source: *Vitis aestivalis*; Title: "Expressed sequence tags of young leaf tissues of a disease-resistant *Vitis aestivalis* var. Norton"(Unpublished (2003)).

CB289366 NCBI acc. No. CB289366 (gi: 28603107) (Feb. 27, 2003); Hou,H.S., et al. "V-B-116B09 VAN-Baker-1 *Vitis aestivalis* cDNA clone V-B-116B09 5', mRNA sequence"; source: *Vitis aestivalis*; Title: "Expressed sequence tags of young leaf tissues of a disease-resistant *Vitis aestivalis* var. Norton" (Unpublished (2003)).

CB289523 NCBI acc. No. CB289523 (gi: 28603264) (Feb. 27, 2003): Hou,H.S., et al. "V-B-118A07 VAN-Baker-1 *Vitis aestivalis* cDNA clone V-B-118A07 5', mRNA sequence"; source: *Vitis aestivalis*; Title: "Expressed sequence tags of young leaf tissues of a disease-resistant *Vitis aestivalis* var. Norton" (Unpublished (2003)).

CB292286 NCBI acc. No. CB292286 (gi: 28617743) (Feb. 28, 2003); Close,T.J., et al. "UCRCS01_04ba10_g1 Washington Navel orange cold acclimated flavedo & albedo cDNA library *Citrus sinensis* cDNA clone UCRCS01_04ba10, mRNA sequence"; source: *Citrus sinensis*.

CB322190 NCBI acc. No. C8322190 (gi: 28856848) (Mar. 5, 2003); Burns,J.K., et al. "EST0312 Mature leaf blade cDNA subtraction library *Citrus sinensis* cDNA clone 24LB271 similar to pathogenesis-related transcriptional activator PTI5 (acc# AAC49740), mRNA sequence"; source: *Citrus sinensis*.

CB341794 NCBI acc. No. CB341794 (gi: 28962761) (Mar. 14, 2003); Goes Da Silva,F., et al. "CA32EN0002_IIIbF_A03 Cabernet Sauvignon Leaf—CA32EN *Vitis vinifera* cDNA clone CA32EN0002_IIIbF_A03 5', mRNA sequence"; source: *Vitis vinifera*.

(56) References Cited

OTHER PUBLICATIONS

CB342848 NCBI acc. No. CB342848 (gi: 28963815) (Mar. 14, 2003); Goes Da Silva,F., et al. "CA32EN0004_IIIaF_C01 Cabernet Sauvignon Leaf—CA32EN *Vitis vinifera* cDNA clone CA32EN0004_IIIaF_C01 5', mRNA sequence"; source: *Vitis vinifera*.
CB342920 NCBI acc. No. CB342920 (gi: 28963887) (Mar. 14, 2003); Goes Da Silva,F., et al. "CA32EN0004_IIIbR_C01 Cabernet Sauvignon Leaf—CA32EN *Vitis vinifere* cDNA clone CA32EN0004_IIIbR_C01 3', mRNA sequence"; source: *Vitis vinifera*.
CB350627 NCBI acc. No. CB350627 (gi: 28985410) (Mar. 17, 2003); Wen, T.J., et al. "MEST253-F08.univ ISUM5-RN *Zea mays* cDNA clone MEST253-F08 3', mRNA sequence"; source: *Zea mays*.
CRO238740 NCBI acc. No. AJ238740 (gi: 8346774) (Jun. 7, 2000); Menke,F.L.H., et al. "*Catharanthus roseus* mRNA for AP2-domain DNA-binding protein ORCA2"; source: *Catharanthus roseus* (Madagascar periwinkle).
CRO251249 NCBI acc. No. AJ251249 (gi: 8980312) (Jul. 8, 2000); Van Der Fits,L. et al. "*Catharanthus roseus* mRNA for AP2-domain DNA-binding protein (orca3 gene)"; source: *Catharanthus roseus* (Madagascar periwinkle); Title: ORCA3, a jasmonate-responsive master regulator of multiple genes in plant primary and.
CRO251250 NCBI acc. No. AJ251250 (gi: 8980314) (Jul. 8, 2000); Van Der Fits,L., et al. "*Catharanthus roseus* orca3 gene for AP2-domain DNA-binding protein"; source: *Catharanthus roseus* (Madagascar periwinkle).
LEU89255 NCBI acc. No. U89255 (gi: 2213780) (Jun. 25, 1997); Zhou,J., et al. "*Lycopersicon esculentum* DNA-binding protein Pti4 mRNA, complete cds"; source: *Lycopersicon esculentum* (tomato).
LEU89256 NCBI acc. No. U89256 (gi: 2213782) (Jun. 25, 1997); Zhou,J., et al. "*Lycopersicon esculentum* DNA-binding protein Pti5 mRNA, complete cds"; source: *Lycopersicon esculentum* (tomato).
NTA299252 NCBI acc. No. AJ299252 (gi: 10798643) (Oct. 11, 2000); Shen,W.H., et al. "*Nicotiana tabacum* partial mRNA for AP2 domain-containing transcription factor (ap2 gene)"; source: *Nicotiana tabacum* (common tobacco); Title: "Nicotiana tabacum cDNA (partial) encoding AP2 domain-containing protein" (Unpublished).
NTU81157 NCBI acc. No. U81157 (gi: 1732405) (Dec. 16, 1996); Xu,P., et al. "*Nicotiana tabacum* S25-XP1 DNA binding protein mRNA, complete cds"; source: *Nicotiana tabacum* (common tobacco); Title: "Direct Submission" (Submitted (Dec. 6, 1996).
OSA307662 NCBI acc. No. AJ307662 (gi: 14140112) (May 17, 2001); Mayerr,K., et al. "*Oryza saliva genomic* DNA fragment, chromosome 2"; source: *Oryza sativa*; Title: Conservation of microstructure bewtween a sequenced region of the genome of rice and multiple segments of the genome of *Arabidopsis*.
OSJN00126 NCBI acc. No. AL607006 (gi: 15799247) (Sep. 27, 2001); Han,B., et al. "*Oryza sativa* chromosome 4 clone OSJNBA0079A21, * Sequencing in Progress *"; source: *Oryza sativa*; Title: "Direct Submission".
SHU91857 NCBI acc. No. U91857 (gi: 4099913) (Jan. 5, 1999); Gardner,R.C., et al. "*Stylosanthes hamata* ethylene-responsive element binding protein homolog gene, complete cds"; source: *Stylosanthes hamata*; Title: "Aluminium Tolerance in Yeast Conferred by Over-expression of *Stylosanthes* genes" (Unpublished).
STU77655 NCBI acc. No. U77655 (gi: 1688232) (Nov. 28, 1996); Stidd,J.E., et al. "*Solanum tuberosum* DNA binding protein homolog (STWAAEIRD) mRNA, complete cds"; source: *Solanum tuberosum* (potato); Title: "cDNA sequence from a log-phase cell suspension culture with similarity to DNA binding proteins" (Unpublished).
TOBBY4A NCBI acc. No. D38123 (gi: 790359) (May 1, 1995); Ohme-Takagi,M., et al. "Tobacco mRNA"; source: Unknown.; Title: "Etylene-inducible DNA binding proteins that interact with an ethylene responsive element" (The Plant Cell 7, 173-182 (1995)).

TOBBY4B NCBI acc. No. D38124 (gi: 790360) (May 1, 1995); Ohme-Takagi,M., et al. "Tobacco mRNA"; source: Unknown.; Title: "Etylene-Inducible DNA binding proteins that interact with an ethylene responsive element" (The Plant Cell 7, 173-182 (1995)).
TOBBY4C NCBI acc. No. D38125 (gi: 790361) (May 1, 1995); Ohme-Takagi,M., et al. "Tobacco mRNA"; source:.Unknown.; Title: "Etylene-inducible DNA binding proteins that interact with an ethylene responsive element" (The Plant Cell 7, 173-182 (1995)).
TOBBY4D NCBI acc. No. D38126 (gi: 790362) (May 1, 1995); Ohme-Takagi,M., et al. "Tobacco mRNA"; source: Unknown.; Title: "Etylene-inducible DNA binding proteins that interact with an ethylene responsive element" (The Plant Cell 7, 173-182 (1995)).
AAG43545 NCBI acc. No. AAG43545 (gi: 12003376) (Jan. 2, 2001); Durrant,W.E., et al. "Avr9/Cf-9 rapidly elicited protein 1 [*Nicotiana tabacum*]"; source: *Nicotiana tabacum* (common tobacco).
BAA07324 NCBI acc. No. BAA07324 (gi: 1208498) (Feb. 28, 1996); Ohme-Takagi,M., et al. "EREBP-2"; source: *Nicotiana tabacum* (common tobacco); Title: "Direct Submission" (Submitted (Sep. 1, 1994) Maseru Ohme-Takagl, National Institute of Bioscience and Human Thechnology, Plant Moplecular Biology Laboratory.
AAG60182 NCBI acc. No. AAG60182 (gi: 12597874) (Jan. 30, 2001); Buell, C.R., et al. "putative ethylene-responsive element binding protein [*Oryza sativa*]"; source: *Oryza sativa*; Title: "*Oryza sativa* chromosome 10 BAC OSJN8a0027P10 genomic sequence" (Unpublished).
AAK31279 NCBI acc. No. AAK31279 (gi: 13569995) (Apr. 10, 2001); Buell, C.R., et al. "putative ethylene-responsive element binding protein [*Oryza sativa*]"; source: *Oryza sativa*; Title: "*Oryza sativa* chromosome 10 BAC OSJNBb0089A17 genomic sequence" (Unpublished).
CAC39058 NCBI acc. No. CAC39058 (gi: 14140141) (May 17, 2001); Mayer,K., et al. "putative AP2-related transcription factor [*Oryza sativa*]"; source: *Oryza sativa*; Title: Conservation of microstructure bewtween a sequenced region of the genome of rice and multiple segments of the genome of *Arabidopsis*.
CAC39060 NCBI acc. No. CAC39060 (gi: 14140143) (May 17, 2001); Mater,K., et al. "putative ethylene responsive element binding factor [*Oryza sativa*]"; source: *Oryza sativa*; Title: Conservation of microstructure bewtween a sequenced region of the genome of rice and multiple segments of the genome of *Arabidopsis*.
BAB67922 NCBI acc. No. BAB87922 (gi: 15623883) (Sep. 14, 2001); Sasaki,T., et al. "contains EST-hypothetical protein [*Oryza sativa*]"; source: *Oryza sativa*; Title: "*Oryza sativa* nipponbare(GA3) genomic DNA, chromosome 1, PAC clone:P0046E05" (Published Only in Database (2001) in press).
AAB38748 NCBI acc. No. AAB38748 (gi: 1732406) (Dec. 16, 1996); Xu,P., et al. "S25-XP1 DNA binding protein [*Nicotiana tabacum*]"; source: *Nicotiana tabacum* (common tobacco); Title: "Direct Submission" (Submitted Dec. 6, 1996) Biotechnology Institute, Zhejiang Agriculture Unversity, Hangzhou, Zhejiang 310029, P.R.China).
BAA87068 NCBI acc. No. BAA87068 (gi: 6478845) (Nov. 30, 1999); Achida,Y., et al. "ethylene-responsive element binding protein1 homolog [*Matricaria chamomilla*]"; source: *Matricaria chamomilla*; Title: "ethylene-responsive element binding protein 1 (EREBP) homolog, *Matricaria chamomilla*".
BAB89538 NCBI acc. No. BAB89538 (gi: 20160591) (Apr. 16, 2002); Sasaki,T., et al. "hypothetical protein [*Oryza sativa* (japonica cultivar-group)]"; source: *Oryza sativa* (japonica cuitivar-group); Title: "*Oryza sativa* nipponbare(GA3) genomic DNA, chromosome 1, PAC clone:P0435B05" (Published Only in Database (2001)).
AAC49740 NCBI acc. No. (gi: 2213783) (Jun. 25, 1997); Zhouj., et al. "Pti5 [*Lycopersicon esculentum*]"; source: *Lycopersicon esculentum* (tomato); Title: "The Pto Kinase Conferring Resistance to Tomato Bacterial Speck Disease Interacts with Proteins that Bind a Cis-Element of Pathogenesis-Related Genes".
AAN32899 NCBI acc. No. AAN32899 (gi: 23452024) (Oct. 2, 2002); Zhang,H., et al. "transcdription factor TSRF1 [*Lycopersicon esculentum*]"; source: *Lycopersicon esculentum* (tomato); Title: "A tomato transcdription factor regulating expression of stress responsive genes" (Unpublished).

(56) References Cited

OTHER PUBLICATIONS

BAC21532 NCBI acc. No. BAC21532 (gi: 24060081) (Oct. 16, 2002); Sasaki,T., et al. "putative ethylene response factor ERF1 [*Oryza sativa* (japonica cultivar-group)]"; source: *Oryza sativa* (japonica cultivar-group); Title: "*Oryza sativa* nipponbare(GA3) genomic DNA, chromosome 7, PAC clone:P0710F09".

AAN77067 NCBI acc. No. AAN77067 (gi: 25992126) (Dec. 2, 2002); Cheng,X.G., et al. "ethylene responsive element binding protein [*Lycopersicon esculentum*]"; source: *Solanum lycopersicum* (*Lycopersicon esculentum*); Title: "Direct Submission" (Submitted (Apr. 13, 2002).

AAN87744 NCBI acc. No. AAN87744 (gi: 27261478) (Dec. 19, 2002): Wing,R.A., et al. "Hypothetical protein [*Oryza sativa* (japonica cultivar-group)]"; source: *Oryza sativa* (japonica cultivar-group); Title: "Rice Genomic Sequence" (Unpublished).

BAC55991 NCBI acc. No. BAC55991 (gi: 28071302) (Jan. 29, 2003); Sasaki,T., et al. "P0705A05.4 [*Oryza sativa* (japonica cultivar-group)]"; source: *Oryza sativa* (japonica cdtivar-group); Title: "*Oryza sativa* nipponbare(GA3) genomic DNA, chromosome 8, PAC clone:P0705A05" (Published Only in Database (2002)).

BAA87088 NCBI acc. No. BAA87068 (gi: 6478845) (Nov. 30, 1999); Ashida,Y., et al. "ethylene-responsive element binding protein1 homolog [*Matricaria chamomilla*]"; source: *Matricaria chamomilla*; Title: "ethylene-responsive element binding protein1 (EREBP) homolog, *Matricaria chemomilla*".

T07689 NCBI acc. No. T07689 (gi: 7489078) (Apr. 6, 2000); Zhou,J., et al. "transcription factor Pti5—tomato"; source: *Lycopersicon esculentum* (tomato); Title: "The Pto kinase conferring resistance to tomato bacterial speck disease interacts with proteins that bind a cis-element of pathogenesis-related genes".

T02590 NCBI acc. No. T02590 (gi: 7489113) (Apr. 6, 2000); Ohme-Takagi,M., et al. "DNA binding protein EREBP-2-common tobacco"; source: *Nicotiana tabacum* (common tobacco); Title: "Ethylene-inducible DNA binding proteins that interact with an ethylene-responsive element" (Plant Cell 7 (2), 173-182 (1995)).

T03927 NCBI acc. No. T03927 (gi: 7489116) (Apr. 6, 2000); Xu.P., et al. "DNA binding protein S25-XP1—common tobacco"; source: *Nicotiana tabacum* (common tobacco); Title: "Direct Submission" (Submitted (Dec. 1996) to the EMBL Data Library).

AAF63205 NCBI acc. No. AAF63205 (gi: 7528276) (Apr. 9, 2000); Scharte,J., et al. "AP2-related transcription factor [*Mesembryanthemum crystallinum*]"; source: *Mesembryanthemum crystallinum* (common iceplant).

O04681 NCBI acc. No. O04681 (gi: 7531180) (Apr. 10, 2000); Zhou,J., et al. "Pathogenesis-Related Genes Transcriptional Activator PTI5"; source: *Lycopersicon esculentum* (tomato).

BAA97122 NCBI acc. No. BAA97122 (gi: 8809571) (Jun. 28, 2000); Kitajima,S., et al. "ethylene-responsive element binding factor [*Nicotiana sylvestris*]"; source: *Nicotiana sylvestris* (wood tobacco).

CAB96899 NCBI acc. No. CAB96899 (gi: 8980313) (Jul. 8, 2000); Van Der Fits,L., et al. "AP2-domain DNA-binding protein [*Catharanthus roseus*]"; source: *Catharanthus roseus* (Madagascar periwinkle).

CAB96900 NCBI acc. No. CAB96900 (gi: 8980315) (Jul. 8, 2000); Van Der Fits,L., et al. "AP2-domain DNA-binding protein [*Catharanthus roseus*]"; source: *Catharanthus roseus* (Madagascar periwinkle).

AAB70439 NCBI acc. No. AAB70439 (gi: 1903358) (Mar. 21, 1997); Van Der Fits,L., et al. "F19P19.18 [*Arabidopsis thaliana*]"; source: *Arabidopsis thaliana* (thale cress); Title: "Sequence of BAC F19P19 from *Arabidopsis thaliana* chromosome 1" (Unpublished (1997)).

AC000104 CBI acc. No. AC000104 (gi: 1764158) (Jan. 6, 1997); Vysotskaia,V., et al. *Arabidopsis thaliana* chromosome 1, \*\*\* Sequencing in Progress \*\*\*; source: *Arabidopsis thaliana* (thale cress); Title: "Sequence of BAC F19P19 from *Arabidopsis thaliana* chromosome 1" (Unpublished (1997)).

AB025608 CBI acc. No. AB025608 (gi: 4589414) (Apr. 20, 1999); Nakamura,Y., et al. "*Arabidopsis thaliana* genomic DNA, chromosome 3, TAC clone: K13B15, complete sequence"; source: *Arabidopsis thaliana* (Thale cress); Title: "Structural Analysis of *Arabidopsis thaliana* Chromosome 3. II" (Unpublishe (1999)).

AB025638 NCBI acc. No. AB025638 (gi: 4589444) (Apr. 20, 1999); Nakamura,Y., et al. "*Arabidopsis thaliana* genomic DNA, chromosome 5, P1 clone: MWF20, complete sequence"; source: *Arabidopsis thaliana* (thale cress); Title: "Structural Analysis of *Arabidopsis thaliana* Chromosome 5.XIII" (Unpublished (1999)).

CC669146 NCBI acc. No. CC669146 (gi: 32073332) (Jun. 19, 2003); Whitelaw,C.A., et al. "OGUBT28TVZM_0.7_1.5_KB *Zea mays* genomic clone ZMMBMa0403E08, genomic survey sequence"; source: *Zea mays*; Title: "Consortium for Maize Genomics" (Unpublished (2002)).

BT009060 NCBI acc. No. BT009060 (gi: 32128611) (Jun. 20, 2003); Tingey, S.V., et al. "*Triticum aestivum* clone wdr1f.pk003.I5:fis, full insert mRNA sequence"; source: *Triticum aestivum* (bread wheat); Title: "Direct Submission" (Submitted (Jun. 20, 2003) Crop Genetics, E. I. DuPont de Nemours and Company.

AK107745 NCBI acc. No. AK107745 (gi: 32992954) (Jul. 19, 2003); Kikuchi,S., et al. "*Oryza sativa* (japonica cultivar-group) cDNA clone: 002-132-H03, full insert sequence"; source: *Oryza sativa* (japonica cultivar-group); Title: "Rice full-length cDNA" (Unpublished).

CG262446 NCBI acc. No. CG262446 (gi: 34174058) (Aug. 25, 2003); Whitelaw,C.A., et al. "OGWGY72THZM_0.7_1.5_KB *Zea mays* genomic clone ZMMBMa0576K23, genomic survey sequence"; source: *Zea mays*; Title: "Consortium for Maize Genomics" (Unpublished (2002)).

CB967722 NCBI acc. No. CB967722 (gi: 30229857) (Apr. 29, 2003); Kirst,M., et al. "egx20b12_F Differentiating xylem *Eucalyptus grandis* cDNA clone egx20b12 5', mRNA sequence"; source: *Eucalyptus grandis*; Title: "Gene Discovery in *Eucalyptus grandis* Xylem" (Unpublished (2003)).

CC690315 NCBI acc. No. CC690315 (gi: 32095091) (Jun. 19, 2003); Whitelaw, C.A. et al. "OGVB192TVZM_0.7_1.5_KB *Zea mays* genomic clone ZMMBMa0495P15, genomic survey sequence"; source: *Zea mays*; Title: "Consortium for Maize Genomics" (Unpublished (2002)).

CAE45639 NCBI acc. No. CAE45639 (gi: 34221729) (Aug. 25, 2003); Gong,W., e•al. "putative ethylene responsive element binding protein [*Arabidopsis thaliana*]"; source: *Arabidopsis thaliana* (thale cress).

BAA95735 NCBI acc. No. BAA95735 (gi: 7939532) (May 19, 2000); Nakamura, Y., et al. "contains similarity to ethylene response element binding protein EREBP-gene_id:K14B15.13 [*Arabidopsis thaliana*]"; source: *Arabidopsis thaliana* (thale cress); Title: Structural Analysis of *Arabidopsis thaliana* Chromosome 3.

AJ580377 EMBL acc. No. AJ580377 (Aug. 24, 2003); Gong W., et al. "*Arabidopsis thaliana* mRNA for putative ethylene responsive element binding protein".

AB008103 EMBL acc. No. AB008103 (Aug. 21, 1998); "*Arabidopsis thaliana* AtERF-1 mRNA for ethylene responsive element binding factor 1, complete cds".

O80337 EMBL acc. No. O80337 (May 30, 2000); "Ethylene responsive element bnding factor 1 (AtERF1) (EREBP-2 protein)".

AB008104 EMBL acc. No. A8008104 (Aug. 21, 1998); "*Arabidopsis thaliana* AtERF-2 mRNA for ethylene responsive element binding factor 2, complete cds".

AL161546 EMBL acc. No. AL161546 (Mar. 16, 2000); "*Arabidopsis thaliana* DNA chromosome 4, contig fragment No. 46".

AB025608 EMBL acc. No. AB025608 (Apr. 9, 1999); "*Arabidopsis thaliana* genomic DNA, chromosme 3, TAC clone: K14B15".

A1776626 EMBL acc. No. AB025608 (Jun. 30, 1999); "EST257726 tomato resistant, Cornell *Lycopersicon esculentum* cDNA clone cLER19A14, mRNA sequence".

AF245119 EMBL acc. No. AF245119 (Apr. 9, 2000); "*Mesembryanthemum crystallinum* AP2-related transciprtion factor (CDBP) mRNA, complete cds".

Allen, M.D., et al. (1998). A novel mode of DNA recognition by a beta-sheet revealed by the solution structure of the GCC-box binding domain in complex with DNA. Embo J 17, 5484-5496.

Ashida, et al. (2002); Molecular cloning and mRNA expression of geraniol-inducible genes in cultured soot primordia of *Matricaria chamomilia*. Biosci. Biotechnol. Biochem. 66 (11), 2511-2514.

(56) References Cited

OTHER PUBLICATIONS

Berrocal-Lobo, M., and Molina, A. (Jul. 2004). Ethylene response factor 1 mediates *Arabidopsis* resistance to the soilborne fungus *Fusarium oxysporum*. Mol Plant Microbe Interact 17, 763-770.
Brown, R.L., et al. (2003). A role for the GCC-box in jasmonate-mediated activation of the PDF1.2 gene of *Aribidopsis*. Plant Physiol 132, 1020-1032.
Campbell, et al. (1998) Isolation of a cDNA from potato with structural similarity to the AP2 gene superfamily (Accession No. U77655) (PGR98-129). Plant Physiol. 117 (3), 1127 (1998).
Chakravarthy, S., et al. (2003). The tomato transcription factor Pti4 regulates defense-related gene expression via GCC box and non-GCC box cis elements. Plant Cell 15, 3033-3050.
Chen, W., et al. (2002). Expression profile matrix of *Aribidopsis* transcription factor genes suggests their putative functions in response to environmental stresses. Plant Cell 14, 559-574.
Da Costa E Silva et al. (Jul. 1993) BPF-1, a pathogen-induced DNA-binding protein involved in the plant defense response. Plant J. 4:125-135.
Fujimoto, et al. (Mar. 2000). *Arabidopsis* ethylene-responsive element binding factors act as transcriptional activators or repressors of BCC box-mediated gene expression. Plant Cell (2000), 12(3), 393-404.
Guo, H., and Ecker, J.R. (Feb. 2004). The ethylene signaling pathway: new insights. Curr Opin Plant Biol 7, 40-49.
Guo, Z.J., et al. (Jul. 2004). Overexpression of the AP2/EREBP transcription factor OPBP1 enhances disease resistance and salt tolerance in tobacco. Plant Mol Blol 55, 607-618.
Hao, D., et al. (1998). Unique mode of GCC box recognition by the DNA-binding domain of ethylene-responsive element-binding factor (ERF domain) in plant. J Biol Chem 273, 26857-26861.
Hao, D., et al. (2002), Determinants in the sequence specific binding of two plant transcription factors, CBF1 and NtERF2, to the DRE and GCC motifs. Biochemistry 41, 4202-4208.
He, P., et al. (2001). Overexpression of Pti5 in tomato potentiates pathogen-induced defense gene expression and enhances disease resistance to *Pseudomonas syringae* pv. tomato. Mol Plant Microbe Interact 14, 1453-1457.
Kitajima, Sakihito et al (Jun. 2000) "Characterization of gene expression of NsERFs, transcription factors of basic PR genes from *Nicotiana sylvestris*" Plant and Cell Physiology, vol. 41, No. 6, pp. 817-824.
Lee, J.H., et al. (May 2004). The ethylene-responsive factor like protein 1 (CaERFLP1) of hot pepper (*Capsicum annuum* L.) interacts in vitro with both GCC and DRE/CRT sequences with different binding affinities: possible biological roles of CaERFLP1 in response to pathogen infection and high salinity condi . . . Plant Mol Biol 55, 61-81.
Liu, Q., et al. (1998). Two transcription factors, DREB1 and DREB2, with an EREBP/AP2 DNA binding domain separate two cellular signal transduction pathways in drought- and low-temperature-responsive gene expression, respectively, in *Arabidopsis*. Plant Cell 10, 1391-1406.
Lorenzo, O., et al. (2003). Ethylene response factor1 integrates signals from ethylene and jasmonate pathways in plant defense. Plant Cell 15, 165-178.
Mazarei, et al. (Jun. 2002) Identification and characterization of a soybean ethylene-responsive element-binding protein gene whose mRNA expression changes during soybean cyst nematode infection. Mol. Plant Microbe Interact. 15(6):577-86.
Menke, et al. (1999) A novel jasmonate-and elicitor-responsive element in the periwinkle secondary metabolite biosynthetic gene Str interacts with a jasmonate-and elicitor-inducible AP2-domain transcription factor, ORCA2. EMBO J. 18 (16), 4455-4463.
Ohme-Takagi, M., and Shinshl, H. (1995). Ethylene-Inducible DNA binding proteins that interact with an ethylene-responsive element. Plant Cell 7, 173-182.
Ohta, et al. (2001) Repression domains of class II ERF transcriptional repressors share an essential motif for active repression. Plant Cell 13 (8), 1959-1968.
Okamura, et al. (Jun. 24, 1997). The AP2 domain of APETALA2 defines a large new family of DNA binding proteins in Arabidopsis. Proc. Natl Acad Sci USA (1997), 94(13), 7076-7081.
Onate-Sanchez, L., and Singh, K.B. (2002). Identification of *Arabidopsis* ethylene-responsive element binding factors with distinct induction kinetics after pathogen infection. Plant Physiol 128, 1313-1322.
Riechmann, J.L., et al. (2000). *Arabidopsis* transcription factors: genome-wide comparative analysis among eukaryotes. Science 290, 2105-2110.
Riechmann, J.L., and Meyerowitz, E.M. (Jun. 1998). The AP2/EREBP family of plant transcription factors. Biol Chem 379, 633-646.
Sakuma, Y., et al. (2002). DNA-binding specificity of the ERF/AP2 domain of Arabidopsis DREBs, transcription factors Involved in dehydration and cold-inducible gene expression. Biochem Biophys Res Commun 290, 998-1009.
Solano, et al. (Dec. 1, 1998). Nuclear events in ethylene signaling: a transcriptional cascade mediated by Ethylene-Insensitive3 an Ethylene-Response-Factor1. Genes & Development (1998), 12(23), 3703-3714.
Suzuki, et al. (1998). Immediate early induction of mRNAs for ethylene-responsive transcription factors in tobacco leaf strips after cutting. Plant Journal vol. 15, No. 5, 1998, pp. 657-665.
Tao, Y., et al. (2003). Quantitative nature of Arabidopsis responses during compatible and incompatible interactions with the bacterial pathogen *Pseudomonas syringae*. Plant Cell 15, 317-330.
Van Der Fits, L. and Memelink, J. (2000) ORCA3, a jasmonate-responsive transcriptional regulator of plant primary and secondary metabolism. Science 289 (5477), 295-297 (2000).
Van Der Fits, et al. (Jan. 2001). The jasmonate-inducible AP2/ERF-domain transcription factor ORCA3 activates gene expression via interaction with a jasmonate-responsive promoter element. Plant Journal (2001), 25(1), 43-53.
Xu, et al. (Nov. 1998). A nitrilase-like protein interacts with GCC box DNA-binding proteins involved in ethylene and defense responses. Plant Physiology (1998), 118(3), 867-874.
Zhang, et al. (Aug. 2004). Tomato stress-responsive factor TSRF1 interacts with ethylene responsive element GCC box and regulates pathogen resistance to *Ralstonia solanacearum*. Plant Mol. Biol. 55 (6), 825-834.
Zhou, J., et al. (1997). The Pto kinase conferring resistance to tomato bacterial speck disease interacts with proteins that bind a cis-element of pathogenesis-related genes. Embo J 16, 3207-3218.
Daly et al. (Dec. 2001). Plant Systematics in the Age of Genomics. Plant Physiology 127:1328-1333.

\* cited by examiner

|          | 10 | 20 | 30 | 40 |
|----------|----|----|----|----|
| G1752_At |    |    |    |    |
| G1791_At |    |    |    |    |
| G1795_At |    |    |    |    |
| G30_At   |    |    |    |    |
| G3380_Os |    |    |    |    |
| G3794_Zm |    |    |    |    |
| G3736_Ta |    |    |    |    |
| G3381_Os |    |    |    |    |
| G3517_Zm |    |    |    |    |
| G3739_Zm |    |    |    |    |
| G3520_Gm |    |    |    |    |
| G3383_Os |    |    |    |    |
| G3737_Os |    |    |    |    |
| G3515_Os |    |    |    |    |
| G3516_Zm |    |    |    |    |
| G3735_Mt |    | M S - - - - | M H S G K R P L S P E | S M A G N R - |
| G1792_At |    | M Y G Q C N I E | S S D S V N N G V N | S R M Y F R - |
| G3518_Gm |    | M S M T A D S Q | S D Y A F L E S I R | R H L L G G |
| G3519_Gm |    |    |    | M E S S - - N R S S - |
| G26_At   |    |    | S S D D Y A L L E | S I T R H L L G G |
| G22_At   |    |    |    |    |
| G1006_At |    |    |    |    |
| G28_At   |    |    |    |    |
| G1751_At | M H Y P N N R T E F V G A P A P T R Y Q K E Q L S | P E Q E L S V I V S A |
| G45_At   | M V R V C V Y T Q K T P D F M W N L K P S M K C G | Q Y L R T Q V S P T V L P N Y |
| G1266_At | M H Y C V Y T Q K T P D F M W N L K P S M K C G |    |    |
| G2512_At |    |    |    |    |

FIG. 3A

|          | 50 | 60 | 70 | 80 |
|---|---|---|---|---|
| G1752_At |   |   |   |   |
| G1791_At |   |   |   |   |
| G1795_At |   |   |   |   |
| G30_At |   |   |   |   |
| G3380_Os |   |   |   |   |
| G3794_Zm |   |   |   |   |
| G3736_Ta |   |   |   |   |
| G3381_Os |   |   |   |   |
| G3517_Zm |   |   |   |   |
| G3739_Zm |   |   |   |   |
| G3520_Gm |   |   |   |   |
| G3383_Os |   |   |   |   |
| G3737_Os |   |   |   |   |
| G3515_Os |   |   |   |   |
| G3516_Zm |   |   |   |   |
| G1792_At | - - - - - - - - - - N N Q - - - - - - - - - - - - - - - - - - |
| G3518_Gm |   |   |   |   |
| G3519_Gm |   |   |   |   |
| G3735_Mt |   |   |   |   |
| G26_At | E E K K E L C C C S T L S E S D - - - - - - - - - - - - - - - - - |
| G22_At | - - - N P S F S N V - - - - - - - - - - - - - - - - - - - - - - |
| G1006_At | G G E N E L R L N E S T P S S - - - - - - - - - - - - - - - - - |
| G28_At | - E S E P I L S E S T A S S V T Q S C V T G Q S I K P V Y G R N P S F S K L - |
| G1751_At | L Q H V I S G E N E T A P C Q G F S S D S T V I S A G M P R L D S D T C Q V C R - |
| G45_At | P A A D S T M A F G N I Q E L D G E I L K N V W A N Y I G T P Q T D T R S I Q - |
| G1266_At |   |   |   |   |
| G2512_At |   |   |   |   |

FIG. 3B

|  | 90 | 100 | 110 | 120 |
|---|---|---|---|---|
| G1752_At | | M E Y S | – Q S S M Y S | – – – S |
| G1791_At | | M E R I | | |
| G1795_At | | M D Q G | | |
| G30_At | | M D Q G | | |
| G3380_Os | | M D G · | | |
| G3794_Zm | | M D – · | | |
| G3736_Ta | | M E G G | | |
| G3381_Os | | M D H H | | |
| G3517_Zm | | M D G · | | |
| G3739_Zm | | M D G · | | |
| G3520_Gm | | M E E · | | |
| G3383_Os | | M E D · | | |
| G3737_Os | | M E D · | | |
| G3515_Os | | M E D · | | |
| G3516_Zm | | M E D · | | |
| G1792_At | – – – – – – – – – – – – – – – – | S Q D D | | |
| G3518_Gm | V S D F V S E L T G Q P I P S S | M E G · | | |
| G3519_Gm | – – I L N D N W S D L P – – L S V D D S | | | |
| G3735_Mt | – – C F T E S W G G L P – – L K E N D S | M E G · | | |
| G26_At | – Y P C F T E S W G D L P – – L K E N D S | | | |
| G22_At | I E G C L G C N Y F F A P N – Q R I E K N H Q | S Q D D Q | | |
| G1006_At | – V P E V S R T W E A L P T L D D I P E G · | M E G · | | |
| G28_At | | M D P F L I Q S P F S G – – F S P E Y S I G S | Q D M A I Y | |
| G1751_At | | M E Y · | – – – – – E D M L V Y | |
| G45_At | | M | – – – – – E D M L V Y | |
| G1266_At | | | – – – – – – – – Q | |
| G2512_At | | Q T N F L S G E F S P E N S S S S | | – G S |

FIG. 3C

|          | 130               | 140             | 150             | 160      |
|----------|-------------------|-----------------|-----------------|----------|
| G1752_At | SWSSSQESLLWNESC-  | FLDQSSEPQAFFC-  | -PNYDYSDDF      |          |
| G1791_At | ES------YNTNEM-   | --------------- | ---------       |          |
| G1795_At | GR------GVGAEHG-  | --------------- | ---------       |          |
| G30_At   | GRSSGS-GGGGAEQG   | --------------- | ---------       |          |
| G3380_Os | DGGGGWDDQGNGGG    | --------------- | ---------       |          |
| G3794_Zm | DGG------------   | --------------- | ---------       |          |
| G3736_Ta | EGS------GGGG-    | --------------- | ---------       |          |
| G3381_Os | HQQQ----QQEGG-    | --------------- | ---------       |          |
| G3517_Zm | EWSK-D---GGGGG-   | --------------- | ---------       |          |
| G3739_Zm | DWSK-D---GGGGG-   | --------------- | ---------       |          |
| G3520_Gm | SKEK-----KKDT-    | --------------- | ---------       |          |
| G3383_Os | NRS------KDT-     | --------------- | ---------       |          |
| G3737_Os | DK-------KEA      | --------------- | ---------       |          |
| G3515_Os | DKS------KEG-     | --------------- | ---------       |          |
| G3516_Zm | DK-------KEG-     | --------------- | ---------       |          |
| G1792_At | ---------------   | --------------- | ---------       |          |
| G3518_Gm | GRSSVS---NGN-     | --------------- | ---------       |          |
| G3519_Gm | GRSSVS---NGN-     | --------------- | ---------       |          |
| G3735_Mt | DHKLVSNS--TNGNG   | --------------- | ---------       |          |
| G26_At   | SSS---LTLQEKS-    | --------------- | ---------       |          |
| G22_At   | NTLRDAVSSGWTPSVP- | --PVT---PVT---  | -SPAEENKPPATKA  |          |
| G1006_At | GLLKDAFH-FDTSSS-  | -DLSCLFDFPAVKVE | PTENFT          |          |
| G28_At   | GILNDAFHGGWEPSSS  | SDEDRS--SFPSVKI | ETPESFA         |          |
| G1751_At | EEEITSSNRRRESSP-  | --------------- | -----VA         |          |
| G45_At   | SREMLQSLDMSTEDQE  | WTEILDAIASFPN-- | KTNHDPLTN       |          |
| G1266_At | SPDSFSSSNNYSLPF   | NENDSE-EMFLYGLI | EQSTQQTY        |          |
| G2512_At | SWSS-QESFLWEES-   | FLHQSFD-QSFLLSS | PTDNYCDDF       |          |

|       | 450 | 460 | 470 | 480 |
|---|---|---|---|---|
| G1752_At |  |  |  |  |
| G1791_At |  |  |  |  |
| G1795_At | - - - - G K K K |  |  |  |
| G30_At |  |  |  |  |
| G3380_Os |  |  |  |  |
| G3794_Zm |  |  |  |  |
| G3736_Ta |  |  |  |  |
| G3381_Os |  |  |  |  |
| G3517_Zm |  |  |  |  |
| G3739_Zm |  |  |  |  |
| G3520_Gm |  |  |  |  |
| G3383_Os |  |  |  |  |
| G3737_Os |  |  |  |  |
| G3515_Os |  |  |  |  |
| G3516_Zm |  |  |  |  |
| G1792_At |  |  |  |  |
| G3518_Gm |  |  |  |  |
| G3519_Gm |  |  |  |  |
| G3735_Mt |  |  |  |  |
| G26_At |  |  |  |  |
| G22_At |  |  |  |  |
| G1006_At |  |  |  |  |
| G28_At |  |  |  |  |
| G1751_At |  |  |  |  |
| G45_At |  |  |  |  |
| G1266_At |  |  |  |  |
| G2512_At |  |  |  |  |

FIG. 3L

| | | | | | | | | | | | | | | |
|---|---|---|---|---|---|---|---|---|---|---|---|---|---|---|
| G1752_At | L | V | V | F | E | D | L | G | A | E | Y | L | E | Q | L | L |
| G1791_At | V | I | E | F | E | Y | L | D | D | S | L | L | E | E | L | L |
| G1795_At | V | F | E | F | E | Y | L | D | D | S | V | L | E | E | L | L |
| G30_At | V | F | E | F | E | Y | L | D | D | S | V | L | D | E | L | L |
| G3380_Os | V | I | E | L | E | C | L | D | D | Q | V | L | Q | E | M | L |
| G3794_Zm | V | I | E | L | E | C | L | D | D | Q | V | L | Q | E | M | L |
| G3736_Ta | V | I | E | F | E | Y | L | D | D | D | V | L | Q | S | M | L |
| G3381_Os | P | I | E | F | E | Y | L | D | D | H | V | L | Q | E | M | L |
| G3517_Zm | V | I | E | F | E | Y | L | D | D | E | V | L | Q | E | M | L |
| G3739_Zm | V | I | E | L | E | Y | L | D | D | E | V | L | Q | E | M | L |
| G3520_Gm | V | I | E | F | E | C | L | D | D | K | L | L | E | D | L | L |
| G3383_Os | K | I | E | F | E | Y | L | D | D | K | V | L | D | D | L | L |
| G3737_Os | K | V | E | L | V | Y | L | D | D | K | V | L | D | E | L | L |
| G3515_Os | K | V | E | L | E | C | L | D | D | K | V | L | E | D | L | L |
| G3516_Zm | K | V | E | L | E | C | L | D | D | R | V | L | E | E | L | L |
| G1792_At | V | F | E | F | E | Y | L | D | D | K | V | L | E | E | L | L |
| G3518_Gm | T | F | E | L | E | Y | F | D | N | K | L | L | E | E | L | L |
| G3519_Gm | T | F | E | L | E | Y | L | D | N | K | L | L | E | E | L | L |
| G3735_Mt | - | - | E | L | E | F | L | D | N | K | L | L | Q | E | L | L |
| G26_At | S | S | S | S | S | S | L | N | H | Q | G | L | R | P | N | L |
| G22_At | E | L | D | F | T | V | D | Q | F | Y | F | D | G | S | L | L |
| G1006_At | K | C | E | V | - | G | D | E | T | R | V | D | - | E | L | L |
| G28_At | T | V | K | C | E | - | V | E | V | A | R | G | - | R | L | L |
| G1751_At | C | N | M | E | E | W | M | N | M | M | M | M | M | D | F | G |
| G45_At | L | F | E | F | E | D | L | G | S | D | Y | L | E | T | L | L |
| G1266_At | V | V | V | F | E | D | L | G | E | Q | Y | L | E | E | L | L |
| G2512_At | L | V | V | L | E | D | L | G | A | E | Y | L | E | E | L | - |
| | | | | | E | | D | | | | L | | | | L | |

G1792 clade (braces G1791_At through G3735_Mt)

FIG. 4

TRANSCRIPTIONAL REGULATION OF PLANT DISEASE TOLERANCE

RELATIONSHIP TO COPENDING APPLICATIONS

This application (the "instant application")is a continuation-in-part of prior U.S. application Ser. No. 10/666,642, filed Sep. 18, 2003 (pending), which claims the benefit of U.S. Provisional Application No. 60/411,837, filed Sep. 18, 2002 (expired) and U.S. Provisional Application No. 60/465,809, filed Apr. 24,2003 (expired); and, the instant application is a continuation-in-part of prior U.S. application Ser. No. 10/714,887, filed Nov. 13, 2003 (pending), which is a continuation-in-part of prior U.S. application Ser. No. 10/374,780, filed Feb. 25, 2003 (pending) which is a continuation-in-part of prior U.S. application Ser. No. 09/837,944, filed Apr. 18, 2001 (abandoned) and prior U.S. application Ser. No. 10/171,468, filed Jun. 14, 2002 (abandoned); and, the instant application is a continuation-in-part of prior U.S. application Ser. No. 10/456,882, filed Jun. 6, 2003 (pending), which is a continuation-in-part of prior U.S. application Ser. No. 10/171,468, filed Jun. 14, 2002 (abandoned) and prior U.S. application Ser. No. 09/934,455, filed Aug. 22, 2001 (abandoned); and, the instant application is a continuation-in-part of prior U.S. application Ser. No. 10/255,068, filed Aug. 9, 2002 (pending), which claims the benefit of U.S. Provisional Application No. 60/310,847, filed Aug. 9, 2001 (expired) and prior U.S. application Ser. No. 10/255,068, is also a continuation-in-part of prior U.S. application Ser. No. 09/837,944, filed Apr. 18, 2001 (abandoned) and prior U.S. application Ser. No. 10/171,468, filed Jun. 14, 2002, (abandoned); and, the instant application is a continuation-in-part of prior U.S. application Ser. No. 10/255,066, filed Aug. 9, 2002 (pending); and, the instant application is a continuation-in-part of prior PCT Application No. PCT/US04/005654, filed Feb. 25, 2004 (pending); and, the instant application is a continuation-in-part of prior U.S. application Ser. No. 10/374,780, filed Feb. 25, 2003 (pending), which is a continuation-in-part of prior U.S. application Ser. No. 09/837,944, filed Apr. 18, 2001 (abandoned). The entire contents of these applications are hereby incorporated by reference.

FIELD OF THE INVENTION

The present invention relates to increasing a plant's tolerance to disease and abiotic stress tolerance, and the plant product quality yield that may be obtained from a plant.

BACKGROUND OF THE INVENTION

Studies from a diversity of prokaryotic and eukaryotic organisms suggest a gradual evolution of biochemical and physiological mechanisms and metabolic pathways. Despite different evolutionary pressures, proteins that regulate the cell cycle in yeast, plant, nematode, fly, rat, and man have common chemical or structural features and modulate the same general cellular activity. A comparison of gene sequences with known structure and/or function from one plant species, for example, *Arabidopsis thaliana*, with those from other plants, allows researchers to develop models for manipulating a plant's traits and developing varieties with valuable properties.

A plant's traits may be controlled through a number of cellular processes. One important way to manipulate that control is through transcription factors proteins that influence the expression of a particular gene or sets of genes. Because transcription factors are key controlling elements of biological pathways, altering the expression levels of one or more transcription factors can change entire biological pathways in an organism. Strategies for manipulating a plant's biochemical, developmental, or phenotypic characteristics by altering a transcription factor expression can result in plants and crops with new and/or improved commercially valuable properties, including traits that improve yield under non-stressed conditions, or survival and yield during periods of abiotic stress. Examples of the latter include, for example, germination in cold conditions, and osmotic stresses such as desiccation, drought, excessive heat, and salt stress.

We have identified polynucleotides encoding transcription factors, including *Arabidopsis* sequences G1792, G1791, G1795, G30, and equivalogs listed in the Sequence Listing from a variety of other species, developed transgenic plants using some of these polynucleotides from diverse species, and analyzed the plants for their tolerance to disease and abiotic stress. In so doing, we have identified important polynucleotide and polypeptide sequences for producing commercially valuable plants and crops as well as the methods for making them and using them. Other aspects and embodiments of the invention are described below and can be derived from the teachings of this disclosure as a whole.

SUMMARY OF THE INVENTION

The present invention describes polynucleotides that may be introduced into plants. The polynucleotides encode transcription factor polypeptides that have the useful properties of increasing disease tolerance or resistance, increased abiotic stress, and/or altered sensing of carbon-nitrogen (C/N) balance. The present invention thus may be used to increase a plant's tolerance to disease, including multiple pathogens, which may further include fungal pathogens. This method is accomplished by first providing an expression vector and then introducing the expression vector into a plant to produce a transformed plant. The expression vector contains both a regulatory element and a polynucleotide sequence. The regulatory element controls the expression of the polynucleotide sequence. The polynucleotide encodes a member of the G1792 clade of transcription factor polypeptides, which are shown in the present invention to comprise two distinct conserved domains: an AP2 domain and an EDLL domain, in order from N-terminal to C-terminal. The EDLL domain is characterized by, in order from N-terminal to C-terminal, a glutamic acid residue, an aspartic acid residue, and two leucine residues. The consensus sequence for the EDLL domain is represented by SEQ ID NO: 55. After a target plant is transformed with the expression vector, which confers increased tolerance by virtue of the overexpression of the G1792 clade member, the transformed plant is grown.

The invention also pertains to a method for producing a plant with greater disease tolerance than a control plant. This method is performed by providing the expression vector just described. After transforming a target plant with this expression vector, a transformed plant with greater disease tolerance than a control plant is the result.

The invention also encompasses transgenic plants that have greater tolerance to multiple fungal pathogens than a control plant, wherein the transgenic plants are produced by the above methods.

The invention is also directed to seed produced from any of the transformed plants produced by the methods disclosed or claimed herein.

The methods encompassed by the invention may also be extended to propagation techniques used to generate plants.

For example, a target plant that has been transformed with a polynucleotide encoding a G1792 polypeptide clade member and that has greater disease and/or abiotic stress tolerance than a wild-type or non-transformed control may be "selfed" (i.e., self-pollinated) or crossed with another plant to produce seed. Progeny plants may be grown from this seed, thus generating transformed progeny plants with increased tolerance to disease and/or abiotic stress, as compared to wild-type, control or non-transformed plants of the same species.

BRIEF DESCRIPTION OF THE SEQUENCE LISTING AND DRAWINGS

The file of this patent contains at least one drawing executed in color. Copies of this patent with color drawing(s) will be provided by the Patent and Trademark Office upon request and payment of the necessary fee.

The Sequence Listing provides exemplary polynucleotide and polypeptide sequences of the invention. The traits associated with the use of the sequences are included in the Examples.

CD-ROM1 and CD-ROM2 are identical read-only memory computer-readable compact discs and each contains a copy of the Sequence Listing in ASCII text format. The Sequence Listing is named "MBI0062 CIP.ST25.txt", is 73 kilobytes in size, and was created on Jul. 29, 2004. The copies of the Sequence Listing on the CD-ROM disc are hereby incorporated by reference in their entirety.

FIG. 1 shows a conservative estimate of phylogenetic relationships among the orders of flowering plants (modified from Angiosperm Phylogeny Group (1998) *Ann. Missouri Bot. Gard.* 84: 1-49). Those plants with a single cotyledon (monocots) are a monophyletic clade nested within at least two major lineages of dicots; the eudicots are further divided into rosids and asterids. *Arabidopsis* is a rosid eudicot classified within the order Brassicales; rice is a member of the monocot order Poales. FIG. 1 was adapted from Daly et al. (2001) *Plant Physiol.* 127: 1328-1333.

Figure 2:
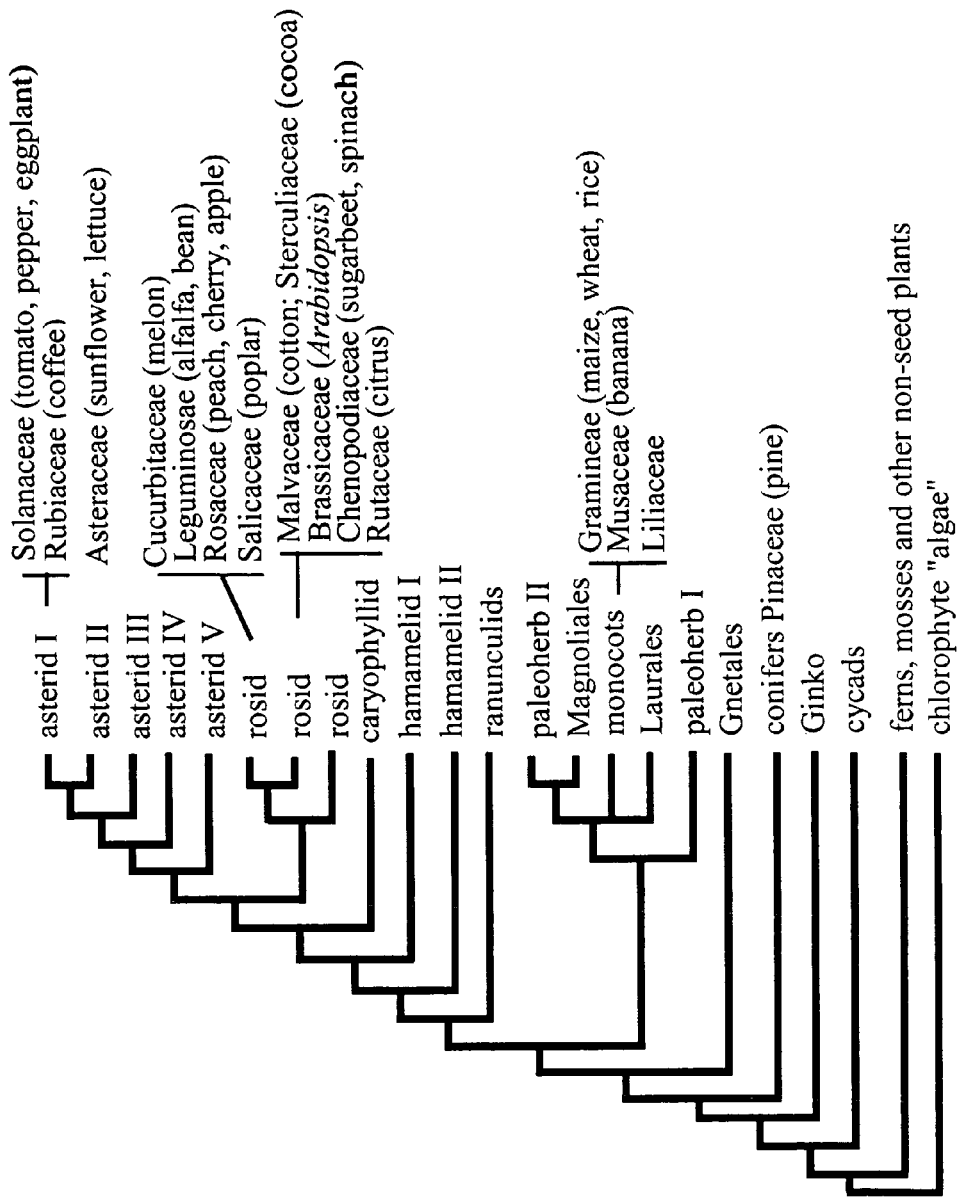

FIG. 2 shows a phylogenic dendogram depicting phylogenetic relationships of higher plant taxa, including clades containing tomato and *Arabidopsis*; adapted from Ku et al. (2000) *Proc. Natl. Acad. Sci. U.S.A.* 97: 9121-9126; and Chase et al. (1993) *Ann. Missouri Bot. Gard.* 80: 528-580.

Figure 3E:
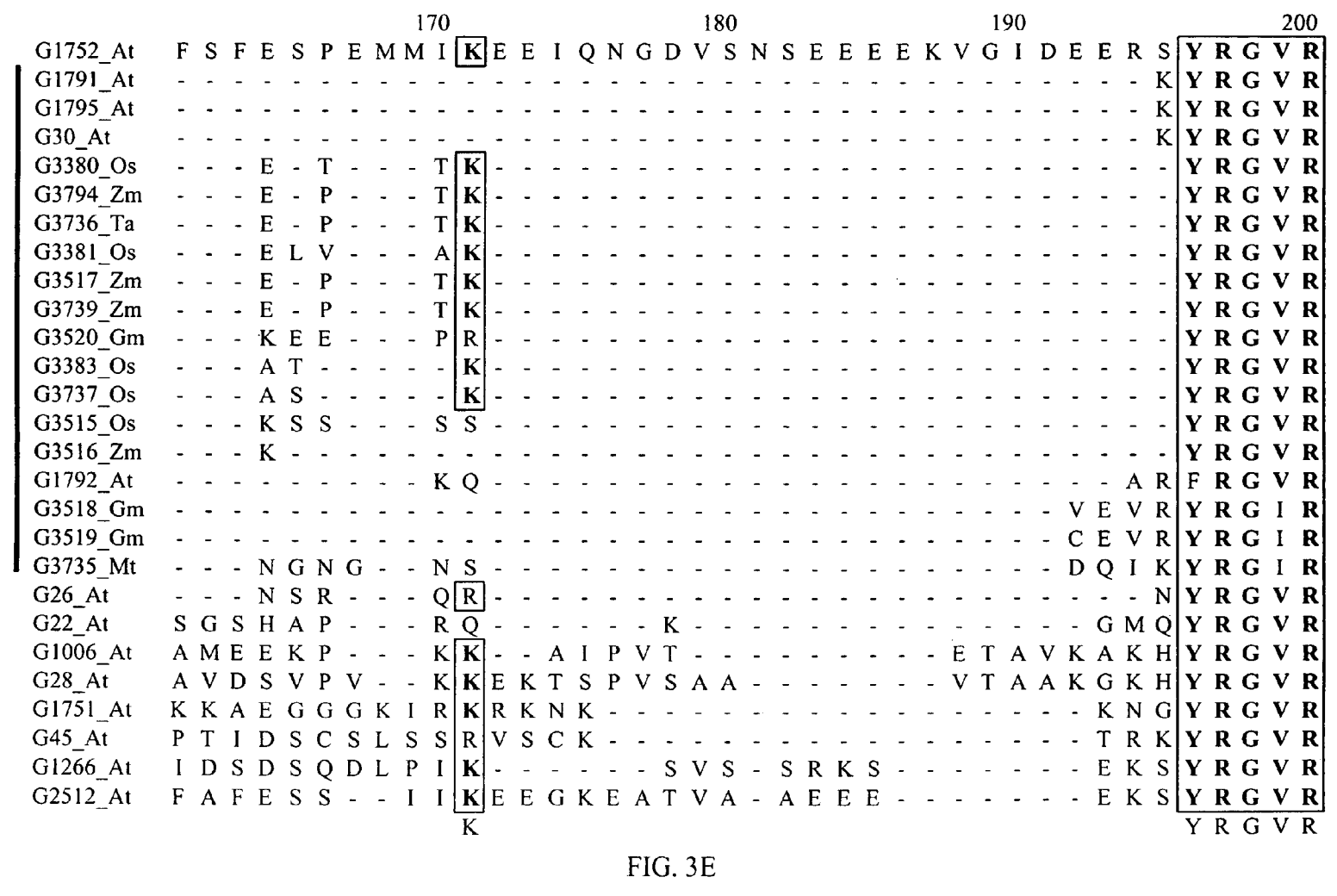
Figure 3F:
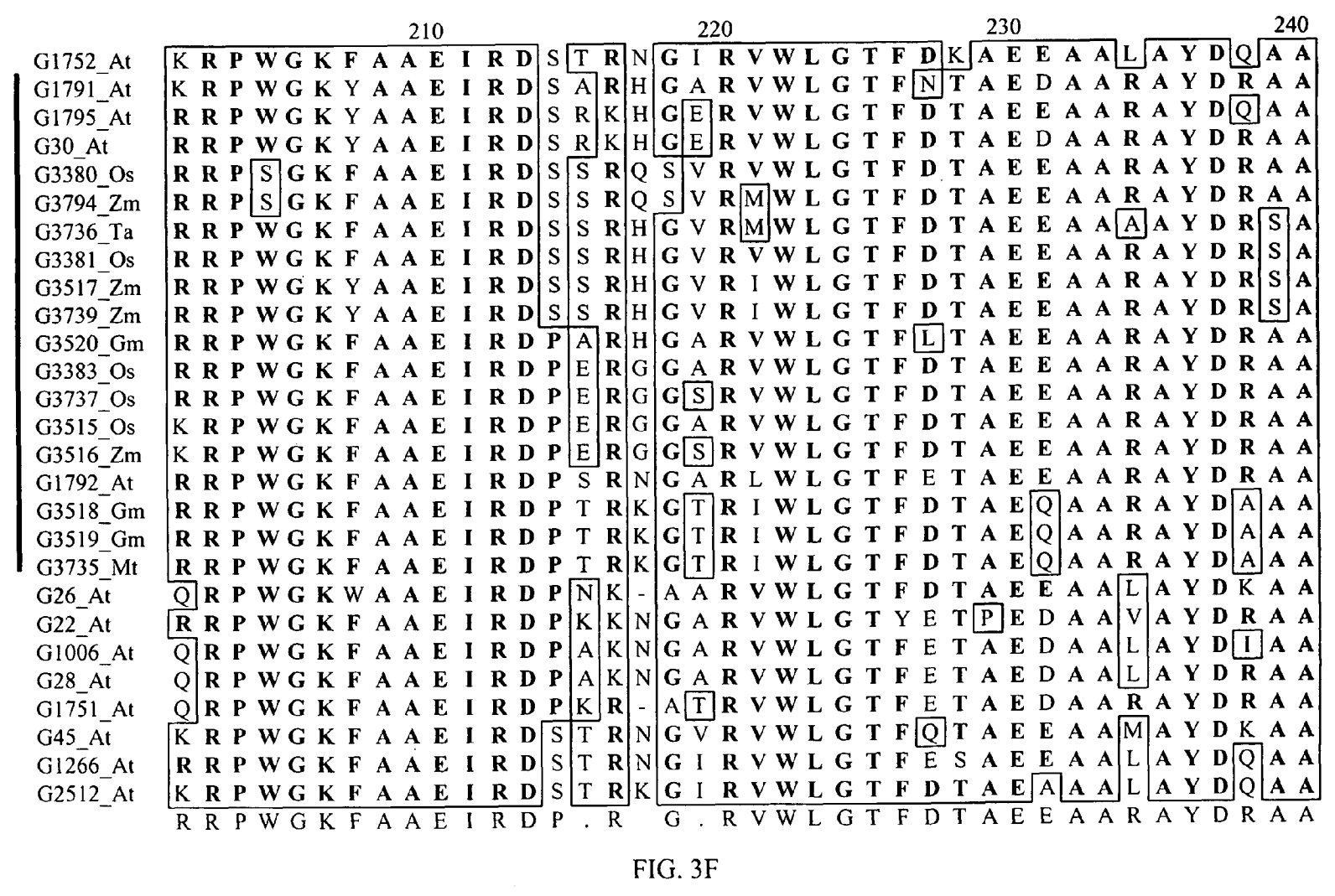
Figure 3G:
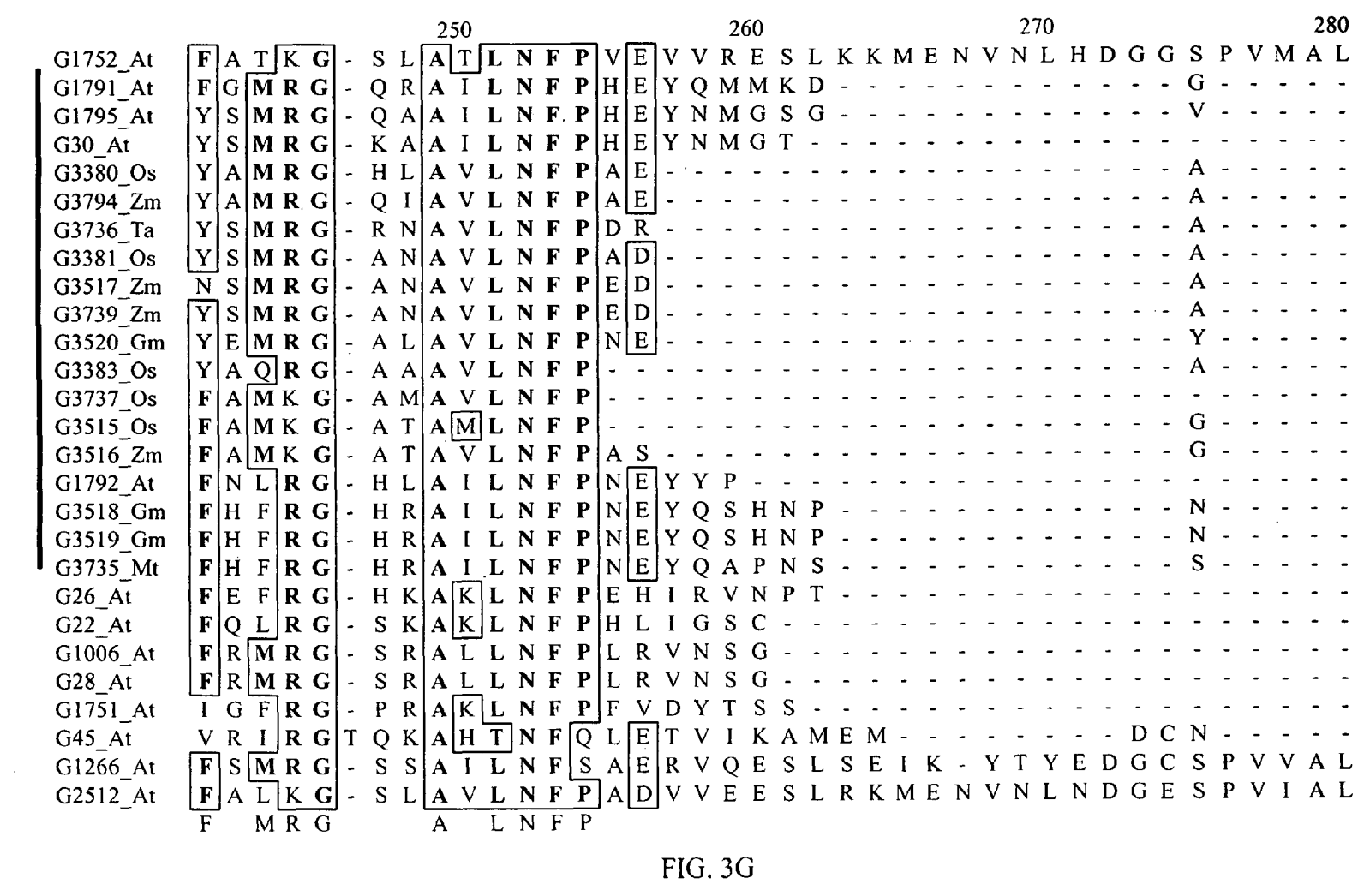
Figure 3H:
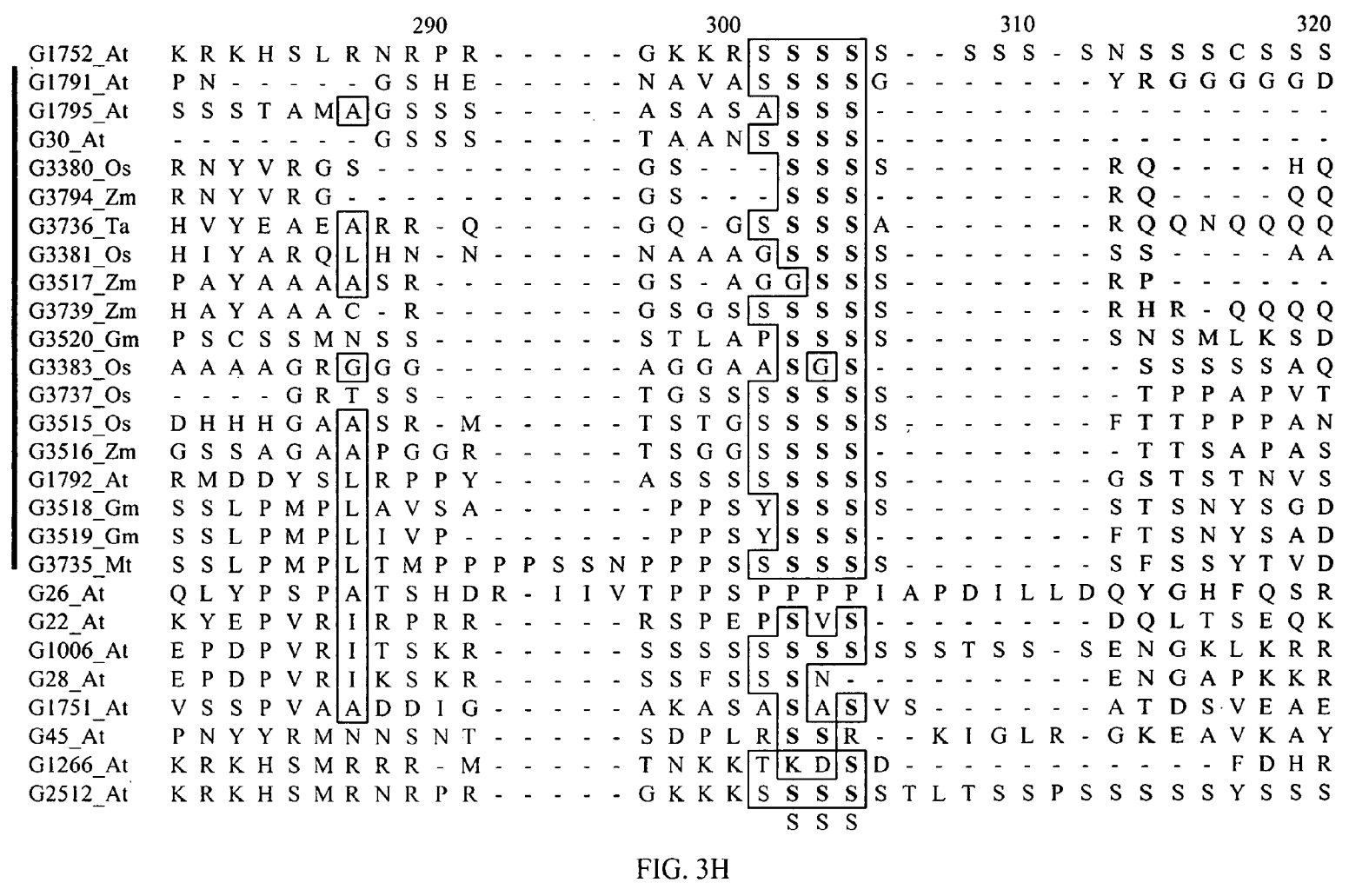
Figure 3I:
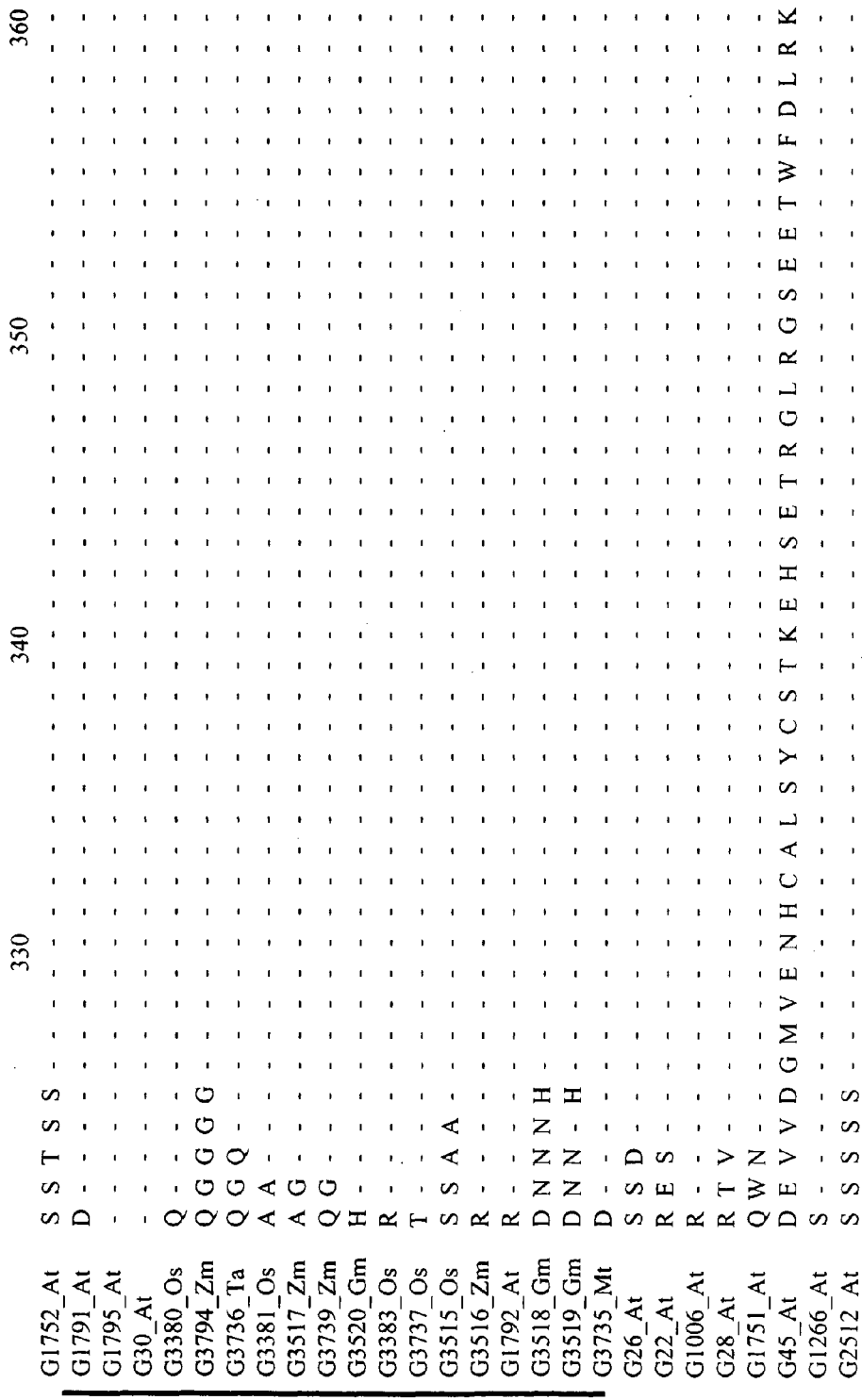
Figure 3J:
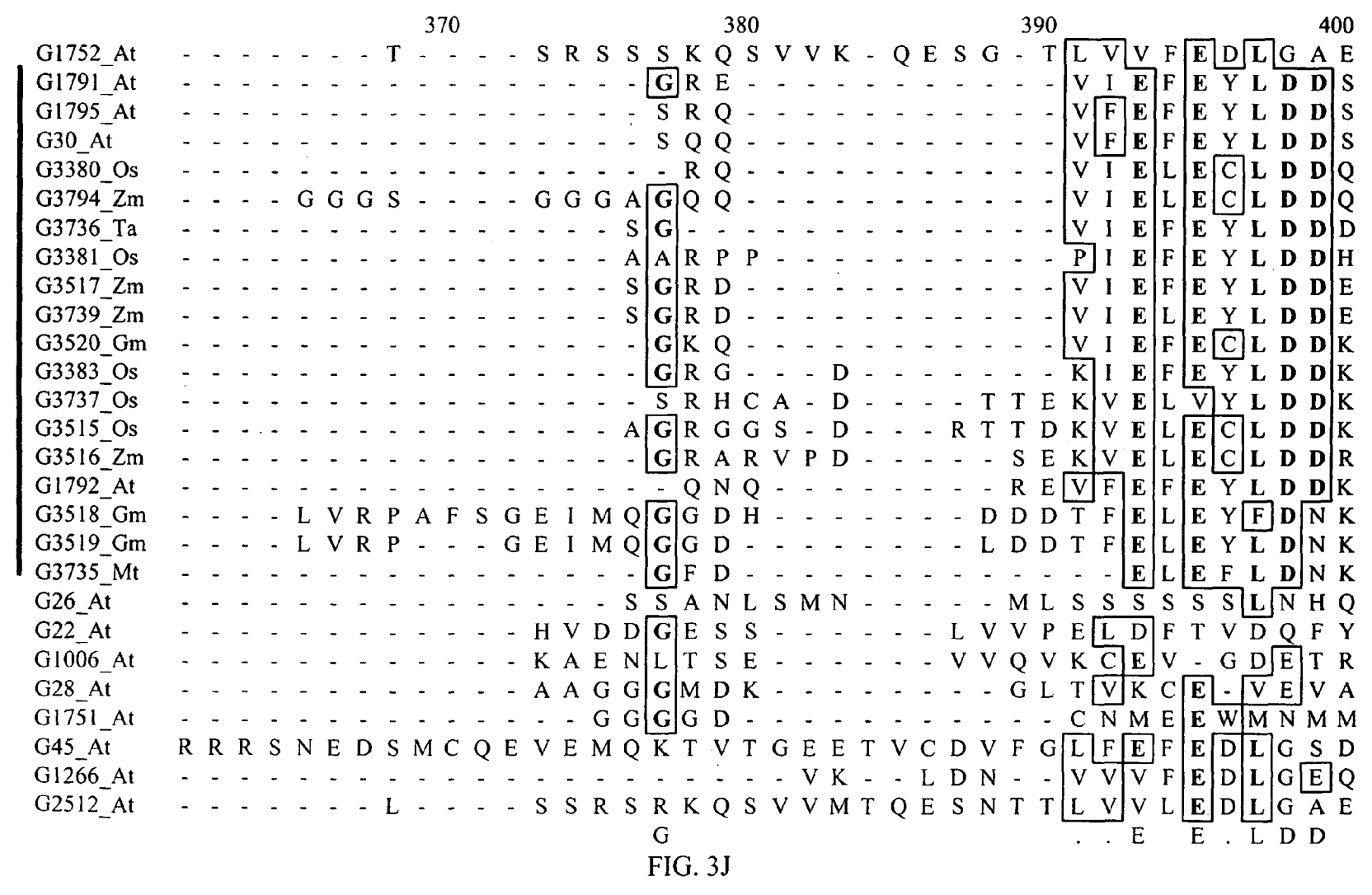
Figure 3K:
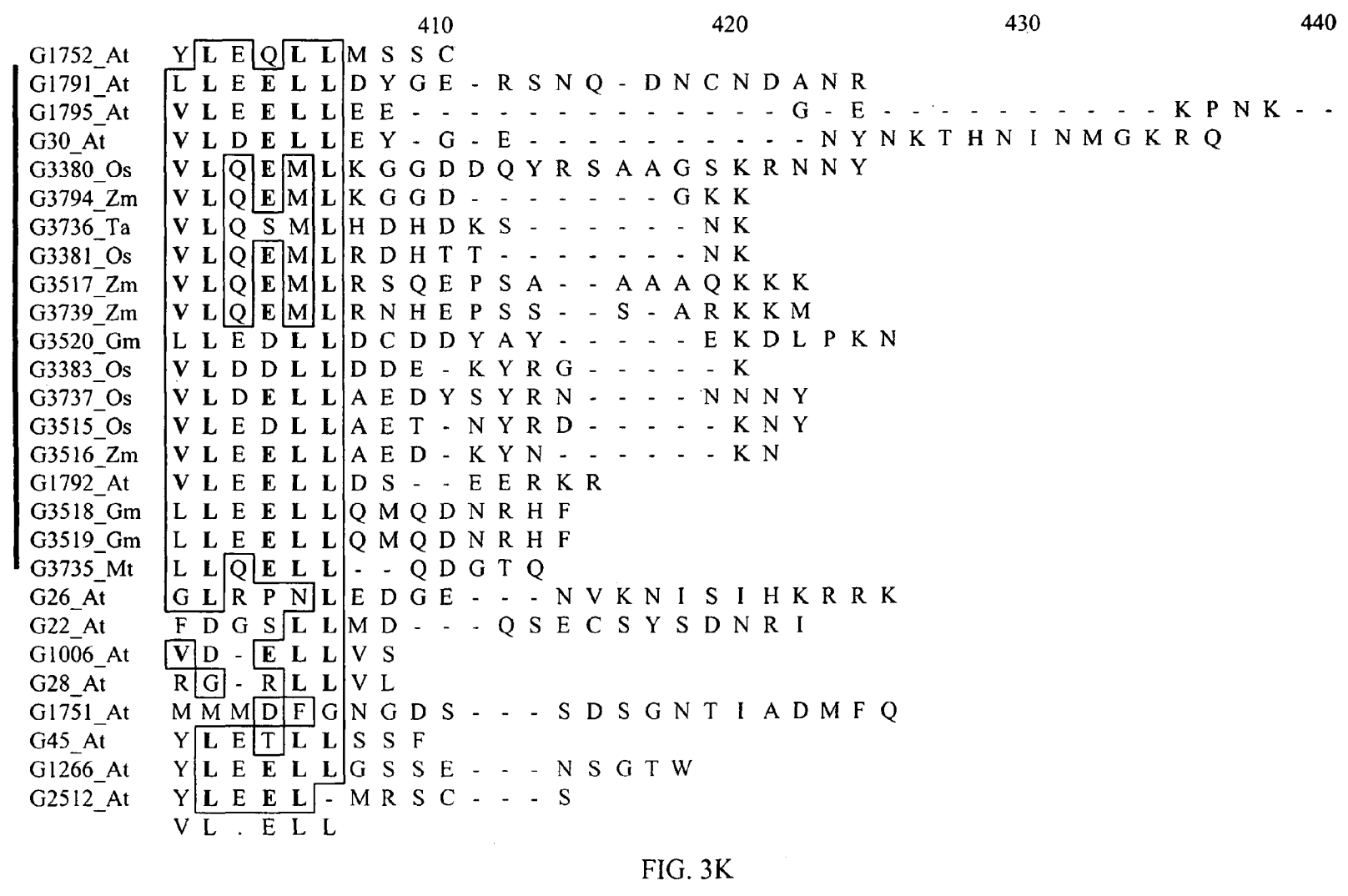

FIGS. 3A-3L represent a multiple amino acid sequence alignment of G1792 orthologs and paralogs. Clade orthologs and paralogs are indicated by the black bar on the left side of the figure. Conserved regions of identity are boxed and appear in boldface, while conserved sequences of similarity are boxed and appear as plain text. The AP2 conserved domains span alignment coordinates 196-254. The S conserved domain spans alignment coordinates of 301-304. The EDLL conserved domain spans the alignment coordinates of 391-406 (FIGS. 3J-3K; see also FIG. 4). The sequences listed in FIGS. 3A-3L may be found in the sequence Listing as SEQ ID NO: 42 (G1752), SEQ ID NO: 4 (G1791), SEQ ID NO: 6 (G1795), SEQ ID NO: 8 (G30), SEQ ID NO: 10 (G3380), SEQ ID NO: 36 (G3794), SEQ ID NO: 30 (G3736), SEQ ID NO: 12 (G3381), SEQ ID NO: 20 (G3517), SEQ ID NO: 34 (G3739), SEQ ID NO: 26 (G3520), SEQ ID NO: 14 (G3383) SEQ ID NO: 32 (G3737) SEQ ID NO: 16 (G3515), SEQ ID NO: 18 (G3516), SEQ ID NO: 2 (G1792), SEQ ID NO: 22 (G3518),SEQ ID NO: 24 (G3519), SEQ ID NO: 28 (G3735), SEQ ID NO: 52 (G26), SEO ID NO: 50 (G22), SEQ ID NO: 46 (G1006), SEQ ID NO: 48 (G28), SEQ ID NO: 54 (G1751), SEQID NO: 40 (G45), SEQ ID NO: 38 (G1266), and SEQ ID NO: 44 (G2512). Abbreviations in these figures include: At *Arabidopsis thaliana;* Os *Oryza sativa;* Zm *Zea mays;* Ta *Triticum aestivum;* Gm *Glycine max;* Mt *Medicago truncatula.*

FIG. 4 shows a novel conserved domain for the G1792 clade, herein referred to as the "EDLL domain" (SEQ ID NO: 55). All clade members contain a glutamic acid residue at position 3, an aspartic acid residue at position 8, and leucine residues at positions 12 and 16 of the domain. The sequences listed in FIG. 4 may be found in the sequence Listing as SEQ ID NO: 42 (G1752), SEQ ID NO: 4 (G1791), SEQ ID NO: 6 (G1795), SEQ ID NO: 8 (G30), SEQ ID NO: 10 (G3380), SEQ ID NO: 36 (G3794), SEQ ID NO: 30 (G3736), SEQ ID NO: 12 (G3381), SEQ ID NO: 20 (G3517), SEQ ID NO: 34 (G3739), SEQ ID NO: 26 (G3520), SEQ ID NO: 14 (G3381), SEQ ID NO: 32 (G3737), SEQ ID NO: 16 (G3515), SEQ ID NO: 18 (G3516), SEQ ID NO: 2 (G1792), SEQ ID NO: 22 (G3518), SEQ ID NO: 24 (G3519), SEQ ID NO: 28 (G3735), SEQ ID NO: 52 (G26), SEQ ID NO: 50 (G22), SEQ ID NO: 46 (G1006), SEQ ID NO: 48 (G28), SEQ ID NO: 54 (G1751), SEP ID NO: 40 (G45), SEQ ID NO: 38 (G1266), and SEQ ID NO: 44 (G2512).

Figure 5:
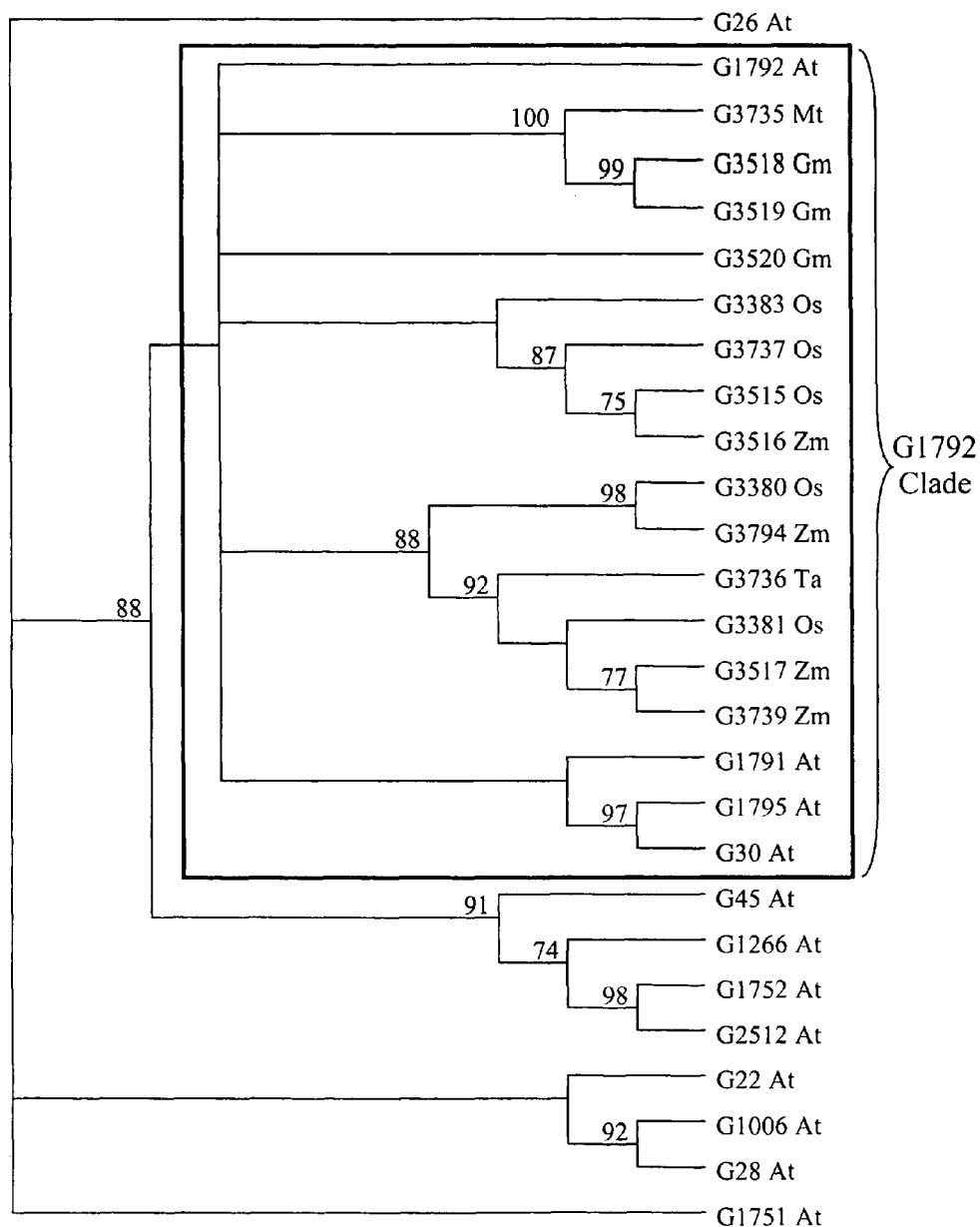

FIG. 5 illustrates the relationship of G1792 and related sequences in this phylogenetic tree of the G1792 clade. The tree building method used was "Neighbor Joining" with "Systematic Tie-Breaking" and Bootstrapping with 1000 replicates. The AP2 domains (as listed in Table 1) were used to build the phylogeny. The members of the G1792 clade are shown within the large box. The sequences listed in FIG. 4 may be found in the sequence Listing as SEQ ID NO: 52 (G26), SEQ ID NO: 2 (G1792), SEQ ID NO: 28 (G3735), SEQ ID NO: 22 (G3518), SEQ ID NO: 24 (G3519), SEQ ID NO: 26 (G3520), SEQ ID NO: 14 (G3383), SEQ ID NO: 32 (G3737), SEQ ID NO: 16 (G3515), SEQ ID NO: 18 (G3516), SEQ ID NO: 10 (G3380), SEQ ID NO: 36 (G3794), SEQ ID NO: 30 (G3736), SEQ ID NO: 12 (G3381), SEQ ID NO: 20 (G3517), SEQ ID NO: 34 (G3739), SEQ ID NO: 4 (G1791), SEQ ID NO: 6 (G1795), SEQ ID NO: 8 (G30), SEQ ID NO: 40 (G45), SEQ ID NO: 38 (G1266), SEQ ID NO: 42 (G1752), SEQ ID NO: 44 (G2512), SEQ ID NO: 50 (G22), SEQ ID NO: 46 (G1006), SEQ ID NO: 48 (G28), and SEQ ID NO: 54 (G1751).

Figure 6:
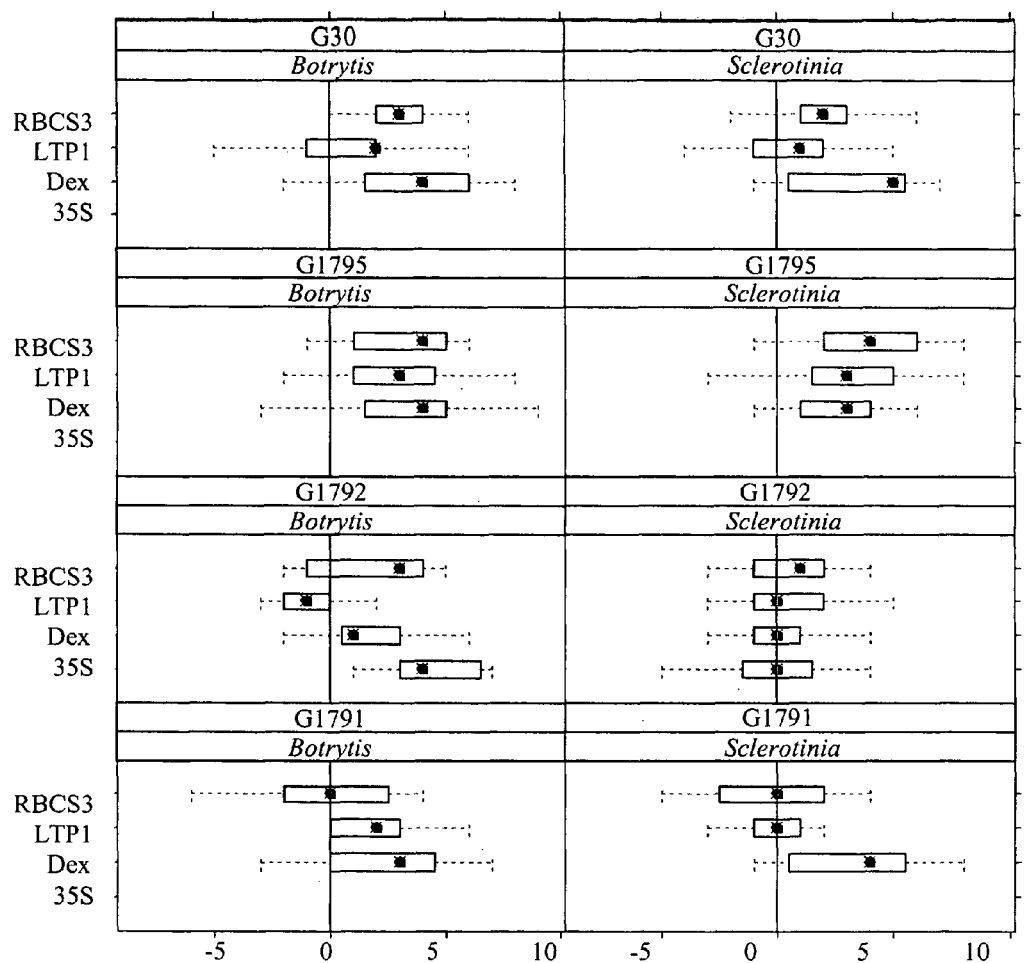

FIG. 6 shows the distribution of test plants surviving in a pathogen assay. The data plotted were collected from all of the lines tested. Increased tolerance is shown as the positive number of living plants greater than the number of surviving control plants (the latter value appears as the center line in each category). 35S::G1792 plants are included for comparison. The median of each determination, that is, the number of overexpressing plants greater than the number of surviving controls, is represented by the point within the rectangular box, the rectangular box delineates the 25th to 75th percentiles, and the dotted lines represent the 10th to 90th percentiles. The sequences in FIG. 4 may be found in the sequence Listing as SEQ ID NO: 8 (G30), SEQ ID NO: 6 (G1795), SEQ ID NO: 2 (G1792), and SEQ ID NO: 4 (G1791).

Figure 7:
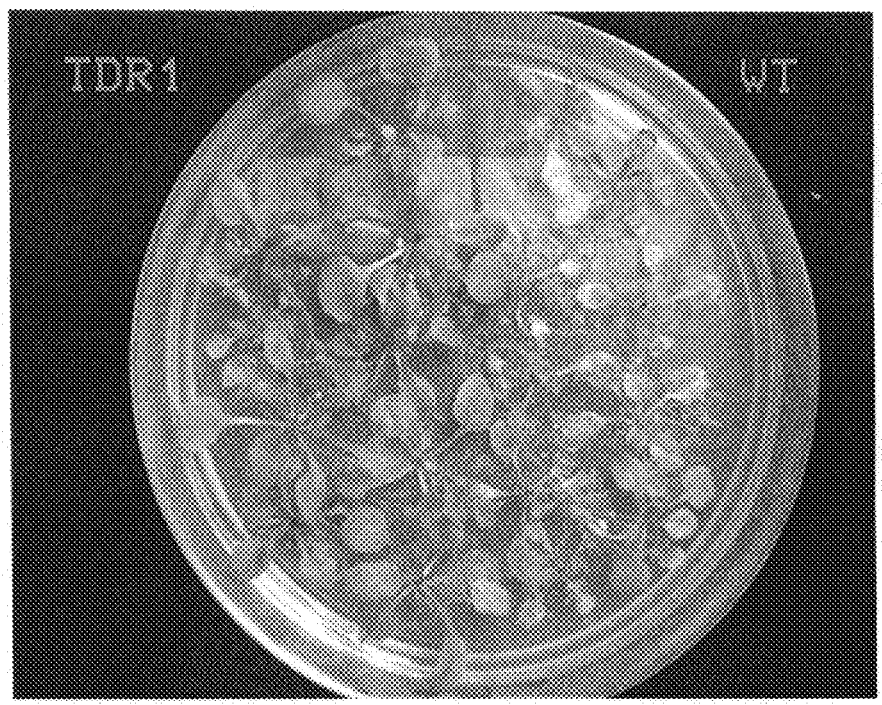
Figure 8:

FIGS. 7 and 8 show the results of plate-based disease assays with controls and *Arabidopsis* plants overexpressing members of the G1792 clade. In FIGS. 7 and 8, plants overexpressing *Arabidopsis* sequence G1792 and rice sequence G3381, respectively, on the left half of the plates were significantly more tolerant to *Botrytis cinerea* than the control plants on the right half of the plates, as evidenced by significant growth of the pathogen only on the susceptible plants.

DETAILED DESCRIPTION

The present invention relates to polynucleotides and polypeptides for modifying phenotypes of plants, particularly those associated with increased tolerance to disease and abiotic stress. Throughout this disclosure, various information sources are referred to and/or are specifically incorporated. The information sources include scientific journal articles, patent documents, textbooks, and World Wide Web browser-inactive page addresses, for example. While the reference to these information sources clearly indicates that they can be used by one of skill in the art, each and every one of the information sources cited herein are specifically incorporated in their entirety, whether or not a specific mention of "incorporation by reference" is noted. The contents and teachings of each and every one of the information sources can be relied on and used to make and use embodiments of the invention.

As used herein and in the appended claims, the singular forms "a", "an", and "the" include the plural reference unless the context clearly dictates otherwise. Thus, for example, a reference to "a host cell" includes a plurality of such host cells, and a reference to "a stress" is a reference to one or more stresses and equivalents thereof known to those skilled in the art, and so forth.

Definitions

"Nucleic acid molecule" refers to an oligonucleotide, polynucleotide or any fragment thereof. It may be DNA or RNA of genomic or synthetic origin, double-stranded or single-stranded, and combined with carbohydrate, lipids, protein, or other materials to perform a particular activity such as transformation or form a useful composition such as a peptide nucleic acid (PNA).

"Polynucleotide" is a nucleic acid molecule comprising a plurality of polymerized nucleotides, e.g., at least about 15 consecutive polymerized nucleotides, optionally at least about 30 consecutive nucleotides, at least about 50 consecutive nucleotides. A polynucleotide may be a nucleic acid, oligonucleotide, nucleotide, or any fragment thereof. In many instances, a polynucleotide comprises a nucleotide sequence encoding a polypeptide (or protein) or a domain or fragment thereof. Additionally, the polynucleotide may comprise a promoter, an intron, an enhancer region, a polyadenylation site, a translation initiation site, 5' or 3' untranslated regions, a reporter gene, a selectable marker, or the like. The polynucleotide can be single stranded or double stranded DNA or RNA. The polynucleotide optionally comprises modified bases or a modified backbone. The polynucleotide can be, e.g., genomic DNA or RNA, a transcript (such as an mRNA), a cDNA, a PCR product, a cloned DNA, a synthetic DNA or RNA, or the like. The polynucleotide can be combined with carbohydrate, lipids, protein, or other materials to perform a particular activity such as transformation or form a useful composition such as a peptide nucleic acid (PNA). The polynucleotide can comprise a sequence in either sense or antisense orientations. "Oligonucleotide" is substantially equivalent to the terms amplimer, primer, oligomer, element, target, and probe and is preferably single stranded.

"Gene" or "gene sequence" refers to the partial or complete coding sequence of a gene, its complement, and its 5' or 3' untranslated regions. A gene is also a functional unit of inheritance, and in physical terms is a particular segment or sequence of nucleotides along a molecule of DNA (or RNA, in the case of RNA viruses) involved in producing a polypeptide chain. The latter may be subjected to subsequent processing such as splicing and folding to obtain a functional protein or polypeptide. A gene may be isolated, partially isolated, or be found with an organism's genome. By way of example, a transcription factor gene encodes a transcription factor polypeptide, which may be functional or require processing to function as an initiator of transcription.

Operationally, genes may be defined by the cis-trans test, a genetic test that determines whether two mutations occur in the same gene and which may be used to determine the limits of the genetically active unit (Rieger et al. (1976) *Glossary of Genetics and Cytogenetics: Classical and Molecular,* 4th ed., Springer Verlag, Berlin). A gene generally includes regions preceding ("leaders"; upstream) and following ("trailers"; downstream) the coding region. A gene may also include intervening, non-coding sequences, referred to as "introns", located between individual coding segments, referred to as "exons". Most genes have an associated promoter region, a regulatory sequence 5' of the transcription initiation codon (there are some genes that do not have an identifiable promoter). The function of a gene may also be regulated by enhancers, operators, and other regulatory elements.

A "recombinant polynucleotide" is a polynucleotide that is not in its native state, e.g., the polynucleotide comprises a nucleotide sequence not found in nature, or the polynucleotide is in a context other than that in which it is naturally found, e.g., separated from nucleotide sequences with which it typically is in proximity in nature, or adjacent (or contiguous with) nucleotide sequences with which it typically is not in proximity. For example, the sequence at issue can be cloned into a vector, or otherwise recombined with one or more additional nucleic acid.

An "isolated polynucleotide" is a polynucleotide whether naturally occurring or recombinant, that is present outside the cell in which it is typically found in nature, whether purified or not. Optionally, an isolated polynucleotide is subject to one or more enrichment or purification procedures, e.g., cell lysis, extraction, centrifugation, precipitation, or the like.

A "polypeptide" is an amino acid sequence comprising a plurality of consecutive polymerized amino acid residues e.g., at least about 15 consecutive polymerized amino acid residues. In many instances, a polypeptide comprises a polymerized amino acid residue sequence that is a transcription factor or a domain or portion or fragment thereof. Additionally, the polypeptide may comprise 1) a localization domain, 2) an activation domain, 3) a repression domain, 4) an oligomerization domain, or 5) a DNA-binding domain, or the like. The polypeptide optionally comprises modified amino acid residues, naturally occurring amino acid residues not encoded by a codon, non-naturally occurring amino acid residues.

"Protein" refers to an amino acid sequence, oligopeptide, peptide, polypeptide or portions thereof whether naturally occurring or synthetic.

"Portion", as used herein, refers to any part of a protein used for any purpose, but especially for the screening of a library of molecules which specifically bind to that portion or for the production of antibodies.

A "recombinant polypeptide" is a polypeptide produced by translation of a recombinant polynucleotide. A "synthetic polypeptide" is a polypeptide created by consecutive polymerization of isolated amino acid residues using methods well known in the art. An "isolated polypeptide," whether a naturally occurring or a recombinant polypeptide, is more enriched in (or out of) a cell than the polypeptide in its natural state in a wild-type cell, e.g., more than about 5% enriched, more than about 10% enriched, or more than about 20%, or more than about 50%, or more, enriched, i.e., alternatively denoted: 105%, 110%, 120%, 150% or more, enriched relative to wild type standardized at 100%. Such an enrichment is not the result of a natural response of a wild-type plant. Alternatively, or additionally, the isolated polypeptide is separated from other cellular components with which it is typically associated, e.g., by any of the various protein purification methods herein.

"Homology" refers to sequence similarity between a reference sequence and at least a fragment of a newly sequenced clone insert or its encoded amino acid sequence.

"Hybridization complex" refers to a complex between two nucleic acid molecules by virtue of the formation of hydrogen bonds between purines and pyrimidines.

"Identity" or "similarity" refers to sequence similarity between two or more polynucleotide sequences, or two or more polypeptide sequences, with identity being a more strict comparison. The phrases "percent identity" and "% identity" refer to the percentage of identical bases or residues at corresponding positions found in a comparison of two or more sequences (when a position in the compared sequence is occupied by the same nucleotide base or amino acid, then the molecules are identical at that position). "Sequence similarity" refers to the percentage of bases that are similar in the corresponding positions of two or more polynucleotide sequences. A degree of homology or similarity of polypeptide sequences is a function of the number of similar amino acid residues (see Table 3) at positions shared by the polypeptide sequences. Two or more sequences can be anywhere from 0-100% similar, or any integer value therebetween. Identity or similarity can be determined by comparing a position in each sequence that may be aligned for purposes of comparison.

"Alignment" refers to a number of nucleotide bases or amino acid residue sequences aligned by lengthwise comparison so that components in common (i.e., nucleotide bases or amino acid residues) may be visually and readily identified. The fraction or percentage of components in common is related to the homology or identity between the sequences. Alignments such as those of FIGS. 3A-L or FIG. 4 may be used to identify conserved domains and relatedness within these domains. An alignment may suitably be determined by means of computer programs known in the art, such as MACVECTOR software (1999) (Accelrys, Inc., San Diego, Calif.).

A "conserved domain" or "conserved region" as used herein refers to a region in heterologous polynucleotide or polypeptide sequences where there is a relatively high degree of sequence identity between the distinct sequences. An "AP2 domain", such as is found in a member of AP2 transcription factor family, is an example of a conserved domain. With respect to polynucleotides encoding presently disclosed transcription factors, a conserved domain is preferably at least 10 base pairs (bp) in length. A "conserved domain", with respect to presently disclosed AP2 polypeptides refers to a domain within a transcription factor family that exhibits a higher degree of sequence homology, such as at least 62% sequence identity including conservative substitutions, and more preferably at least 65% sequence identity, and even more preferably at least 69%, or at least about 70%, or at least about 72%, or at least about 72%, or at least about 73%, or at least about 74%, or at least about 75%, or at least about 76%, or at least about 77%, or at least about 78%, or at least about 79%, or at least about 80%, , or at least about 90%, or at least about 95%, or at least about 98% amino acid residue sequence identity to the conserved domain. A fragment or domain can be referred to as outside a conserved domain, outside a consensus sequence, or outside a consensus DNA-binding site that is known to exist or that exists for a particular transcription factor class, family, or sub-family. In this case, the fragment or domain will not include the exact amino acids of a consensus sequence or consensus DNA-binding site of a transcription factor class, family or sub-family, or the exact amino acids of a particular transcription factor consensus sequence or consensus DNA-binding site. Furthermore, a particular fragment, region, or domain of a polypeptide, or a polynucleotide encoding a polypeptide, can be "outside a conserved domain" if all the amino acids of the fragment, region, or domain fall outside of a defined conserved domain(s) for a polypeptide or protein. Sequences having lesser degrees of identity but comparable biological activity are considered to be equivalents.

As one of ordinary skill in the art recognizes, conserved domains may be identified as regions or domains of identity to a specific consensus sequence (for example, Riechmann et al. (2000) *Science* 290: 2105-2110). Thus, by using alignment methods well known in the art, the conserved domains of the plant transcription factors for the AP2 proteins may be determined.

Conserved domains for members of the G1792 clade of transcription factor polypeptides (or simply the "G1792 clade"), including SEQ ID NO: 2, 4, 6, 8, 10, 12, 14, 16, 18, 20, 22, 24, 26, 28, 30, 32, 34 and 36, are listed in Table 1. A comparison of these conserved domains with other sequences would allow one of skill in the art to identify AP2 or EDLL domains in the polypeptides listed or referred to in this disclosure, as well as other polypeptides not presented in this disclosure, but which comprise these domains.

"Complementary" refers to the natural hydrogen bonding by base pairing between purines and pyrimidines. For example, the sequence A-C-G-T (5'→3') forms hydrogen bonds with its complements A-C-G-T (5'→3') or A-C-G-U (5'→3'). Two single-stranded molecules may be considered partially complementary, if only some of the nucleotides bond, or "completely complementary" if all of the nucleotides bond. The degree of complementarity between nucleic acid strands affects the efficiency and strength of the hybridization and amplification reactions. "Fully complementary" refers to the case where bonding occurs between every base pair and its complement in a pair of sequences, and the two sequences have the same number of nucleotides.

The terms "highly stringent" or "highly stringent condition" refer to conditions that permit hybridization of DNA strands whose sequences are highly complementary, wherein these same conditions exclude hybridization of significantly mismatched DNAs. Polynucleotide sequences capable of hybridizing under stringent conditions with the polynucleotides of the present invention may be, for example, variants of the disclosed polynucleotide sequences, including allelic or splice variants, or sequences that encode orthologs or paralogs of presently disclosed polypeptides. Nucleic acid hybridization methods are disclosed in detail by Kashima et al. (1985) *Nature* 313:402-404, and Sambrook et al. (1989) *Molecular Cloning: A Laboratory Manual*, 2nd Ed., Cold Spring Harbor Laboratory, Cold Spring Harbor, N.Y.; and by Haymes et al. "*Nucleic Acid Hybridization: A Practical Approach*", IRL Press, Washington, D.C. (1985), which references are incorporated herein by reference.

In general, stringency is determined by the temperature, ionic strength, and concentration of denaturing agents (e.g., formamide) used in a hybridization and washing procedure (a more detailed description of establishing and determining stringency is disclosed below). The degree to which two nucleic acids hybridize under various conditions of stringency is correlated with the extent of their similarity. Thus, similar nucleic acid sequences from a variety of sources, such as within a plant's genome (as in the case of paralogs) or from another plant (as in the case of orthologs) that may perform similar functions can be isolated on the basis of their ability to hybridize with known transcription factor sequences. Numerous variations are possible in the conditions and means by which nucleic acid hybridization can be performed to isolate transcription factor sequences having similarity to transcription factor sequences known in the art and are not limited to those explicitly disclosed herein. Such an approach may be used to isolate polynucleotide sequences having various degrees of similarity with disclosed transcription factor sequences, such as, for example, encoded transcription factors having 62% or greater identity with the AP2 domain of disclosed transcription factors.

Regarding the terms "paralog" and "ortholog", homologous polynucleotide sequences and homologous polypeptide sequences may be paralogs or orthologs of the claimed polynucleotide or polypeptide sequence. Orthologs and paralogs are evolutionarily related genes that have similar sequence and similar functions. Orthologs are structurally related genes in different species that are derived by a speciation event. Paralogs are structurally related genes within a single species that are derived by a duplication event. Sequences that are sufficiently similar to one another will be appreciated by those of skill in the art and may be based upon percentage identity of the complete sequences, percentage identity of a conserved domain or sequence within the complete sequence, percentage similarity to the complete sequence, percentage similarity to a conserved domain or sequence within the complete sequence, and/or an arrangement of contiguous nucleotides or peptides particular to a conserved domain or complete sequence. Sequences that are sufficiently similar to one another will also bind in a similar manner to the same DNA binding sites of transcriptional regulatory elements using methods well known to those of skill in the art.

The term "equivalog" describes members of a set of homologous proteins that are conserved with respect to function since their last common ancestor. Related proteins are grouped into equivalog families, and otherwise into protein families with other hierarchically defined homology types. This definition is provided at the Institute for Genomic Research (TIGR) World Wide Web (www) website, "tigr.org" under the heading "Terms associated with TIGRFAMs".

The term "variant", as used herein, may refer to polynucleotides or polypeptides that differ from the presently disclosed polynucleotides or polypeptides, respectively, in sequence from each other, and as set forth below.

With regard to polynucleotide variants, differences between presently disclosed polynucleotides and polynucleotide variants are limited so that the nucleotide sequences of the former and the latter are closely similar overall and, in many regions, identical. Due to the degeneracy of the genetic code, differences between the former and latter nucleotide sequences may be silent (i.e., the amino acids encoded by the polynucleotide are the same, and the variant polynucleotide sequence encodes the same amino acid sequence as the presently disclosed polynucleotide. Variant nucleotide sequences may encode different amino acid sequences, in which case such nucleotide differences will result in amino acid substitutions, additions, deletions, insertions, truncations or fusions with respect to the similar disclosed polynucleotide sequences. These variations result in polynucleotide variants encoding polypeptides that share at least one functional characteristic. The degeneracy of the genetic code also dictates that many different variant polynucleotides can encode identical and/or substantially similar polypeptides in addition to those sequences illustrated in the Sequence Listing.

Also within the scope of the invention is a variant of a transcription factor nucleic acid listed in the Sequence Listing, that is, one having a sequence that differs from the one of the polynucleotide sequences in the Sequence Listing, or a complementary sequence, that encodes a functionally equivalent polypeptide (i.e., a polypeptide having some degree of equivalent or similar biological activity) but differs in sequence from the sequence in the Sequence Listing, due to degeneracy in the genetic code. Included within this definition are polymorphisms that may or may not be readily detectable using a particular oligonucleotide probe of the polynucleotide encoding polypeptide, and improper or unexpected hybridization to allelic variants, with a locus other than the normal chromosomal locus for the polynucleotide sequence encoding polypeptide.

"Allelic variant" or "polynucleotide allelic variant" refers to any of two or more alternative forms of a gene occupying the same chromosomal locus. Allelic variation arises naturally through mutation, and may result in phenotypic polymorphism within populations. Gene mutations may be "silent" or may encode polypeptides having altered amino acid sequence. "Allelic variant" and "polypeptide allelic variant" may also be used with respect to polypeptides, and in this case the term refer to a polypeptide encoded by an allelic variant of a gene.

"Splice variant" or "polynucleotide splice variant" as used herein refers to alternative forms of RNA transcribed from a gene. Splice variation naturally occurs as a result of alternative sites being spliced within a single transcribed RNA molecule or between separately transcribed RNA molecules, and may result in several different forms of mRNA transcribed from the same gene. Thus, splice variants may encode polypeptides having different amino acid sequences, which may or may not have similar functions in the organism. "Splice variant" or "polypeptide splice variant" may also refer to a polypeptide encoded by a splice variant of a transcribed mRNA.

As used herein, "polynucleotide variants" may also refer to polynucleotide sequences that encode paralogs and orthologs of the presently disclosed polypeptide sequences. "Polypeptide variants" may refer to polypeptide sequences that are paralogs and orthologs of the presently disclosed polypeptide sequences.

Differences between presently disclosed polypeptides and polypeptide variants are limited so that the sequences of the former and the latter are closely similar overall and, in many regions, identical. Presently disclosed polypeptide sequences and similar polypeptide variants may differ in amino acid sequence by one or more substitutions, additions, deletions, fusions and truncations, which may be present in any combination. These differences may produce silent changes and result in a functionally equivalent transcription factor. Thus, it will be readily appreciated by those of skill in the art, that any of a variety of polynucleotide sequences is capable of encoding the transcription factors and transcription factor homolog polypeptides of the invention. A polypeptide sequence variant may have "conservative" changes, wherein a substituted amino acid has similar structural or chemical properties. Deliberate amino acid substitutions may thus be made on the basis of similarity in polarity, charge, solubility, hydrophobicity, hydrophilicity, and/or the amphipathic nature of the residues, as long as the functional or biological activity of the transcription factor is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine (more detail on conservative substitutions appears in Table 3). More rarely, a variant may have "non-conservative" changes, e.g., replacement of a glycine with a tryptophan. Similar minor variations may also include amino acid deletions or insertions, or both. Related polypeptides may comprise, for example, additions and/or deletions of one or more N-linked or O-linked glycosylation sites, or an addition and/or a deletion of one or more cysteine residues. Guidance in determining which and how many amino acid residues may be substituted, inserted or deleted without abolishing functional or biological activity may be found using computer programs well known in the art, for example, DNASTAR software (U.S. Pat. No. 5,840,544).

"Fragment", with respect to a polynucleotide, refers to a clone or any part of a polynucleotide molecule that retains a usable, functional characteristic. Useful fragments include oligonucleotides and polynucleotides that may be used in hybridization or amplification technologies or in the regulation of replication, transcription or translation. A "polynucleotide fragment" refers to any subsequence of a polynucleotide, typically, of at least about 9 consecutive nucleotides, preferably at least about 30 nucleotides, more preferably at least about 50 nucleotides, of any of the sequences provided herein. Exemplary polynucleotide fragments are the first sixty consecutive nucleotides of the transcription factor polynucleotides listed in the Sequence Listing. Exemplary fragments also include fragments that comprise a region that encodes an AP2 domain of a transcription factor. Exemplary fragments also include fragments that comprise a conserved domain of a transcription factor. Exemplary fragments include fragments that comprise an AP2 conserved domain, for example, amino acid residues 16-80 of G1792 (SEQ ID NO: 2), or an EDLL domain, amino acid residues 117-132, as noted in Table 1.

Fragments may also include subsequences of polypeptides and protein molecules, or a subsequence of the polypeptide. Fragments may have uses in that they may have antigenic potential. In some cases, the fragment or domain is a subsequence of the polypeptide which performs at least one biological function of the intact polypeptide in substantially the same manner, or to a similar extent, as does the intact polypeptide. For example, a polypeptide fragment can comprise a recognizable structural motif or functional domain such as a DNA-binding site or domain that binds to a DNA promoter region, an activation domain, or a domain for protein-protein interactions, and may initiate transcription. Fragments can vary in size from as few as 3 amino acid residues to the full length of the intact polypeptide, but are preferably at least about 30 amino acid residues in length and more preferably at least about 60 amino acid residues in length.

The invention also encompasses production of DNA sequences that encode transcription factors and transcription factor derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding transcription factors or any fragment thereof.

"Derivative" refers to the chemical modification of a nucleic acid molecule or amino acid sequence. Chemical modifications can include replacement of hydrogen by an alkyl, acyl, or amino group or glycosylation, pegylation, or any similar process that retains or enhances biological activity or lifespan of the molecule or sequence.

The term "plant" includes whole plants, shoot vegetative organs/structures (for example, leaves, stems and tubers), roots, flowers and floral organs/structures (for example, bracts, sepals, petals, stamens, carpels, anthers and ovules), seed (including embryo, endosperm, and seed coat), fruit (the mature ovary), plant tissue (for example, vascular tissue or ground tissue), cells (for example, guard cells, egg cells, and the like), and progeny of plants. The class of plants that can be used in the method of the invention is generally as broad as the class of higher and lower plants amenable to transformation techniques, including angiosperms (monocotyledonous and dicotyledonous plants), gymnosperms, ferns, horsetails, psilophytes, lycophytes, bryophytes, and multicellular algae (as shown in FIG. 1, adapted from Daly et al. (2001) *Plant Physiol.* 127: 1328-1333; FIG. 2, adapted from Ku et al. (2000) *Proc. Natl. Acad. Sci. U.S.A.* 97: 9121-9126; and also Tudge in *The Variety of Life*, Oxford University Press, New York, N.Y. (2000) pp. 547-606).

A "transgenic plant" refers to a plant that contains genetic material not found in a wild-type plant of the same species, variety or cultivar. The genetic material may include a transgene, an insertional mutagenesis event (such as by transposon or T-DNA insertional mutagenesis), an activation tagging sequence, a mutated sequence, a homologous recombination event or a sequence modified by chimeraplasty. Typically, the foreign genetic material has been introduced into the plant by human manipulation, but any method can be used as one of skill in the art recognizes.

A transgenic plant may contain an expression vector or cassette. The expression cassette typically comprises a polypeptide-encoding sequence operably linked (i.e., under regulatory control of) to appropriate inducible or constitutive regulatory sequences that allow for the expression of polypeptide. The expression cassette can be introduced into a plant by transformation or by breeding after transformation of a parent plant. A plant refers to a whole plant as well as to a plant part, such as seed, fruit, leaf, or root, plant tissue, plant cells or any other plant material, e.g., a plant explant, as well as to progeny thereof, and to in vitro systems that mimic biochemical or cellular components or processes in a cell.

"Wild type" or "wild-type", as used herein, refers to a plant cell, seed, plant component, plant tissue, plant organ or whole plant that has not been genetically modified or treated in an experimental sense. Wild-type cells, seed, components, tissue, organs or whole plants may be used as controls to compare levels of expression and the extent and nature of trait modification with cells, tissue or plants of the same species in which a transcription factor expression is altered, e.g., in that it has been knocked out, overexpressed, or ectopically expressed.

A "control plant" as used in the present invention refers to a plant cell, seed, plant component, plant tissue, plant organ or whole plant used to compare against transgenic or genetically modified plant for the purpose of identifying an enhanced phenotype in the transgenic or genetically modified plant. A control plant may in some cases be a transgenic plant line that comprises an empty vector or marker gene, but does not contain the recombinant polynucleotide of the present invention that is expressed in the transgenic or genetically modified plant being evaluated. In general, a control plant is a plant of the same line or variety as the transgenic or genetically modified plant being tested. A suitable control plant would include a genetically unaltered or non-transgenic plant of the parental line used to generate a transgenic plant herein.

A "trait" refers to a physiological, morphological, biochemical, or physical characteristic of a plant or particular plant material or cell. In some instances, this characteristic is visible to the human eye, such as seed or plant size, or can be measured by biochemical techniques, such as detecting the protein, starch, or oil content of seed or leaves, or by observation of a metabolic or physiological process, e.g. by measuring tolerance to water deprivation or particular salt or sugar concentrations, or by the observation of the expression level of a gene or genes, e.g., by employing Northern analysis, RT-PCR, microarray gene expression assays, or reporter gene expression systems, or by agricultural observations such as osmotic stress tolerance or yield. Any technique can be used to measure the amount of, comparative level of, or difference in any selected chemical compound or macromolecule in the transgenic plants, however.

"Trait modification" refers to a detectable difference in a characteristic in a plant ectopically expressing a polynucleotide or polypeptide of the present invention relative to a plant not doing so, such as a wild-type plant. In some cases, the trait modification can be evaluated quantitatively. For example, the trait modification can entail at least about a 2% or greater increase or decrease in an observed trait compared with a wild-type or control plant. It is known that there can be a natural variation in the modified trait. Therefore, the trait modification observed entails a change of the normal distribution of the trait in the plants compared with the distribution observed in wild-type plants.

When two or more plants are "morphologically similar" they have comparable forms or appearances, including analogous features such as dimension, height, width, mass, root mass, shape, glossiness, color, stem diameter, leaf size, leaf dimension, leaf density, internode distance, branching, root branching, number and form of inflorescences, and other macroscopic characteristics.

"Modulates" refers to a change in activity (biological, chemical, or immunological) or lifespan resulting from specific binding between a molecule and either a nucleic acid molecule or a protein.

The term "transcript profile" refers to the expression levels of a set of genes in a cell in a particular state, particularly by comparison with the expression levels of that same set of genes in a cell of the same type in a reference state. For example, the transcript profile of a particular transcription factor in a suspension cell is the expression levels of a set of genes in a cell knocking out or overexpressing that transcription factor compared with the expression levels of that same set of genes in a suspension cell that has normal levels of that transcription factor. The transcript profile can be presented as a list of those genes whose expression level is significantly different between the two treatments, and the difference ratios. Differences and similarities between expression levels may also be evaluated and calculated using statistical and clustering methods.

"Ectopic expression or altered expression" in reference to a polynucleotide indicates that the pattern of expression in, e.g., a transgenic plant or plant tissue, is different from the expression pattern in a wild-type plant or a reference plant of the same species. The pattern of expression may also be compared with a reference expression pattern in a wild-type plant of the same species. For example, the polynucleotide or polypeptide is expressed in a cell or tissue type other than a cell or tissue type in which the sequence is expressed in the wild-type plant, or by expression at a time other than at the time the sequence is expressed in the wild-type plant, or by a response to different inducible agents, such as hormones or environmental signals, or at different expression levels (either higher or lower) compared with those found in a wild-type plant. The term also refers to altered expression patterns that are produced by lowering the levels of expression to below the detection level or completely abolishing expression. The resulting expression pattern can be transient or stable, constitutive or inducible. In reference to a polypeptide, the term "ectopic expression or altered expression" further may relate to altered activity levels resulting from the interactions of the polypeptides with exogenous or endogenous modulators or from interactions with factors or as a result of the chemical modification of the polypeptides.

The term "overexpression" as used herein refers to a greater expression level of a gene in a plant, plant cell or plant tissue, compared to expression in a wild-type plant, cell or tissue, at any developmental or temporal stage for the gene. Overexpression can occur when, for example, the genes encoding one or more transcription factors are under the control of a strong expression signal, such as one of the promoters described herein (e.g., the cauliflower mosaic virus 35S transcription initiation region). Overexpression may occur throughout a plant or in specific tissues of the plant, depending on the promoter used, as described below.

Overexpression may take place in plant cells normally lacking expression of polypeptides functionally equivalent or identical to the present transcription factors. Overexpression may also occur in plant cells where endogenous expression of the present transcription factors or functionally equivalent molecules normally occurs, but such normal expression is at a lower level. Overexpression thus results in a greater than normal production, or "overproduction" of the transcription factor in the plant, cell or tissue.

The term "transcription regulating region" refers to a DNA regulatory sequence that regulates expression of one or more genes in a plant when a transcription factor having one or more specific binding domains binds to the DNA regulatory sequence. Transcription factors of the present invention possess an AP2 domain. Examples of AP2 or EDLL conserved domains of the sequences of the invention may be found in Table 1. The transcription factors of the invention also comprise an amino acid subsequence that forms a transcription activation domain that regulates expression of one or more abiotic stress or disease tolerance genes in a plant when the transcription factor binds to the regulating region.

"Substantially purified" refers to nucleic acid molecules or proteins that are removed from their natural environment and are isolated or separated, and are at least about 60% free, preferably about 75% free, and most preferably about 90% free, from other components with which they are naturally associated.

DESCRIPTION OF THE SPECIFIC EMBODIMENTS

Transcription Factors Modify Expression of Endogenous Genes

A transcription factor may include, but is not limited to, any polypeptide that can activate or repress transcription of a single gene or a number of genes. As one of ordinary skill in the art recognizes, transcription factors can be identified by the presence of a region or domain of structural similarity or identity to a specific consensus sequence or the presence of a specific consensus DNA-binding site or DNA-binding site motif (for example, Riechmann et al. (2000) supra). The plant transcription factors of the present invention belong to the AP2 transcription factor family (Riechmann and Meyerowitz (1998) *Biol. Chem.* 379: 633-646).

Generally, the transcription factors encoded by the present sequences are involved in cell differentiation and proliferation and the regulation of growth. Accordingly, one skilled in the art would recognize that by expressing the present sequences in a plant, one may change the expression of autologous genes or induce the expression of introduced genes. By affecting the expression of similar autologous sequences in a plant that have the biological activity of the present sequences, or by introducing the present sequences into a plant, one may alter a plant's phenotype to one with improved traits related to osmotic stresses. The sequences of the invention may also be used to transform a plant and introduce desirable traits not found in the wild-type cultivar or strain. Plants may then be selected for those that produce the most desirable degree of over- or under-expression of target genes of interest and coincident trait improvement.

The sequences of the present invention may be from any species, particularly plant species, in a naturally occurring form or from any source whether natural, synthetic, semi-synthetic or recombinant. The sequences of the invention may also include fragments of the present amino acid sequences. Where "amino acid sequence" is recited to refer to an amino acid sequence of a naturally occurring protein molecule, "amino acid sequence" and like terms are not meant to limit the amino acid sequence to the complete native amino acid sequence associated with the recited protein molecule.

In addition to methods for modifying a plant phenotype by employing one or more polynucleotides and polypeptides of the invention described herein, the polynucleotides and polypeptides of the invention have a variety of additional uses. These uses include their use in the recombinant production (i.e., expression) of proteins; as regulators of plant gene expression, as diagnostic probes for the presence of complementary or partially complementary nucleic acids (including for detection of natural coding nucleic acids); as substrates for further reactions, e.g., mutation reactions, PCR reactions, or the like; as substrates for cloning e.g., including digestion or ligation reactions; and for identifying exogenous or endogenous modulators of the transcription factors. In many instances, a polynucleotide comprises a nucleotide sequence encoding a polypeptide (or protein) or a domain or fragment thereof. Additionally, the polynucleotide may comprise a promoter, an intron, an enhancer region, a polyadenylation site, a translation initiation site, 5' or 3' untranslated regions, a reporter gene, a selectable marker, or the like. The polynucleotide can be single stranded or double stranded DNA or RNA. The polynucleotide optionally comprises modified bases or a modified backbone. The polynucleotide can be, e.g., genomic DNA or RNA, a transcript (such as an mRNA), a cDNA, a PCR product, a cloned DNA, a synthetic DNA or RNA, or the like. The polynucleotide can comprise a sequence in either sense or antisense orientations.

Expression of genes that encode transcription factors that modify expression of endogenous genes, polynucleotides, and proteins are well known in the art. In addition, transgenic plants comprising isolated polynucleotides encoding transcription factors may also modify expression of endogenous genes, polynucleotides, and proteins. Examples include Peng et al. (1997) *Genes Development* 11: 3194-3205, and Peng et al. (1999) *Nature*, 400: 256-261. In addition, many others have demonstrated that an *Arabidopsis* transcription factor expressed in an exogenous plant species elicits the same or very similar phenotypic response (for example, Fu et al. (2001) *Plant Cell* 13: 1791-1802; Nandi et al. (2000) *Curr. Biol.* 10: 215-218; Coupland (1995) *Nature* 377: 482-483; and Weigel and Nilsson (1995) *Nature* 377: 482-500).

In another example, a transcription factor expressed in another plant species elicits the same or very similar phenotypic response of the endogenous sequence, as often predicted in earlier studies of *Arabidopsis* transcription factors in *Arabidopsis* (Mandel et al. (1992) *Cell* 71:133-143) and Suzuki et al. (2001) *Plant J.* 28: 409-418). Other examples include Muller et al. (2001) *Plant J.* 28: 169-179; Kim et al. (2001) *Plant J.* 25: 247-259; Kyozuka and Shimamoto (2002) *Plant Cell Physiol.* 43: 130-135; Boss and Thomas (2002) *Nature*, 416: 847-850; He et al. (2000) *Transgenic Res.* 9: 223-227; and Robson et al. (2001) *Plant J.* 28: 619-631.

In yet another example, Gilmour et al. ((1998) *Plant J.* 16: 433-442) teach an *Arabidopsis* AP2 transcription factor, CBF1, that increases plant freezing tolerance when overexpressed in transgenic plants. Jaglo et al. ((2001) *Plant Physiol.* 127: 910-917) further identified sequences in *Brassica napus* which encode CBF-like genes and that transcripts for these genes accumulated rapidly in response to low temperature. Transcripts encoding CBF-like proteins were also found to accumulate rapidly in response to low temperature in wheat, as well as in tomato. An alignment of the CBF proteins from *Arabidopsis, B. napus*, wheat, rye, and tomato revealed the presence of conserved consecutive amino acid residues, PKK/RPAGRxKFxETRHP (SEQ ID NO: 56 or 57) and DSAWR (SEQ ID NO: 58), which bracket the AP2/EREBP DNA binding domains of the proteins and distinguish them from other members of the AP2/EREBP protein family (Jaglo et al. (2001) supra).

Transcription factors mediate cellular responses and control traits through altered expression of genes containing cis-acting nucleotide sequences that are targets of the introduced transcription factor. It is well appreciated in the Art that the effect of a transcription factor on cellular responses or a cellular trait is determined by the particular genes whose expression is either directly or indirectly (e.g., by a cascade of transcription factor binding events and transcriptional changes) altered by transcription factor binding. In a global analysis of transcription comparing a standard condition with one in which a transcription factor is overexpressed, the resulting transcript profile associated with transcription factor overexpression is related to the trait or cellular process controlled by that transcription factor. For example, the PAP2 gene and other genes in the MYB family have been shown to control anthocyanin biosynthesis through regulation of the expression of genes known to be involved in the anthocyanin biosynthetic pathway (Bruce et al. (2000) *Plant Cell* 12: 65-79; and Borevitz et al. (2000) *Plant Cell* 12: 2383-2393). Further, global transcript profiles have been used successfully as diagnostic tools for specific cellular states (e.g., cancerous vs. non-cancerous; Bhattacharjee et al. (2001) *Proc. Natl. Acad. Sci. U.S.A.* 98: 13790-13795; and Xu et al. (2001) *Proc. Natl. Acad. Sci. U.S.A.* 98: 15089-15094). Consequently, it is evident to one skilled in the art that similarity of transcript profile upon overexpression of different transcription factors would indicate similarity of transcription factor function.

Polypeptides and Polynucleotides of the Invention

The present invention provides, among other things, transcription factors (TFs), and transcription factor homolog polypeptides, and isolated or recombinant polynucleotides encoding the polypeptides, or novel sequence variant polypeptides or polynucleotides encoding novel variants of transcription factors derived from the specific sequences provided in the Sequence Listing. Also provided are methods for increasing a plant's tolerance to one or more pathogens or abiotic stresses. These methods are based on the ability to alter the expression of critical regulatory molecules that may be conserved between diverse plant species. Related conserved regulatory molecules may be originally discovered in a model system such as *Arabidopsis* and homologous, functional molecules then discovered in other plant species. The latter may then be used to confer tolerance to one or more pathogens or abiotic stresses in diverse plant species.

Exemplary polynucleotides encoding the polypeptides of the invention were identified in the *Arabidopsis thaliana* GenBank database using publicly available sequence analysis programs and parameters. Sequences initially identified were then further characterized to identify sequences comprising specified sequence strings corresponding to sequence motifs present in families of known transcription factors. In addition, further exemplary polynucleotides encoding the polypeptides of the invention were identified in the plant GenBank database using publicly available sequence analysis programs and parameters. Sequences initially identified were then further characterized to identify sequences comprising specified sequence strings corresponding to sequence motifs present in families of known transcription factors. Polynucleotide sequences meeting such criteria were confirmed as transcription factors.

Additional polynucleotides of the invention were identified by screening *Arabidopsis thaliana* and/or other plant cDNA libraries with probes corresponding to known transcription factors under low stringency hybridization conditions. Additional sequences, including full length coding sequences were subsequently recovered by the rapid amplification of cDNA ends (RACE) procedure, using a commercially available kit according to the manufacturer's instructions. Where necessary, multiple rounds of RACE are performed to isolate 5' and 3' ends. The full-length cDNA was then recovered by a routine end-to-end polymerase chain reaction (PCR) using primers specific to the isolated 5' and 3' ends. Exemplary sequences are provided in the Sequence Listing.

These sequences and others derived from diverse species and found in the sequence listing have been ectopically expressed in overexpressor plants. The changes in the characteristic(s) or trait(s) of the plants were then observed and found to confer increased abiotic stress or disease tolerance. Therefore, the polynucleotides and polypeptides can be used to improve desirable characteristics of plants.

The polynucleotides of the invention were also ectopically expressed in overexpressor plant cells and the changes in the expression levels of a number of genes, polynucleotides, and/or proteins of the plant cells observed. Therefore, the polynucleotides and polypeptides can be used to change expression levels of a genes, polynucleotides, and/or proteins of plants.

The AP2 family, including the G1792 clade. AP2 (APETALA2) and EREBPs (Ethylene-Responsive Element Binding Proteins) are the prototypic members of a family of transcription factors unique to plants, whose distinguishing characteristic is that they contain AP2 DNA-binding domain (a review appears in Riechmann and Meyerowitz (1998) *Biol. Chem.* 379: 633-646). The AP2 domain was first recognized as a repeated motif within the *Arabidopsis thaliana* AP2 protein (Jofuku et al. (1994) *Plant Cell* 6: 1211-1225). Shortly afterwards, four DNA-binding proteins from tobacco were identified that interact with a sequence that is essential for the responsiveness of some promoters to the plant hormone ethylene, and were designated as ethylene-responsive element binding proteins (EREBPs; Ohme-Takagi et al. (1995) *Plant Cell* 7: 173-182). The DNA-binding domain of EREBP-2 was mapped to a region that was common to all four proteins (Ohme-Takagi et al (1995) supra), and that was found to be closely related to the AP2 domain (Weigel (1995) *Plant Cell* 7: 388-389) but that did not bear sequence similarity to previously known DNA-binding motifs.

AP2/EREBP genes form a large family, with many members known in several plant species (Okamuro et al. (1997) *Proc. Natl. Acad. Sci. U.S.A.* 94: 7076-7081; Riechmann and Meyerowitz (1998) supra). The number of AP2/EREBP genes in the *Arabidopsis thaliana* genome is approximately 145 (Riechmann et al. (2000) *Science* 290: 2105-2110). The APETALA2 class is characterized by the presence of two AP2 DNA binding domains, and contains 14 genes. The AP2/ERF is the largest subfamily, and includes 125 genes which are involved in abiotic (DREB subgroup) and biotic (ERF subgroup) stress responses and the RAV subgroup includes 6 genes which all have a B3 DNA binding domain in addition to the AP2 DNA binding domain (Kagaya et al. (1999) *Nucleic Acids Res.* 27: 470-478).

*Arabidopsis* AP2 is involved in the specification of sepal and petal identity through its activity as a homeotic gene that forms part of the combinatorial genetic mechanism of floral organ identity determination and it is also required for normal ovule and seed development (Bowman et al. (1991) *Development* 112: 1-20; Jofuku et al. (1994) supra). *Arabidopsis* ANT is required for ovule development and it also plays a role in floral organ growth (Elliott et al. (1996) *Plant Cell* 8: 155-168; Klucher et al. (1996) *Plant Cell* 8: 137-153). Finally, maize G115 regulates leaf epidermal cell identity (Moose et al. (1996) *Genes Dev.* 10: 3018-3027).

The attack of a plant by a pathogen may induce defense responses that lead to resistance to the invasion, and these responses are associated with transcriptional activation of defense-related genes, among them those encoding pathogenesis-related (PR) proteins. The involvement of EREBP-like genes in controlling the plant defense response is based on the observation that many PR gene promoters contain a short cis-acting element that mediates their responsiveness to ethylene (ethylene appears to be one of several signal molecules controlling the activation of defense responses). Tobacco EREBP-1, -2, -3, and -4, and tomato Pti4, Pti5 and Pti6 proteins have been shown to recognize such cis-acting elements (Ohme-Takagi (1995) supra; Zhou et al. (1997) *EMBO J.* 16: 3207-3218). In addition, Pti4, Pti5, and Pti6 proteins have been shown to directly interact with Pto, a protein kinase that confers resistance against *Pseudomonas syringae* pv tomato (Zhou et al. (1997) supra). Plants are also challenged by adverse environmental conditions like cold or drought, and EREBP-like proteins appear to be involved in the responses to these abiotic stresses as well. COR (for cold-regulated) gene expression is induced during cold acclimation, the process by which plants increase their resistance to freezing in response to low unfreezing temperatures. The *Arabidopsis* EREBP-like gene CBF1 (Stockinger et al. (1997) *Proc. Natl. Acad. Sci. U.S.A.* 94: 1035-1040) is a regulator of the cold acclimation response, because ectopic expression of CBF1 in *Arabidopsis* transgenic plants induced COR gene expression in the absence of a cold stimulus, and the plant freezing tolerance was increased (Jaglo-Ottosen et al. (1998) *Science* 280: 104-106). Finally, another *Arabidopsis* EREBP-like gene, ABI4, is involved in abscisic acid (ABA) signal transduction, because abi4 mutants are insensitive to ABA (ABA is a plant hormone that regulates many agronomically important aspects of plant development; Finkelstein et al. (1998) *Plant Cell* 10: 1043-1054).

We first identified G1792 (AT3G23230) as a putative transcription factor in the sequence of BAC clone K14B15 (AB025608, gene K14B15.14). We have assigned the name TRANSCRIPTIONAL REGULATOR OF DEFENSE RESPONSE 1 (TDR1) to this gene, based on its apparent role in disease responses. The G1792 protein and other polypeptides within the G1792 clade contain a single AP2 domain and belong to the ERF class of AP2 proteins.

The primary amino acid sequence of G1792 and other members of the G1792 clade, showing the relative positions of the AP2 domain, are presented in FIGS. 3A-3L. In addition to the AP2 domain, the G1792 clade of transcription factor polypeptides contains a putative activation domain designated the "EDLL domain". Four amino acids are highly conserved in the paralogs and orthologs of G1792 within this domain. These conserved residues comprise glutamic acid, aspartic acid, and two leucine residues (hence the "EDLL" designation) in the subsequence:

Glu-(Xaa)$_4$-Asp-(Xaa)$_3$-Leu-(Xaa)$_3$-Leu (SEQ ID NO: 55)

where Xaa can be any amino acid, including those represented in FIG. 4.

AtERF Type Transcription Factors Respond to Abiotic Stress

While ERF type transcription factors are primarily recognized for responding to a variety of biotic stresses (such as pathogen infection), some ERFs have been characterized as being responsive to abiotic stress. Fujimoto et. al. (2000) *Plant Cell* 12: 393-404 have shown that AtERF1-5 (corresponding to G28, SEQ ID NO: 48, G1006, SEQ ID NO: 46, G1005, G6 and G1004 respectively) can respond to various abiotic stresses, including cold, heat, drought, ABA, CHX, and wounding. Genes normally associated with the plant defense response (PR1, PR2, PR5, and peroxidases) have also been shown to be regulated by water stress (Zhu et. al. (1995) *Plant Physiol.* 108: 929-937; Ingram and Bartels (1996). *Annu Rev. Plant Physiol. Plant Mol. Biol.* 47:377-403) suggesting some overlap between the two responses. A target sequence for ERF-type transcription factors has been identified and extensively studied (Hao et al. (1998) *J. Biol. Chem.* 273: 26857-26861). This target sequence consists of AGC-CGCC and has been found in the 5' upstream regions of genes responding to disease and regulated by ERFs. However, it is also certainly the case that several genes (ARSK1 and dehydrin) known to be induced by ABA, NaCl, cold and wounding, also possess a GCC box regulatory element in their 5' upstream regions (Hwang and Goodman (1995) *Plant J.* 8: 37-43) suggesting that ERF type transcription factors may regulate also regulate abiotic stress associated genes.

ERF Type Transcription Factors in Other Species

ERF type transcription factors have been characterized in other species. Tsi1, a tobacco AtERF ortholog has been shown to be responsive to NaCl, drought (mildly responsive), wounding, salicylic acid (SA), ethephon, abscisic acid (ABA), and methyl jasmonate (MeJA; Park et. al. (2001) *Plant Cell* 13: 1035-1046). Tsi1 is most closely related by BLAST to At4g27950 (G1750) in *Arabidopsis*. RT data suggest that At4g27950 may also have a similar function although overexpression of At4g27950 causes some deleterious effects. In tobacco plants, however, overexpression of Tsi1 enhances resistance to both pathogen challenge and osmotic stress (Park et. al. (2001) supra). Interestingly, Tsi1 has also been shown to interact specifically with both GCC and DRE regulatory elements. Genes containing DRE elements are known to be regulated in response to abiotic stresses; as such, it is possible that Tsi1 has the ability to regulate the transcription of genes involved in abiotic stresses such as drought.

ERF-type transcription factors are well known to be transcriptional activators of disease responses (Fujimoto et. al. (2000) supra; Gu et al. (2000) *Plant Cell* 12: 771-786; Chen et al. (2002) *Plant Cell* 14: 559-574; Cheong et al. (2002) *Plant Physiol.* 129: 661-677; Onate-Sanchez and Singh (2002) *Plant Physiol.* 128: 1313-1322; Brown et al. (2003) *Plant Physiol.* 132: 1020-1032; Lorenzo et al. (2003) *Plant Cell* 15: 165-178) but have not been well characterized as being involved in response to abiotic stress conditions such as drought. Other AP2 transcription factors (DREBs), including the CBF class, are known to bind DRE elements in genes responding to abiotic stresses such as drought, high salt, and cold (Haake et al. (2002) *Plant Physiol.* 130: 639-648; Thomashow (2001) *Plant Physiol.* 125: 89-93, Liu et al. (1998) *Plant Cell* 10: 1391-1406; Gilmour et al. (2000) *Plant Physiol.* 124: 1854-1865; and Shinozaki and Yamaguchi-Shinozaki (2000) *Curr. Opin. Plant Biol.* 3: 217-223).

The Role of ERF Type Transcription Factors in Disease Responses

Pti4, Pti5 and Pti6 were identified as interactors with the tomato disease resistance protein Pto in yeast 2-hybrid assays (Zhou et al, (1997) *EMBO J.* 16: 3207-3218). Since that time, several ERF genes have been shown to enhance disease resistance when overexpressed in *Arabidopsis* or other species. These ERF genes include ERF1 (G1266) of *Arabidopsis* (Berrocal-Lobo et al. (2002) *Plant J.* 29: 23-32, Pti4 (Gu et al. (2002) *Plant Cell* 14: 817-831 and Pti5 (He et al. (2001) *Mol. Plant Microbe Interact.* 14: 1453-1457) of tomato, Tsi1 of tobacco (Park et. al. (2001) supra; Shin et al. (2002) *Mol. Plant Microbe Interact.* 15: 983-989, and AtERF1 (G28, SEQ ID NO: 48) and TDR1 (G1792, SEQ ID NO: 2) of *Arabidopsis* (included in the present data).

Regulation of ERF TFs by Pathogen and Small Molecule Signaling

ERF genes show a variety of stress-regulated expression patterns. Regulation by disease-related stimuli such as ethylene (ET), jasmonic acid (JA), salicylic acid (SA), and infection by virulent or avirulent pathogens has been shown for a number of ERF genes (Fujimoto et. al. (2000) supra; Gu et al. (2000) supra; Chen et al. (2002) stipra; Cheong et al. (2002) supra; Onate-Sanchez and Singh (2002) supra; Brown et al. (2003) supra; Lorenzo et al. (2003) supra). However, some ERF genes are also induced by wounding and abiotic stresses (Fujimoto et. al. (2000) supra; Park et al. (2001) *Plant Cell* 13: 1035-1046; Chen et al. (2002) supra; Tournier et al. (2003) *FEBS Lett.* 550: 149-154). Currently, it is difficult to assess the overall picture of ERF regulation in relation to phylogeny, since different studies have concentrated on different ERF genes, treatments and time points. Significantly, several ERF transcription factors that confer enhanced disease resistance when overexpressed, such as ERF1, Pti4, and AtERF1, are transcriptionally regulated by pathogens, ET, and JA (Fujimoto et. al. (2000) supra; Onate-Sanchez and Singh (2002) supra; Brown et al. (2003) supra; Lorenzo et al. (2003) supra). ERF1 is induced synergistically by ET and JA, and induction by either hormone is dependent on an intact signal transduction pathway for both hormones, indicating that ERF1 may be a point of integration for ET and JA (Lorenzo et al. (2003) supra). At least 4 other ERFs are also induced by JA and ET (Brown et al. (2003) supra), implying that other ERFs are probably also important in ET/JA signal transduction. A number of the genes in subgroup 1, including AtERF3 and AtERF4, are thought to act as transcriptional repressors (Fujimoto et. al. (2000) supra), and these two genes were found to be induced by ET, JA, and an incompatible pathogen (Brown et al. (2003) supra).

The SA signal transduction pathway can act antagonistically to the ET/JA pathway. Interestingly, Pti4 and AtERF1 are induced by SA as well as by JA and ET (Gu et al. (2000) supra; Onate-Sanchez and Singh (2002) supra). Pti4, Pti5 and Pti6 have been implicated indirectly in regulation of the SA response, perhaps through interaction with other transcription factors, since overexpression of these genes in *Arabidopsis* induced SA-regulated genes without SA treatment and enhanced the induction seen after SA treatment (Gu et al. (2002) supra).

Post-transcriptional regulation of ERF genes by phosphorylation may be a significant form of regulation. Pti4 has been shown to be phosphorylated specifically by the Pto kinase, and this phosphorylation enhances binding to its target sequence (Gu et al. (2000) supra). Recently, the OsEREBP1 gene of rice has been shown to be phosphorylated by the pathogen-induced MAP kinase BWMK1, and this phosphorylation was shown to enhance its binding to the GCC box (Cheong et al. (2003) *Plant Physiol.* 132: 1961-1972), suggesting that phosphorylation of ERF proteins maybe a common theme. A potential MAPK phosphorylation site has been noted in AtERF5 (Fujimoto et. al. (2000) supra).

Target Genes Regulated by ERF TFs

Binding of ERF transcription factors to the target sequence AGCCGCC (the GCC box) has been extensively studied (Hao et al. (1998) supra). This element is found in a number of promoters of pathogenesis-related and ET- or JA-induced genes. However, it is unclear how much overlap there is in target genes for particular ERFs. Recent studies have profiled genes induced in Arabidopsis plants overexpressing ERF1 (Lorenzo et al. (2003) supra) and Pti4 (Chakravarthy et al. (2003) *Plant Cell* 15: 3033-3050). However, these studies were done with different technology (Affymetrix GeneChip vs. serial analysis of gene expression) and under different conditions, and it is therefore difficult to compare the results directly. There is evidence that flanking sequences can affect the binding of ERFs to the GCC box (Gu et al. (2002) supra; Tournier et al. (2003) supra), so it is likely that different ERFs will regulate somewhat different gene sets.

Protein Structure and Properties: Tertiary Structure

The solution structure of an ERF type transcription factor domain in complex with the GCC box has been determined (Allen et. al. (1998) *EMBO J.* 17: 5484-5496). It consists of a β-sheet composed of three strands and an α-helix. Flanking sequences of the AP2 domain of this protein were replaced with the flanking sequences of the related CBF1 protein and the chimeric protein was found to contain the same arrangement of secondary structural elements as the native ERF type protein (Allen, M. D., personal communication). This implies that the secondary structural motifs may be conserved for similar ERF type transcription factors within the family.

Protein Structure and Properties: DNA Binding Motifs

Two positions have been identified as defining ERF class transcription factors. These consist of amino acids Ala-14 and Asp-19 in the AP2 domain (Sakuma et. al. (2002) *Biochem. Biophys. Res. Commun.* 290: 998-1009). Recent work indicates that these two amino acids (Ala-14 and Asp-19) have a key function in determining the target specificity (Sakuma et. al. (2002) supra; Hao et al. (2002) *Biochemistry* 41: 4202-4208) and interact directly with the DNA. The 3-dimensional structure/GCC box complex indicates the interaction of the second strand of the β-sheet with the DNA. The GCC box binding motif of ERF type transcription factors consists of a core sequence of AGCCCGCC.

Table 1 shows the polypeptides identified by: polypeptide SEQ ID NO (first column); the Gene ID (GID) No. and species (second column); the conserved domain coordinates for the AP2 and EDLL domains in amino acid residue coordinates (third column); AP2 domain sequences of the respective polypeptides (fourth column); the identity in percentage terms of the respective AP2 domains to the AP2 domain of G1792 (fifth column); EDLL domain sequences of the respective polypeptides (sixth column); and the percent identity of the respective EDLL domains to the EDLL domain of G1792 (seventh column). Polypeptide sequences that are shown herein to confer disease tolerance include *Arabidopsis* G30, G1791, G1792, and G1795, soybean G3520, and rice G3381. These sequences have AP2 domains with 76% or greater identity to the AP2 domain of G1792, and 75% or greater identity to the EDLL domain of G1792.

TABLE 1

Gene families and conserved domains of G1792 clade members

| SEQ ID NO: | GID No./ Species | AP2 and EDLL Domains in AA Coordinates | AP2 domain | % ID to AP2 Domain of G1792 | EDLL Domain | % ID to EDLL Domain of G1792 |
|---|---|---|---|---|---|---|
| 2 | G1792 At | 16-80; 117-132 | KQARFRGVRRRPWGKFAA EIRDPSRNGARLWLGTFET AEEAARAYDRAAFNLRGH LAILNFPNEY | 100% | VFEFEYLD DKVLEELL | 100% |
| 6 | G1795 At | 11-75; 104-119 | EHGKYRGVRRRPWGKYA AEIRDSRKHGERVWLGTF DTAEEAARAYDQAAYSM RGQAAILNFPHEY | 69% | VFEFEYLD DSVLEELL | 93% |
| 8 | G30 At | 16-80; 100-115 | EQGKYRGVRRRPWGKYA AEIRDSRKHGERVWLGTF DTAEDAARAYDRAAYSM RGKAAILNFPHEY | 70% | VFEFEYLD DSVLDELL | 87% |
| 14 | G3383 Os | 9-73; 101-116 | TATKYRGVRRRPWGKFAA EIRDPERGGARVWLGTFD TAEEAARAYDRAAYAQR GAAAVLNFPAAA | 79% | KIEFEYLD DKVLDDLL | 85% |
| 4 | G1791 At | 10-74; 108-123 | NEMKYRGVRKRPWGKYA AEIRDSARHGARVWLGTF NTAEDAARAYDRAAFGM RGQRAILNFPHEY | 73% | VIEFEYLD DSLLEELL | 81% |
| 24 | G3519 Gm | 13-77; 128-143 | CEVRYRGIRRRPWGKFAA EIRDPTRKGTRIWLGTFDT AEQAARAYDAAAFHFRGH RAILNFPNEY | 78% | TFELEYLD NKLLEELL | 80% |

TABLE 1-continued

Gene families and conserved domains of G1792 clade members

| SEQ ID NO: | GID No./ Species | AP2 and EDLL Domains in AA Coordinates | AP2 domain | % ID to AP2 Domain of G1792 | EDLL Domain | % ID to EDLL Domain of G1792 |
|---|---|---|---|---|---|---|
| 12 | G3381 Os | 14-78; 109-124 | LVAKYRGVRRRPWGKFA AEIRDSSRHGVRVWLGTF DTAEEAARAYDRSAYSMR GANAVLNFPADA | 76% | PIEFEYLDD HVLQEML | 78% |
| 32 | G3737 Os | 8-72; 101-116 | AASKYRGVRRRPWGKFA AEIRDPERGGSRVWLGTFD TAEEAARAYDRAAFAMK GAMAVLNFPGRT | 76% | KVELVYLD DKVLDELL | 78% |
| 16 | G3515 Os | 11-75; 116-131 | SSSSYRGVRKRPWGKAA EIRDPERGGARVWLGTFD TAEEAARAYDRAAFAMK GATAMLNFPGDH | 75% | KVELECLD DKVLEDLL | 78% |
| 18 | G3516 Zm | 6-70; 107-122 | KEGKYRGVRKRPWGKFA AEIRDPERGGSRVWLGTFD TAEEAARAYDRAAFAMK GATAVLNFPASG | 74% | KVELECLD DRVLEELL | 78% |
| 26 | G3520 Gm | 14-78; 109-124 | EEPRYRGVRRRPWGKAA EIRDPARHGARVWLGTFL TAEEAARAYDRAAYEMR GALAVLNFPNEY | 80% | VIEFECLD DKLLEDLL | 75% |
| 20 | G3517 Zm | 13-77; 103-118 | EPTKYRGVRRRPWGKYAA EIRDSSRHGVRIWLGTFDT AEEAARAYDRSANSMRGA NAVLNFPEDA | 72% | VIEFEYLD DEVLQEM L | 75% |
| 22 | G3518 Gm | 13-77; 135-150 | VEVRYRGIRRRPWGKFAA EIRDPTRKGTRIWLGTFDT AEQAARAYDAAAFHFRGH RAILNFPNEY | 78% | TFELEYFD NKLLEELL | 73% |
| 30 | G3736 Ta | 12-76; 108-123 | EPTKYRGVRRRPWGKFAA EIRDSSRHGVRMWLGTFD TAEEAAAAYDRSAYSMRG RNAVLNFPDRA | 73% | VIEFEYLD DDVLQSM L | 68% |
| 34 | G3739 Zm | 13-77; 107-122 | EPTKYRGVRRRPWGKYAA EIRDSSRHGVRIWLGTFDT AEEAARAYDRSAYSMRGA NAVLNFPEDA | 72% | VIELEYLD DEVLQEM L | 68% |
| 28 | G3735 Mt | 23-87; 131-144 | DQIKYRGIRRRPWGKFAA EIRDPTRKGTRIWLGTFDT AEQAARAYDAAAFHFRGH RAILNFPNEY | 78% | ELEFLDNK LLQELL | 64% |
| 10 | G3380 Os | 18-82; 103-118 | ETTKYRGVRRRPSGKFAA EIRDSSRQSVRVWLGTFDT AEEAARAYDRAAYAMRG HLAVLNFPAEA | 77% | VIELECLD DQVLQEM L | 62% |
| 36 | G3794 Zm | 6-70; 102-117 | EPTKYRGVRRRPSGKFAA EIRDSSRQSVRMWLGTFDT AEEAARAYDRAAYAMRG QIAVLNFPAEA | 73% | VLELECLD DQVLQEM L | 62% |

Abbreviations:
At - *Arabidopsis thaliana*
Gm - *Glycine max*
Mt - *Medicago truncatula*
Os - *Oryza sativa*
Ta - *Triticum aestivum*
Zm - *Zea mays*

The transcription factors of the invention each possess an AP2 domain and an EDLL domain, and include paralogs and orthologs of G1792 found by BLAST analysis, as described below.

As shown in Table 1, the AP2 domains of G1792 clade members are at least 69% identical to the AP2 domain of G1792, and the EDLL domains of G1792 clade members are at least 62% identical to the EDLL domain of G1792. These transcription factors rely on the binding specificity and functions of their conserved domains.

Producing Polypeptides

The polynucleotides of the invention include sequences that encode transcription factors and transcription factor homolog polypeptides and sequences complementary thereto, as well as unique fragments of coding sequence, or sequence complementary thereto. Such polynucleotides can be, e.g., DNA or RNA, e.g., mRNA, cRNA, synthetic RNA, genomic DNA, cDNA synthetic DNA, oligonucleotides, etc. The polynucleotides are either double-stranded or single-stranded, and include either, or both sense (i.e., coding) sequences and antisense (i.e., non-coding, complementary) sequences. The polynucleotides include the coding sequence of a transcription factor, or transcription factor homolog polypeptide, in isolation, in combination with additional coding sequences (e.g., a purification tag, a localization signal, as a fusion-protein, as a pre-protein, or the like), in combination with non-coding sequences (e.g., introns or inteins, regulatory elements such as promoters, enhancers, terminators, and the like), and/or in a vector or host environment in which the polynucleotide encoding a transcription factor or transcription factor homolog polypeptide is an endogenous or exogenous gene.

A variety of methods exist for producing the polynucleotides of the invention. Procedures for identifying and isolating DNA clones are well known to those of skill in the art and are described in, e.g., Berger and Kimmel (1987) *Guide to Molecular Cloning Techniques, Methods Enzymol*. vol. 152, Academic Press, Inc., San Diego, Calif.; Sambrook et al. (1989) supra, vol. 1-3, Cold Spring Harbor Laboratory, Cold Spring Harbor, N.Y., and Ausubel et al. (supplemented through 2000), eds., *Current Protocols in Molecular Biology*, Greene Publishing Associates, Inc. and John Wiley & Sons, Inc.

Alternatively, polynucleotides of the invention, can be produced by a variety of in vitro amplification methods adapted to the present invention by appropriate selection of specific or degenerate primers. Examples of protocols sufficient to direct persons of skill through in vitro amplification methods, including the polymerase chain reaction (PCR) the ligase chain reaction (LCR), Qβ-replicase amplification and other RNA polymerase mediated techniques (e.g., NASBA), e.g., for the production of the homologous nucleic acids of the invention are found in Berger and Kimmel (1987) supra, Sambrook (1989) supra, and Ausubel (2000) supra, as well as Mullis et al. (1990) *PCR Protocols A Guide to Methods and Applications* (Innis et al., eds) Academic Press Inc. San Diego, Calif. Improved methods for cloning in vitro amplified nucleic acids are described in Wallace et al. U.S. Pat. No. 5,426,039. Improved methods for amplifying large nucleic acids by PCR are summarized in Cheng et al. (1994) *Nature* 369: 684-685 and the references cited therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase (e.g., Ausubel (2000) supra, Sambrook (1989) supra, and Berger and Kimmel (1987) supra).

Alternatively, polynucleotides and oligonucleotides of the invention can be assembled from fragments produced by solid-phase synthesis methods. Typically, fragments of up to approximately 100 bases are individually synthesized and then enzymatically or chemically ligated to produce a desired sequence, e.g., a polynucleotide encoding all or part of a transcription factor. For example, chemical synthesis using the phosphoramidite method is described, e.g., by Beaucage et al. (1981) *Tetrahedron Letters* 22: 1859-1869; and Matthes et al. (1984) *EMBO J*. 3: 801-805. According to such methods, oligonucleotides are synthesized, purified, annealed to their complementary strand, ligated and then optionally cloned into suitable vectors. And if so desired, the polynucleotides and polypeptides of the invention can be custom ordered from any of a number of commercial suppliers.

Homologous Sequences

Sequences homologous to those provided in the Sequence Listing derived from *Arabidopsis thaliana* or from other plants of choice, are also an aspect of the invention. Homologous sequences can be derived from any plant including monocots and dicots and in particular agriculturally important plant species, including but not limited to, crops such as soybean, wheat, corn (maize), potato, cotton, rice, rape, oil-seed rape (including canola), sunflower, alfalfa, clover, sugarcane, and turf; or fruits and vegetables, such as banana, blackberry, blueberry, strawberry, and raspberry, cantaloupe, carrot, cauliflower, coffee, cucumber, eggplant, grapes, honeydew, lettuce, mango, melon, onion, papaya, peas, peppers, pineapple, pumpkin, spinach, squash, sweet corn, tobacco, tomato, tomatillo, watermelon, rosaceous fruits (such as apple, peach, pear, cherry and plum) and vegetable brassicas (such as broccoli, cabbage, cauliflower, Brussels sprouts, and kohlrabi). Other crops, including fruits and vegetables, whose phenotype can be changed and which comprise homologous sequences include barley; rye; millet; sorghum; currant; avocado; citrus fruits such as oranges, lemons, grapefruit and tangerines, artichoke, cherries; nuts such as the walnut and peanut; endive; leek; roots such as arrowroot, beet, cassava, turnip, radish, yam, and sweet potato; and beans. The homologous sequences may also be derived from woody species, such as pine, poplar and eucalyptus, or mint or other labiates. In addition, homologous sequences may be derived from plants that are evolutionarily-related to crop plants, but which may not have yet been used as crop plants. Examples include deadly nightshade (*Atropa belladona*), related to tomato; jimson weed (*Datura strommium*), related to peyote; and teosinte (*Zea* species), related to corn (maize).

Orthologs and Paralogs

Homologous sequences as described above can comprise orthologous or paralogous sequences. Several different methods are known by those of skill in the art for identifying and defining these functionally homologous sequences. Three general methods for defining orthologs and paralogs are described; an ortholog or paralog, including equivalogs, may be identified by one or more of the methods described below.

Within a single plant species, gene duplication may cause two copies of a particular gene, giving rise to two or more genes with similar sequence and often similar function known as paralogs. A paralog is therefore a similar gene formed by duplication within the same species. Paralogs typically cluster together or in the same lade (a group of similar genes) when a gene family phylogeny is analyzed using programs such as CLUSTAL (Thompson et al. (1994) *Nucleic Acids Res*. 22: 4673-4680; Higgins et al. (1996) *Methods Enzymol*. 266: 383-402). Groups of similar genes can also be identified with pair-wise BLAST analysis (Feng and Doolittle (1987) *J. Mol. Evol*. 25: 351-360). For example, a clade of very similar MADS domain transcription factors from *Arabidopsis* all share a common function in flowering time (Ratcliffe et al. (2001) *Plant Physiol.* 126: 122-132), and a group of very similar AP2 domain transcription factors from *Arabidopsis* are involved in tolerance of plants to freezing (Gilmour et al. (1998) *Plant J.* 16: 433-442). Analysis of groups of similar genes with similar function that fall within one clade can yield sub-sequences that are particular to the clade. These sub-sequences, known as consensus sequences, can not only be used to define the sequences within each lade, but define the functions of these genes; genes within a clade may contain paralogous sequences, or orthologous sequences that share the same function (for example, Mount (2001), in *Bioinformatics: Sequence and Genome Analysis*, Cold Spring Harbor Laboratory Press, Cold Spring Harbor, N.Y., page 543).

Speciation, the production of new species from a parental species, can also give rise to two or more genes with similar sequence and similar function. These genes, termed orthologs, often have an identical function within their host plants and are often interchangeable between species without losing function. Because plants have common ancestors, many genes in any plant species will have a corresponding orthologous gene in another plant species. Once a phylogenic tree for a gene family of one species has been constructed using a program such as CLUSTAL (Thompson et al. (1994) *Nucleic Acids Res.* 22: 4673-4680; Higgins et al. (1996) supra) potential orthologous sequences can be placed into the phylogenetic tree and their relationship to genes from the species of interest can be determined. Orthologous sequences can also be identified by a reciprocal BLAST strategy. Once an orthologous sequence has been identified, the function of the ortholog can be deduced from the identified function of the reference sequence.

Transcription factor gene sequences are conserved across diverse eukaryotic species lines (Goodrich et al. (1993) *Cell* 75: 519-530; Lin et al. (1991) *Nature* 353: 569-571; Sadowski et al. (1988) *Nature* 335: 563-564). Plants are no exception to this observation; diverse plant species possess transcription factors that have similar sequences and functions.

Orthologous genes from different organisms have highly conserved functions, and very often essentially identical functions (Lee et al. (2002) *Genome Res.* 12: 493-502; Remm et al. (2001) *J. Mol. Biol.* 314: 1041-1052). Paralogous genes, which have diverged through gene duplication, may retain similar functions of the encoded proteins. In such cases, paralogs can be used interchangeably with respect to certain embodiments of the instant invention (for example, transgenic expression of a coding sequence). An example of such highly related paralogs is the CBF family, with three well-defined members in *Arabidopsis* and at least one ortholog in Brassica napus (U.S. patent application 20040098764), all of which control pathways involved in both freezing and drought stress (Gilmour et al. (1998) *Plant J.* 16: 433-442; Jaglo et al. (1998) *Plant Physiol.* 127: 910-917).

The following references represent a small sampling of the many studies that demonstrate that conserved transcription factor genes from diverse species are likely to function similarly (i.e., regulate similar target sequences and control the same traits), and that transcription factors may be transformed into diverse species to confer or improve traits.

(1) Distinct *Arabidopsis* transcription factors, including G28 (SEQ ID NO: 48, U.S. Pat. No. 6,664,446), G482 (U.S. patent application 20040045049), G867 (U.S. patent application 20040098764), and G1073 (U.S. Pat. No. 6,717,034), have been shown to confer abiotic stress tolerance when the sequences are overexpressed. The polypeptides sequences belong to distinct clades of transcription factor polypeptides that include members from diverse species. In each case, a significant number of sequences derived from both dicots and monocots have been shown to confer tolerance to various abiotic stresses when the sequences were overexpressed (unpublished data).

(2) The *Arabidopsis* NPR1 gene regulates systemic acquired resistance (SAR); over-expression of NPR1 leads to enhanced resistance in *Arabidopsis*. When either *Arabidopsis* NPR1 or the rice NPR1 ortholog was overexpressed in rice (which, as a monocot, is diverse from *Arabidopsis*), challenge with the rice bacterial blight pathogen *Xanthomonas oryzae* pv. *Oryzae*, the transgenic plants displayed enhanced resistance (Chern et al. (2001) *Plant J.* 27: 101-113). NPR1 acts through activation of expression of transcription factor genes, such as TGA2 (Fan and Dong (2002) *Plant Cell* 14: 1377-1389).

(3) E2F genes are involved in transcription of plant genes for proliferating cell nuclear antigen (PCNA). Plant E2Fs share a high degree of similarity in amino acid sequence between monocots and dicots, and are even similar to the conserved domains of the animal E2Fs. Such conservation indicates a functional similarity between plant and animal E2Fs. E2F transcription factors that regulate meristem development act through common cis-elements, and regulate related (PCNA) genes (Kosugi and Ohashi (2002) *Plant J.* 29: 45-59).

(4) The ABI5 gene (abscisic acid (ABA) insensitive 5) encodes a basic leucine zipper factor required for ABA response in the seed and vegetative tissues. Co-transformation experiments with ABI5 cDNA constructs in rice protoplasts resulted in specific transactivation of the ABA-inducible wheat, *Arabidopsis*, bean, and barley promoters. These results demonstrate that sequentially similar ABI5 transcription factors are key targets of a conserved ABA signaling pathway in diverse plants (Gampala et al. (2001) *J. Biol. Chem.* 277: 1689-1694).

(5) Sequences of three *Arabidopsis* GAMYB-like genes were obtained on the basis of sequence similarity to GAMYB genes from barley, rice, and *L. temulentum*. These three *Arabidopsis* genes were determined to encode transcription factors (AtMYB33, AtMYB65, and AtMYB101) and could substitute for a barley GAMYB and control alpha-amylase expression (Gocal et al. (2001) *Plant Physiol.* 127: 1682-1693).

(6) The floral control gene LEAFY from *Arabidopsis* can dramatically accelerate flowering in numerous dicotyledonous plants. Constitutive expression of *Arabidopsis* LEAFY also caused early flowering in transgenic rice (a monocot), with a heading date that was 26-34 days earlier than that of wild-type plants. These observations indicate that floral regulatory genes from *Arabidopsis* are useful tools for heading date improvement in cereal crops (He et al. (2000) *Transgenic Res.* 9: 223-227).

(7) Bioactive gibberellins (GAs) are essential endogenous regulators of plant growth. GA signaling tends to be conserved across the plant kingdom. GA signaling is mediated via GAI, a nuclear member of the GRAS family of plant transcription factors. *Arabidopsis* GAI has been shown to function in rice to inhibit gibberellin response pathways (Fu et al. (2001) *Plant Cell* 13: 1791-1802).

(8) The *Arabidopsis* gene SUPERMAN (SUP), encodes a putative transcription factor that maintains the boundary between stamens and carpels. By over-expressing *Arabidopsis* SUP in rice, the effect of the gene's presence on whorl boundaries was shown to be conserved. This demonstrated that SUP is a conserved regulator of floral whorl boundaries and affects cell proliferation (Nandi et al. (2000) *Curr. Biol.* 10: 215-218).

(9) Maize, petunia and *Arabidopsis* myb transcription factors that regulate flavonoid biosynthesis are genetically similar and affect the same trait in their native species. Therefore, sequence and function of these myb transcription factors correlate with each other in these diverse species (Borevitz et al. (2000) *Plant Cell* 12: 2383-2394).

(10) Wheat reduced height-1 (Rht-B1/Rht-D1) and maize dwarf-8 (d8) genes are orthologs of the *Arabidopsis* gibberellin insensitive (GAI) gene. Both of these genes have been used to produce dwarf grain varieties that have improved grain yield. These genes encode proteins that resemble nuclear transcription factors and contain an SH2-like domain, indicating that phosphotyrosine may participate in gibberellin signaling. Transgenic rice plants containing a mutant GAI allele from *Arabidopsis* have been shown to produce reduced responses to gibberellin and are dwarfed, indicating that mutant GAI orthologs could be used to increase yield in a wide range of crop species (Peng et al. (1999) *Nature* 400: 256-261).

Transcription factors that are homologous to the listed AP2 transcription factors will typically share at least about 69% and 62% amino acid sequence identity in their AP2 and EDLL domains, respectively, as seen by the examples shown to confer disease or abiotic stress tolerance in Table 1. Transcription factors that are homologous to the listed sequences should share at least 40% amino acid sequence identity over the entire length of the polypeptide.

At the nucleotide level, the sequences of the invention will typically share at least about 40% or greater nucleotide sequence identity to one or more of the listed full-length sequences, or to a listed sequence but excluding or outside of the region(s) encoding a known consensus sequence or consensus DNA-binding site, or outside of the region(s) encoding one or all conserved domains. The degeneracy of the genetic code enables major variations in the nucleotide sequence of a polynucleotide while maintaining the amino acid sequence of the encoded protein.

Percent identity can be determined electronically, e.g., by using the MEGALIGN program (DNASTAR, Inc. Madison, Wis.). The MEGALIGN program can create alignments between two or more sequences according to different methods, for example, the clustal method (for example, Higgins and Sharp (1988) *Gene* 73: 237-244). The clustal algorithm groups sequences into clusters by examining the distances between all pairs. The clusters are aligned pairwise and then in groups. Other alignment algorithms or programs may be used, including FASTA, BLAST, or ENTREZ, FASTA and BLAST, and which may be used to calculate percent similarity. These are available as a part of the GCG sequence analysis package (University of Wisconsin, Madison, Wis.), and can be used with or without default settings. ENTREZ is available through the National Center for Biotechnology Information. In one embodiment, the percent identity of two sequences can be determined by the GCG program with a gap weight of 1, e.g., each amino acid gap is weighted as if it were a single amino acid or nucleotide mismatch between the two sequences (U.S. Pat. No. 6,262,333).

Other techniques for alignment are described in Methods in Enzymology, vol. 266, *Computer Methods for Macromolecular Sequence Analysis* (1996), ed. Doolittle, Academic Press, Inc., San Diego, Calif., U.S.A. Preferably, an alignment program that permits gaps in the sequence is utilized to align the sequences. The Smith-Waterman is one type of algorithm that permits gaps in sequence alignments (Shpaer (1 997) *Methods Mol. Biol.* 70: 173-187). Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer. This approach improves ability to pick up distantly related matches, and is especially tolerant of small gaps and nucleotide sequence errors. Nucleic acid-encoded amino acid sequences can be used to search both protein and DNA databases.

The percentage similarity between two polypeptide sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no similarity between the two amino acid sequences are not included in determining percentage similarity. Percent identity between polynucleotide sequences can also be counted or calculated by other methods known in the art, e.g., the Jotun Hein method (for example, Hein (1990) *Methods Enzymol.* 183: 626-645). Identity between sequences can also be determined by other methods known in the art, e.g., by varying hybridization conditions (U.S. patent application No. 20010010913).

Thus, the invention provides methods for identifying a sequence similar or paralogous or orthologous or homologous to one or more polynucleotides as noted herein, or one or more target polypeptides encoded by the polynucleotides, or otherwise noted herein and may include linking or associating a given plant phenotype or gene function with a sequence. In the methods, a sequence database is provided (locally or across an internet or intranet) and a query is made against the sequence database using the relevant sequences herein and associated plant phenotypes or gene functions.

In addition, one or more polynucleotide sequences or one or more polypeptides encoded by the polynucleotide sequences may be used to search against a BLOCKS (Bairoch et al. (1997) *Nucleic Acids Res.* 25: 217-221), PFAM, and other databases which contain previously identified and annotated motifs, sequences and gene functions. Methods that search for primary sequence patterns with secondary structure gap penalties (Smith et al. (1992) *Protein Engineering* 5: 35-51) as well as algorithms such as Basic Local Alignment Search Tool (BLAST; Altschul (1993) *J. Mol. Evol.* 36: 290-300; Altschul et al. (1990) *J. Mol. Biol.* 215: 403-410), BLOCKS (Henikoff and Henikoff (1991) *Nucleic Acids Res.* 19: 6565-6572), Hidden Markov Models (HMM; Eddy (1996) *Curr. Opin. Str. Biol.* 6: 361-365; Sonnhammer et al. (1997) *Proteins* 28: 405-420), and the like, can be used to manipulate and analyze polynucleotide and polypeptide sequences encoded by polynucleotides. These databases, algorithms and other methods are well known in the art and are described in Ausubel et al. (1997) *Short Protocols in Molecular Biology,* John Wiley & Sons, New York, N.Y., unit 7.7; and in Meyers (1995) *Molecular Biology and Biotechnology,* Wiley VCH, New York, N.Y., p 856-853.

A further method for identifying or confirming that specific homologous sequences control the same function is by comparison of the transcript profile(s) obtained upon overexpression or knockout of two or more related transcription factors. Since transcript profiles are diagnostic for specific cellular states, one skilled in the art will appreciate that genes that have a highly similar transcript profile (e.g., with greater than 50% regulated transcripts in common, more preferably with greater than 70% regulated transcripts in common, most preferably with greater than 90% regulated transcripts in common) will have highly similar functions. Fowler et al. (2002) *Plant Cell*, 14: 1675-1679, have shown that three paralogous AP2 family genes (CBF1, CBF2 and CBF3), each of which is induced upon cold treatment, and each of which can condition improved freezing tolerance, have highly similar transcript profiles. Once a transcription factor has been shown to provide a specific function, its transcript profile becomes a diagnostic tool to determine whether putative paralogs or orthologs have the same function.

Furthermore, methods using manual alignment of sequences similar or homologous to one or more polynucleotide sequences or one or more polypeptides encoded by the polynucleotide sequences may be used to identify regions of similarity and AP2 domains. Such manual methods are well-known of those of skill in the art and can include, for example, comparisons of tertiary structure between a polypeptide sequence encoded by a polynucleotide with a known function, and a polypeptide sequence encoded by a polynucleotide sequence for which a function has not yet been determined. Such examples of tertiary structure may comprise predicted α-helices, β-sheets, amphipathic helices, leucine zipper motifs, zinc finger motifs, proline-rich regions, cysteine repeat motifs, and the like.

Orthologs and paralogs of presently disclosed transcription factors may be cloned using compositions provided by the present invention according to methods well known in the art. cDNAs can be cloned using mRNA from a plant cell or tissue that expresses one of the present transcription factors. Appropriate MRNA sources may be identified by interrogating Northern blots with probes designed from the present transcription factor sequences, after which a library is prepared from the mRNA obtained from a positive cell or tissue. Transcription factor-encoding cDNA is then isolated using, for example, PCR, using primers designed from a presently disclosed transcription factor gene sequence, or by probing with a partial or complete cDNA or with one or more sets of degenerate probes based on the disclosed sequences. The cDNA library may be used to transform plant cells. Expression of the cDNAs of interest is detected using, for example, methods disclosed herein such as microarrays, Northern blots, quantitative PCR, or any other technique for monitoring changes in expression. Genomic clones may be isolated using similar techniques to those.

Examples of orthologs of the *Arabidopsis* polypeptide sequences SEQ ID NOs: 2, 4, 6, and 8 include SEQ ID NOs: 10, 12, 14, 16, 18, 20, 22, 24, 26, 28, 30, 32, 34 and 36, and other functionally similar orthologs that may be discovered using the methods found in Examples X and XI. In addition to the sequences in the Sequence Listing, the invention encompasses isolated nucleotide sequences that are sequentially and structurally similar to G1792, G1791, G1795, G30, G3381, and G3520 (SEQ ID NO: 1, 3, 5, 7, 11, and 25, respectively) and can function in a plant by increasing disease or abiotic stress tolerance, particularly when overexpressed. These polypeptide sequences represent clade members that function similarly to G1792 by conferring disease and abiotic stress tolerance, and show significant sequence similarity to G1792, as shown by their respective identities to the AP2 and EDLL domains of G1792, as shown in Table 1.

Since a number of these polynucleotide sequences in the G1792 clade of transcription factor polypeptides are phylogenetically related (FIG. 5), similar in sequence, are derived from diverse plant species, and have been shown to increase a plant's disease and/or abiotic stress tolerance, one skilled in the art would predict that other similar, phylogenetically related sequences would also increase a plant's tolerance to abiotic and biotic stresses.

Identifying Polynucleotides or Nucleic Acids by Hybridization

Polynucleotides homologous to the sequences illustrated in the Sequence Listing and tables can be identified, e.g., by hybridization to each other under stringent or under highly stringent conditions. Single stranded polynucleotides hybridize when they associate based on a variety of well characterized physical-chemical forces, such as hydrogen bonding, solvent exclusion, base stacking and the like. The stringency of a hybridization reflects the degree of sequence identity of the nucleic acids involved, such that the higher the stringency, the more similar are the two polynucleotide strands. Stringency is influenced by a variety of factors, including temperature, salt concentration and composition, organic and non-organic additives, solvents, etc. present in both the hybridization and wash solutions and incubations (and number thereof), as described in more detail in the references cited above.

Encompassed by the invention are polynucleotide sequences that are capable of hybridizing to the claimed polynucleotide sequences, including any of the transcription factor polynucleotides within the Sequence Listing, and fragments thereof under various conditions of stringency (for example, Wahl and Berger, in Berger and Kimmel (1987) supra, pages 399-407, and Kimmel, in and Berger and Kimmel (1987) supra, pages 507-511). In addition to the nucleotide sequences listed in the Sequence Listing, full length cDNA, orthologs, and paralogs of the present nucleotide sequences may be identified and isolated using well-known methods. The cDNA libraries, orthologs, and paralogs of the present nucleotide sequences may be screened using hybridization methods to determine their utility as hybridization target or amplification probes.

With regard to hybridization, conditions that are highly stringent, and means for achieving them, are well known in the art (for example, in Sambrook et al. (1989) supra; Berger and Kimmel (1987) supra, pages 467-469; and Anderson and Young (1985) "Quantitative Filter Hybridisation." In: Hames and Higgins, ed., *Nucleic Acid Hybridisation, A Practical Approach*, Oxford, IRL Press, 73-111.

Stability of DNA duplexes is affected by such factors as base composition, length, and degree of base pair mismatch. Hybridization conditions may be adjusted to allow DNAs of different sequence relatedness to hybridize. The melting temperature ($T_m$) is defined as the temperature when 50% of the duplex molecules have dissociated into their constituent single strands. The melting temperature of a perfectly matched duplex, where the hybridization buffer contains formamide as a denaturing agent, may be estimated by the following equations:

DNA-DNA:

$$T_m(°\text{C.}) = 81.5 + 16.6(\log[\text{Na}+]) + 0.41(\%\text{ G}+\text{C}) - 0.62(\%\text{ formamide}) - 500/L \quad (I)$$

DNA-RNA:

$$T_m(°\text{C.}) = 79.8 + 18.5(\log[\text{Na}+]) + 0.58(\%\text{ G}+\text{C}) + 0.12(\%\text{ G}+\text{C})^2 - 0.5(\%\text{ formamide}) - 820/L \quad (II)$$

RNA-RNA:

$$T_m(°\text{C.}) = 79.8 + 18.5(\log[\text{Na}+]) + 0.58(\%\text{ G}+\text{C}) + 0.12(\%\text{ G}+\text{C})^2 - 0.35(\%\text{ formamide}) - 820/L \quad (III)$$

where L is the length of the duplex formed, [Na+] is the molar concentration of the sodium ion in the hybridization or washing solution, and % G+C is the percentage of (guanine+ cytosine) bases in the hybrid. For imperfectly matched hybrids, approximately 1° C. is required to reduce the melting temperature for each 1% mismatch.

Hybridization experiments are generally conducted in a buffer of pH between 6.8 to 7.4, although the rate of hybridization is nearly independent of pH at ionic strengths likely to be used in the hybridization buffer (Anderson et al. (1985) supra). In addition, one or more of the following may be used to reduce non-specific hybridization: sonicated salmon sperm DNA or another non-complementary DNA, bovine serum albumin, sodium pyrophosphate, sodium dodecyl sulfate (SDS), polyvinyl-pyrrolidone, ficoll and Denhardt's solution. Dextran sulfate and polyethylene glycol 6000 act to exclude DNA from solution, thus raising the effective probe DNA concentration and the hybridization signal within a given unit of time. In some instances, conditions of even greater stringency may be desirable or required to reduce non-specific and/or background hybridization. These conditions may be created with the use of higher temperature, lower ionic strength and higher concentration of a denaturing agent such as formamide.

Stringency conditions can be adjusted to screen for moderately similar fragments such as homologous sequences from distantly related organisms, or to highly similar fragments such as genes that duplicate functional enzymes from closely related organisms. The stringency can be adjusted either during the hybridization step or in the post-hybridization washes. Salt concentration, formamide concentration, hybridization temperature and probe lengths are variables that can be used to alter stringency (as described by the formula above). As a general guidelines high stringency is typically performed at $T_m$-5° C. to $T_m$-20° C., moderate stringency at $T_m$-20° C. to $T_m$-35° C. and low stringency at $T_m$-35° C. to $T_m$-50° C. for duplex >150 base pairs. Hybridization may be performed at low to moderate stringency (25-50° C. below $T_m$), followed by post-hybridization washes at increasing stringencies. Maximum rates of hybridization in solution are determined empirically to occur at $T_m$-25° C. for DNA-DNA duplex and $T_m$-15° C. for RNA-DNA duplex. Optionally, the degree of dissociation may be assessed after each wash step to determine the need for subsequent, higher stringency wash steps.

High stringency conditions may be used to select for nucleic acid sequences with high degrees of identity to the disclosed sequences. An example of stringent hybridization conditions obtained in a filter-based method such as a Southern or northern blot for hybridization of complementary nucleic acids that have more than 100 complementary residues is about 5° C. to 20° C. lower than the thermal melting point ($T_m$) for the specific sequence at a defined ionic strength and pH. Conditions used for hybridization may include about 0.02 M to about 0.15 M sodium chloride, about 0.5% to about 5% casein, about 0.02% SDS or about 0.1% N-laurylsarcosine, about 0.001 M to about 0.03 M sodium citrate, at hybridization temperatures between about 50° C. and about 70° C. More preferably, high stringency conditions are about 0.02 M sodium chloride, about 0.5% casein, about 0.02% SDS, about 0.001 M sodium citrate, at a temperature of about 50° C. Nucleic acid molecules that hybridize under stringent conditions will typically hybridize to a probe based on either the entire DNA molecule or selected portions, e.g., to a unique subsequence, of the DNA.

Stringent salt concentration will ordinarily be less than about 750 mM NaCl and 75 mM trisodium citrate. Increasingly stringent conditions may be obtained with less than about 500 mM NaCl and 50 mM trisodium citrate, to even greater stringency with less than about 250 mM NaCl and 25 mM trisodium citrate. Low stringency hybridization can be obtained in the absence of organic solvent, e.g., formamide, whereas high stringency hybridization may be obtained in the presence of at least about 35% formamide, and more preferably at least about 50% formamide. Stringent temperature conditions will ordinarily include temperatures of at least about 30° C., more preferably of at least about 37° C, and most preferably of at least about 42° C. with formamide present. Varying additional parameters, such as hybridization time, the concentration of detergent, e.g., sodium dodecyl sulfate (SDS) and ionic strength, are well known to those skilled in the art. Various levels of stringency are accomplished by combining these various conditions as needed.

The washing steps that follow hybridization may also vary in stringency; the post-hybridization wash steps primarily determine hybridization specificity, with the most critical factors being temperature and the ionic strength of the final wash solution. Wash stringency can be increased by decreasing salt concentration or by increasing temperature. Stringent salt concentration for the wash steps will preferably be less than about 30 mM NaCl and 3 mM trisodium citrate, and most preferably less than about 15 mM NaCl and 1.5 mM trisodium citrate.

Thus, hybridization and wash conditions that may be used to bind and remove polynucleotides with less than the desired homology to the nucleic acid sequences or their complements that encode the present transcription factors include, for example:

6×SSC at 65° C.;
50% formamide, 4×SSC at 42° C.; or
0.5×SSC, 0.1% SDS at 65° C.;

with, for example, two wash steps of 10-30 minutes each. Useful variations on these conditions will be readily apparent to those skilled in the art.

A person of skill in the art would not expect substantial variation among polynucleotide species encompassed within the scope of the present invention because the highly stringent conditions set forth in the above formulae yield structurally similar polynucleotides.

If desired, one may employ wash steps of even greater stringency, including about 0.2×SSC, 0.1% SDS at 65° C. and washing twice, each wash step being about 30 minutes, or about 0.1×SSC, 0.1% SDS at 65° C. and washing twice for 30 minutes. The temperature for the wash solutions will ordinarily be at least about 25° C., and for greater stringency at least about 42° C. Hybridization stringency may be increased further by using the same conditions as in the hybridization steps, with the wash temperature raised about 3° C. to about 5° C., and stringency may be increased even further by using the same conditions except the wash temperature is raised about 6° C. to about 9° C. For identification of less closely related homologs, wash steps may be performed at a lower temperature, e.g., 50° C.

An example of a low stringency wash step employs a solution and conditions of at least 25° C. in 30 mM NaCl, 3 mM trisodium citrate, and 0.1% SDS over 30 minutes. Greater stringency may be obtained at 42° C. in 15 mM NaCl, with 1.5 mM trisodium citrate, and 0.1% SDS over 30 minutes. Even higher stringency wash conditions are obtained at 65° C.-68° C. in a solution of 15 mM NaCl, 1.5 mM trisodium citrate, and 0.1% SDS. Wash procedures will generally employ at least two final wash steps. Additional variations on these conditions will be readily apparent to those skilled in the art (for example, U.S. patent application No. 20010010913).

Stringency conditions can be selected such that an oligonucleotide that is perfectly complementary to the coding oligonucleotide hybridizes to the coding oligonucleotide with at least about a 5-10× higher signal to noise ratio than the ratio for hybridization of the perfectly complementary oligonucleotide to a nucleic acid encoding a transcription factor known as of the filing date of the application. It may be desirable to select conditions for a particular assay such that a higher signal to noise ratio, that is, about 15× or more, is obtained. Accordingly, a subject nucleic acid will hybridize to a unique coding oligonucleotide with at least a 2× or greater signal to noise ratio as compared to hybridization of the coding oligonucleotide to a nucleic acid encoding known polypeptide. The particular signal will depend on the label used in the relevant assay, e.g., a fluorescent label, a colorimetric label, a radioactive label, or the like. Labeled hybridization or PCR probes for detecting related polynucleotide sequences may be produced by oligolabeling, nick translation, end-labeling, or PCR amplification using a labeled nucleotide.

Identifying Polynucleotides or Nucleic Acids with Expression Libraries

In addition to hybridization methods, transcription factor homolog polypeptides can be obtained by screening an expression library using antibodies specific for one or more transcription factors. With the provision herein of the disclosed transcription factor, and transcription factor homolog nucleic acid sequences, the encoded polypeptide(s) can be expressed and purified in a heterologous expression system (for example, *E. coli*) and used to raise antibodies (monoclonal or polyclonal) specific for the polypeptide(s) in question. Antibodies can also be raised against synthetic peptides derived from the amino acid sequences or subsequences of a transcription factor or transcription factor homolog. Methods of raising antibodies are well known in the art and are described in Harlow and Lane (1988), *Antibodies: A Laboratory Manual*, Cold Spring Harbor Laboratory, New York. Such antibodies can then be used to screen an expression library produced from the plant from which it is desired to clone additional transcription factor homologs, using the methods described above. The selected cDNAs can be confirmed by sequencing and enzymatic activity.

Sequence Variations

It will readily be appreciated by those of skill in the art, that any of a variety of polynucleotide sequences are capable of encoding the transcription factors and transcription factor homolog polypeptides of the invention. Due to the degeneracy of the genetic code, many different polynucleotides can encode identical and/or substantially similar polypeptides in addition to those sequences illustrated in the Sequence Listing. Nucleic acids having a sequence that differs from the sequences shown in the Sequence Listing, or complementary sequences, that encode functionally equivalent peptides (i.e., peptides having some degree of equivalent or similar biological activity) but differ in sequence from the sequence shown in the Sequence Listing due to degeneracy in the genetic code, are also within the scope of the invention.

Altered polynucleotide sequences encoding polypeptides include those sequences with deletions, insertions, or substitutions of different nucleotides, resulting in a polynucleotide encoding a polypeptide with at least one functional characteristic of the instant polypeptides. Included within this definition are polymorphisms which may or may not be readily detectable using a particular oligonucleotide probe of the polynucleotide encoding the instant polypeptides, and improper or unexpected hybridization to allelic variants, with a locus other than the normal chromosomal locus for the polynucleotide sequence encoding the instant polypeptides.

Allelic variant refers to any of two or more alternative forms of a gene occupying the same chromosomal locus. Allelic variation arises naturally through mutation, and may result in phenotypic polymorphism within populations. Gene mutations can be silent (i.e., no change in the encoded polypeptide) or may encode polypeptides having altered amino acid sequence. The term allelic variant is also used herein to denote a protein encoded by an allelic variant of a gene. Splice variant refers to alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Those skilled in the art would recognize that, for example, G1792, SEQ ID NO: 2, represents a single transcription factor; allelic variation and alternative splicing may be expected to occur. Allelic variants of SEQ ID NO: 1 can be cloned by probing cDNA or genomic libraries from different individual organisms according to standard procedures. Allelic variants of the DNA sequence shown in SEQ ID NO: 1, including those containing silent mutations and those in which mutations result in amino acid sequence changes, are within the scope of the present invention, as are proteins which are allelic variants of SEQ ID NO: 2. cDNAs generated from alternatively spliced mRNAs, which retain the properties of the transcription factor are included within the scope of the present invention, as are polypeptides encoded by such cDNAs and mRNAs. Allelic variants and splice variants of these sequences can be cloned by probing cDNA or genomic libraries from different individual organisms or tissues according to standard procedures known in the art (U.S. Pat. No. 6,388,064).

Thus, in addition to the sequences set forth in the Sequence Listing, the invention also encompasses related nucleic acid molecules that include allelic or splice variants, and sequences that are complementary. Related nucleic acid molecules also include nucleotide sequences encoding a polypeptide comprising a substitution, modification, addition and/or deletion of one or more amino acid residues. Such related polypeptides may comprise, for example, additions and/or deletions of one or more N-linked or O-linked glycosylation sites, or an addition and/or a deletion of one or more cysteine residues.

For example, Table 2 illustrates, for example, that the codons AGC, AGT, TCA, TCC, TCG, and TCT all encode the same amino acid: serine. Accordingly, at each position in the sequence where there is a codon encoding serine, any of the above trinucleotide sequences can be used without altering the encoded polypeptide.

TABLE 2

| Amino acid | | | Possible Codons |
|---|---|---|---|
| Alanine | Ala | A | GCA GCC GCG GCU |
| Cysteine | Cys | C | TGC TGT |
| Aspartic acid | Asp | D | GAC GAT |
| Glutamic acid | Glu | E | GAA GAG |
| Phenyl-alanine | Phe | F | TTC TTT |
| Glycine | Gly | G | GGA GGC GGG GGT |

TABLE 2-continued

| Amino acid | | | Possible Codons |
|---|---|---|---|
| Histidine | His | H | CAC CAT |
| Isoleucine | Ile | I | ATA ATC ATT |
| Lysine | Lys | K | AAA AAG |
| Leucine | Leu | L | TTA TTG CTA CTC CTG CTT |
| Methionine | Met | M | ATG |
| Asparagine | Asn | N | AAC AAT |
| Proline | Pro | P | CCA CCC CCG CCT |
| Glutamine | Gln | Q | CAA CAG |
| Arginine | Arg | R | AGA AGG CGA CGC CGG CGT |
| Serine | Ser | S | AGC AGT TCA TCC TCG TCT |
| Threonine | Thr | T | ACA ACC ACG ACT |
| Valine | Val | V | GTA GTC GTG GTT |
| Tryptophan | Trp | W | TGG |
| Tyrosine | Tyr | Y | TAC TAT |

Sequence alterations that do not change the amino acid sequence encoded by the polynucleotide are termed "silent" variations. With the exception of the codons ATG and TGG, encoding methionine and tryptophan, respectively, any of the possible codons for the same amino acid can be substituted by a variety of techniques, e.g., site-directed mutagenesis, available in the art. Accordingly, any and all such variations of a sequence selected from the above table are a feature of the invention.

In addition to silent variations, other conservative variations that alter one, or a few amino acids in the encoded polypeptide, can be made without altering the function of the polypeptide, these conservative variants are, likewise, a feature of the invention.

For example, substitutions, deletions and insertions introduced into the sequences provided in the Sequence Listing, are also envisioned by the invention. Such sequence modifications can be engineered into a sequence by site-directed mutagenesis (Wu, editor; *Methods Enzymol.* (1993) vol. 217, Academic Press) or the other methods noted below. Amino acid substitutions are typically of single residues; insertions usually will be on the order of about from 1 to 10 amino acid residues; and deletions will range about from 1 to 30 residues. In one embodiment, deletions or insertions are made in adjacent pairs, e.g., a deletion of two residues or insertion of two residues. Substitutions, deletions, insertions or any combination thereof can be combined to arrive at a sequence. The mutations that are made in the polynucleotide encoding the transcription factor should not place the sequence out of reading frame and should not create complementary regions that could produce secondary mRNA structure. Preferably, the polypeptide encoded by the DNA performs the desired function.

Conservative substitutions are those in which at least one residue in the amino acid sequence has been removed and a different residue inserted in its place. Such substitutions generally are made in accordance with the Table 3 when it is desired to maintain the activity of the protein. Table 3 shows amino acids which can be substituted for an amino acid in a protein and which are typically regarded as conservative substitutions. In one embodiment, transcriptions factors listed in the Sequence Listing may have up to 10 conservative substitutions and retain their function. In another embodiment, transcription factors listed in the Sequence Listing may have more than 10 conservative substitutions and still retain their function.

TABLE 3

| Residue | Conservative Substitutions |
|---|---|
| Ala | Ser |
| Arg | Lys |
| Asn | Gln; His |
| Asp | Glu |
| Gln | Asn |
| Cys | Ser |
| Glu | Asp |
| Gly | Pro |
| His | Asn; Gln |
| Ile | Leu, Val |
| Leu | Ile; Val |
| Lys | Arg; Gln |
| Met | Leu; Ile |
| Phe | Met; Leu; Tyr |
| Ser | Thr; Gly |
| Thr | Ser; Val |
| Trp | Tyr |
| Tyr | Trp; Phe |
| Val | Ile; Leu |

Similar substitutions are those in which at least one residue in the amino acid sequence has been removed and a different residue inserted in its place. Such substitutions generally are made in accordance with the Table 4 when it is desired to maintain the activity of the protein. Table 4 shows amino acids which can be substituted for an amino acid in a protein and which are typically regarded as structural and functional substitutions. For example, a residue in column 1 of Table 4 may be substituted with a residue in column 2; in addition, a residue in column 2 of Table 4 may be substituted with the residue of column 1.

TABLE 4

| Residue | Similar Substitutions |
|---|---|
| Ala | Ser; Thr; Gly; Val; Leu; Ile |
| Arg | Lys; His; Gly |
| Asn | Gln; His; Gly; Ser; Thr |
| Asp | Glu, Ser; Thr |
| Gln | Asn; Ala |
| Cys | Ser; Gly |
| Glu | Asp |
| Gly | Pro; Arg |
| His | Asn; Gln; Tyr; Phe; Lys; Arg |
| Ile | Ala; Leu; Val; Gly; Met |
| Leu | Ala; Ile; Val; Gly; Met |
| Lys | Arg; His; Gln; Gly; Pro |
| Met | Leu; Ile; Phe |
| Phe | Met; Leu; Tyr; Trp; His; Val; Ala |
| Ser | Thr; Gly; Asp; Ala; Val; Ile; His |
| Thr | Ser; Val; Ala; Gly |
| Trp | Tyr; Phe; His |
| Tyr | Trp; Phe; His |
| Val | Ala; Ile; Leu; Gly; Thr; Ser; Glu |

Substitutions that are less conservative than those in Table 4 can be selected by picking residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions which in general are expected to produce the greatest changes in protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine.

Further Modifying Sequences of the Invention B Mutation/Forced Evolution

In addition to generating silent or conservative substitutions as noted, above, the present invention optionally includes methods of modifying the sequences of the Sequence Listing. In the methods, nucleic acid or protein modification methods are used to alter the given sequences to produce new sequences and/or to chemically or enzymatically modify given sequences to change the properties of the nucleic acids or proteins.

Thus, in one embodiment, given nucleic acid sequences are modified, e.g., according to standard mutagenesis or artificial evolution methods to produce modified sequences. The modified sequences may be created using purified natural polynucleotides isolated from any organism or may be synthesized from purified compositions and chemicals using chemical means well known to those of skill in the art. For example, Ausubel (1997, 2000) supra, provides additional details on mutagenesis methods. Artificial forced evolution methods are described, for example, by Stemmer (1994; Nature 370: 389-391), Stemmer (1994; Proc. Natl. Acad. Sci. U.S.A. 91: 10747-10751), and U.S. Pat. Nos. 5,811,238, 5,837,500, and 6,242,568. Methods for engineering synthetic transcription factors and other polypeptides are described, for example, by Zhang et al. (2000) J. Biol. Chem. 275: 33850-33860, Liu et al. (2001) J. Biol. Chem. 276: 11323-11334, and Isalan et al. (2001) Nature Biotechnol. 19: 656-660. Many other mutation and evolution methods are also available and expected to be within the skill of the practitioner.

Similarly, chemical or enzymatic alteration of expressed nucleic acids and polypeptides can be performed by standard methods. For example, a sequence can be modified by addition of lipids, sugars, peptides, organic or inorganic compounds, by the inclusion of modified nucleotides or amino acids, or the like. For example, protein modification techniques are illustrated in Ausubel (1997, 2000) supra. Further details on chemical and enzymatic modifications can be found herein. These modification methods can be used to modify any given sequence, or to modify any sequence produced by the various mutation and artificial evolution modification methods noted herein.

Accordingly, the invention provides for modification of any given nucleic acid by mutation, evolution, chemical or enzymatic modification, or other available methods, as well as for the products produced by practicing such methods, e.g., using the sequences herein as a starting substrate for the various modification approaches.

For example, optimized coding sequence containing codons preferred by a particular prokaryotic or eukaryotic host can be used e.g., to increase the rate of translation or to produce recombinant RNA transcripts having desirable properties, such as a longer half-life, as compared with transcripts produced using a non-optimized sequence. Translation stop codons can also be modified to reflect host preference. For example, preferred stop codons for Saccharomyces cerevisiae and mammals are TAA and TGA, respectively. The preferred stop codon for monocotyledonous plants is TGA, whereas insects and E. coli prefer to use TAA as the stop codon.

The polynucleotide sequences of the present invention can also be engineered in order to alter a coding sequence for a variety of reasons, including but not limited to, alterations which modify the sequence to facilitate cloning, processing and/or expression of the gene product. For example, alterations are optionally introduced using techniques which are well known in the art, e.g., site-directed mutagenesis, to insert new restriction sites, to alter glycosylation patterns, to change codon preference, to introduce splice sites, etc.

Furthermore, a fragment or domain derived from any of the polypeptides of the invention can be combined with domains derived from other transcription factors or synthetic domains to modify the biological activity of a transcription factor. For instance, a DNA-binding domain derived from a transcription factor of the invention can be combined with the activation domain of another transcription factor or with a synthetic activation domain. A transcription activation domain assists in initiating transcription from a DNA-binding site. Examples include the transcription activation region of VP16 or GAL4 (Moore et al. (1998) Proc. Natl. Acad. Sci. U.S.A. 95: 376-381; Aoyama et al. (1995) Plant Cell 7: 1773-1785), peptides derived from bacterial sequences (Ma and Ptashne (1987) Cell 51: 113-119) and synthetic peptides (Giniger and Ptashne (1987) Nature 330: 670-672).

Expression and Modification of Polypeptides

Typically, polynucleotide sequences of the invention are incorporated into recombinant DNA (or RNA) molecules that direct expression of polypeptides of the invention in appropriate host cells, transgenic plants, in vitro translation systems, or the like. Due to the inherent degeneracy of the genetic code, nucleic acid sequences which encode substantially the same or a functionally equivalent amino acid sequence can be substituted for any listed sequence to provide for cloning and expressing the relevant homolog.

The transgenic plants of the present invention comprising recombinant polynucleotide sequences are generally derived from parental plants, which may themselves be non-transformed (or non-transgenic) plants. These transgenic plants may either have a transcription factor gene "knocked out" (for example, with a genomic insertion by homologous recombination, an antisense or ribozymne construct) or expressed to a normal or wild-type extent. However, overexpressing transgenic "progeny" plants will exhibit greater mRNA levels, wherein the mRNA encodes a transcription factor, that is, a DNA-binding protein that is capable of binding to a DNA regulatory sequence and inducing transcription, and preferably, expression of a plant trait gene. Preferably, the mRNA expression level will be at least three-fold greater than that of the parental plant, or more preferably at least ten-fold greater mRNA levels compared to said parental plant, and most preferably at least fifty-fold greater compared to said parental plant.

Vectors, Promoters, and Expression Systems

The present invention includes recombinant constructs comprising one or more of the nucleic acid sequences herein. The constructs typically comprise a vector, such as a plasmid, a cosmid, a phage, a virus (e.g., a plant virus), a bacterial artificial chromosome (BAC), a yeast artificial chromosome (YAC), or the like, into which a nucleic acid sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available.

General texts that describe molecular biological techniques useful herein, including the use and production of vectors, promoters and many other relevant topics, include Berger and Kimmel (1987) supra, Sambrook (1989) supra, and Ausubel (1997, 2000) supra. Any of the identified sequences can be incorporated into a cassette or vector, e.g., for expression in plants. A number of expression vectors suitable for stable transformation of plant cells or for the establishment of transgenic plants have been described including those described in Weissbach and Weissbach (1989) *Methods for Plant Molecular Biology*, Academic Press, and Gelvin et al. (1990) *Plant Molecular Biology Manual*, Kluwer Academic Publishers. Specific examples include those derived from a Ti plasmid of *Agrobacterium tumefaciens*, as well as those disclosed by Herrera-Estrella et al. (1983) *Nature* 303: 209, Bevan (1984) *Nucleic Acids Res.* 12: 8711-8721, Klee (1985) *Bio/Technology* 3: 637-642, for dicotyledonous plants.

Alternatively, non-Ti vectors can be used to transfer the DNA into monocotyledonous plants and cells by using free DNA delivery techniques. Such methods can involve, for example, the use of liposomes, electroporation, microprojectile bombardment, silicon carbide whiskers, and viruses. By using these methods transgenic plants such as wheat, rice (Christou (1991) *Bio/Technology* 9: 957-962) and corn (Gordon-Kamm (1990) *Plant Cell* 2: 603-618) can be produced. An immature embryo can also be a good target tissue for monocots for direct DNA delivery techniques by using the particle gun (Weeks et al. (1993) *Plant Physiol.* 102: 1077-1084; Vasil (1993) *Bio/Technology* 10: 667-674; Wan and Lemeaux (1994) *Plant Physiol.* 104: 37-48, and for *Agrobacterium*-mediated DNA transfer (Ishida et al. (1996) *Nature Biotechnol.* 14: 745-750).

Typically, plant transformation vectors include one or more cloned plant coding sequence (genomic or cDNA) under the transcriptional control of 5' and 3' regulatory sequences and a dominant selectable marker. Such plant transformation vectors typically also contain a promoter (e.g., a regulatory region controlling inducible or constitutive, environmentally-or developmentally-regulated, or cell- or tissue-specific expression), a transcription initiation start site, an RNA processing signal (such as intron splice sites), a transcription termination site, and/or a polyadenylation signal.

A potential utility for the transcription factor polynucleotides disclosed herein is the isolation of promoter elements from these genes that can be used to program expression in plants of any genes. Each transcription factor gene disclosed herein is expressed in a unique fashion, as determined by promoter elements located upstream of the start of translation, and additionally within an intron of the transcription factor gene or downstream of the termination codon of the gene. As is well known in the art, for a significant portion of genes, the promoter sequences are located entirely in the region directly upstream of the start of translation. In such cases, typically the promoter sequences are located within 2.0 kb of the start of translation, or within 1.5 kb of the start of translation, frequently within 1.0 kb of the start of translation, and sometimes within 0.5 kb of the start of translation.

The promoter sequences can be isolated according to methods known to one skilled in the art.

Examples of constitutive plant promoters which can be useful for expressing the TF sequence include: the cauliflower mosaic virus (CaMV) 35S promoter, which confers constitutive, high-level expression in most plant tissues (for example, Odell et al. (1985) *Nature* 313: 810-812); the nopa-line synthase promoter (An et al. (1988) *Plant Physiol.* 88: 547-552); and the octopine synthase promoter (Fromm et al. (1989) *Plant Cell* 1: 977-984).

The transcription factors of the invention may be operably linked with a specific promoter that causes the transcription factor to be expressed in response to environmental, tissue-specific or temporal signals. A variety of plant gene promoters are known to regulate gene expression in response to environmental, hormonal, chemical, developmental signals, and in a tissue-active manner; many of these may be used for expression of a TF sequence in plants. Choice of a promoter is based largely on the phenotype of interest and is determined by such factors as tissue (e.g., seed, fruit, root, pollen, vascular tissue, flower, carpel, etc.), inducibility (e.g., in response to wounding, heat, cold, drought, light, pathogens, etc.), timing, developmental stage, and the like. Numerous known promoters have been characterized and can favorably be employed to promote expression of a polynucleotide of the invention in a transgenic plant or cell of interest. For example, tissue specific promoters include: seed-specific promoters (such as the napin, phaseolin or DC3 promoter described in U.S. Pat. No. 5,773,697), fruit-specific promoters that are active during fruit ripening, such as the dru 1 promoter (U.S. Pat. No. 5,783,393), or the 2A11 promoter (U.S. Pat. No. 4,943,674) and the tomato polygalacturonase promoter (Bird et al. (1988) *Plant Mol. Biol.* 11: 651-662), root-specific promoters, such as ARSK1, and those disclosed in U.S. Pat. Nos. 5,618,988, 5,837,848 and 5,905,186, epidermis-specific promoters, including CUT1 (Kunst et al. (1999) *Biochem. Soc. Tians.* 28: 651-654), pollen-active promoters such as PTA29, PTA26 and PTA 13 (U.S. Pat. No. 5,792,929), promoters active in vascular tissue (Ringli and Keller (1998) *Plant Mol. Biol.* 37: 977-988), flower-specific (Kaiser et al. (1995) *Plant Mol. Biol.* 28: 231-243), pollen (Baerson et al. (1994) *Plant Mol. Biol.* 26: 1947-1959), carpels (Ohl et al. (1990) *Plant Cell* 2: 837-848), pollen and ovules (Baerson et al. (1993) *Plant Mol. Biol.* 22: 255-267), auxin-inducible promoters (such as that described in van der Kop et al. (1999) *Plant Mol. Biol.* 39: 979-990 or Baumann et al. (1999)*Plant Cell* 11: 323-334), cytokinin-inducible promoter (Guevara-Garcia (1998) *Plant Mol. Biol.* 38: 743-753), promoters responsive to gibberellin (Shi et al. (1998) *Plant Mol. Biol.* 38: 1053-1060, Willmott et al. (1998) *Plant Mol. Biol.* 38: 817-825) and the like. Additional promoters are those that elicit expression in response to heat (Ainley et al. (1993) *Plant Mol. Biol.* 22: 13-23), light (e.g., the pea rbcS-3A promoter, described in Kuhlemeier et al. (1989) *Plant Cell* 1: 471-478, and the maize rbcS promoter, described in Schaffier and Sheen (1991) *Plant Cell* 3: 997-1012); wounding (e.g., wun1, described in Siebertz et al. (1989) *Plant Cell* 1: 961-968), pathogens (such as the PR-1 promoter described in Buchel et al. (1999) *Plant Mol. Biol.* 40: 387-396, and the PDF1.2 promoter described in Manners et al. (1998) *Plant Mol. Biol.* 38: 1071-1080), and chemicals such as methyl jasmonate or salicylic acid (Gatz (1997) *Annu. Rev. Plant Physiol. Plant Mol. Biol.* 48: 89-108). In addition, the timing of the expression can be controlled by using promoters such as those acting at senescence (Gan and Amasino (1995) *Science* 270: 1986-1988); or late seed development (Odell et al. (1994) *Plant Physiol.* 106: 447-458).

Plant expression vectors can also include RNA processing signals that can be positioned within, upstream or downstream of the coding sequence. In addition, the expression vectors can include additional regulatory sequences from the 3'-untranslated region of plant genes, e.g., a 3' terminator region to increase mRNA stability of the mRNA, such as the PI-II terminator region of potato or the octopine or nopaline synthase 3' terminator regions.

Additional Expression Elements

Specific initiation signals can aid in efficient translation of coding sequences. These signals can include, e.g., the ATG initiation codon and adjacent sequences. When a coding sequence, its initiation codon and upstream sequences are inserted into the appropriate expression vector, no additional translational control signals may be needed. However, in cases where only coding sequence (e.g., a mature protein coding sequence) or a portion thereof is inserted, exogenous transcriptional control signals including the ATG initiation codon can be separately provided. The initiation codon is provided in the correct reading frame to facilitate transcription. Exogenous transcriptional elements and initiation codons can be of various origins, both natural and synthetic. The efficiency of expression can be enhanced by the inclusion of enhancers appropriate to the cell system in use.

Expression Hosts

The present invention also relates to host cells which are transduced with vectors of the invention, and the production of polypeptides of the invention (including fragments thereof) by recombinant techniques. Host cells are genetically engineered (i.e., nucleic acids are introduced, e.g., transduced, transformed or transfected) with the vectors of this invention, which may be, for example, a cloning vector or an expression vector comprising the relevant nucleic acids herein. The vector is optionally a plasmid, a viral particle, a phage, a naked nucleic acid, etc. The engineered host cells can be cultured in conventional nutrient media modified as appropriate for activating promoters, selecting transformants, or amplifying the relevant gene. The culture conditions, such as temperature, pH and the like, are those previously used with the host cell selected for expression, and will be apparent to those skilled in the art and in the references cited herein, including, Sambrook (1989) supra and Ausubel (1997, 2000) supra.

The host cell can be a eukaryotic cell, such as a yeast cell, or a plant cell, or the host cell can be a prokaryotic cell, such as a bacterial cell. Plant protoplasts are also suitable for some applications. For example, the DNA fragments are introduced into plant tissues, cultured plant cells or plant protoplasts by standard methods including electroporation (Fromm et al. (1985) *Proc. Natl. Acad. Sci. U.S.A.* 82: 5824-5828), infection by viral vectors such as cauliflower mosaic virus (CaMV) (Hohn et al. (1982) *Molecular Biology of Plant Tumors*, Academic Press, New York, N.Y., pp. 549-560; U.S. Pat. No. 4,407,956), high velocity ballistic penetration by small particles with the nucleic acid either within the matrix of small beads or particles, or on the surface (Klein et al. (1987) *Nature* 327: 70-73), use of pollen as vector (WO 85/01856), or use of *Agrobacterium tumefaciens* or *A. rhizogenes* carrying a T-DNA plasmid in which DNA fragments are cloned. The T-DNA plasmid is transmitted to plant cells upon infection by *Agrobacterium tumefaciens*, and a portion is stably integrated into the plant genome (Horsch et al. (1984) *Science* 233: 496-498; Fraley et al. (1 983) *Proc. Natl. Acad. Sci. U.S.A.* 80: 4803-4807).

The cell can include a nucleic acid of the invention that encodes a polypeptide, wherein the cell expresses a polypeptide of the invention. The cell can also include vector sequences, or the like. Furthermore, cells and transgenic plants that include any polypeptide or nucleic acid above or throughout this specification, e.g., produced by transduction of a vector of the invention, are an additional feature of the invention.

For long-term, high-yield production of recombinant proteins, stable expression can be used. Host cells transformed with a nucleotide sequence encoding a polypeptide of the invention are optionally cultured under conditions suitable for the expression and recovery of the encoded protein from cell culture. The protein or fragment thereof produced by a recombinant cell may be secreted, membrane-bound, or contained intracellularly, depending on the sequence and/or the vector used. As will be understood by those of skill in the art, expression vectors containing polynucleotides encoding mature proteins of the invention can be designed with signal sequences which direct secretion of the mature polypeptides through a prokaryotic or eukaryotic cell membrane.

Modified Amino Acid Residues

Polypeptides of the invention may contain one or more modified amino acid residues. The presence of modified amino acids may be advantageous in, for example, increasing polypeptide half-life, reducing polypeptide antigenicity or toxicity, increasing polypeptide storage stability, or the like. Amino acid residue(s) are modified, for example, co-translationally or post-translationally during recombinant production or modified by synthetic or chemical means.

Non-limiting examples of a modified amino acid residue include incorporation or other use of acetylated amino acids, glycosylated amino acids, sulfated amino acids, prenylated (e.g., farnesylated, geranylgeranylated) amino acids, PEG modified (for example, "PEGylated") amino acids, biotinylated amino acids, carboxylated amino acids, phosphorylated amino acids, etc. References adequate to guide one of skill in the modification of amino acid residues are replete throughout the literature.

The modified amino acid residues may prevent or increase affinity of the polypeptide for another molecule, including, but not limited to, polynucleotide, proteins, carbohydrates, lipids and lipid derivatives, and other organic or synthetic compounds.

Identification of Additional Protein Factors

A transcription factor provided by the present invention can also be used to identify additional endogenous or exogenous molecules that can affect a phenotype or trait of interest. Such molecules include endogenous molecules that are acted upon either at a transcriptional level by a transcription factor of the invention to modify a phenotype as desired. For example, the transcription factors can be employed to identify one or more downstream genes that are subject to a regulatory effect of the transcription factor. In one approach, a transcription factor or transcription factor homolog of the invention is expressed in a host cell, e.g., a transgenic plant cell, tissue or explant, and expression products, either RNA or protein, of likely or random targets are monitored, e.g., by hybridization to a microarray of nucleic acid probes corresponding to genes expressed in a tissue or cell type of interest, by two-dimensional gel electrophoresis of protein products, or by any other method known in the art for assessing expression of gene products at the level of RNA or protein. Alternatively, a transcription factor of the invention can be used to identify promoter sequences (such as binding sites on DNA sequences) involved in the regulation of a downstream target. After identifying a promoter sequence, interactions between the transcription factor and the promoter sequence can be modified by changing specific nucleotides in the promoter sequence or specific amino acids in the transcription factor that interact with the promoter sequence to alter a plant trait. Typically, transcription factor DNA-binding sites are identified by gel shift assays. After identifying the promoter regions, the promoter region sequences can be employed in double-stranded DNA arrays to identify molecules that affect the interactions of the transcription factors with their promoters (Bulyk et al. (1999) *Nature Biotechnol.* 17: 573-577).

The identified transcription factors are also useful to identify proteins that modify the activity of the transcription factor. Such modification can occur by covalent modification, such as by phosphorylation, or by protein-protein (homo or-heteropolymer) interactions. Any method suitable for detecting protein-protein interactions can be employed. Among the methods that can be employed are co-immunoprecipitation, cross-linking and co-purification through gradients or chromatographic columns, and the two-hybrid yeast system.

The two-hybrid system detects protein interactions in vivo and has been previously described (Chien et al. (1991) *Proc. Natl. Acad. Sci. U.S.A.* 88: 9578-9582), and is commercially available from Clontech (Palo Alto, Calif.). In such a system, plasmids are constructed that encode two hybrid proteins: one consists of the DNA-binding domain of a transcription activator protein fused to the TF polypeptide and the other consists of the transcription activator protein's activation domain fused to an unknown protein that is encoded by a cDNA that has been recombined into the plasmid as part of a cDNA library. The DNA-binding domain fusion plasmid and the cDNA library are transformed into a strain of the yeast *Saccharomyces cerevisiae* that contains a reporter gene (e.g., lacZ) whose regulatory region contains the transcription activator's binding site. Either hybrid protein alone cannot activate transcription of the reporter gene. Interaction of the two hybrid proteins reconstitutes the functional activator protein and results in expression of the reporter gene, which is detected by an assay for the reporter gene product. Then, the library plasmids responsible for reporter gene expression are isolated and sequenced to identify the proteins encoded by the library plasmids. After identifying proteins that interact with the transcription factors, assays for compounds that interfere with the TF protein-protein interactions can be performed.

Subsequences

Also contemplated are uses of polynucleotides, also referred to herein as oligonucleotides, typically having at least 12 to 50 bases that hybridize under stringent conditions to a polynucleotide sequence described above. The polynucleotides may be used as probes, primers, sense and antisense agents, and the like, according to methods as noted supra.

Subsequences of the polynucleotides of the invention, including polynucleotide fragments and oligonucleotides are useful as nucleic acid probes and primers. An oligonucleotide suitable for use as a probe or primer is at least about 15 nucleotides in length, more often at least about 18 nucleotides, often at least about 21 nucleotides, frequently at least about 30 nucleotides, or about 40 nucleotides, or more in length. A nucleic acid probe is useful in hybridization protocols, for example, to identify additional polypeptide homologs of the invention, including protocols for microarray experiments. Primers can be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods (for example, in Sambrook (1989) supra, and Ausubel (1997, 2000) supra).

In addition, the invention includes an isolated or recombinant polypeptide including a subsequence of at least about 15 contiguous amino acids encoded by the recombinant or isolated polynucleotides of the invention. For example, such polypeptides, or domains or fragments thereof, can be used as immunogens, e.g., to produce antibodies specific for the polypeptide sequence, or as probes for detecting a sequence of interest. A subsequence can range in size from about 15 amino acids in length up to and including the full length of the polypeptide.

To be encompassed by the present invention, an expressed polypeptide which comprises such a polypeptide subsequence performs at least one biological function of the intact polypeptide in substantially the same manner, or to a similar extent, as does the intact polypeptide. For example, a polypeptide fragment can comprise a recognizable structural motif or functional domain such as a DNA binding domain that activates transcription, for example, by binding to a specific DNA promoter region an activation domain, or a domain for protein-protein interactions.

Production of Transgenic Plants
Modification of Traits

The polynucleotides of the invention are favorably employed to produce transgenic plants with various traits, or characteristics, that have been modified in a desirable manner, e.g., to improve the seed characteristics of a plant. For example, alteration of expression levels or patterns (e.g., spatial or temporal expression patterns) of one or more of the transcription factors (or transcription factor homologs) of the invention, as compared with the levels of the same protein found in a wild-type plant, can be used to modify a plant's traits. An illustrative example of trait modification, improved characteristics, by altering expression levels of a particular transcription factor is described further in the Examples and the Sequence Listing.

*Arabidopsis* as a Model System

*Arabidopsis thaliana* is the object of rapidly growing attention as a model for genetics and metabolism in plants. *Arabidopsis* has a small genome, and well-documented studies are available. It is easy to grow in large numbers and mutants defining important genetically controlled mechanisms are either available, or can readily be obtained. Various methods to introduce and express isolated homologous genes are available (Koncz et al., editors, *Methods in Arabidopsis Research* (1992) World Scientific, New Jersey N.J., in "Preface"). Because of its small size, short life cycle, obligate autogamy and high fertility, *Arabidopsis* is also a choice organism for the isolation of mutants and studies in morphogenetic and development pathways, and control of these pathways by transcription factors (Koncz (1992) supra, p. 72). A number of studies introducing transcription factors into *A. thaliana* have demonstrated the utility of this plant for understanding the mechanisms of gene regulation and trait alteration in plants (for example, Koncz (1992) supra, and U.S. Pat. No. 6,417,428).

*Arabidopsis* Genes in Transgenic Plants

Expression of genes encoding transcription factors that modify expression of endogenous genes, polynucleotides, and proteins are well known in the art. In addition, transgenic plants comprising isolated polynucleotides encoding transcription factors may also modify expression of endogenous genes, polynucleotides, and proteins. Examples include Peng et al. (1997) et al. *Genes and Development* 11: 3194-3205, and Peng et al. (1999) *Nature* 400: 256-261. In addition, many others have demonstrated that an *Arabidopsis* transcription factor expressed in an exogenous plant species elicits the same or very similar phenotypic response (for example, Fu et al. (2001) *Plant Cell* 13: 1791-1802; Nandi et al. (2000) *Curr. Biol.* 10: 215-218; Coupland (1995) *Nature* 377: 482-483; and Weigel and Nilsson (1995) *Nature* 377: 482-500).

Homologous Genes Introduced into Transgenic Plants

Homologous genes that may be derived from any plant, or from any source whether natural, synthetic, semi-synthetic or recombinant, and that share significant sequence identity or similarity to those provided by the present invention, may be introduced into plants, for example, crop plants, to confer desirable or improved traits. Consequently, transgenic plants may be produced that comprise a recombinant expression vector or cassette with a promoter operably linked to one or more sequences homologous to presently disclosed sequences. The promoter may be, for example, a plant or viral promoter.

The invention thus provides for methods for preparing transgenic plants, and for modifying plant traits. These methods include introducing into a plant a recombinant expression vector or cassette comprising a functional promoter operably linked to one or more sequences homologous to presently disclosed sequences. Plants and kits for producing these plants that result from the application of these methods are also encompassed by the present invention.

Transcription Factors of Interest for the Modification of Plant Traits

Currently, the existence of a series of maturity groups for different latitudes represents a major barrier to the introduction of new valuable traits. Any trait (e.g. increased tolerance to an abiotic or biotic stress) has to be bred into each of the different maturity groups separately, a laborious and costly exercise. The availability of single strain, which could be grown at any latitude, would therefore greatly increase the potential for introducing new traits to crop species such as soybean and cotton.

For the specific effects, traits and utilities conferred to plants, one or more transcription factor genes of the present invention may be used to increase or decrease, or improve or prove deleterious to a given trait. For example, knocking out a transcription factor gene that naturally occurs in a plant, or suppressing the gene (with, for example, antisense suppression), may cause decreased tolerance to an osmotic stress relative to non-transformed or wild-type plants. By overexpressing this gene, the plant may experience increased tolerance to the same stress. More than one transcription factor gene may be introduced into a plant, either by transforming the plant with one or more vectors comprising two or more transcription factors, or by selective breeding of plants to yield hybrid crosses that comprise more than one introduced transcription factor.

Genes, Traits and Utilities that Affect Plant Characteristics

Plant transcription factors can modulate gene expression, and, in turn, be modulated by the environmental experience of a plant. Significant alterations in a plant's environment invariably result in a change in the plant's transcription factor gene expression pattern. Altered transcription factor expression patterns generally result in phenotypic changes in the plant. Transcription factor gene product(s) in transgenic plants then differ(s) in amounts or proportions from that found in wild-type or non-transformed plants, and those transcription factors likely represent polypeptides that are used to alter the response to the environmental change. By way of example, it is well accepted in the art that analytical methods based on altered expression patterns may be used to screen for phenotypic changes in a plant far more effectively than can be achieved using traditional methods.

Plants overexpressing members of the G1792 clade of transcription factor polypeptides, including sequences from diverse species of monocots and dicots, such as *Arabidopsis thaliana* polypeptides G1792, G1791, G1795 and G30, *Oryza sativa* polypeptide G3381, and *Glycine max* polypeptide G3520, were shown to be more disease tolerant than control plants (Example VIII).

The invention also provides polynucleotides that encode G1792 clade polypeptides, fragments thereof, conserved domains thereof, paralogs, orthologs, equivalogs, and fragments thereof. Examples of these sequences are listed in the Sequence Listing, and due to the high degree of structural similarity to the sequences of the invention, it is expected that many of the sequences for which data have not been generated will also function to increase disease tolerance. The invention also encompasses the complements of the polynucleotides. The polynucleotides are also useful for screening libraries of molecules or compounds for specific binding and for identifying other sequences of G1792 clade member by identifying orthologs having similar sequences, particularly in the conserved domains.

Antisense and Co-Suppression

In addition to expression of the nucleic acids of the invention as gene replacement or plant phenotype modification nucleic acids, the nucleic acids are also useful for sense and anti-sense suppression of expression, e.g., to down-regulate expression of a nucleic acid of the invention, e.g., as a further mechanism for modulating plant phenotype. That is, the nucleic acids of the invention, or subsequences or anti-sense sequences thereof, can be used to block expression of naturally occurring homologous nucleic acids. A variety of sense and anti-sense technologies are known in the art, e.g., as set forth in Lichtenstein and Nellen (1997) *Antisense Technology: A Practical Approach* IRL Press at Oxford University Press, Oxford, U.K. Antisense regulation is also described in Crowley et al. (1985) *Cell* 43: 633-641; Rosenberg et al. (1985) *Nature* 313: 703-706; Preiss et al. (1985) *Nature* 313: 27-32; Melton (1985) *Proc. Natl. Acad. Sci. U.S.A.* 82: 144-148; Izant and Weintraub (1985) *Science* 229: 345-352; and Kim and Wold (1 985) *Cell* 42: 129-138. Additional methods for antisense regulation are known in the art. Antisense regulation has been used to reduce or inhibit expression of plant genes in, for example in European Patent Publication No. 271988. Antisense RNA may be used to reduce gene expression to produce a visible or biochemical phenotypic change in a plant (Smith et al. (1988) *Nature* 334: 724-726; Smith et al. (1990) *Plant Mol. Biol.* 14: 369-379). In general, sense or anti-sense sequences are introduced into a cell, where they are optionally amplified, for example, by transcription. Such sequences include both simple oligonucleotide sequences and catalytic sequences such as ribozymes.

For example, a reduction or elimination of expression (i.e., a "knock-out") of a transcription factor or transcription factor homolog polypeptide in a transgenic plant, e.g., to modify a plant trait, can be obtained by introducing an antisense construct corresponding to the polypeptide of interest as a cDNA. For antisense suppression, the transcription factor or homolog cDNA is arranged in reverse orientation (with respect to the coding sequence) relative to the promoter sequence in the expression vector. The introduced sequence need not be the full length cDNA or gene, and need not be identical to the cDNA or gene found in the plant type to be transformed. Typically, the antisense sequence need only be capable of hybridizing to the target gene or RNA of interest. Thus, where the introduced sequence is of shorter length, a higher degree of homology to the endogenous transcription factor sequence will be needed for effective antisense suppression. While antisense sequences of various lengths can be utilized, preferably, the introduced antisense sequence in the vector will be at least 30 nucleotides in length, and improved antisense suppression will typically be observed as the length of the antisense sequence increases. Preferably, the length of the antisense sequence in the vector will be greater than 100 nucleotides. Transcription of an antisense construct as described results in the production of RNA molecules that are the reverse complement of mRNA molecules transcribed from the endogenous transcription factor gene in the plant cell.

Suppression of endogenous transcription factor gene expression can also be achieved using a ribozyme. Ribozymes are RNA molecules that possess highly specific endoribonuclease activity. The production and use of ribozymes are disclosed in U.S. Pat. Nos. 4,987,071 and 5,543,508. Synthetic ribozyme sequences including antisense RNAs can be used to confer RNA cleaving activity on the antisense RNA, such that endogenous mRNA molecules that hybridize to the antisense RNA are cleaved, which in turn leads to an enhanced antisense inhibition of endogenous gene expression.

Vectors in which RNA encoded by a transcription factor or transcription factor homolog cDNA is over-expressed can also be used to obtain co-suppression of a corresponding endogenous gene, for example, in the manner disclosed in U.S. Pat. No. 5,231,020. Such co-suppression (also termed sense suppression) does not require that the entire transcription factor cDNA be introduced into the plant cells, nor does it require that the introduced sequence be exactly identical to the endogenous transcription factor gene of interest. However, as with antisense suppression, the suppressive efficiency will be enhanced as specificity of hybridization is increased, e.g., as the introduced sequence is lengthened, and/or as the sequence similarity between the introduced sequence and the endogenous transcription factor gene is increased.

Vectors expressing an untranslatable form of the transcription factor mRNA (e.g., sequences comprising one or more stop codon, or nonsense mutation) can also be used to suppress expression of an endogenous transcription factor, thereby reducing or eliminating its activity and modifying one or more traits. Methods for producing such constructs are described in U.S. Pat. No. 5,583,021. Preferably, such constructs are made by introducing a premature stop codon into the transcription factor gene. Alternatively, a plant trait can be modified by gene silencing using double-stranded RNA (Sharp (1999) *Genes and Development* 13: 139-141). Another method for abolishing the expression of a gene is by insertion mutagenesis using the T-DNA of *Agrobacterium tumefaciens*. After generating the insertion mutants, the mutants can be screened to identify those containing the insertion in a transcription factor or transcription factor homolog gene. Plants containing a single transgene insertion event at the desired gene can be crossed to generate homozygous plants for the mutation. Such methods are well known to those of skill in the art (for example, in Koncz et al. (1992) supra).

Suppression of endogenous transcription factor gene expression can also be achieved using RNA interference, or RNAi. RNAi is a post-transcriptional, targeted gene-silencing technique that uses double-stranded RNA (dsRNA) to incite degradation of messenger RNA (mRNA) containing the same sequence as the dsRNA (Constans (2002) *The Scientist* 16:36). Small interfering RNAs, or siRNAs are produced in at least two steps: an endogenous ribonuclease cleaves longer dsRNA into shorter, 21-23 nucleotide-long RNAs. The siRNA segments then mediate the degradation of the target mRNA (Zamore (2001) *Nature Struct. Biol.* 8: 746-50). RNAi has been used for gene function determination in a manner similar to antisense oligonucleotides (Constans (2002) supra). Expression vectors that continually express siRNAs in transiently and stably-transfected cells have been engineered to express small hairpin RNAs (shRNAs), which get processed in vivo into siRNAs-like molecules capable of carrying out gene-specific silencing (Brummelkamp et al. (2002) *Science* 296:550-553, and Paddison et al. (2002) *Genes & Dev.* 16:948-958). Post-transcriptional gene silencing by double-stranded RNA is discussed in further detail by Hammond et al. (2001) *Nature Rev Gen* 2: 110-119, Fire et al. (I 998) *Nature* 391: 806-811 and Timmons and Fire (1998) *Nature* 395: 854.

Alternatively, a plant phenotype can be altered by eliminating an endogenous gene, such as a transcription factor or transcription factor homolog, e.g., by homologous recombination (Kempin et al. (1997) *Nature* 389: 802-803).

A plant trait can also be modified by using the Cre-lox system (for example, as described in U.S. Pat. No. 5,658, 772). A plant genome can be modified to include first and second lox sites that are then contacted with a Cre recombinase. If the lox sites are in the same orientation, the intervening DNA sequence between the two sites is excised. If the lox sites are in the opposite orientation, the intervening sequence is inverted.

The polynucleotides and polypeptides of this invention can also be expressed in a plant in the absence of an expression cassette by manipulating the activity or expression level of the endogenous gene by other means, such as, for example, by ectopically expressing a gene by T-DNA activation tagging (Ichikawa et al. (1997) *Nature* 390 698-701; Kakimoto et al. (1996) *Science* 274: 982-985). This method entails transforming a plant with a gene tag containing multiple transcriptional enhancers and once the tag has inserted into the genome, expression of a flanking gene coding sequence becomes deregulated. In another example, the transcriptional machinery in a plant can be modified so as to increase transcription levels of a polynucleotide of the invention (for example, in PCT Publications WO 96/06166 and WO 98/53057 which describe the modification of the DNA-binding specificity of zinc finger proteins by changing particular amino acids in the DNA-binding motif).

The transgenic plant can also include the machinery necessary for expressing or altering the activity of a polypeptide encoded by an endogenous gene, for example, by altering the phosphorylation state of the polypeptide to maintain it in an activated state.

Transgenic plants (or plant cells, or plant explants, or plant tissues) incorporating the polynucleotides of the invention and/or expressing the polypeptides of the invention can be produced by a variety of well established techniques as described above. Following construction of a vector, most typically an expression cassette, including a polynucleotide, e.g., encoding a transcription factor or transcription factor homolog, of the invention, standard techniques can be used to introduce the polynucleotide into a plant, a plant cell, a plant explant or a plant tissue of interest. Optionally, the plant cell, explant or tissue can be regenerated to produce a transgenic plant.

The plant can be any higher plant, including gymnosperms, monocotyledonous and dicotyledonous plants. Suitable protocols are available for *Leguminosae* (alfalfa, soybean, clover, etc.), *Umbelliferae* (carrot, celery, parsnip), *Cruciferae* (cabbage, radish, rapeseed, broccoli, etc.), *Curcurbitaceae* (melons and cucumber), *Gramineae* (wheat, corn, rice, barley, millet, etc.), *Solanaceae* (potato, tomato, tobacco, peppers, etc.), and various other crops. See protocols described in Ammirato et al., Editors, (1984) *Handbook of Plant Cell Culture Crop Species*, Macmillan Publ. Co., New York NY;

Shimamoto et al. (1989) *Nature* 338: 274-276; Fromm et al. (1990) *Bio/Technol.* 8: 833-839; and Vasil et al. (1990) *Bio/Technol.* 8: 429-434.

Transformation and regeneration of both monocotyledonous and dicotyledonous plant cells are now routine, and the selection of the most appropriate transformation technique will be determined by the practitioner. The choice of method will vary with the type of plant to be transformed; those skilled in the art will recognize the suitability of particular methods for given plant types. Suitable methods can include, but are not limited to: electroporation of plant protoplasts; liposome-mediated transformation; polyethylene glycol (PEG) mediated transformation; transformation using viruses; micro-injection of plant cells; micro-projectile bombardment of plant cells; vacuum infiltration; and *Agrobacterium tumefaciens*-mediated transformation. Transformation means introducing a nucleotide sequence into a plant in a manner to cause stable or transient expression of the sequence.

Successful examples of the modification of plant characteristics by transformation with cloned sequences which serve to illustrate the current knowledge in this field of technology, and which are herein incorporated by reference, include: U.S. Pat. Nos. 5,571,706; 5,677,175; 5,510,471; 5,750,386; 5,597,945; 5,589,615; 5,750,871; 5,268,526; 5,780,708; 5,538,880; 5,773,269; 5,736,369 and 5,610,042.

Following transformation, plants are preferably selected using a dominant selectable marker incorporated into the transformation vector. Typically, such a marker will confer antibiotic or herbicide resistance on the transformed plants, and selection of transformants can be accomplished by exposing the plants to appropriate concentrations of the antibiotic or herbicide.

After transformed plants are selected and grown to maturity, those plants showing a modified trait are identified. The modified trait can be any of those traits described above. Additionally, to confirm that the modified trait is due to changes in expression levels or activity of the polypeptide or polynucleotide of the invention can be determined by analyzing mRNA expression using Northern blots, RT-PCR or microarrays, or protein expression using immunoblots or Western blots or gel shift assays.

Integrated Systems B Sequence Identity

In addition to providing compositions and methods to improve plant traits, the present invention may be an integrated system, computer or computer readable medium that comprises an instruction set for determining the identity of one or more sequences in a database. In addition, the instruction set can be used to generate or identify sequences that meet any specified criteria. Furthermore, the instruction set may be used to associate or link certain functional benefits, such improved characteristics, with one or more identified sequence.

For example, the instruction set can include, e.g., a sequence comparison or other alignment program, e.g., an available program such as, for example, the Wisconsin Package Version 10.0, such as BLAST, FASTA, PILEUP, FINDPATTERNS or the like (GCG, Madison, Wis.). Public sequence databases such as GenBank, EMBL, Swiss-Prot and PIR or private sequence databases such as PHYTOSEQ sequence database (Incyte Genomics, Wilmington, Del.) can be searched.

Alignment of sequences for comparison can be conducted by the local homology algorithm of Smith and Waterman (1981) *Adv. Appl. Math.* 2: 482-489, by the homology alignment algorithm of Needleman and Wunsch (1970) *J. Mol. Biol.* 48: 443-453, by the search for similarity method of Pearson and Lipman (1988) *Proc. Natl Acad. Sci. U.S.A.* 85: 2444-2448, by computerized implementations of these algorithms. After alignment, sequence comparisons between two (or more) polynucleotides or polypeptides are typically performed by comparing sequences of the two sequences over a comparison window to identify and compare local regions of sequence similarity. The comparison window can be a segment of at least about 20 contiguous positions, usually about 50 to about 200, more usually about 100 to about 150 contiguous positions. A description of the method is provided in Ausubel et al. (1997, 2000) supra.

A variety of methods for determining sequence relationships can be used, including manual alignment and computer assisted sequence alignment and analysis. This later approach is a preferred approach in the present invention, due to the increased throughput afforded by computer assisted methods. As noted above, a variety of computer programs for performing sequence alignment are available, or can be produced by one of skill.

One example algorithm that is suitable for determining percent sequence identity and sequence similarity is the BLAST algorithm, which is described in Altschul et al. (1990) supra. Software for performing BLAST analyses is publicly available, e.g., through the National Library of Medicine's National Center for Biotechnology Information (National Institutes of Health U.S. government website at www.ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990, 1993) supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (Henikoff and Henikoff (1992) *Proc. Natl. Acad. Sci. U.S.A.* 89: 10915-10919). Unless otherwise indicated, "sequence identity" here refers to the % sequence identity generated from a tblastx using the NCBI version of the algorithm at the default settings using gapped alignments with the filter "off" (for example, at the NIH website at www.ncbi.nlm.nih.gov, supra).

In addition to calculating percent sequence identity, the BLAST algorithm also performs a statistical analysis of the similarity between two sequences (for example, Karlin and Altschul (1993) *Proc. Natl. Acad. Sci. U.S.A.* 90: 5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence (and, therefore, in this context, homologous) if the smallest sum probability in a comparison of the test nucleic acid to the reference nucleic acid is less than about 0.1, or less than about 0.01, and or even less than about 0.001. An additional example of a useful sequence alignment algorithm is PILEUP. PILEUP creates a multiple sequence alignment from a group of related sequences using progressive, pairwise alignments. The program can align, for example, up to 300 sequences of a maximum length of 5,000 letters.

The integrated system, or computer typically includes a user input interface allowing a user to selectively view one or more sequence records corresponding to the one or more character strings, as well as an instruction set which aligns the one or more character strings with each other or with an additional character string to identify one or more region of sequence similarity. The system may include a link of one or more character strings with a particular phenotype or gene function. Typically, the system includes a user readable output element that displays an alignment produced by the alignment instruction set.

The methods of this invention can be implemented in a localized or distributed computing environment. In a distributed environment, the methods may be implemented on a single computer comprising multiple processors or on a multiplicity of computers. The computers can be linked, e.g. through a common bus, but more preferably the computer(s) are nodes on a network. The network can be a generalized or a dedicated local or wide-area network and, in certain preferred embodiments, the computers may be components of an intra-net or an internet.

Thus, the invention provides methods for identifying a sequence similar or homologous to one or more polynucleotides as noted herein, or one or more target polypeptides encoded by the polynucleotides, or otherwise noted herein and may include linking or associating a given plant phenotype or gene function with a sequence. In the methods, a sequence database is provided (locally or across an inter or intra net) and a query is made against the sequence database using the relevant sequences herein and associated plant phenotypes or gene functions.

Any sequence herein can be entered into the database, before or after querying the database. This provides for both expansion of the database and, if done before the querying step, for insertion of control sequences into the database. The control sequences can be detected by the query to ensure the general integrity of both the database and the query. As noted, the query can be performed using a web browser based interface. For example, the database can be a centralized public database such as those noted herein, and the querying can be done from a remote terminal or computer across an internet or intranet.

Any sequence herein can be used to identify a similar, homologous, paralogous, or orthologous sequence in another plant. This provides means for identifying endogenous sequences in other plants that may be useful to alter a trait of progeny plants, which results from crossing two plants of different strain. For example, sequences that encode an ortholog of any of the sequences herein that naturally occur in a plant with a desired trait can be identified using the sequences disclosed herein. The plant is then crossed with a second plant of the same species but which does not have the desired trait to produce progeny which can then be used in further crossing experiments to produce the desired trait in the second plant. Therefore the resulting progeny plant contains no transgenes; expression of the endogenous sequence may also be regulated by treatment with a particular chemical or other means, such as EMR. Some examples of such compounds well known in the art include: ethylene; cytokinins; phenolic compounds, which stimulate the transcription of the genes needed for infection; specific monosaccharides and acidic environments that potentiate vir gene induction; acidic polysaccharides which induce one or more chromosomal genes; and opines; other mechanisms include light or dark treatment (reviews of such treatments appears in Winans (1992) *Microbiol. Rev.* 56: 12-31; Eyal et al. (1992) *Plant Mol. Biol.* 19: 589-599; Chrispeels et al. (2000) *Plant Mol. Biol.* 42: 279-290; and Piazza et al. (2002) *Plant Physiol.* 128: 1077-1086).

Molecular Modeling

Another means that may be used to confirm the utility and function of transcription factor sequences that are orthologous or paralogous to presently disclosed transcription factors is through the use of molecular modeling software. Molecular modeling is routinely used to predict polypeptide structure, and a variety of protein structure modeling programs, such as "Insight II" (Accelrys, Inc.) are commercially available for this purpose. Modeling can thus be used to predict which residues of a polypeptide can be changed without altering function (Crameri et al. (2003) U.S. Pat. No. 6,521,453). Thus, polypeptides that are sequentially similar can be shown to have a high likelihood of similar function by their structural similarity, which may, for example, be established by comparison of regions of superstructure. The relative tendencies of amino acids to form regions of superstructure (for example, α-helices and β-sheets) are well established. For example, O'Neil et al. (1990) *Science* 250: 646-651, have discussed in detail the helix forming tendencies of amino acids. Tables of relative structure forming activity for amino acids can be used as substitution tables to predict which residues can be functionally substituted in a given region, for example, in DNA-binding domains of known transcription factors and equivalogs. Homologs that are likely to be functionally similar can then be identified.

Of particular interest is the structure of a transcription factor in the region of its conserved domains, such as those identified in Table 1. Structural analyses may be performed by comparing the structure of the known transcription factor around its conserved domain with those of orthologs and paralogs. Analysis of a number of polypeptides within a transcription factor group or lade, including the functionally or sequentially similar polypeptides provided in the Sequence Listing, may also provide an understanding of structural elements required to regulate transcription within a given family.

EXAMPLES

It is to be understood that this invention is not limited to the particular devices, machines, materials and methods described. Although particular embodiments are described, equivalent embodiments may be used to practice the invention. The examples below are provided to enable the subject invention and are not included for the purpose of limiting the invention.

The invention, now being generally described, will be more readily understood by reference to the following examples, which are included merely for purposes of illustration of certain aspects and embodiments of the present invention and are not intended to limit the invention. It will be recognized by one of skill in the art that a transcription factor that is associated with a particular first trait may also be associated with at least one other, unrelated and inherent second trait which was not predicted by the first trait.

Example I

Full Length Gene Identification and Cloning

Putative transcription factor sequences (genomic or ESTs) related to known transcription factors were identified in the Arabidopsis thaliana GenBank database using the tblastn sequence analysis program using default parameters and a P-value cutoff threshold of 4 or 5 or lower, depending on the length of the query sequence. Putative transcription factor sequence hits were then screened to identify those containing particular sequence strings. If the sequence hits contained such sequence strings, the sequences were confirmed as transcription factors.

Alternatively, Arabidopsis thaliana cDNA libraries derived from different tissues or treatments, or genomic libraries were screened to identify novel members of a transcription family using a low stringency hybridization approach. Probes were synthesized using gene specific primers in a standard PCR reaction (annealing temperature 60° C.) and labeled with $^{32}$P dCTP using the High Prime DNA Labeling Kit (Roche Diagnostics Corp., Indianapolis, Ind.). Purified radiolabelled probes were added to filters immersed in Church hybridization medium (0.5 M $NaPO_4$ pH 7.0, 7% SDS, 1% w/v bovine serum albumin) and hybridized overnight at 60° C. with shaking. Filters were washed two times for 45 to 60 minutes with 1×SSC, 1% SDS at 60° C.

To identify additional sequence 5' or 3' of a partial cDNA sequence in a cDNA library, 5' and 3' rapid amplification of cDNA ends (RACE) was performed using the MARATHON cDNA amplification kit (Clontech, Palo Alto, Calif.). Generally, the method entailed first isolating poly(A) mRNA, performing first and second strand cDNA synthesis to generate double stranded cDNA, blunting cDNA ends, followed by ligation of the MARATHON Adaptor to the cDNA to form a library of adaptor-ligated ds cDNA.

Gene-specific primers were designed to be used along with adaptor specific primers for both 5' and 3' RACE reactions. Nested primers, rather than single primers, were used to increase PCR specificity. Using 5' and 3' RACE reactions, 5' and 3' RACE fragments were obtained, sequenced and cloned. The process can be repeated until 5' and 3' ends of the full-length gene were identified. Then the full-length cDNA was generated by PCR using primers specific to 5' and 3' ends of the gene by end-to-end PCR.

Example II

Construction of Expression Vectors

The sequence was amplified from a genomic or cDNA library using primers specific to sequences upstream and downstream of the coding region. The expression vector was pMEN20 or pMEN65, which are both derived from pMON316 (Sanders et al. (1987) Nucleic Acids Res. 15:1543-1558) and contain the CaMV 35S promoter to express transgenes. To clone the sequence into the vector, both pMEN20 and the amplified DNA fragment were digested separately with SalI and NotI restriction enzymes at 37° C. for 2 hours. The digestion products were subject to electrophoresis in a 0.8% agarose gel and visualized by ethidium bromide staining. The DNA fragments containing the sequence and the linearized plasmid were excised and purified by using a QIAQUICK gel extraction kit (Qiagen, Valencia, Calif.). The fragments of interest were ligated at a ratio of 3:1 (vector to insert). Ligation reactions using T4 DNA ligase (New England Biolabs, Beverly Mass.) were carried out at 16° C. for 16 hours. The ligated DNAs were transformed into competent cells of the E. coli strain DH5alpha by using the heat shock method. The transformations were plated on LB plates containing 50 mg/l kanamycin (Sigma Chemical Co. St. Louis Mo.). Individual colonies were grown overnight in five milliliters of LB broth containing 50 mg/l kanamycin at 37° C. Plasmid DNA was purified by using Qiaquick Mini Prep kits (Qiagen, Valencia, Calif.).

Example III

Transformation of Agrobacterium with the Expression Vector

After the plasmid vector containing the gene was constructed, the vector was used to transform Agrobacterium tumefaciens cells expressing the gene products. The stock of Agrobacterium tumefaciens cells for transformation was made as described by Nagel et al. (1990) FEMS Microbiol Letts. 67: 325-328. Agrobacterium strain ABI was grown in 250 ml LB medium (Sigma) overnight at 28° C. with shaking until an absorbance over 1 cm at 600 nm ($A_{600}$) of 0.5 1.0 was reached. Cells were harvested by centrifugation at 4,000×g for 15 minutes at 4° C. Cells were then resuspended in 250 µl chilled buffer (1 mM HEPES, pH adjusted to 7.0 with KOH). Cells were centrifuged again as described above and resuspended in 125 µl chilled buffer. Cells were then centrifuged and resuspended two more times in the same HEPES buffer as described above at a volume of 100 µl and 750 µl, respectively. Resuspended cells were then distributed into 40 µl aliquots, quickly frozen in liquid nitrogen, and stored at −80° C.

Agrobacterium cells were transformed with plasmids prepared as described above following the protocol described by Nagel et al. 1990) supra. For each DNA construct to be transformed, 50-100 ng DNA (generally resuspended in 10 mM Tris-HCl, 1 mM EDTA, pH 8.0) was mixed with 40 µl of Agrobacterium cells. The DNA/cell mixture was then transferred to a chilled cuvette with a 2 mm electrode gap and subject to a 2.5 kV charge dissipated at 25 µF and 200 µF using a Gene Pulser II apparatus (Bio-Rad, Hercules, Calif.). After electroporation, cells were immediately resuspended in 1.0 ml LB and allowed to recover without antibiotic selection for 2 4 hours at 28° C. in a shaking incubator. After recovery, cells were plated onto selective medium of LB broth containing 100 µg/ml spectinomycin (Sigma) and incubated for 24-48 hours at 28° C. Single colonies were then picked and inoculated in fresh medium. The presence of the plasmid construct was verified by PCR amplification and sequence analysis.

Example IV

Transformation of Arabidopsis Plants with Agrobacterium tumefaciens with Expression Vector After transformation of Agrobacterium tumefaciens with plasmid vectors containing the gene, single Agrobacterium colonies were identified, propagated, and used to transform Arabidopsis plants. Briefly, 500 ml cultures of LB medium containing 50 mg/l kanamycin were inoculated with the colonies and grown at 28° C. with shaking for 2 days until an optical absorbance at 600 nm wavelength over 1 cm ($A_{600}$) of >2.0 is reached. Cells were then harvested by centrifugation at 4,000 ×g for 10 minutes, and resuspended in infiltration medium (½× Murashige and Skoog salts (Sigma Chemical Co., St. Louis, Mo.), 1× Gamborg's B-5 vitamins (Sigma Chemical Co., St. Louis, Mo.), 5.0% (w/v) sucrose, 0.044 µM benzylamino purine (Sigma Chemical Co., St. Louis, Mo.), 200 µl/l Silwet L-77 (Lehle Seeds, Round Rock, Tex.) until an $A_{600}$ of 0.8 was reached).

Prior to transformation, *Arabidopsis thaliana* seeds (ecotype Columbia) were sown at a density of ~10 plants per 4" pot onto Pro-Mix BX potting medium (Hummert International) covered with fiberglass mesh (18 mm×16 mm). Plants were grown under continuous illumination (50-75 µE/m$^2$/second) at 22-23° C. with 65-70% relative humidity. After about 4 weeks, primary inflorescence stems (bolts) are cut off to encourage growth of multiple secondary bolts. After flowering of the mature secondary bolts, plants were prepared for transformation by removal of all siliques and opened flowers.

The pots were then immersed upside down in the mixture of *Agrobacterium infiltration* medium as described above for 30 seconds, and placed on their sides to allow draining into a 1'×2' flat surface covered with plastic wrap. After 24 h, the plastic wrap was removed and pots are turned upright. The immersion procedure was repeated one week later, for a total of two immersions per pot. Seeds were then collected from each transformation pot and analyzed following the protocol described below.

Example V

Identification of *Arabidopsis* Primary Transformants

Seeds collected from the transformation pots were sterilized essentially as follows. Seeds were dispersed into in a solution containing 0.1% (v/v) Triton X-100 (Sigma Chemical Co., St. Louis, Mo.) and sterile water and washed by shaking the suspension for 20 minutes. The wash solution was then drained and replaced with fresh wash solution to wash the seeds for 20 minutes with shaking. After removal of the ethanol/detergent solution, a solution containing 0.1% (v/v) Triton X-100 and 30% (v/v) bleach (CLOROX; Clorox Corp. Oakland, Calif.) was added to the seeds, and the suspension was shaken for 10 minutes. After removal of the bleach/detergent solution, seeds were then washed five times in sterile distilled water. The seeds were stored in the last wash water at 4° C. for 2 days in the dark before being plated onto antibiotic selection medium (1× Murashige and Skoog salts (pH adjusted to 5.7 with 1M KOH), 1× Gamborg's B-5 vitamins, 0.9% phytagar (Life Technologies), and 50 mg/l kanamycin). Seeds were germinated under continuous illumination (50-75 µE/m$^2$/second) at 22-23° C. After 7-10 growth under these conditions, kanamycin-resistant primary transformants ($T_1$ generation) were visible and obtained. These seedlings were transferred first to fresh selection plates where the seedlings continued to grow for 3-5 more days, and then to soil (Pro-Mix BX potting medium).

Primary transformants were crossed and progeny seeds ($T_2$) collected; kanamycin-resistant seedlings were selected and analyzed. The expression levels of the recombinant polynucleotides in the transformants varies from about a 5% expression level increase to a least a 100% expression level increase. Similar observations are made with respect to polypeptide level expression.

Example VI

Identification of *Arabidopsis* Plants with Transcription Factor Gene Knockouts The screening of insertion mutagenized *Arabidopsis* collections for null mutants in a known target gene was essentially as described in Krysan et al. (1999) *Plant Cell* 11: 2283-2290. Briefly, gene-specific primers, nested by 5-250 base pairs to each other, were designed from the 5' and 3' regions of a known target gene. Similarly, nested sets of primers were also created specific to each of the T-DNA or transposon ends (the "right" and "left" borders). All possible combinations of gene specific and T-DNA/transposon primers were used to detect by PCR an insertion event within or close to the target gene. The amplified DNA fragments were then sequenced which allows the precise determination of the T-DNA/transposon insertion point relative to the target gene. Insertion events within the coding or intervening sequence of the genes were deconvoluted from a pool comprising a plurality of insertion events to a single unique mutant plant for functional characterization. The method is described in more detail in Yu and Adam, U.S. application Ser. No. 09/177,733 filed Oct. 23, 1998.

Example VII

Identification of Modified Phenotypes in Overexpressing Plants

Experiments were performed to identify those transformants that exhibited a morphological difference relative to wild-type control plants, i.e., a modified structure and/or development characteristics. For such studies, the transformants were observed by eye to identify novel structural or developmental characteristics associated with the ectopic expression of the polynucleotides or polypeptides of the invention. Examples of genes and equivalogs that confer significant improvements to overexpressing plants are noted in the following Examples.

Experiments were also performed to identify those transformants that exhibited an improved pathogen tolerance, with results provided in Example VIII. All four TRANSCRIPTIONAL REGULATOR OF DEFENSE RESPONSE (TDR) sequences were tested under the regulatory control of tissue-specific and inducible promoters using a two-component system. The goal of these experiments was to determine if disease resistance could be achieved while reducing detrimental pleiotropic effects of ectopic expression of the TDR genes. Three different promoters were tested in combination with all four paralogs: tomato RBCS3 (Sugita et al. (1987) *Mol. Gen. Genet.* 209: 247-256), *Arabidopsis* LTPI (Thoma et al. (1994) *Plant Physiol.* 105: 35-45), and a transgenic glucocorticoid-inducible promoter (Aoyama and Chua (1997) *Plant J.* 11: 605-612). To test the spectrum of resistance in the two-component lines, we performed assays for *Botrytis cinerea, Fusarium oxysporum*, and *Sclerotinia sclerotiorum*. The 35S:: G1792 lines had not shown resistance to *Sclerotinia* in previous experiments, but this fungus was included to determine if any of the paralog genes gave enhanced resistance to a broader or different spectrum of pathogens.

For the LTP1 and RBCS3 projects, the first component (promoter::LexA/GAL4) comprised a LexA DNA binding domain fused to a GAL4 activation domain, cloned behind one of these promoters. These constructs are contained within vector backbone pMEN48 that also carried a kanamycin resistance marker, along with an opLexA::GFP reporter. The green fluorescent protein (GFP) used was EGFP, a variant available from Clontech (Palo Alto, Calif.) with enhanced signal. EGFP is soluble in the cytoplasm. Transgenic "driver lines" were first obtained containing the promoter::LexA/GAL4 component. For each promoter driver, a line was selected that showed reproducible expression of the GFP reporter gene in the desired pattern through a number of generations. A homozygous population was then established.

Having established a promoter panel, it was then possible to overexpress any transcription factor in the G1792 clade by super-transforming or crossing in a second construct (opLex-A::transcription factor) carrying the transcription factor of interest cloned behind a LexA operator site. In each case this second construct carried a sulfonamide selectable marker and was contained within vector backbone.

For the preparation of dexamethasone inducible lines, a kanamycin-resistant 35S::LexA-GAL4-transactivator driver line was established and was supertransforned with opLexA:: transcription factor constructs carrying a sulfonamide-resistance gene for each of the transcription factors of interest. 35S::LexA-GAL4-transactivator independent driver lines were generated at the outset of the experiment. Primary transformants were selected on kanamycin plates and screened for GFP fluorescence at the seedling stage. Any lines that showed constitutive GFP activity were discarded. At ten days, lines that showed no GFP activity were transferred onto MS agar plates containing 5μM dexamethasone. Lines that showed strong GFP activation by two to three days following the dexamethasone treatments were marked for follow-up in the T2 generation. Following similar experiments in the T2 generation, a single line, 65, was selected for future studies. Line 65 lacked any obvious background expression and all plants showed strong GFP fluorescence following dexamethasone application. A homozygous population for line 65 was then obtained, re-checked to ensure that it still exhibited induction following dexamethasone application, and bulked. 35S:: LexA-GAL4-transactivator line 65 was also crossed to an opLexA::GUS line to demonstrate that it could drive activation of targets arranged in trans.

Five T1 lines from each promoter/gene combination were selected for plate-based disease assays on the T2 generation. T2 seeds from each line (segregating for the target transgene construct) were surface sterilized and grown on MS plates supplemented with 0.3% sucrose. Plants homozygous for each activator line and supertransformed with the target construct vector containing GUS (no transcription factor gene) were used as controls and treated in the same manner as test lines. Plants were grown in a 22° C. growth chamber under constant light for ten days. On the 10th day, seedlings were transferred to MS plates without sucrose. The dex-inducible lines were transferred to MS plates supplemented with 5 μm dexamethasone. Each plate was marked in half, with half of the plate containing nine seedlings of an experimental line and the other half containing nine seedlings of the appropriate control line. For each experimental line, there were three test plates per pathogen plus one uninoculated plate. 35S::G1792 direct promoter/gene fusion lines were included and compared to wild-type plants as a control for the disease assays. Direct 35S/gene fusion lines were also used in the abiotic stress assay experiments, for which results are presented in Tables 7-10.

At 14 days, seedlings were inoculated by spraying the plates with a freshly prepared suspension of spores ($10^5$ spores/ml, *Botrytis*; $10^6$ spores/ml, *Fusarium*) or ground, filtered hyphae (1 gm/300 ml, *Sclerotinia*). Plates were returned to a growth chamber with dimmed lighting on a 12 hour dark/12 hour light regimen; disease symptoms were assessed over a period of two weeks after inoculation. All lines were initially tested with *Botrytis* and *Sclerotinia*. Tolerance was quantitatively scored as the number of living plants. Numbers were plotted on a "box and whisker" diagram (FIG. 6) to determine increased survivorship of particular promoter/gene combinations. To illustrate the spread of the data, results from all lines per combination were plotted together; lines that were potentially sense-suppressed (based on disease phenotype) may skew the median towards wild type in some cases. Also, all two-component lines were segregating for the target transgene. Lines that showed tolerance to *Botrytis* or *Sclerotinia* were then tested with *Fusarium*. *Fusarium* tolerance was determined by a reduction in chlorosis and damping off symptoms.

In some instances, expression patterns of the pathogen-induced genes (such as defense genes) may be monitored by microarray experiments. In these experiments, cDNAs are generated by PCR and resuspended at a final concentration of about 100 ng/μl in 3×SSC or 150 mM Na-phosphate (Eisen and Brown (1999) *Methods Enzymol.* 303: 179-205). The cDNAs are spotted on microscope glass slides coated with polylysine. The prepared cDNAs are aliquoted into 384 well plates and spotted on the slides using, for example, an Omni-Grid x-y-z gantry (GeneMachines, Menlo Park, Calif.) outfitted with quill type pins (Telechem International, Sunnyvale, Calif.). After spotting, the arrays are cured for a minimum of one week at room temperature, rehydrated and blocked following the protocol recommended by Eisen and Brown (1999) supra.

Sample total RNA (10 μg) samples are labeled using fluorescent Cy3 and Cy5 dyes. Labeled samples are resuspended in 4×SSC/0.03% SDS/4 μg salmon sperm DNA/2 μg tRNA/ 50 mM Na-pyrophosphate, heated for 95° C. for 2.5 minutes, spun down and placed on the array. The array is then covered with a glass coverslip and placed in a sealed chamber. The chamber is then kept in a water bath at 62° C. overnight. The arrays are washed as described in Eisen and Brown (1999) supra, and scanned on a General Scanning 3000 laser scanner. The resulting files are subsequently quantified using IMA-GENE, software (BioDiscovery, Los Angeles, Calif.).

Modified phenotypes observed for particular overexpressing plants may include increased disease tolerance or resistance. For a particular overexpressor that shows a less beneficial characteristic, such as reduced disease resistance or tolerance, it may be more useful to select a plant with a decreased expression of the particular transcription factor, for example, in a knockout plant. For a particular knockout plant that shows a less beneficial characteristic, such as decreased disease tolerance, it may be more useful to select a plant with an increased expression of the particular transcription factor.

The germination assays in Example IX followed modifications of the same basic protocol. Sterile seeds were sown on the conditional media listed below. Plates were incubated at 22° C. under 24-hour light (120-130 μEin/m$^2$/s) in a growth chamber. Evaluation of germination and seedling vigor was conducted 3 to 15 days after planting. The basal media was 80% Murashige-Skoog medium (MS)+vitamins.

For stress experiments conducted with more mature plants, seeds were germinated and grown for seven days on MS+vitamins+1% sucrose at 22° C. and then transferred to cold and heat stress conditions. The plants were either exposed to cold stress (6 hour exposure to 4-8° C.), or heat stress (32° C. was applied for five days, after which the plants were transferred back 22° C. for recovery and evaluated after 5 days relative to controls not exposed to the depressed or elevated temperature).

The salt stress assays were intended to find genes that confer better germination, seedling vigor or growth in high salt. Evaporation from the soil surface causes upward water movement and salt accumulation in the upper soil layer where the seeds are placed. Thus, germination normally takes place at a salt concentration much higher than the mean salt concentration of the whole soil profile. Plants differ in their tolerance to NaCl depending on their stage of development, therefore seed germination, seedling vigor, and plant growth responses were evaluated.

Osmotic stress assays (including NaCl and mannitol assays) were conducted to determine if an osmotic stress phenotype was NaCl-specific or if it was a general osmotic stress related phenotype. Plants tolerant to osmotic stress could also have more tolerance to drought and/or freezing.

For salt and osmotic stress germination experiments, the medium was supplemented with 150 mM NaCl or 300 mM mannitol. Growth regulator sensitivity assays were performed in MS media, vitamins, and either 0.3 µM ABA, 9.4% sucrose, or 5% glucose.

Desiccation and drought assays were performed to find genes that mediate better plant survival after short-term, severe water deprivation. Ion leakage was measured if needed.

For plate-based desiccation assays, wild-type and control seedlings were grown for 14 days on MS+Vitamins+1% Sucrose at 22° C. The plates were then left open in the sterile hood for 3 hr for hardening, and the seedlings were removed from the media and dried for 1.5 h in the sterile hood. The seedlings were transferred back to plates and incubated at 22° C. for recovery. The plants were then evaluated after another five days.

Soil-based drought screens were performed with *Arabidopsis* plants overexpressing the transcription factors listed in the Sequence Listing, where noted below. Seeds from wild-type *Arabidopsis* plants, or plants overexpressing a polypeptide of the invention, were stratified for three days at 4° C. in 0.1% agarose. Fourteen seeds of each overexpressor or wild-type were then sown in three inch clay pots containing a 50:50 mix of vermiculite:perlite topped with a small layer of Metro-Mix 200 and grown for fifteen days under 24 hr light. Pots containing wild-type and overexpressing seedlings were placed in flats in random order. Drought stress was initiated by placing pots on absorbent paper for seven to eight days. The seedlings were considered to be sufficiently stressed when the majority of the pots containing wild-type seedlings within a flat had become severely wilted. Pots were then re-watered and survival was scored four to seven days later. Plants were ranked against wild-type controls for each of two criteria: tolerance to the drought conditions and recovery (survival) following re-watering.

At the end of the initial drought period, each pot was assigned a numeric value score depending on the above criteria. A low value was assigned to plants with an extremely poor appearance (i.e., the plants were uniformly brown) and a high value given to plants that were rated very healthy in appearance (i.e., the plants were all green). After the plants were rewatered and incubated an additional four to seven days, the plants were reevaluated to indicate the degree of recovery from the water deprivation treatment.

An analysis was then conducted to determine which plants best survived water deprivation, identifying the transgenes that consistently conferred drought-tolerant phenotypes and their ability to recover from this treatment. The analysis was performed by comparing overall and within-flat tabulations with a set of statistical models to account for variations between batches. Several measures of survival were tabulated, including: (a) the average proportion of plants surviving relative to wild-type survival within the same flat; (b) the median proportion surviving relative to wild-type survival within the same flat; (c) the overall average survival (taken over all batches, flats, and pots); (d) the overall average survival relative to the overall wild-type survival; and (e) the average visual score of plant health before rewatering.

Sugar sensing assays were intended to find genes involved in sugar sensing by germinating seeds on high concentrations of sucrose and glucose and looking for degrees of hypocotyl elongation. The germination assay on mannitol controlled for responses related to osmotic stress. Sugars are key regulatory molecules that affect diverse processes in higher plants including germination, growth, flowering, senescence, sugar metabolism and photosynthesis. Sucrose is the major transport form of photosynthate and its flux through cells has been shown to affect gene expression and alter storage compound accumulation in seeds (source-sink relationships). Glucose-specific hexose-sensing has also been described in plants and is implicated in cell division and repression of "famine" genes (photosynthetic or glyoxylate cycles).

Temperature stress assays were carried out to find genes that confer better germination, seedling vigor or plant growth under temperature stress (cold, freezing and heat). Temperature stress cold germination experiments were carried out at 8° C. Heat stress germination experiments were conducted at 32° C. to 37° C. for 6 hours of exposure.

For nitrogen utilization assays, sterile seeds were sown onto plates containing media based on 80% MS without a nitrogen source (tolerance to low nitrogen assay). For carbon/nitrogen balance (C/N) sensing assays, the media also contained 3% sucrose (−N/+G). The −N/+Gln media was identical but was supplemented with 1 mM glutamine. Plates were incubated in a 24-hour light C (120-130 µEins$^{-2}$ m$^{-1}$) growth chamber at 22° C. Evaluation of germination and seedling vigor was done five days after planting for C/N assays. The production of less anthocyanin on these media is generally associated with increased tolerance to nitrogen limitation, and a transgene responsible for the altered response is likely involved in the plant's ability to perceive their carbon and nitrogen status.

The transcription factor sequences of the Sequence Listing, or those in the present Tables or Figures, and their equivalogs, can be used to prepare transgenic plants and plants with altered traits. The specific transgenic plants listed below are produced from the sequences of the Sequence Listing, as noted. The Sequence Listing, Tables 2 and 5 and Example VIII provide exemplary polynucleotide and polypeptide sequences of the invention.

Example VIII

Results Identifying Genes that Confer Significant Disease Tolerance

This example provides experimental evidence for increased disease tolerance controlled by the transcription factor polypeptides and polypeptides of the invention.

The transcription factor sequences of the Sequence Listing can be used to prepare transgenic plants with altered traits. From the experimental results of the plate-based and growth assays presented in the tables of this Example, it may be inferred that a representative number of sequences from diverse plant species imparted increased disease tolerance to a number of pathogens. These comparable effects indicate that sequences found within the G1792 clade of transcription factor polypeptides are functionally related and can be used to confer various types of disease stress tolerance in plants. A number of these genes conferred increased tolerance to multiple pathogens.

As determined from experimental assays, a number of members of the G1792 clade of transcription factor polypeptides from diverse plant species, including G1792 (SEQ ID NO: 2), G1791 (SEQ ID NO: 4), G1795 (SEQ ID NO: 6), G30 (SEQ ID NO: 8), G3381 (SEQ ID NO: 12), and G3520 (SEQ ID NO: 26), increase disease tolerance when these sequences are overexpressed.

In initial studies, 35S::G1792 plants were found to be more tolerant to the fungal pathogens *Fusarium oxysporum* and *Botrytis cinerea* and showed fewer symptoms after inoculation with a low dose of each pathogen. This result was confirmed using individual T2 lines. The effect of G1792 overexpression in increasing tolerance to pathogens received further, incidental confirmation. T2 plants of two 35S::G1792 lines had been growing in a room that suffered a serious powdery mildew infection. For each line, a pot of six plants was present in a flat containing nine other pots of lines from unrelated genes. In either of the two different flats, the only plants that were free from infection (that is, showing a 100% reduction in symptoms) were those from the 35S::G1792 line. This observation suggested that G1792 overexpression may be used to increase resistance to powdery mildew. Additional experiments confirmed that 35S::G1792 plants showed significantly increased tolerance to *Erysiphe*; a significant number of these plants had exhibited a 100% reduction in disease symptoms, and appeared to be disease-free. G1792 was ubiquitously expressed, but appeared to be induced by salicylic acid.

We then predicted that other sequences within the G1792 clade may also confer similar functions, including disease tolerance, based on the phylogenetic relatedness and structural similarities of these sequences. A summary of the disease assay results for four *Arabidopsis* sequences and two non-*Arabidopsis* sequences in this clade is presented in Table 5. At least six sequences in the clade derived from diverse species, including two non-*Arabidopsis* orthologs, G3520 (soybean) and G3381 (rice), provided significantly enhanced tolerance to *Sclerotinia* when overexpressed in Arabidopsis using various regulatory controls. Many of the plants overexpressing G1792 paralogs showed a considerable reduction in disease symptoms, and a number appeared to be 100% free. Other sequences are being investigated.

TABLE 5

Disease screening of G1792 and paralogs under different promoters

| | G1792 | | | G1791 | | | G1795 | | | G30 | | | G3381 | | | G3520 | | |
|---|---|---|---|---|---|---|---|---|---|---|---|---|---|---|---|---|---|---|
| | B | S | F | B | S | F | B | S | F | B | S | F | B | S | F | B | S | F |
| 35S | ++ | wt | + | | | | | | | | | | | + | | | + | |
| RBCS3 | + | wt | + | wt | wt | wt | ++ | ++ | wt | + | + | wt | | | | | | |
| LTP1 | wt | wt | | + | wt | wt | ++ | + | wt | + | wt | wt | | | | | | |
| Dex-ind. | ++ | wt | + | ++ | ++ | wt | ++ | ++ | wt | ++ | ++ | wt | | | | | | |

Abbreviations:
B *Botrytis cinerea*
S *Sclerotinia sclerotiorum*
F *Fusarium oxysporum*
Scoring:
++ significant improvement in tolerance
+ mild to moderate improvement in tolerance
wt no difference in tolerance from wild-type controls (susceptible)
empty cell: not done Utilities for G1792 clade members under non-constitutive regulatory control. The results of these studies with the non-constitutive regulatory control of several G1792 clade members indicate that the polynucleotide and polypeptide sequences can be used to improve disease or biotic stress tolerance.

Example IX

Results Identifying Genes that Confer Significant Abiotic Stress Tolerance

This example provides experimental evidence for increased abiotic stress tolerance and altered C/N sensing when G1792 clade members are overexpressed.

Our previous studies with 35S direct promoter fusion resulted in G1792 overexpressing plants with greater abiotic stress tolerance and drought tolerance in soil-based assays. As seen in the table below, plants overexpressing G1792 clade members displayed a markedly increased tolerance to osmotic stress, cold, desiccation and low nitrogen during germination, and exhibited altered C/N sensing.

As noted in Table 6 and subsequent tables in this example, we have obtained similar physiological phenotypes from overexpression of the related *Arabidopsis* genes (G1792), rice (G3515, G3381) and corn genes (G3517), indicating that these genes are likely to be functionally related, with their function or stress tolerance preserved in diverse species.

Abbreviations in the tables in this example include:
Germ germination;
mann mannitol;
ABA abscisic acid;
N– 80% MS media without a nitrogen source;
N–/S+ 80% MS media without a nitrogen source and with 3% sucrose; and
N–/S+/G+ 80% MS media without a nitrogen source, with 3% sucrose and 1 mM glutamine.
Scoring of results is given as:
++ significant tolerance;
+ mild to moderate tolerance;
wt no perceived difference in tolerance from wild-type controls; and
empty cell not done.

TABLE 6

Results of abiotic stress assays in 35S::G1792 (*Arabidopsis*) direct promoter fusion experiments

| Line | Germ in high salt | Germ in mann | Germ in sucrose | Germ in ABA | Germ in heat | Germ in cold | Growth in heat | Desiccation | Growth in cold | N−/S+ | N−/S+/G+ | N− |
|---|---|---|---|---|---|---|---|---|---|---|---|---|
| 301 | wt | wt | wt | wt | wt | wt | wt | + | wt | + | + | + |
| 305 | wt | wt | wt | wt | wt | wt | + | + | wt | + | + | ++ |
| 307 | wt | wt | wt | wt | wt | wt | wt | + | wt | wt | wt | wt |
| 309 | wt | wt | wt | wt | wt | wt | wt | wt | wt | wt | wt | wt |
| 310 | wt | wt | wt | wt | wt | wt | wt | wt | wt | wt | wt | + |
| 311 | wt | wt | + | wt | wt | ++ | wt | wt | wt | + | + | + |
| 312 | wt | wt | wt | wt | wt | + | wt | wt | wt | + | + | ++ |
| 313 | wt | wt | wt | wt | wt | wt | wt | + | wt | wt | wt | wt |
| 318 | wt | wt | wt | wt | wt | wt | wt | wt | wt | + | + | wt |
| 320 | wt | wt | wt | wt | wt | wt | wt | wt | wt | + | + | + |
| 12 | wt | wt | wt | wt | wt | wt | + | wt | wt | wt | wt | wt |
| 5-1-5 | wt | wt | wt | wt | wt | + | wt | wt | wt | wt | wt | wt |
| 6 | wt | wt | wt | wt | wt | wt | wt | wt | + | + | + | + |

TABLE 7

Results of abiotic stress and CN sensing assays in 35S::G3381 (rice) direct promoter fusion experiments

| Line | Germ in high salt | Germ in mann | Germ in sucrose | Germ in ABA | Germ in heat | Germ in cold | Growth in heat | Desiccation | Growth in cold | N−/S+ | N−/S+/G+ | N− |
|---|---|---|---|---|---|---|---|---|---|---|---|---|
| 301 | wt | wt | wt | wt | wt | wt | wt | wt | wt | wt | wt | wt |
| 302 | wt | + | wt | + | wt | ++ | wt | wt | wt | wt | wt | wt |
| 304 | + | + | wt | wt | wt | + | wt | wt | wt | wt | wt | wt |
| 306 | wt | wt | wt | wt | + | + | wt | wt | wt | + | + | + |

TABLE 8

Results of abiotic stress and CN sensing assays in 35S::G3515 (rice) direct promoter fusion experiments

| Line | Germ in high salt | Germ in mann | Germ in sucrose | Germ in ABA | Germ in heat | Germ in cold | Growth in heat | Desiccation | Growth in cold | N−/S+ | N−/S+/G+ | N− |
|---|---|---|---|---|---|---|---|---|---|---|---|---|
| 304 | wt | wt | wt | wt | wt | wt | wt | wt | wt | wt | wt | + |
| 306 | wt | wt | wt | wt | wt | wt | wt | wt | wt | wt | wt | ++ |
| 308 | wt | wt | wt | wt | wt | wt | wt | wt | wt | wt | wt | wt |
| 309 | wt | wt | wt | wt | wt | wt | wt | wt | wt | wt | wt | wt |
| 310 | wt | wt | wt | wt | wt | wt | wt | wt | + | wt | wt | wt |
| 313 | wt | + | wt | wt | wt | wt | wt | wt | + | wt | wt | wt |
| 314 | wt | + | wt | wt | wt | wt | wt | wt | wt | wt | wt | wt |
| 315 | wt | wt | wt | wt | wt | wt | wt | wt | wt | wt | wt | wt |
| 319 | wt | wt | wt | wt | wt | + | + | wt | wt | wt | wt | wt |
| 320 | wt | wt | wt | wt | wt | wt | wt | wt | wt | wt | wt | wt |

TABLE 9

Results of abiotic stress and CN sensing assays in 35S::G3517 (corn) direct promoter fusion experiments

| Line | Germ in high salt | Germ in mann | Germ in sucrose | Germ in ABA | Germ in heat | Germ in cold | Growth in heat | Desiccation | Growth in cold | N−/S+ | N−/S+/G+ | N− |
|---|---|---|---|---|---|---|---|---|---|---|---|---|
| 301 | wt | wt | wt | wt | + | wt | wt | wt | wt | wt | wt | wt |
| 302 | wt | wt | wt | wt | wt | wt | wt | wt | wt | wt | wt | wt |
| 305 | wt | wt | wt | + | wt | wt | wt | wt | + | wt | wt | wt |
| 308 | wt | wt | wt | wt | wt | wt | + | wt | wt | wt | wt | wt |
| 310 | wt | wt | wt | wt | wt | wt | + | wt | + | wt | wt | wt |
| 311 | wt | wt | wt | wt | wt | wt | wt | wt | + | wt | wt | wt |

TABLE 9-continued

Results of abiotic stress and CN sensing assays in 35S::G3517 (corn) direct promoter fusion experiments

| Line | Germ in high salt | Germ in mann | Germ in sucrose | Germ in ABA | Germ in heat | Germ in cold | Growth in heat | Desiccation | Growth in cold | N−/ S+ | N−/ S+/G+ | N− |
|------|------|------|------|------|------|------|------|------|------|------|------|------|
| 312 | wt | wt | wt | wt | + | wt | wt | wt | wt | wt | wt | + |
| 318 | wt | wt | wt | wt | wt | wt | wt | wt | wt | wt | wt | wt |
| 319 | wt | wt | wt | wt | wt | + | wt | wt | wt | wt | wt | wt |
| 320 | wt | wt | wt | wt | wt | + | wt | wt | wt | wt | wt | wt |

G1792 overexpression increases survivability in a soil-based drought assay. Plants overexpressing G1792 were observed to be rather dark and shiny and in some cases showed delayed flowering. Lines were later analyzed in a soil-based drought screen. 35S::G1792 lines exhibited markedly enhanced drought tolerance compared to wild-type, both in terms of their appearance at the end of the drought period, and in survivability following re-watering.

G1792 (and related genes) respond in baseline microarray experiments. G1792 and related genes have been identified as responding to abiotic stresses in microarray experiments in which wild-type Columbia plants were been treated with various abiotic stresses. G1792 transcript in roots peaks four hours after mannitol treatment, reaching an expression level approximately 24-fold higher than mock treated plants. G1792 transcript levels in roots in NaCl treated plants reach levels eight-fold higher than mock treated plants at eight hours. Interestingly, G1792 expression is down-regulated in both soil-based drought experiments and upon treatment with ABA. Expression levels in both cases are down-regulated approximately three-fold.

G1792 clade member overexpression increases tolerance to growth on nitrogen-limiting conditions. 35S::G1792, 35S::G3381 and 35S::G3515 transformants showed more tolerance to growth under nitrogen-limiting conditions. In a root growth assay under conditions of limiting nitrogen, 35S::G1792, 35S::G3381 and 35S::G3515 lines were less stunted. In a germination assay that monitors the effect of carbon on nitrogen signaling through anthocyanin production on media with high sucrose and with or without glutamine (Hsieh et al. (1998) Proc. Natl. Acad .Sci. U.S.A. 95: 13965-13970), the 35S::G1792, 35S::G3381 and 35S::G3515 lines made less anthocyanin on high sucrose with glutamine, indicating that these sequences are likely involved in monitoring carbon and nitrogen status in plants.

Utilities for G1792 clade members under constitutive and non-constitutive regulatory control. The results of these studies with the constitutive regulatory control of several G1792 clade members indicate that the polynucleotide and polypeptide sequences can be used to improve abiotic stress tolerance. The data in this and the previous Example confirm our conclusions that G1792 and other G1792 clade members may be valuable tools for the purpose of increasing yield and quality of plant products.

Example X

Identification of Homologous Sequences by Computer Homology Search

This example describes identification of genes that are orthologous to *Arabidopsis thaliana* G1792 clade member transcription factors from a computer homology search.

Homologous sequences, including those of paralogs and orthologs from *Arabidopsis* and other plant species, were identified using database sequence search tools, such as the Basic Local Alignment Search Tool (BLAST) (Altschul et al. (1990) supra; and Altschul et al. (1997) *Nucleic Acid Res.* 25: 3389-3402). The tblastx sequence analysis programs were employed using the BLOSUM-62 scoring matrix (Henikoff and Henikoff (1992) *Proc. Natl. Acad. Sci. U.S.A.* 89: 10915-10919). The entire NCBI GenBank database was filtered for sequences from all plants except *Arabidopsis thaliana* by selecting all entries in the NCBI GenBank database associated with NCBI taxonomic ID 33090 (Viridiplantae; all plants) and excluding entries associated with taxonomic ID 3701 (*Arabidopsis thaliana*).

These sequences are compared to sequences representing transcription factor genes presented in the Sequence Listing, using the Washington University TBLASTX algorithm (version 2.0a19MP) at the default settings using gapped alignments with the filter "off". For each transcription factor gene in the Sequence Listing, individual comparisons were ordered by probability score (P-value), where the score reflects the probability that a particular alignment occurred by chance. For example, a score of 3.6e-59 is $3.6 \times 10^{-59}$. In addition to P-values, comparisons were also scored by percentage identity. Percentage identity reflects the degree to which two segments of DNA or protein are identical over a particular length. Examples of sequences so identified are presented in, for example, the Sequence Listing and Table 1. Paralogous or orthologous sequences may be readily identified and available in GenBank by Accession number (Sequence Identifier or Accession Number). The percent sequence identity among these sequences can be as low as 49%, or even lower sequence identity.

Candidate paralogous sequences were identified among *Arabidopsis* transcription factors through alignment, identity, and phylogenic relationships. G1791, G1795 and G30 (SEQ ID NO: 4, 6, and 8, respectively), paralogs of G1792, may be found in the Sequence Listing.

Candidate orthologous sequences were identified from proprietary unigene sets of plant gene sequences in *Zea mays*, *Glycine max* and *Oryza sativa* based on significant homology to *Arabidopsis* transcription factors. These candidates were reciprocally compared to the set of *Arabidopsis* transcription factors. If the candidate showed maximal similarity in the protein domain to the eliciting transcription factor or to a paralog of the eliciting transcription factor, then it was considered to be an ortholog. Identified non-*Arabidopsis* sequences that were shown in this manner to be orthologous to the *Arabidopsis* sequences are provided in, for example, Table 1.

Example XI

Identification of Orthologous and Paralogous Sequences by PCR

Orthologs to *Arabidopsis* G1792 clade members may be identified by several methods in addition to the method provided in Example X, including hybridization or amplification. This example describes how equivalogs to the *Arabidopsis* AP2 family transcription factor CBF1, which confers tolerance to abiotic stresses (Thomashow et al. (2002) U.S. Pat. No. 6,417,428), were identified. In this example, orthologs to CBF1 were found in canola (*Brassica napus*) using polymerase chain reaction (PCR).

Degenerate primers were designed for regions of AP2 binding domain and outside of the AP2 (carboxyl terminal domain):

```
                                         (SEQ ID NO: 59)
Mol 368      5'- CAY CCN ATH TAY MGN GGN GT -3'
(reverse)
(United States Patent Application 20040098764)

(SEQ ID NO: 60)
Mol 378      5'- GGN ARN ARC ATN CCY TCN GCC -3'
(forward)
(United States Patent Application 20040098764)
(Y: C/T, N: A/C/G/T, H: A/C/T, M: A/C, R: A/G)
```

Primer Mol 368 is in the AP2 binding domain of CBF1 (amino acid sequence: His-Pro-Ile-Tyr-Arg-Gly-Val; SEQ ID NO: 61) while primer Mol 378 is outside the AP2 domain (carboxyl terminal domain; amino acid sequence: Met-Ala-Glu-Gly-Met-Leu-Leu-Pro; SEQ ID NO: 62).

The genomic DNA isolated from *B. napus* was PCR-amplified by using these primers following these conditions: an initial denaturation step of 2 minutes at 93° C.; 35 cycles of 93° C. for 1 minute, 55° C. for 1 minute, and 72° C. for 1 minute; and a final incubation of 7 minutes at 72° C. at the end of cycling.

The PCR products were separated by electrophoresis on a 1.2% agarose gel and transferred to nylon membrane and hybridized with the AT CBF1 probe prepared from *Arabidopsis* genomic DNA by PCR amplification. The hybridized products were visualized by colorimetric detection system (Boehringer Mannheim) and the corresponding bands from a similar agarose gel were isolated using the Qiagen Extraction Kit (Qiagen, Valencia, Calif.). The DNA fragments were ligated into the TA clone vector from TOPO TA Cloning Kit (Invitrogen Corporation, Carlsbad, Calif.) and transformed into *E. coli* strain TOP10 (Invitrogen).

Seven colonies were picked and the inserts were sequenced on an ABI 377 machine from both strands of sense and antisense after plasmid DNA isolation. The DNA sequence was edited by sequencer and aligned with the AtCBF1 by GCG software and NCBI blast searching.

The nucleic acid sequence and amino acid sequence of one canola ortholog found in this manner (bnCBF1) identified by this process is shown in U.S. patent application 20040098764.

The aligned amino acid sequences show that the bnCBF1 gene has 88% identity with the *Arabidopsis* sequence in the AP2 domain region and 85% identity with the *Arabidopsis* sequence outside the AP2 domain when aligned for two insertion sequences that are outside the AP2 domain.

Similarly, paralogous sequences to *Arabidopsis* genes, such as CBF1, may also be identified.

Two paralogs of CBF1 from *Arabidopsis thaliana*: CBF2 and CBF3. CBF2 and CBF3 have been cloned and sequenced as described below.

A lambda cDNA library prepared from RNA isolated from *Arabidopsis thaliana* ecotype Columbia (Lin and Thomashow (1992) *Plant Physiol.* 99: 519-525) was screened for recombinant clones that carried inserts related to the CBF1 gene (Stockinger et al. (1997) *Proc. Natl. Acad. Sci. U.S.A.* 94: 1035-1040). CBF1 was $^{32}$P-radiolabeled by random priming (Sambrook et al. (1989) supra) and used to screen the library by the plaque-lift technique using standard stringent hybridization and wash conditions (Hajela et al. (1990) *Plant Physiol.* 93:1246-1252; Sambrook et al. (1989) supra) 6×SSPE buffer, 60° C. for hybridization and 0.1×SSPE buffer and 60° C. for washes). Twelve positively hybridizing clones were obtained and the DNA sequences of the cDNA inserts were determined. The results indicated that the clones fell into three classes. One class carried inserts corresponding to CBF1. The two other classes carried sequences corresponding to two different homologs of CBF1, designated CBF2 and CBF3. The nucleic acid sequences and predicted protein coding sequences for *Arabidopsis* CBF1, CBF2 and CBF3 may be found, for example, in U.S. patent application 20040098764, as are the nucleic acid sequences and predicted protein coding sequence for the *Brassica napus* CBF ortholog bnCBF 1.

A comparison of the nucleic acid sequences of *Arabidopsis* CBF1, CBF2 and CBF3 indicate that they are 83 to 85% identical as shown in Table 10.

TABLE 10

| | Percent identity[a] | |
|---|---|---|
| | DNA[b] | Polypeptide |
| cbf1/cbf2 | 85 | 86 |
| cbf1/cbf3 | 83 | 84 |
| cbf2/cbf3 | 84 | 85 |

[a]Percent identity was determined using the Clustal algorithm from the Megalign program (DNASTAR, Inc.).
[b]Comparisons of the nucleic acid sequences of the open reading frames are shown.

Similarly, the amino acid sequences of the three CBF polypeptides range from 84 to 86% identity. An alignment of the three amino acid sequences reveals that most of the differences in amino acid sequence occur in the acidic C-terminal half of the polypeptide. This region of CBF1 serves as an activation domain in both yeast and *Arabidopsis* (not shown).

Residues 47 to 106 of CBF1 correspond to the AP2 domain of the protein, a DNA binding motif that to date, has only been found in plant proteins. A comparison of the AP2 domains of CBF1, CBF2 and CBF3 indicates that there are a few differences in amino acid sequence. These differences in amino acid sequence might have an effect on DNA binding specificity.

Example XII

Transformation of Canola with a Plasmid Containing CBF1, CBF2, or CBF3

After identifying homologous genes to CBF 1, canola was transformed with a plasmid containing the *Arabidopsis* CBF1, CBF2, or CBF3 genes cloned into the vector pGA643 (An (1987) *Methods Enzymol.* 253: 292). In these constructs the CBF genes were expressed constitutively under the CaMV 35S promoter. In addition, the CBF1 gene was cloned under the control of the *Arabidopsis* COR15 promoter in the same vector pGA643. Each construct was transformed into *Agrobacterium* strain GV3101. Transformed agrobacteria were grown for 2 days in minimal AB medium containing appropriate antibiotics.

Spring canola (*B. napus* cv. Westar) was transformed using the protocol of Moloney et al. (1989) *Plant Cell Reports* 8: 238, with some modifications as described. Briefly, seeds were sterilized and plated on half strength MS medium, containing 1% sucrose. Plates were incubated at 24° C. under 60-80 µE/m$^2$ s light using a 16 hour light/8 hour dark photoperiod. Cotyledons from 4-5 day old seedlings were collected, the petioles cut and dipped into the *Agrobacterium* solution. The dipped cotyledons were placed on co-cultivation medium at a density of 20 cotyledons/plate and incubated as described above for 3 days. Explants were transferred to the same media, but containing 300 mg/l timentin (Smith-Kline Beecham, PA) and thinned to 10 cotyledons/plate. After 7 days explants were transferred to Selection/Regeneration medium. Transfers were continued every 2-3 weeks (2 or 3 times) until shoots had developed. Shoots were transferred to Shoot-Elongation medium every 2-3 weeks. Healthy looking shoots were transferred to rooting medium. Once good roots had developed, the plants were placed into moist potting soil.

The transformed plants were then analyzed for the presence of the NPTII gene/kanamycin resistance by ELISA, using the ELISA NPTII kit from 5Prime-3Prime Inc. (Boulder, Colo.). Approximately 70% of the screened plants were NPTII positive. Only those plants were further analyzed.

From Northern blot analysis of the plants that were transformed with the constitutively expressing constructs, showed expression of the CBF genes and all CBF genes were capable of inducing the *Brassica napus* cold-regulated gene BN 115 (homolog of the *Arabidopsis* COR15 gene). Most of the transgenic plants appear to exhibit a normal growth phenotype. As expected, the transgenic plants are more freezing tolerant than the wild-type plants. Using the electrolyte leakage of leaves test, the control showed a 50% leakage at −2 to −3° C. Spring canola transformed with either CBF1 or CBF2 showed a 50% leakage at −6 to −7° C. Spring canola transformed with CBF3 shows a 50% leakage at about −10 to −15° C. Winter canola transformed with CBF3 may show a 50% leakage at about −16 to −20° C. Furthermore, if the spring or winter canola are cold acclimated the transformed plants may exhibit a further increase in freezing tolerance of at least −2° C.

To test salinity tolerance of the transformed plants, plants were watered with 150 mM NaCl. Plants overexpressing CBF1, CBF2, or CBF3 grew better compared with plants that had not been transformed with CBF1, CBF2, or CBF3.

These results demonstrate that equivalogs of *Arabidopsis* transcription factors can be identified and shown to confer similar functions in non-*Arabidopsis* plant species.

Example XIII

Transformation of Dicots

Crop species overexpressing members of the G1792 clade of transcription factor polypeptides have been shown experimentally to produce plants with increased tolerance to disease. This observation indicates that these genes, when overexpressed, will result in larger yields of various plant species, particularly during conditions of biotic stress.

Thus, transcription factor sequences listed in the Sequence Listing recombined into pMEN20 or pMEN65 expression vectors may be transformed into a plant for the purpose of modifying plant traits. The cloning vector may be introduced into a variety of cereal plants by means well known in the art such as, for example, direct DNA transfer or *Agrobacterium tumefaciens*-mediated transformation. It is now routine to produce transgenic plants using most dicot plants (see Weissbach and Weissbach, (1989) supra; Gelvin et al. (1990) supra; Herrera-Estrella et al. (1983) supra; Bevan (1984) supra; and Klee (1985) supra). Methods for analysis of traits are routine in the art and examples are disclosed above.

Methods for transforming cotton may be found in U.S. Pat. Nos. 5,004,863, 5,159,135 and 5,518,908; for transforming brassica species may be found in U.S. Pat. No. 5,463,174; for transforming peanut plants may be found in Cheng et al. (1996) *Plant Cell Rep.* 15: 653-657, and McKently et al. (1995) *Plant Cell Rep.* 14: 699-703; and for transforming pea may be found in Grant et al. (1995) *Plant Cell Rep.* 15: 254-258.

Numerous protocols for the transformation of tomato and soy plants have been previously described, and are well known in the art. Gruber et al. ((1993) in *Methods in Plant Molecular Biology and Biotechnology*, p. 89-119, Glick and Thompson, eds., CRC Press, Inc., Boca Raton) describe several expression vectors and culture methods that may be used for cell or tissue transformation and subsequent regeneration. For soybean transformation, methods are described by Miki et al. (1993) in *Methods in Plant Molecular Biology and Biotechnology*, p. 67-88, Glick and Thompson, eds., CRC Press, Inc., Boca Raton; and U.S. Pat. No. 5,563,055, (Townsend and Thomas), issued Oct. 8, 1996.

There are a substantial number of alternatives to *Agrobacterium*-mediated transformation protocols, other methods for the purpose of transferring exogenous genes into soybeans or tomatoes. One such method is microprojectile-mediated transformation, in which DNA on the surface of microprojectile particles is driven into plant tissues with a biolistic device (see, for example, Sanford et al., (1987) *Part. Sci. Technol.* 5:27-37; Christou et al. (1992) *Plant. J.* 2: 275-281; Sanford (1993) *Methods Enzymol.* 217: 483-509; Klein et al. (1987) *Nature* 327: 70-73; U.S. Pat. No. 5,015,580 (Christou et al), issued May 14, 1991; and U.S. Pat. No. 5,322,783 (Tomes et al.), issued Jun. 21, 1994.

Alternatively, sonication methods (see, for example, Zhang et al. (1991) *Bio/Technology* 9: 996-997); direct uptake of DNA into protoplasts using $CaCl_2$ precipitation, polyvinyl alcohol or poly-L-ornithine (see, for example, Hain et al. (1985) *Mol. Gen. Genet.* 199: 161-168; Draper et al., *Plant Cell Physiol.* 23: 451-458 (1982)); liposome or spheroplast fusion (see, for example, Deshayes et al. (1985) *EMBO J.*, 4: 2731-2737; Christou et al. (1987) *Proc. Natl. Acad. Sci. U.S.A.* 84: 3962-3966); and electroporation of protoplasts and whole cells and tissues (see, for example, Donn et al.(1990) in *Abstracts of VIIth International Congress on Plant Cell and Tissue Culture IAPTC*, A2-38: 53; D'Halluin et al. (1992) *Plant Cell* 4: 1495-1505; and Spencer et al. (1994) *Plant Mol. Biol.* 24: 51-61) have been used to introduce foreign DNA and expression vectors into plants.

After a plant or plant cell is transformed (and the latter regenerated into a plant), the transformed plant may be crossed with itself or a plant from the same line, a non-transformed or wild-type plant, or another transformed plant from a different transgenic line of plants. Crossing provides the advantages of producing new and often stable transgenic varieties. Genes and the traits they confer that have been introduced into a tomato or soybean line may be moved into distinct line of plants using traditional backcrossing techniques well known in the art. Transformation of tomato plants may be conducted using the protocols of Koornneef et al (1986) In *Tomato Biotechnology:* Alan R. Liss, Inc., 169-178, and in U.S. Pat. No. 6,613,962, the latter method described in brief here. Eight day old cotyledon explants are precultured for 24 hours in Petri dishes containing a feeder layer of Petunia hybrida suspension cells plated on MS medium with 2% (w/v) sucrose and 0.8% agar supplemented with 10 µM α-naphthalene acetic acid and 4.4 µM 6-benzylaminopurine. The explants are then infected with a diluted overnight culture of *Agrobacterium tumefaciens* containing an expression vector comprising a polynucleotide of the invention for 5-10 minutes, blotted dry on sterile filter paper and cocultured for 48 hours on the original feeder layer plates. Culture conditions are as described above. Overnight cultures of *Agrobacterium tumefaciens* are diluted in liquid MS medium with 2% (w/v/) sucrose, pH 5.7) to an $OD_{600}$ of 0.8.

Following cocultivation, the cotyledon explants are transferred to Petri dishes with selective medium comprising MS medium with 4.56 µM zeatin, 67.3 µM vancomycin, 418.9 µM cefotaxime and 171.6 µM kanamycin sulfate, and cultured under the culture conditions described above. The explants are subcultured every three weeks onto fresh medium. Emerging shoots are dissected from the underlying callus and transferred to glass jars with selective medium without zeatin to form roots. The formation of roots in a kanamycin sulfate-containing medium is a positive indication of a successful transformation.

Transformation of soybean plants may be conducted using the methods found in, for example, U.S. Pat. No. 5,563,055. In this method, soybean seed is surface sterilized by exposure to chlorine gas evolved in a glass bell jar. Seeds are germinated by plating on 1/10 strength agar solidified medium without plant growth regulators and culturing at 28° C. with a 16 hour day length. After three or four days, seed may be prepared for cocultivation. The seedcoat is removed and the elongating radicle removed 3-4 mm below the cotyledons.

Overnight cultures of *Agrobacterium tumefaciens* harboring the expression vector comprising a polynucleotide of the invention are grown to log phase, pooled, and concentrated by centrifugation. Inoculations are conducted in batches such that each plate of seed was treated with a newly resuspended pellet of *Agrobacterium*. The pellets are resuspended in 20 ml inoculation medium. The inoculum is poured into a Petri dish containing prepared seed and the cotyledonary nodes are macerated with a surgical blade. After 30 minutes the explants are transferred to plates of the same medium that has been solidified. Explants are embedded with the adaxial side up and level with the surface of the medium and cultured at 22° C. for three days under white fluorescent light. These plants may then be regenerated according to methods well established in the art, such as by moving the explants after three days to a liquid counter-selection medium (see U.S. Pat. No. 5,563,055).

The explants may then be picked, embedded and cultured in solidified selection medium. After one month on selective media transformed tissue becomes visible as green sectors of regenerating tissue against a background of bleached, less healthy tissue. Explants with green sectors are transferred to an elongation medium. Culture is continued on this medium with transfers to fresh plates every two weeks. When shoots are 0.5 cm in length they may be excised at the base and placed in a rooting medium.

Example XIV

Increased Biotic and Abiotic Stress Tolerance in Monocots

Cereal plants such as, but not limited to, corn, wheat, rice, sorghum, or barley, may be transformed with the present polynucleotide sequences, including monocot or dicot-derived sequences such as those presented in Tables 1 or 5, cloned into a vector such as pGA643 and containing a kanamycin-resistance marker, and expressed constitutively under, for example, the CaMV 35S or COR15 promoters. pMEN20 or pMEN65 and other expression vectors may also be used for the purpose of modifying plant traits. For example, pMEN020 may be modified to replace the NptII coding region with the BAR gene of *Streptomyces hygroscopicus* that confers resistance to phosphinothricin. The KpnI and BglII sites of the Bar gene are removed by site-directed mutagenesis with silent codon changes.

The cloning vector may be introduced into a variety of cereal plants by means well known in the art including direct DNA transfer or *Agrobacterium tumefaciens*-mediated transformation. The latter approach may be accomplished by a variety of means, including, for example, that of U.S. Pat. No. 5,591,616, in which monocotyledon callus is transformed by contacting dedifferentiating tissue with the *Agrobacterium* containing the cloning vector.

The sample tissues are immersed in a suspension of $3\times10^{-9}$ cells of *Agrobacterium* containing the cloning vector for 3-10 minutes. The callus material is cultured on solid medium at 25° C. in the dark for several days. The calli grown on this medium are transferred to Regeneration medium. Transfers are continued every 2-3 weeks (2 or 3 times) until shoots develop. Shoots are then transferred to Shoot-Elongation medium every 2-3 weeks. Healthy looking shoots are transferred to rooting medium and after roots have developed, the plants are placed into moist potting soil.

The transformed plants are then analyzed for the presence of the NPTII gene/kanamycin resistance by ELISA, using the ELISA NPTII kit from 5Prime-3Prime Inc. (Boulder, Colo.).

It is also routine to use other methods to produce transgenic plants of most cereal crops (Vasil (1994) *Plant Mol. Biol.* 25: 925-937) such as corn, wheat, rice, sorghum (Cassas et al. (1993) *Proc. Natl. Acad. Sci. U.S.A.* 90: 11212-11216, and barley (Wan and Lemeaux (1994) *Plant Physiol.* 104:37-48). DNA transfer methods such as the microprojectile method can be used for corn (Fromm et al. (1990) *Bio/Technol.* 8: 833-839); Gordon-Kamm et al. (1990) *Plant Cell* 2: 603-618; Ishida (1990) *Nature Biotechnol.* 14:745-750), wheat (Vasil et al. (1992) *Bio/Technol.* 10:667-674; Vasil et al. (1993) *Bio/Technol.* 11:1553-1558; Weeks et al. (1993) *Plant Physiol.* 102:1077-1084), and rice (Christou (1991) *Bio/Technol.* 9:957-962; Hiei et al. (1994) *Plant J.* 6:271-282; Aldemita and Hodges (1996) *Planta* 199:612-617; and Hiei et al. (1997) *Plant Mol. Biol.* 35:205-218). For most cereal plants, embryogenic cells derived from immature scutellum tissues are the preferred cellular targets for transformation (Hiei et al. (1997) *Plant Mol. Biol.* 35:205-218; Vasil (1994) *Plant Mol. Biol.* 25: 925-937). For transforming corn embryogenic cells derived from immature scutellar tissue using microprojectile bombardment, the A188XB73 genotype is the preferred genotype (Fromm et al. (1990) *Bio/Technol.* 8: 833-839; Gordon-Kamm et al. (1990) *Plant Cell* 2: 603-618). After microprojectile bombardment the tissues are selected on phosphinothricin to identify the transgenic embryogenic cells (Gordon-Kamm et al. (1990) *Plant Cell* 2: 603-618). Transgenic plants are regenerated by standard corn regeneration techniques (Fromm et al. (1990) *Bio/Technol.* 8: 833-839; Gordon-Kamm et al. (1990) *Plant Cell* 2: 603-618).

Northern blot analysis, RT-PCR or microarray analysis of the regenerated, transformed plants may be used to show expression of G1792 and related genes that are capable of conferring tolerance to biotic or abiotic stress.

To verify the ability to confer abiotic stress tolerance, mature plants overexpressing a G1792 clade member, or alternatively, seedling progeny of these plants, may be challenged by a biotic stress, such as a fungal pathogen, or abiotic stress, such as drought, heat, high salt, or freezing. Alternatively, these plants may be challenged in an osmotic stress condition that may also measure altered sugar sensing, such as a high sugar condition. By comparing wild type and transgenic plants similarly treated, the transgenic plants may be shown to have greater tolerance to biotic and/or abiotic stress.

By comparing wild type and transgenic plants similarly treated, the transgenic plants may be shown to have less fungal growth when inoculated with one or more fungal pathogens, or also fewer adverse effects from disease caused by Pseudomonas syringae, nematodes, mollicutes, parasites, or herbivorous arthropods.

The transgenic plants may also have greater yield relative to a control plant when both are faced with the same pathogen challenge. Since members of the G1792 clade may be tolerant or resistant to one or multiple pathogens, plants overexpressing a member of the G1792 clade may incur a smaller yield loss and/or reduced disease symptoms than control plants when the overexpressors and control plants are faced with similar pathogen challenges, including fungal pathogen challenges. Methods for reducing yield loss alleviate some or all of these symptoms by, for example, reducing defoliation, distortions, stunting, necrosis, lesion size or number, pathogen growth or sporulation (in the case of fungal pathogens) by at least about 5%, or at least 10%, or at least 20% or more, up to 100%, relative to a control plant exposed to the same pathogen challenge, or increasing chlorophyll content or photosynthesis by at least about 5%, or at least 10%, or at least 20% or more relative to a control plant subjected to the same pathogen challenge. As indicated in Example VIII, a number of plants overexpressing members of the G1792 clade showed significantly greater disease symptom reduction (up to and including 100%) and significantly fewer or reduced symptoms compared to control plants.

After a monocot plant or plant cell has been transformed (and the latter regenerated into a plant) and shown to have greater tolerance to biotic or abiotic stress, or produce greater yield relative to a control plant under the stress conditions, the transformed monocot plant may be crossed with itself or a plant from the same line, a non-transformed or wild-type monocot plant, or another transformed monocot plant from a different transgenic line of plants.

Example XV

Sequences that Confer Significant Improvements to Non-*Arabidopsis* Species

The function of specific orthologs of G1792 has been analyzed and may be further characterized by incorporation into crop plants. The ectopic overexpression of these orthologs may be regulated using constitutive, inducible, or tissue specific regulatory elements, as disclosed above. Genes that have been examined and have been shown to modify plant traits (including increasing disease tolerance and tolerance to multiple pathogens) encode members of the G1792 clade of transcription factor polypeptides, such as those found in *Arabidopsis thaliana* (SEQ ID NO: 2, 4, 6 and 8), *Glycine max* (22, 24, and 26), *Medicago truncatala* (30), *Oryza sativa* (SEQ ID NO: 10, 12, 14, 16, and 32), *Triticum aestivum* (30), and *Zea mays* (SEQ ID NO: 18, 20, 34 and 36). In addition to these sequences, it is expected that related polynucleotide sequences encoding polypeptides found in the Sequence Listing can also induce altered traits, including increased tolerance to disease and biotic stresses, when transformed into a considerable variety of plants of different species, and including dicots and monocots. The polynucleotide and polypeptide sequences derived from monocots (e.g., the rice or corn sequences) may be used to transform both monocot and dicot plants, and those derived from dicots (e.g., the *Arabidopsis* and soy genes) may be used to transform either group, although it is expected that some of these sequences will function best if the gene is transformed into a plant from the same group as that from which the sequence is derived.

These experiments demonstrate that a number of representative members of the G1792 clade of transcription factor polypeptides, including G1792, G1791, G1795, G30, G3381, G3515, and G3517 can be identified and shown to increase disease tolerance. It is expected that the same methods may be applied to identify and eventually make use of other members of the clade from a diverse range of species.

All publications and patent applications mentioned in this specification are herein incorporated by reference to the same extent as if each individual publication or patent application was specifically and individually indicated to be incorporated by reference.

The present invention is not limited by the specific embodiments described herein. The invention now being fully described, it will be apparent to one of ordinary skill in the art that many changes and modifications can be made thereto without departing from the spirit or scope of the appended claims. Modifications that become apparent from the foregoing description and accompanying figures fall within the scope of the claims.

What is claimed is:

1. A method for increasing a plant's tolerance or resistance to a fungal pathogen, the method comprising:
   (a) providing an expression vector comprising a regulatory element and a polynucleotide sequence;
      wherein the polynucleotide encodes a polypeptide comprises SEQ ID NO: 6, and
      the polynucleotide sequence is operably linked to the regulatory element, and the regulatory element controls expression of the polynucleotide sequence; and
   (b) transforming a target plant with the expression vector to produce a transformed plant, wherein the polypeptide is overexpressed in the transformed plant, and said overexpression results in the transformed plant having greater tolerance or resistance to a fungal disease as compared to a control plant;
   (c) growing the plant in an environment that contains at least a fungal pathogen; and
   (d) selecting a transgenic plant having greater tolerance or resistance to the fungal pathogen as compared to the control plant as a result of expression of the polypeptide.

2. The method of claim 1, wherein the fungal pathogen is selected from the group consisting of *Botrytis, Sclerotinia*, and *Erysiphe*.

3. The method of claim 1 wherein the regulatory element is a constitutive, inducible or tissue-specific promoter.

4. The method of claim 3, wherein the tissue-specific promoter is a leaf promoter or an epidermal tissue-specific promoter.

5. The method of claim 3, wherein the constitutive, inducible or tissue-specific promoter is a cauliflower mosaic 35S promoter, an RBCS3 promoter, or an LTP1 promoter.

6. The method of claim 1, the method steps further comprising:
   (d) selfing or crossing the transformed plant with itself or another plant, respectively, to produce seed; and
   (e) growing a progeny plant from the seed;
      wherein the progeny plant has greater tolerance or resistance to a fungal pathogen than a control plant.

7. A method for producing a plant with greater tolerance or resistance to a fungal pathogen than a control plant, the method comprising:
   (a) providing an expression vector comprising a regulatory element and a polynucleotide sequence; wherein
      the polynucleotide encodes a polypeptide that comprises SEQ ID NO: 6;
      the polynucleotide sequence is operably linked to the regulatory element, and the regulatory element controls expression of the polynucleotide sequence; and
   (b) transforming a target plant with the expression vector to produce a transformed plant, wherein the polypeptide is overexpressed in the transformed plant, and said overexpression results in the transformed plant having greater fungal disease tolerance or resistance than the control plant; and
   (c) growing the plant in an environment that contains a fungal pathogen.

8. The method of claim 7, wherein the fungal pathogen is selected from the group consisting of *Botrytis, Sclerotinia*, and *Erysiphe*.

9. The method of claim 7, the method steps further comprising:
   (d) selfing or crossing the transformed plant with itself or another plant, respectively, to produce seed; and
   (e) growing a progeny plant from the seed;
      wherein the progeny plant has greater tolerance or resistance to a fungal pathogen than the control plant.

10. A transgenic seed produced from the transformed plant produced by the method according to claim 7, wherein the transgenic seed comprises the expression vector of claim 7.

11. A transgenic plant comprising an expression vector comprising:
   (i) a polynucleotide sequence encoding SEQ ID NO: 6; and
   (ii) a regulatory element that controls expression of the polynucleotide sequence.

12. The transgenic plant of claim 11, wherein the transgenic plant has greater tolerance or resistance to a fungal pathogen than a control plant exposed to the same pathogen and the transgenic plant has at least 5% reduced defoliation, distortions, stunting, necrosis, lesion size or number, pathogen growth or sporulation, or 5% increased chlorophyll content or photosynthesis, relative to the control plant.

13. The transgenic plant of claim 12, wherein the fungal pathogen is selected from the group consisting of *Botrytis, Sclerotinia*, and *Erysiphe*.

14. The transgenic plant of claim 11, wherein the regulatory element is a constitutive, inducible or tissue-specific promoter.

15. The transgenic plant of claim 14, wherein the tissue-specific promoter is a leaf promoter or an epidermal tissue-specific promoter.

16. The transgenic plant of claim 14, wherein the constitutive, inducible or tissue-specific promoter is a cauliflower mosaic 35S promoter, an RBCS3promoter, or an LTP1promoter.

* * * * *

SEQUENCE LISTING

```
<160> NUMBER OF SEQ ID NOS: 62

<210> SEQ ID NO 1
<211> LENGTH: 696
<212> TYPE: DNA
<213> ORGANISM: Arabidopsis thaliana
<220> FEATURE:
<223> OTHER INFORMATION: G1792

<400> SEQUENCE: 1
aatccataga tctcttatta aataacagtg ctgaccaagc tcttacaaag caaaccaatc      60
tagaacacca aagttaatgg agagctcaaa caggagcagc aacaaccaat cacaagatga     120
caagcaagct cgtttccggg gagttcgaag aaggccttgg ggaaagtttg cagcagagat     180
```

```
tcgagacccg tcgagaaacg gtgcccgtct ttggctcggg acatttgaga ccgctgagga      240
ggcagcaagg gcttatgacc gagcagcctt taaccttagg ggtcatctcg ctatactcaa      300
cttccctaat gagtattatc cacgtatgga cgactactcg cttcgccctc cttatgcttc      360
ttcttcttcg tcgtcgtcat cgggttcaac ttctactaat gtgagtcgac aaaaccaaag      420
agaagttttc gagtttgagt atttggacga taaggttctt gaagaacttc ttgattcaga      480
agaaaggaag agataatcac gattagtttt gttttgatat tttatgtggc actgttgtgg      540
ctacctacgt gcattatgtg catgtatagg tcgcttgatt agtactttat aacatgcatg      600
ccacgaccat aaattgtaag agaagacgta ctttgcgttt tcatgaaata tgaatgttag      660
atggtttgag tacaaaaaaa aaaaaaaaaa aaaaaa                                696

<210> SEQ ID NO 2
<211> LENGTH: 139
<212> TYPE: PRT
<213> ORGANISM: Arabidopsis thaliana
<220> FEATURE:
<223> OTHER INFORMATION: G1792 polypeptide

<400> SEQUENCE: 2

Met Glu Ser Ser Asn Arg Ser Ser Asn Asn Gln Ser Gln Asp Asp Lys
1               5                   10                  15

Gln Ala Arg Phe Arg Gly Val Arg Arg Arg Pro Trp Gly Lys Phe Ala
            20                  25                  30

Ala Glu Ile Arg Asp Pro Ser Arg Asn Gly Ala Arg Leu Trp Leu Gly
        35                  40                  45

Thr Phe Glu Thr Ala Glu Glu Ala Ala Arg Ala Tyr Asp Arg Ala Ala
    50                  55                  60

Phe Asn Leu Arg Gly His Leu Ala Ile Leu Asn Phe Pro Asn Glu Tyr
65                  70                  75                  80

Tyr Pro Arg Met Asp Asp Tyr Ser Leu Arg Pro Pro Tyr Ala Ser Ser
                85                  90                  95

Ser Ser Ser Ser Ser Ser Gly Ser Thr Ser Thr Asn Val Ser Arg Gln
            100                 105                 110

Asn Gln Arg Glu Val Phe Glu Phe Glu Tyr Leu Asp Asp Lys Val Leu
        115                 120                 125

Glu Glu Leu Leu Asp Ser Glu Glu Arg Lys Arg
    130                 135

<210> SEQ ID NO 3
<211> LENGTH: 549
<212> TYPE: DNA
<213> ORGANISM: Arabidopsis thaliana
<220> FEATURE:
<223> OTHER INFORMATION: G1791

<400> SEQUENCE: 3
atgtacatgc aaaaacaaaa accttaaaag ctttcatgga acgtatagag tcttataaca       60
cgaatgagat gaaatacaga ggcgtacgaa agcgtccatg gggaaaatat gcggcggaga      120
ttcgcgactc agctagacac ggtgctcgtg tttggcttgg gacgtttaac acagcggaag      180
acgcggctcg ggcttatgat agagcagctt tcggcatgag aggccaaagg gccattctca      240
attttcctca cgagtatcaa atgatgaagg acggtccaaa tggcagccac gagaatgcag      300
tggcttcctc gtcgtcggga tatagaggag gaggtggtgg tgatgatggg agggaagtta      360
ttgagttcga gtatttggat gatagtttat tggaggagct tttagattat ggtgagagat      420
```

```
ctaaccaaga caattgtaac gacgcaaacc gctagatcat cactacttac ttacagtgta    480 atgttttttgg agtaaagagt aataatcaat ataatatact ttagtttagg aaaaaaaaaa    540
aaaaaaaaa                                                              549
```

<210> SEQ ID NO 4
<211> LENGTH: 139
<212> TYPE: PRT
<213> ORGANISM: Arabidopsis thaliana
<220> FEATURE:
<223> OTHER INFORMATION: G1791 polypeptide

<400> SEQUENCE: 4

```
Met Glu Arg Ile Glu Ser Tyr Asn Thr Asn Glu Met Lys Tyr Arg Gly
1               5                   10                  15

Val Arg Lys Arg Pro Trp Gly Lys Tyr Ala Ala Glu Ile Arg Asp Ser
            20                  25                  30

Ala Arg His Gly Ala Arg Val Trp Leu Gly Thr Phe Asn Thr Ala Glu
        35                  40                  45

Asp Ala Ala Arg Ala Tyr Asp Arg Ala Ala Phe Gly Met Arg Gly Gln
    50                  55                  60

Arg Ala Ile Leu Asn Phe Pro His Glu Tyr Gln Met Met Lys Asp Gly
65                  70                  75                  80

Pro Asn Gly Ser His Glu Asn Ala Val Ala Ser Ser Ser Gly Tyr
                85                  90                  95

Arg Gly Gly Gly Gly Asp Gly Arg Glu Val Ile Glu Phe Glu
            100                 105                 110

Tyr Leu Asp Asp Ser Leu Leu Glu Glu Leu Leu Asp Tyr Gly Glu Arg
        115                 120                 125

Ser Asn Gln Asp Asn Cys Asn Asp Ala Asn Arg
    130                 135
```

<210> SEQ ID NO 5
<211> LENGTH: 450
<212> TYPE: DNA
<213> ORGANISM: Arabidopsis thaliana
<220> FEATURE:
<223> OTHER INFORMATION: G1795

<400> SEQUENCE: 5

```
acaaacacgc aaaagtcat taatatatgg atcaaggagg tcgaggtgtc ggtgccgagc    60
atggaaagta ccggggagtt cggagacgac cttggggaaa atatgcagca gagatacgag   120
attcgaggaa gcacggtgaa cgtgtgtggc ttggaacgtt cgatacggca gaggaagcgg   180
ctagagccta tgaccaagct gcttactcca tgagaggcca agcagcaatc cttaacttcc   240
ctcatgagta taacatgggg agtggtgtct cttcttccac cgccatggct ggatcttcct   300
ccgcctccgc ctccgcttct tcttcttcta ggcaagtttt tgaatttgag tacttggatg   360
atagtgtttt ggaggagctc cttgaggaag agagaaaacc taacaagggc aagaagaaat   420
gagcgagata taattcatga ttatttctaa                                     450
```

<210> SEQ ID NO 6
<211> LENGTH: 131
<212> TYPE: PRT
<213> ORGANISM: Arabidopsis thaliana
<220> FEATURE:
<223> OTHER INFORMATION: G1795 polypeptide

<400> SEQUENCE: 6

```
Met Asp Gln Gly Gly Arg Gly Val Gly Ala Glu His Gly Lys Tyr Arg
1               5                   10                  15

Gly Val Arg Arg Arg Pro Trp Gly Lys Tyr Ala Ala Glu Ile Arg Asp
            20                  25                  30

Ser Arg Lys His Gly Glu Arg Val Trp Leu Gly Thr Phe Asp Thr Ala
        35                  40                  45

Glu Glu Ala Ala Arg Ala Tyr Asp Gln Ala Tyr Ser Met Arg Gly
    50                  55                  60

Gln Ala Ala Ile Leu Asn Phe Pro His Glu Tyr Asn Met Gly Ser Gly
65                  70                  75                  80

Val Ser Ser Ser Thr Ala Met Ala Gly Ser Ser Ala Ser Ala Ser
                85                  90                  95

Ala Ser Ser Ser Arg Gln Val Phe Glu Phe Glu Tyr Leu Asp Asp
            100                 105                 110

Ser Val Leu Glu Glu Leu Leu Glu Gly Glu Lys Pro Asn Lys Gly
        115                 120                 125

Lys Lys Lys
    130
```

<210> SEQ ID NO 7
<211> LENGTH: 553
<212> TYPE: DNA
<213> ORGANISM: Arabidopsis thaliana
<220> FEATURE:
<223> OTHER INFORMATION: G30

<400> SEQUENCE: 7

```
ctcttctgac gcacaacagt atatacacat acacagatat atggatcaag gaggtcgtag      60
cagtggtagt ggaggaggag gagccgagca agggaagtac cgtggagtaa ggagacgacc     120
ttggggtaaa tacgccgcgg aaataagaga ttcgaggaag cacggagagc gtgtgtggct     180
agggacattc gacactgcgg aagacgcggc tcgagcctat gaccgagccg cctattcaat     240
gagaggcaaa gctgccattc tcaacttccc tcacgagtat aacatgggaa ccggatcctc     300
atccactgcg gctaattctt cttcctcgtc gcagcaagtt tttgagtttg agtacttgga     360
cgatagcgtt ttggatgaac ttcttgaata tggagagaac tataacaaga ctcataatat     420
caacatgggc aagaggcaat aaagggaata caatcggtat taactgaaag ttatgtgaaa     480
gaccattttc agttataaca aataaataa atcccaagc gtacaaagct gtttctaaaa     540
aaaaaaaaaa aaa                                                        553
```

<210> SEQ ID NO 8
<211> LENGTH: 133
<212> TYPE: PRT
<213> ORGANISM: Arabidopsis thaliana
<220> FEATURE:
<223> OTHER INFORMATION: G30 polypeptide

<400> SEQUENCE: 8

```
Met Asp Gln Gly Gly Arg Ser Ser Gly Ser Gly Gly Gly Ala Glu
1               5                   10                  15

Gln Gly Lys Tyr Arg Gly Val Arg Arg Pro Trp Gly Lys Tyr Ala
            20                  25                  30

Ala Glu Ile Arg Asp Ser Arg Lys His Gly Glu Arg Val Trp Leu Gly
        35                  40                  45

Thr Phe Asp Thr Ala Glu Asp Ala Ala Arg Ala Tyr Asp Arg Ala Ala
    50                  55                  60
```

Tyr Ser Met Arg Gly Lys Ala Ala Ile Leu Asn Phe Pro His Glu Tyr
65                  70                  75                  80

Asn Met Gly Thr Gly Ser Ser Ser Thr Ala Ala Asn Ser Ser Ser Ser
                85                  90                  95

Ser Gln Gln Val Phe Glu Phe Glu Tyr Leu Asp Asp Ser Val Leu Asp
            100                 105                 110

Glu Leu Leu Glu Tyr Gly Glu Asn Tyr Asn Lys Thr His Asn Ile Asn
        115                 120                 125

Met Gly Lys Arg Gln
    130

<210> SEQ ID NO 9
<211> LENGTH: 579
<212> TYPE: DNA
<213> ORGANISM: Oryza sativa (japonica cultivar-group)
<220> FEATURE:
<223> OTHER INFORMATION: G3380

<400> SEQUENCE: 9
ggtccgatcc gtaacagtag tagctagtta atttgattat tgtccgtccg cggccggtca        60
gtggtcgcaa tcgatcgatc gatatcatgg acggcgacgg cggcggcgga tgggacgatc       120
agggcaacgg cggcggcgag acgaccaagt accgtggcgt gcgtcgccgg ccttctggca       180
agttcgcggc ggagatccgt gactccagca ggcagagcgt ccgcgtctgg ctgggaacct       240
tcgacaccgc cgaggaggct gcgcgggctt acgaccgcgc cgcctacgcc atgcgcggcc       300
acctcgccgt cctcaacttc cctgctgagg cgcgcaacta cgtgcgggga tcaggctcgt       360
cgtcctcgtc ccgacagcat cagcagcggc aggtgatcga gctggagtgc ctagacgacc       420
aagtgctgca agagatgctc aagggtggcg acgatcagta caggtcagca gctgggagca       480
agaggaataa ctactagcta tatatgctgc taacctactt acaatcgcga tacatatcga       540
ggtttgggga ttttcttctc acctgtgtgc agaggctgc                              579

<210> SEQ ID NO 10
<211> LENGTH: 136
<212> TYPE: PRT
<213> ORGANISM: Oryza sativa (japonica cultivar-group)
<220> FEATURE:
<223> OTHER INFORMATION: G3380 polypeptide

<400> SEQUENCE: 10

Met Asp Gly Asp Gly Gly Gly Trp Asp Asp Gln Gly Asn Gly Gly
1               5                   10                  15

Gly Glu Thr Thr Lys Tyr Arg Gly Val Arg Arg Pro Ser Gly Lys
                20                  25                  30

Phe Ala Ala Glu Ile Arg Asp Ser Ser Arg Gln Ser Val Arg Val Trp
            35                  40                  45

Leu Gly Thr Phe Asp Thr Ala Glu Glu Ala Ala Arg Ala Tyr Asp Arg
        50                  55                  60

Ala Ala Tyr Ala Met Arg Gly His Leu Ala Val Leu Asn Phe Pro Ala
65                  70                  75                  80

Glu Ala Arg Asn Tyr Val Arg Gly Ser Gly Ser Ser Ser Ser Ser Arg
                85                  90                  95

Gln His Gln Gln Arg Gln Val Ile Glu Leu Glu Cys Leu Asp Asp Gln
            100                 105                 110

Val Leu Gln Glu Met Leu Lys Gly Gly Asp Asp Gln Tyr Arg Ser Ala
        115                 120                 125

```
Ala Gly Ser Lys Arg Asn Asn Tyr
    130                 135

<210> SEQ ID NO 11
<211> LENGTH: 514
<212> TYPE: DNA
<213> ORGANISM: Oryza sativa (japonica cultivar-group)
<220> FEATURE:
<223> OTHER INFORMATION: G3381

<400> SEQUENCE: 11
atcgatcatc tgctacgaac tcaccctata tatatatact ccatcttagg agctgcttga    60
tcgatcgaca tatatataac taatggatca tcatcatcag cagcagcagc aggagggtga   120
gctggtggcc aagtacaggg gcgtgcggcg gcggccgtgg ggcaaattcg cggcagagat   180
ccgcgactcg agccggcacg gcgtccgcgt gtggctgggc accttcgaca cagccgagga   240
ggccgctcgc gcctacgacc gctccgccta ctccatgcgc ggcgccaacg ccgtcctcaa   300
cttccccgcc gacgcccaca tctacgcccg tcaactacac aataataacg ccgctgctgg   360
ctcttcatct tcctcttccg ccgccgccgc agcagccagg ccgccgccga tcgagttcga   420
gtacctcgat gaccacgtcc tgcaggagat gctccgagac cacaccacca acaagtagct   480
tactactcca ctatatatgc tgcctgctgc ttgt                              514

<210> SEQ ID NO 12
<211> LENGTH: 131
<212> TYPE: PRT
<213> ORGANISM: Oryza sativa (japonica cultivar-group)
<220> FEATURE:
<223> OTHER INFORMATION: G3381 polypeptide

<400> SEQUENCE: 12

Met Asp His His His Gln Gln Gln Gln Glu Gly Glu Leu Val Ala
1               5                   10                  15

Lys Tyr Arg Gly Val Arg Arg Arg Pro Trp Gly Lys Phe Ala Ala Glu
            20                  25                  30

Ile Arg Asp Ser Ser Arg His Gly Val Arg Val Trp Leu Gly Thr Phe
        35                  40                  45

Asp Thr Ala Glu Glu Ala Ala Arg Ala Tyr Asp Arg Ser Ala Tyr Ser
    50                  55                  60

Met Arg Gly Ala Asn Ala Val Leu Asn Phe Pro Ala Asp Ala His Ile
65                  70                  75                  80

Tyr Ala Arg Gln Leu His Asn Asn Asn Ala Ala Ala Gly Ser Ser Ser
                85                  90                  95

Ser Ser Ser Ala Ala Ala Ala Ala Ala Arg Pro Pro Ile Glu Phe
            100                 105                 110

Glu Tyr Leu Asp Asp His Val Leu Gln Glu Met Leu Arg Asp His Thr
        115                 120                 125

Thr Asn Lys
    130

<210> SEQ ID NO 13
<211> LENGTH: 375
<212> TYPE: DNA
<213> ORGANISM: Oryza sativa (japonica cultivar-group)
<220> FEATURE:
<223> OTHER INFORMATION: G3383

<400> SEQUENCE: 13
atggaggaca accggagcaa ggacacggcg accaagtacc gcggcgtgag gaggcggccg    60
```

```
tggggcaagt tcgcggcgga gatccgcgac ccggagcgcg gcggggcgcg cgtctggctc    120
ggcaccttcg acaccgccga ggaggcggcg cgtgcctacg accgcgcggc ctacgcccag    180
cgcggcgccg ccgccgtgct caacttcccg gccgccgccg ccgccggcag gggtggagga    240
gccggcggcg ccgcttccgg gtcgtcgtcg tcgtcgtccg cgcagcgcgg caggggcgac    300
aagatcgagt tcgagtacct cgacgacaag gtgctcgacg atctcctcga cgacgagaag    360
taccgtggta aatga                                                    375
```

```
<210> SEQ ID NO 14
<211> LENGTH: 124
<212> TYPE: PRT
<213> ORGANISM: Oryza sativa (japonica cultivar-group)
<220> FEATURE:
<223> OTHER INFORMATION: G3383 polypeptide

<400> SEQUENCE: 14
```

```
Met Glu Asp Asn Arg Ser Lys Asp Thr Ala Thr Lys Tyr Arg Gly Val
1               5                   10                  15

Arg Arg Arg Pro Trp Gly Lys Phe Ala Ala Glu Ile Arg Asp Pro Glu
            20                  25                  30

Arg Gly Gly Ala Arg Val Trp Leu Gly Thr Phe Asp Thr Ala Glu Glu
        35                  40                  45

Ala Ala Arg Ala Tyr Asp Arg Ala Ala Tyr Ala Gln Arg Gly Ala Ala
    50                  55                  60

Ala Val Leu Asn Phe Pro Ala Ala Ala Ala Gly Arg Gly Gly
65                  70                  75                  80

Ala Gly Gly Ala Ala Ser Gly Ser Ser Ser Ser Ser Ala Gln Arg
            85                  90                  95

Gly Arg Gly Asp Lys Ile Glu Phe Glu Tyr Leu Asp Asp Lys Val Leu
            100                 105                 110

Asp Asp Leu Leu Asp Asp Glu Lys Tyr Arg Gly Lys
        115                 120
```

```
<210> SEQ ID NO 15
<211> LENGTH: 466
<212> TYPE: DNA
<213> ORGANISM: Oryza sativa (japonica cultivar-group)
<220> FEATURE:
<223> OTHER INFORMATION: G3515

<400> SEQUENCE: 15
```

```
gtgtgcgagc ggttgcgtcc gcatggagga cgacaagagt aaggagggga aatcgtcgtc     60
gtcgtaccgc ggcgtgcgga agcggccgtg gggcaagttc gcggcggaga tccgcgaccc    120
ggagcgcggg ggagcccgcg tgtggctcgg cacgttcgac accgcggagg aggccgcgcg    180
ggcgtacgac cgcgccgcat tcgccatgaa gggcgccacg gccatgctca acttcccggg    240
agatcatcat cacggcgccg caagcaggat gaccagcacc ggctcttctt cgtcctcctt    300
caccacgcct cctccggcga actcctccgc ggcggcgggc cgcggcggct ccgatcggac    360
gacggacaag gtggagctgg agtgcctcga cgacaaggtc ctggaggacc tcctcgcgga    420
gaccaactat cgtgataaga actactagct agctagctac tatggc                  466
```

```
<210> SEQ ID NO 16
<211> LENGTH: 141
<212> TYPE: PRT
<213> ORGANISM: Oryza sativa (japonica cultivar-group)
<220> FEATURE:
```

<223> OTHER INFORMATION: G3515 polypeptide

<400> SEQUENCE: 16

Met Glu Asp Asp Lys Ser Lys Glu Gly Lys Ser Ser Ser Tyr Arg
1               5                   10                  15

Gly Val Arg Lys Arg Pro Trp Gly Lys Phe Ala Ala Glu Ile Arg Asp
            20                  25                  30

Pro Glu Arg Gly Gly Ala Arg Val Trp Leu Gly Thr Phe Asp Thr Ala
        35                  40                  45

Glu Glu Ala Ala Arg Ala Tyr Asp Arg Ala Ala Phe Ala Met Lys Gly
    50                  55                  60

Ala Thr Ala Met Leu Asn Phe Pro Gly Asp His His Gly Ala Ala
65                  70                  75                  80

Ser Arg Met Thr Ser Thr Gly Ser Ser Ser Ser Phe Thr Thr Pro
                85                  90                  95

Pro Pro Ala Asn Ser Ser Ala Ala Gly Arg Gly Gly Ser Asp Arg
            100                 105                 110

Thr Thr Asp Lys Val Glu Leu Glu Cys Leu Asp Asp Lys Val Leu Glu
            115                 120                 125

Asp Leu Leu Ala Glu Thr Asn Tyr Arg Asp Lys Asn Tyr
    130                 135                 140

<210> SEQ ID NO 17
<211> LENGTH: 393
<212> TYPE: DNA
<213> ORGANISM: Zea mays
<220> FEATURE:
<223> OTHER INFORMATION: G3516

<400> SEQUENCE: 17
atggaggacg acaagaagga gggcaagtac cgcggcgtgc ggaagcggcc gtggggcaag      60
ttcgccgcgg agatccggga cccggagcgc ggcggctccc gcgtctggct cggcaccttc     120
gacaccgccg aggaggccgc cagggcctac gaccgcgccg cattcgccat gaagggcgcc     180
acggccgtgc tcaacttccc cgccagcgga ggatcgtcag ctggcgcggc tcccggcggc     240
cggaccagcg gcggctcctc ctcgtccacc acgtcggctc cggccagcag ggggagggcc     300
cgtgttcccg actcggagaa ggtggagctg gagtgcctcg acgacagggt cttggaagag     360
ctgctcgcgg aagacaagta caacaagaac taa                                  393

<210> SEQ ID NO 18
<211> LENGTH: 130
<212> TYPE: PRT
<213> ORGANISM: Zea mays
<220> FEATURE:
<223> OTHER INFORMATION: G3516 polypeptide

<400> SEQUENCE: 18

Met Glu Asp Asp Lys Lys Glu Gly Lys Tyr Arg Gly Val Arg Lys Arg
1               5                   10                  15

Pro Trp Gly Lys Phe Ala Ala Glu Ile Arg Asp Pro Glu Arg Gly Gly
            20                  25                  30

Ser Arg Val Trp Leu Gly Thr Phe Asp Thr Ala Glu Glu Ala Ala Arg
        35                  40                  45

Ala Tyr Asp Arg Ala Ala Phe Ala Met Lys Gly Ala Thr Ala Val Leu
    50                  55                  60

Asn Phe Pro Ala Ser Gly Gly Ser Ser Ala Gly Ala Ala Pro Gly Gly
65                  70                  75                  80

Arg Thr Ser Gly Gly Ser Ser Ser Thr Thr Ser Ala Pro Ala Ser
            85                  90                  95

Arg Gly Arg Ala Arg Val Pro Asp Ser Glu Lys Val Glu Leu Glu Cys
            100                 105                 110

Leu Asp Asp Arg Val Leu Glu Glu Leu Leu Ala Glu Asp Lys Tyr Asn
        115                 120                 125

Lys Asn
    130

<210> SEQ ID NO 19
<211> LENGTH: 477
<212> TYPE: DNA
<213> ORGANISM: Zea mays
<220> FEATURE:
<223> OTHER INFORMATION: G3517

<400> SEQUENCE: 19
tacgtccgat ccacagccat catcgccacc cgcgcgctta tggatggcga gtggtccaag       60
gacggcggag gcggcgagcc gaccaagtac cgcggcgtgc ggcgtcggcc ctggggcaag      120
tacgcggcgg agatccgcga ctcgagccgg cacggcgtcc gcatctggct cggcacgttc      180
gacaccgccg aggaggccgc cagggcgtac gaccgctccg ccaactccat gcgcggcgcc      240
aacgccgtgc tcaacttccc ggaggacgcg cccgcctacg ccgccgccgc ctcccgtggc      300
tccgccggcg gatcctcgtc cagaccggcg ggctccggcc gggacgtgat cgagtttgag      360
tacctcgacg acgaggtgct gcaggagatg ctcaggagcc aggagccgtc ggcggcggcg      420
gcgcagaaga agaagtagcg cgagcgccac aggtggcgaa acggccgctt ttccaaa       477

<210> SEQ ID NO 20
<211> LENGTH: 132
<212> TYPE: PRT
<213> ORGANISM: Zea mays
<220> FEATURE:
<223> OTHER INFORMATION: G3517 polypeptide

<400> SEQUENCE: 20

Met Asp Gly Glu Trp Ser Lys Asp Gly Gly Gly Glu Pro Thr Lys
1               5                   10                  15

Tyr Arg Gly Val Arg Arg Arg Pro Trp Gly Lys Tyr Ala Ala Glu Ile
            20                  25                  30

Arg Asp Ser Ser Arg His Gly Val Arg Ile Trp Leu Gly Thr Phe Asp
        35                  40                  45

Thr Ala Glu Glu Ala Ala Arg Ala Tyr Asp Arg Ser Ala Asn Ser Met
    50                  55                  60

Arg Gly Ala Asn Ala Val Leu Asn Phe Pro Glu Asp Ala Pro Ala Tyr
65                  70                  75                  80

Ala Ala Ala Ala Ser Arg Gly Ser Ala Gly Gly Ser Ser Arg Pro
            85                  90                  95

Ala Gly Ser Gly Arg Asp Val Ile Glu Phe Glu Tyr Leu Asp Asp Glu
            100                 105                 110

Val Leu Gln Glu Met Leu Arg Ser Gln Glu Pro Ser Ala Ala Ala Ala
        115                 120                 125

Gln Lys Lys Lys
    130

<210> SEQ ID NO 21
<211> LENGTH: 717

```
<212> TYPE: DNA
<213> ORGANISM: Glycine max
<220> FEATURE:
<223> OTHER INFORMATION: G3518

<400> SEQUENCE: 21
ctaacacaca taacaataac ttagcaacat ttttccttc cttctttctt tctttctata    60
cttttgttg ttaattctaa gttctaagag aagaaaaatg gagggtggaa gatcatcagt   120
ttcaaatggg aatgttgagg ttcgttatag agggattaga agaaggccat ggggaaagtt   180
tgcagcagag attcgtgacc ctacaaggaa aggaacaagg atatggcttg gaacatttga   240
cactgctgaa caagctgcac gagcttatga tgctgctgct tttcattttc gtggccacag   300
agcaattctc aacttcccaa atgagtatca atctcataat ccaaactctt ctttgcctat   360
gcctctagct gtgtcagctc ctccttctta ttcttcttct tcttccactt ctaattattc   420
cggtgatgat aataataacc accttgtgag accagctttt tctggagaaa taatgcaagg   480
tggtgatcat gatgatgata cttttgagtt ggagtacttc gataataagt tgctcgagga   540
actccttcag atgcaagata acagacactt ctaaaagtaa aatataacac aagccagcta   600
tgttgtgtta gtcactggca tgaaataaaa tgcaaagaaa tattgttgat tttatttaat   660
atattttgtt tgattttttt tttttttttt gtagctgatc aaagttcttc gaaatga     717

<210> SEQ ID NO 22
<211> LENGTH: 158
<212> TYPE: PRT
<213> ORGANISM: Glycine max
<220> FEATURE:
<223> OTHER INFORMATION: G3518 polypeptide

<400> SEQUENCE: 22

Met Glu Gly Gly Arg Ser Ser Val Ser Asn Gly Asn Val Glu Val Arg
1               5                   10                  15

Tyr Arg Gly Ile Arg Arg Arg Pro Trp Gly Lys Phe Ala Ala Glu Ile
            20                  25                  30

Arg Asp Pro Thr Arg Lys Gly Thr Arg Ile Trp Leu Gly Thr Phe Asp
        35                  40                  45

Thr Ala Glu Gln Ala Ala Arg Ala Tyr Asp Ala Ala Ala Phe His Phe
    50                  55                  60

Arg Gly His Arg Ala Ile Leu Asn Phe Pro Asn Glu Tyr Gln Ser His
65                  70                  75                  80

Asn Pro Asn Ser Ser Leu Pro Met Pro Leu Ala Val Ser Ala Pro Pro
                85                  90                  95

Ser Tyr Ser Ser Ser Ser Thr Ser Asn Tyr Ser Gly Asp Asp Asn
            100                 105                 110

Asn Asn His Leu Val Arg Pro Ala Phe Ser Gly Glu Ile Met Gln Gly
        115                 120                 125

Gly Asp His Asp Asp Asp Thr Phe Glu Leu Glu Tyr Phe Asp Asn Lys
    130                 135                 140

Leu Leu Glu Glu Leu Leu Gln Met Gln Asp Asn Arg His Phe
145                 150                 155

<210> SEQ ID NO 23
<211> LENGTH: 609
<212> TYPE: DNA
<213> ORGANISM: Glycine max
<220> FEATURE:
<223> OTHER INFORMATION: G3519
```

<400> SEQUENCE: 23

```
tttctttctt tctatacttt ttgtggttct gattattaag ttctaagaga ataacaatgg     60
agggtggaag atcatctgtt tcaaatggga attgtgaggt tcggtataga gggattagaa    120
gaaggccatg gggcaagttt gcagcagaga ttcgtgaccc tacgaggaaa gggacaagga    180
tatggcttgg aacatttgac actgcggaac aagctgctcg agcttatgat gctgctgctt    240
ttcattttcg tggtcataga gcaattctca acttcccaaa tgagtaccaa tctcataatc    300
caaactcttc tttgcctatg cctctaattg tgcctcctcc ttcttattct tcttctttca    360
cttctaatta ttctgctgat gataataacc accttgtgag acctggagaa ataatgcaag    420
gtggtgatct tgatgacact tttgagttgg agtacttgga taataagttg ctcgaggaac    480
tccttcagat gcaagataac agacacttct aaaagtaaaa tataacacaa gccagctatg    540
ttgtgttagt cactggcatg aaataaaatg caaagaaata ttgttgattt tatttaatat    600
attttgttt                                                            609
```

<210> SEQ ID NO 24
<211> LENGTH: 151
<212> TYPE: PRT
<213> ORGANISM: Glycine max
<220> FEATURE:
<223> OTHER INFORMATION: G3519 polypeptide

<400> SEQUENCE: 24

```
Met Glu Gly Gly Arg Ser Ser Val Ser Asn Gly Asn Cys Glu Val Arg
1               5                   10                  15

Tyr Arg Gly Ile Arg Arg Pro Trp Gly Lys Phe Ala Ala Glu Ile
            20                  25                  30

Arg Asp Pro Thr Arg Lys Gly Thr Arg Ile Trp Leu Gly Thr Phe Asp
        35                  40                  45

Thr Ala Glu Gln Ala Ala Arg Ala Tyr Asp Ala Ala Ala Phe His Phe
    50                  55                  60

Arg Gly His Arg Ala Ile Leu Asn Phe Pro Asn Glu Tyr Gln Ser His
65                  70                  75                  80

Asn Pro Asn Ser Ser Leu Pro Met Pro Leu Ile Val Pro Pro Ser
                85                  90                  95

Tyr Ser Ser Ser Phe Thr Ser Asn Tyr Ser Ala Asp Asp Asn His
            100                 105                 110

Leu Val Arg Pro Gly Glu Ile Met Gln Gly Gly Asp Leu Asp Asp Thr
        115                 120                 125

Phe Glu Leu Glu Tyr Leu Asp Asn Lys Leu Leu Glu Leu Leu Gln
    130                 135                 140

Met Gln Asp Asn Arg His Phe
145                 150
```

<210> SEQ ID NO 25
<211> LENGTH: 440
<212> TYPE: DNA
<213> ORGANISM: Glycine max
<220> FEATURE:
<223> OTHER INFORMATION: G3520

<400> SEQUENCE: 25

```
aaggcacaca atggaagagg agtcaaagga gaaaagaag gacactaagg aggaaccacg      60
ttatagagga gtgcggcggc ggccgtgggg gaagttcgcg gccgagattc gggacccggc    120
ccggcacggt gcccgagtgt ggctggggac atttctcacg gcggaggagg ctgctagggc    180
```

```
ttatgaccga gctgcctatg agatgagggg cgctttagcc gttctcaatt ttccaaatga      240
gtatccttca tgctcttcta tgaactcatc ttcaacatta gcaccttcat cttcttcttc      300
aaattcaatg cttaaaagtg atcatggtaa acaagttatt gagttcgagt gcttggatga      360
caaattgtta gaggaccttc ttgattgtga tgactatgcc tacgagaaag acttgcctaa      420
gaactgaacg gtttgatcaa                                                  440
```

```
<210> SEQ ID NO 26
<211> LENGTH: 138
<212> TYPE: PRT
<213> ORGANISM: Glycine max
<220> FEATURE:
<223> OTHER INFORMATION: G3520 polypeptide

<400> SEQUENCE: 26
```

Met Glu Glu Glu Ser Lys Glu Lys Lys Lys Asp Thr Lys Glu Glu Pro
1               5                   10                  15

Arg Tyr Arg Gly Val Arg Arg Pro Trp Gly Lys Phe Ala Ala Glu
            20                  25                  30

Ile Arg Asp Pro Ala Arg His Gly Ala Arg Val Trp Leu Gly Thr Phe
        35                  40                  45

Leu Thr Ala Glu Glu Ala Ala Arg Ala Tyr Asp Arg Ala Ala Tyr Glu
    50                  55                  60

Met Arg Gly Ala Leu Ala Val Leu Asn Phe Pro Asn Glu Tyr Pro Ser
65                  70                  75                  80

Cys Ser Ser Met Asn Ser Ser Ser Thr Leu Ala Pro Ser Ser Ser Ser
                85                  90                  95

Ser Asn Ser Met Leu Lys Ser Asp His Gly Lys Gln Val Ile Glu Phe
            100                 105                 110

Glu Cys Leu Asp Asp Lys Leu Leu Glu Asp Leu Leu Asp Cys Asp Asp
        115                 120                 125

Tyr Ala Tyr Glu Lys Asp Leu Pro Lys Asn
    130                 135

```
<210> SEQ ID NO 27
<211> LENGTH: 653
<212> TYPE: DNA
<213> ORGANISM: Medicago truncatula
<220> FEATURE:
<221> NAME/KEY: misc_feature
<222> LOCATION: (605)..(605)
<223> OTHER INFORMATION: n is a, c, g, or t
<220> FEATURE:
<221> NAME/KEY: misc_feature
<222> LOCATION: (610)..(610)
<223> OTHER INFORMATION: n is a, c, g, or t
<220> FEATURE:
<221> NAME/KEY: misc_feature
<222> LOCATION: (615)..(615)
<223> OTHER INFORMATION: n is a, c, g, or t
<220> FEATURE:
<221> NAME/KEY: misc_feature
<222> LOCATION: (625)..(625)
<223> OTHER INFORMATION: n is a, c, g, or t
<220> FEATURE:
<221> NAME/KEY: misc_feature
<222> LOCATION: (647)..(647)
<223> OTHER INFORMATION: n is a, c, g, or t
<220> FEATURE:
<221> NAME/KEY: misc_feature
<222> LOCATION: (652)..(652)
<223> OTHER INFORMATION: n is a, c, g, or t
<220> FEATURE:
<223> OTHER INFORMATION: G3735
```

<400> SEQUENCE: 27

```
ctaatccttc atactaaaga aaacatagac ttataacaaa atattatta tttacttcgt    60
atattttgt gtttcaaatt aatggaggga gatcataaat tagtttcaaa ttcaacaaat   120
ggaaatggaa atggaaatgg aaattcagat caaataaagt atagaggaat tcgtagaaga   180
ccatggggaa aatttgcagc agaaattcgt gacccaacaa ggaaagggac aagaatatgg   240
cttggaacat ttgatactgc tgaacaagct gcaagagctt atgatgctgc tgcttttcat   300
tttcgtggtc atagagctat tctcaatttc cctaatgaat atcaagctcc taattcatct   360
tcttcattac ctatgcctct tactatgcct ccaccacctt cttctaatcc acctccttct   420
tcttcttctt cttcctcttt tcttcttac accgttgatg atggttttga tgagcttgaa   480
ttcttggata taagttgct tcaagaactt cttcaagatg aaacacaata gttaactatt   540
gaagatcaag tggcatgaaa tgtattggtg gtcatttaat tttctcttca ttaatttatt   600
ttggnttggn tatgnatctc atttntatga ataaatgaga atggggnatt ana         653
```

<210> SEQ ID NO 28
<211> LENGTH: 149
<212> TYPE: PRT
<213> ORGANISM: Medicago truncatula
<220> FEATURE:
<223> OTHER INFORMATION: G3735 polypeptide

<400> SEQUENCE: 28

```
Met Glu Gly Asp His Lys Leu Val Ser Asn Ser Thr Asn Gly Asn Gly
1               5                   10                  15
Asn Gly Asn Gly Asn Ser Asp Gln Ile Lys Tyr Arg Gly Ile Arg Arg
            20                  25                  30
Arg Pro Trp Gly Lys Phe Ala Ala Glu Ile Arg Asp Pro Thr Arg Lys
        35                  40                  45
Gly Thr Arg Ile Trp Leu Gly Thr Phe Asp Thr Ala Glu Gln Ala Ala
    50                  55                  60
Arg Ala Tyr Asp Ala Ala Ala Phe His Phe Arg Gly His Arg Ala Ile
65                  70                  75                  80
Leu Asn Phe Pro Asn Glu Tyr Gln Ala Pro Asn Ser Ser Ser Ser Leu
                85                  90                  95
Pro Met Pro Leu Thr Met Pro Pro Pro Ser Ser Asn Pro Pro
            100                 105                 110
Ser Ser Ser Ser Ser Ser Ser Phe Ser Ser Tyr Thr Val Asp Asp Gly
        115                 120                 125
Phe Asp Glu Leu Glu Phe Leu Asp Asn Lys Leu Leu Gln Glu Leu Leu
    130                 135                 140
Gln Asp Gly Thr Gln
145
```

<210> SEQ ID NO 29
<211> LENGTH: 859
<212> TYPE: DNA
<213> ORGANISM: Triticum aestivum
<220> FEATURE:
<223> OTHER INFORMATION: G3736

<400> SEQUENCE: 29

```
gcacgaggct tcattctccc tcgttccatc caagctccac catccatcac tgatttgcac    60
ttacctagct actccgcaac ccccacttcc ggcttcttca tttctcacta ctagtacgta   120
```

-continued

```
gttgagatta tggagggcgg agaaggatcc ggtggcggcg gcgagccgac caagtaccgc    180
ggggtgcgcc gcaggccgtg gggcaagttc gccgcggaga tccgggactc gagccggcac    240
ggcgtgcgca tgtggctcgg caccttcgac accgccgagg aggccgcggc cgcctacgac    300
cgctccgcct actccatgcg cggccgcaac gccgtgctca acttccccga ccgggcgcac    360
gtctacgagg ccgaggccag gcgccagggc cagggctctt cgtcgtcggc gaggcagcag    420
aatcagcagc agcagcaggg gcagagcggg gtgatcgagt tcgagtacct ggacgacgac    480
gtgctgcagt ccatgctcca cgaccacgac aaatccaaca gtagatcga tggatcatcc     540 atccatccat ccatggatcg atccataata cctactgtat catcccggcc cggccggcaa    600
catcgacctg cgtgcatgcg cgggcgcgga tgcaatctac actacctacc tatgcattcc    660
ggccatatat taggtacgta gattatatgt gtacgagagc ctacgagctc gatgaagatc    720
gtacgtggtg cattctgatg catgaggatt ccatcgacac gaccctctac catatatttg    780
atgggtcgat cgagtaattt gcagccagta atccaatcga tgatatgggg ttttcaaaaa    840
aaaaaaaaaa aaaaaaaa                                                  859
```

<210> SEQ ID NO 30
<211> LENGTH: 131
<212> TYPE: PRT
<213> ORGANISM: Triticum aestivum
<220> FEATURE:
<223> OTHER INFORMATION: G3736 polypeptide

<400> SEQUENCE: 30

```
Met Glu Gly Gly Glu Gly Ser Gly Gly Gly Glu Pro Thr Lys Tyr
1               5                  10                  15

Arg Gly Val Arg Arg Arg Pro Trp Gly Lys Phe Ala Ala Glu Ile Arg
            20                  25                  30

Asp Ser Ser Arg His Gly Val Arg Met Trp Leu Gly Thr Phe Asp Thr
        35                  40                  45

Ala Glu Glu Ala Ala Ala Ala Tyr Asp Arg Ser Ala Tyr Ser Met Arg
    50                  55                  60

Gly Arg Asn Ala Val Leu Asn Phe Pro Asp Arg Ala His Val Tyr Glu
65                  70                  75                  80

Ala Glu Ala Arg Arg Gln Gly Gln Gly Ser Ser Ser Ala Arg Gln
                85                  90                  95

Gln Asn Gln Gln Gln Gln Gly Gln Ser Gly Val Ile Glu Phe Glu
            100                 105                 110

Tyr Leu Asp Asp Asp Val Leu Gln Ser Met Leu His Asp His Asp Lys
        115                 120                 125

Ser Asn Lys
    130
```

<210> SEQ ID NO 31
<211> LENGTH: 882
<212> TYPE: DNA
<213> ORGANISM: Oryza sativa (japonica cultivar-group)
<220> FEATURE:
<223> OTHER INFORMATION: G3737

<400> SEQUENCE: 31

```
acacatgcat cgatcattca tggatgccga attgccgcga tccgggcatt atttcgcgcc    60
aggagaccca agatcatcgt gtcgcccacg ctataaatag ctagctagct tgcctttatg    120
ttgcatatgc caactgctac atgcaggacg tctgaaacta tcattagtga cctgcagcgc    180
```

```
ctgcagtata tatatacaag tagtagtgag catggaggac gacaagaagg aggcggcgag     240
caagtaccgc ggcgtacgga ggcggccgtg gggcaaattc gcggcggaga tccgcgaccc     300
ggagcgcggc ggctcacgcg tctggcttgg cacgttcgac accgccgagg aggccgcgcg     360
agcgtacgac cgcgccgcat cgccatgaa gggcgctatg gccgtgctca acttcccagg     420
caggacgagc agcaccggct cttcgtcgtc atcgtcatcc acgccgccag ctccggtgac     480
gacgagccgc cactgcgccg acacgacgga gaaggtggag cttgtgtacc ttgacgacaa     540
ggtgctcgac gagctccttg cggaggacta cagctaccgc aacaacaaca actactgatc     600
cggccgtcga tgaactgaga cggatcgaca tggggccggt cgtcggtacg ctcgctgaaa     660
cgagacccgg attgctatca ataagcaagc agaagaaaac cgtctcctat atatagcttc     720
ttctgttggc acaagcatat atgggcatgc atgacacatg ctactgtgaa ttgacgggtg     780
tgtgctgtgt gcagactact aaaccacgct tgcaagttgc acgtacgacg tggttgtcaa     840
gagcatgcag tccacgaagc agagaaaaac acctggttta tc                        882
```

<210> SEQ ID NO 32
<211> LENGTH: 128
<212> TYPE: PRT
<213> ORGANISM: Oryza sativa (japonica cultivar-group)
<220> FEATURE:
<223> OTHER INFORMATION: G3737 polypeptide

<400> SEQUENCE: 32

```
Met Glu Asp Asp Lys Lys Glu Ala Ala Ser Lys Tyr Arg Gly Val Arg
1               5                   10                  15

Arg Arg Pro Trp Gly Lys Phe Ala Ala Glu Ile Arg Asp Pro Glu Arg
            20                  25                  30

Gly Gly Ser Arg Val Trp Leu Gly Thr Phe Asp Thr Ala Glu Glu Ala
        35                  40                  45

Ala Arg Ala Tyr Asp Arg Ala Ala Phe Ala Met Lys Gly Ala Met Ala
    50                  55                  60

Val Leu Asn Phe Pro Gly Arg Thr Ser Ser Thr Gly Ser Ser Ser Ser
65                  70                  75                  80

Ser Ser Ser Thr Pro Pro Ala Pro Val Thr Thr Ser Arg His Cys Ala
                85                  90                  95

Asp Thr Thr Glu Lys Val Glu Leu Val Tyr Leu Asp Asp Lys Val Leu
            100                 105                 110

Asp Glu Leu Leu Ala Glu Asp Tyr Ser Tyr Arg Asn Asn Asn Asn Tyr
        115                 120                 125
```

<210> SEQ ID NO 33
<211> LENGTH: 899
<212> TYPE: DNA
<213> ORGANISM: Zea mays
<220> FEATURE:
<223> OTHER INFORMATION: G3739

<400> SEQUENCE: 33

```
cgatataatt cactcctctc aacgctcgct gcacacacac accagtgaac ctagccagcc      60
atttgccgca tcgatcatca gtcgctgtca cgcgcgccaa accaaaccaa agcccaaacc     120
cagctgcaag tgctactgac agcagctagc aaacacacac ccgtcgccat cgctatggac     180
ggcgactggt ccaaggacgg cggaggtgga gagccgacca aatatcgcgg cgtgcggcgg     240
cggccctggg gcaagtacgc ggccgagatc cgcgactcga gccgcacgg cgtccgcatc     300 tggctgggca ccttcgacac cgccgaggag gccgccaggg cgtacgaccg gagcgcctac     360
```

```
tccatgcgcg gcgccaacgc cgtcctcaac ttcccggagg acgcgcacgc ctacgccgcc    420
gcctgccgcg gctccggatc ctcctcatcc tcgtccaggc ataggcagca gcagcagcag    480
ggctccggca gggacgtgat cgagctcgag tacctcgacg acgaggtgct gcaggagatg    540
ctcaggaacc acgagccgtc gtcgtctgcg aggaagaaga tgtaatgcaa acgactggt    600 acacgtggcg aatgcacgtt gcacatcaga atgccatgta tgcgtggggg gttacgttca    660
attgtatgca tgcagtgcag tgactaccgg ccggctctcc tggatatgtc ggccatctct    720
ctctatatat tattaaaatg tcagctccct tctctaattt ggcgggagtt acatcagtgg    780
tactatgcag agttgcatac ttgcatatat atgcacatta ttaattaata actcgatctc    840
tcgtggacgg tggaacagtg ataatcatct cattgtcaat taattttgat caaagaaat    899

<210> SEQ ID NO 34
<211> LENGTH: 136
<212> TYPE: PRT
<213> ORGANISM: Zea mays
<220> FEATURE:
<223> OTHER INFORMATION: G3739 polypeptide

<400> SEQUENCE: 34

Met Asp Gly Asp Trp Ser Lys Asp Gly Gly Gly Glu Pro Thr Lys
  1               5                  10                  15

Tyr Arg Gly Val Arg Arg Pro Trp Gly Lys Tyr Ala Ala Glu Ile
             20                  25                  30

Arg Asp Ser Ser Arg His Gly Val Arg Ile Trp Leu Gly Thr Phe Asp
         35                  40                  45

Thr Ala Glu Glu Ala Ala Arg Ala Tyr Asp Arg Ser Ala Tyr Ser Met
     50                  55                  60

Arg Gly Ala Asn Ala Val Leu Asn Phe Pro Glu Asp Ala His Ala Tyr
 65                  70                  75                  80

Ala Ala Ala Cys Arg Gly Ser Gly Ser Ser Ser Ser Ser Arg His
                 85                  90                  95

Arg Gln Gln Gln Gln Gln Gly Ser Gly Arg Asp Val Ile Glu Leu Glu
            100                 105                 110

Tyr Leu Asp Asp Glu Val Leu Gln Glu Met Leu Arg Asn His Glu Pro
        115                 120                 125

Ser Ser Ser Ala Arg Lys Lys Met
    130                 135

<210> SEQ ID NO 35
<211> LENGTH: 918
<212> TYPE: DNA
<213> ORGANISM: Zea mays
<220> FEATURE:
<223> OTHER INFORMATION: G3794

<400> SEQUENCE: 35
attacttgtg cacttgggtg cagtgcctgc agtataatca agttagggtt taaaagaacc     60
tcgaccgcga tcgtatatag atccagatta tcattagtta ttagaccact gtgatatcga    120
tggacgacgg cggcgagcca accaagtacc gcgcgtgcg gcgccggccg tcggggaagt    180
tcgccgccga gatccgcgac tccagccggc agagcgtgcg catgtggctg gcaccttcg    240 acacggccga ggaggccgca agggcgtacg accgcgcggc ctacgccatg cgcggccaaa    300
tcgccgtgct caacttcccc gccgaggcgc gcaactacgt gcgcggcggg tcgtcgtcgt    360
cccgccagca gcagcaggga ggaggaggag gaggaggaag tggcggcggc gccggtcagc    420
```

```
aggtgatcga gctggagtgc ctggacgatc aggtgctgca ggagatgctc aagggcggcg      480
acgggaaaaa atagttgtta gcgtatctga tcacaggtgc acgtgttgaa actgattatg      540
accaggcgat cgatcccatc ttgtgcatgc ggcctgccaa agttgctggg tcttctcatc      600
gacctatata tatatgcttc tcgatccata tatatatcat aaatgcatgc agggtgcatg      660
catgtaccaa gtttggaatt ataatgctct tggtgctgaa ttgaagtata ctagtatata      720
tagtgtgatc catgtattga aaaggttgtt ttgcttaatc gcgtcatgat tgcacacgtg      780
cttgtttctg cttaaacaac ccatatatat agccggctct ggcctttgtc aagtctgcaa      840
tccttataca tcgttggtaa ttcatgcatg agttctatgt aactgcaatt tagataaatt      900
gtagctaata taatagtc                                                   918
```

```
<210> SEQ ID NO 36
<211> LENGTH: 124
<212> TYPE: PRT
<213> ORGANISM: Zea mays
<220> FEATURE:
<223> OTHER INFORMATION: G3794 polypeptide

<400> SEQUENCE: 36

Met Asp Asp Gly Gly Glu Pro Thr Lys Tyr Arg Gly Val Arg Arg
1               5                   10                  15

Pro Ser Gly Lys Phe Ala Ala Glu Ile Arg Asp Ser Ser Arg Gln Ser
                20                  25                  30

Val Arg Met Trp Leu Gly Thr Phe Asp Thr Ala Glu Glu Ala Ala Arg
            35                  40                  45

Ala Tyr Asp Arg Ala Ala Tyr Ala Met Arg Gly Gln Ile Ala Val Leu
        50                  55                  60

Asn Phe Pro Ala Glu Ala Arg Asn Tyr Val Arg Gly Ser Ser Ser
65                  70                  75                  80

Ser Arg Gln Gln Gln Gln Gly Gly Gly Gly Gly Gly Ser Gly Gly
                85                  90                  95

Gly Ala Gly Gln Gln Val Ile Glu Leu Glu Cys Leu Asp Asp Gln Val
            100                 105                 110

Leu Gln Glu Met Leu Lys Gly Gly Asp Gly Lys Lys
        115                 120
```

```
<210> SEQ ID NO 37
<211> LENGTH: 859
<212> TYPE: DNA
<213> ORGANISM: Arabidopsis thaliana
<220> FEATURE:
<223> OTHER INFORMATION: G1266

<400> SEQUENCE: 37
caatccacta acgatcccta accgaaaaca gagtagtcaa gaaacagagt attttttcta       60
catggatcca tttttaattc agtccccatt ctccggcttc tcaccggaat attctatcgg      120
atcttctcca gattctttct catcctcttc ttctaacaat tactctcttc ccttcaacga      180
gaacgactca gaggaaatgt ttctctacgg tctaatcgag cagtccacgc aacaaaccta      240
tattgactcg gatagtcaag accttccgat caaatccgta agctcaagaa agtcagagaa      300
gtcttacaga ggcgtaagac gacggccatg ggggaaattc gcggcggaga taagagattc      360
gactagaaac ggtattaggg tttggctcgg acgttcgaa agcgcggaag aggcggcttt       420
agcctacgat caagctgctt tctcgatgag agggtcctcg gcgattctca ttttttcggc      480
```

```
ggagagagtt caagagtcgc tttcggagat taaatatacc tacgaggatg gttgttctcc    540
ggttgtggcg ttgaagagga aacactcgat gagacggaga atgaccaata gaagacgaa     600 agatagtgac tttgatcacc gctccgtgaa gttagataat gtagttgtct ttgaggattt    660
gggagaacag taccttgagg agcttttggg gtcttctgaa aatagtggga cttggtgaaa    720
gattaggatt tgtattaggg accttaagtt tgaagtggtt gattaatttt aaccctaata    780
tgttttttgt ttgcttaaat atttgattct attgagaaac atcgaaaaca gtttgtatgt    840
acttttgtga tacttggcg                                                 859
```

<210> SEQ ID NO 38
<211> LENGTH: 218
<212> TYPE: PRT
<213> ORGANISM: Arabidopsis thaliana
<220> FEATURE:
<223> OTHER INFORMATION: G1266 polypeptide

<400> SEQUENCE: 38

```
Met Asp Pro Phe Leu Ile Gln Ser Pro Phe Ser Gly Phe Ser Pro Glu
 1               5                  10                  15

Tyr Ser Ile Gly Ser Ser Pro Asp Ser Phe Ser Ser Ser Ser Asn
            20                  25                  30

Asn Tyr Ser Leu Pro Phe Asn Glu Asn Asp Ser Glu Glu Met Phe Leu
        35                  40                  45

Tyr Gly Leu Ile Glu Gln Ser Thr Gln Gln Thr Tyr Ile Asp Ser Asp
     50                  55                  60

Ser Gln Asp Leu Pro Ile Lys Ser Val Ser Ser Arg Lys Ser Glu Lys
 65                  70                  75                  80

Ser Tyr Arg Gly Val Arg Arg Arg Pro Trp Gly Lys Phe Ala Ala Glu
                 85                  90                  95

Ile Arg Asp Ser Thr Arg Asn Gly Ile Arg Val Trp Leu Gly Thr Phe
            100                 105                 110

Glu Ser Ala Glu Glu Ala Ala Leu Ala Tyr Asp Gln Ala Ala Phe Ser
        115                 120                 125

Met Arg Gly Ser Ser Ala Ile Leu Asn Phe Ser Ala Glu Arg Val Gln
    130                 135                 140

Glu Ser Leu Ser Glu Ile Lys Tyr Thr Tyr Glu Asp Gly Cys Ser Pro
145                 150                 155                 160

Val Val Ala Leu Lys Arg Lys His Ser Met Arg Arg Met Thr Asn
                165                 170                 175

Lys Lys Thr Lys Asp Ser Asp Phe Asp His Arg Ser Val Lys Leu Asp
            180                 185                 190

Asn Val Val Phe Glu Asp Leu Gly Glu Gln Tyr Leu Glu Glu Leu
        195                 200                 205

Leu Gly Ser Ser Glu Asn Ser Gly Thr Trp
    210                 215
```

<210> SEQ ID NO 39
<211> LENGTH: 1262
<212> TYPE: DNA
<213> ORGANISM: Arabidopsis thaliana
<220> FEATURE:
<223> OTHER INFORMATION: G45

<400> SEQUENCE: 39

```
attaatactc tgcatctagt cctttttcaag agtacacaat ctgcactttt ttaatgaaaa    60
tagtacacaa tctttatact tcaaactgag gtaacattat taaattaatt tattgaagtt   120
```

```
gacttaagat gatctattca cataatggta cgtgtgtgtg tgtatacaca gaaaacccct    180
gattttatgt ggaacctaaa accctccatg aaatgcggtc agtaccttag aacacaagtt    240
tcaccaactg tacttcccaa ttatcctgcc gcagattcaa caatggcttt tggcaatatc    300
caagaactag acggcgagat cctaaagaac gtttgggcga attacatcgg aacaccacaa    360
accgatacaa gatcaattca agttccagaa gtttctagaa cttgggaagc gttgcctacc    420
cttgatgaca taccagaagg ttctagagaa atgcttcaaa gcctagatat gtcgacggag    480
gaccaggaat ggacagagat tctcgatgct attgcttctt tcccaaacaa aaccaatcat    540
gatccattaa ccaaccctac cattgattca tgttctttgt cttctcgggt tcttgcaaa    600 acaagaaaat acaggggagt acggaagcgt ccgtggggga aatttgcagc cgaaatcagg    660
gattcgacga gaaacggtgt tagggtttgg ctcggaacgt tccaaactgc agaggaagca    720
gctatggctt acgataaagc cgcggttaga attagaggta ctcaaaaagc tcacacaaat    780
tttcagctcg aaacagttat aaaagctatg gaaatggatt gcaacccaaa ctactaccgg    840
atgaacaact caaatacgtc cgatccatta agaagcagcc gcaaaatcgg attgagaaca    900
ggaaaagagg cggttaaggc ttatgatgaa gtcgttgatg ggatggttga aaaccattgt    960
gcccttagct attgttcaac taaggagcac tcggagactc gtggtttgcg tgggagtgaa   1020
gaaacttggt tcgatttaag aaagagacga aggagtaatg aagattctat gtgtcaagaa   1080
gttgaaatgc agaagacggt tactggagaa gagacagtat gtgatgtgtt tggtttgttt   1140
gagtttgagg atttgggaag tgattatttg gagacgttat tatcttcttt ttgacagaaa   1200
tacattgaaa actaccgttg ctaatttgat aggtatacat atatagacat gtatatattg   1260
ta                                                                  1262
```

```
<210> SEQ ID NO 40
<211> LENGTH: 349
<212> TYPE: PRT
<213> ORGANISM: Arabidopsis thaliana
<220> FEATURE:
<223> OTHER INFORMATION: G45 polypeptide

<400> SEQUENCE: 40
```

```
Met Val Arg Val Cys Val Tyr Thr Gln Lys Thr Pro Asp Phe Met Trp
1               5                   10                  15

Asn Leu Lys Pro Ser Met Lys Cys Gly Gln Tyr Leu Arg Thr Gln Val
            20                  25                  30

Ser Pro Thr Val Leu Pro Asn Tyr Pro Ala Ala Asp Ser Thr Met Ala
        35                  40                  45

Phe Gly Asn Ile Gln Glu Leu Asp Gly Glu Ile Leu Lys Asn Val Trp
    50                  55                  60

Ala Asn Tyr Ile Gly Thr Pro Gln Thr Asp Thr Arg Ser Ile Gln Val
65                  70                  75                  80

Pro Glu Val Ser Arg Thr Trp Glu Ala Leu Pro Thr Leu Asp Asp Ile
                85                  90                  95

Pro Glu Gly Ser Arg Glu Met Leu Gln Ser Leu Asp Met Ser Thr Glu
            100                 105                 110

Asp Gln Glu Trp Thr Glu Ile Leu Asp Ala Ile Ala Ser Phe Pro Asn
        115                 120                 125

Lys Thr Asn His Asp Pro Leu Thr Asn Pro Thr Ile Asp Ser Cys Ser
    130                 135                 140

Leu Ser Ser Arg Val Ser Cys Lys Thr Arg Lys Tyr Arg Gly Val Arg
```

```
                145                 150                 155                 160
            Lys Arg Pro Trp Gly Lys Phe Ala Ala Glu Ile Arg Asp Ser Thr Arg
                            165                 170                 175

Asn Gly Val Arg Val Trp Leu Gly Thr Phe Gln Thr Ala Glu Glu Ala
                        180                 185                 190

Ala Met Ala Tyr Asp Lys Ala Ala Val Arg Ile Arg Gly Thr Gln Lys
                        195                 200                 205

Ala His Thr Asn Phe Gln Leu Glu Thr Val Ile Lys Ala Met Glu Met
                    210                 215                 220

Asp Cys Asn Pro Asn Tyr Tyr Arg Met Asn Asn Ser Asn Thr Ser Asp
            225                 230                 235                 240

Pro Leu Arg Ser Ser Arg Lys Ile Gly Leu Arg Thr Gly Lys Glu Ala
                            245                 250                 255

Val Lys Ala Tyr Asp Glu Val Val Asp Gly Met Val Glu Asn His Cys
                        260                 265                 270

Ala Leu Ser Tyr Cys Ser Thr Lys Glu His Ser Glu Thr Arg Gly Leu
                        275                 280                 285

Arg Gly Ser Glu Glu Thr Trp Phe Asp Leu Arg Lys Arg Arg Arg Ser
                    290                 295                 300

Asn Glu Asp Ser Met Cys Gln Glu Val Glu Met Gln Lys Thr Val Thr
            305                 310                 315                 320

Gly Glu Glu Thr Val Cys Asp Val Phe Gly Leu Phe Glu Phe Glu Asp
                            325                 330                 335

Leu Gly Ser Asp Tyr Leu Glu Thr Leu Leu Ser Ser Phe
                        340                 345

<210> SEQ ID NO 41
<211> LENGTH: 933
<212> TYPE: DNA
<213> ORGANISM: Arabidopsis thaliana
<220> FEATURE:
<223> OTHER INFORMATION: G1752

<400> SEQUENCE: 41
aaaaaaaaaa aaaaaaaaaa acttatggaa tattcccaat cttccatgta ttcatctcca      60
agttcttgga gctcatcaca agaatcactc ttatggaacg agagctgttt cttggatcaa     120
tcatctgaac ctcaagcctt cttttgccct aattatgatt actccgatga cttttttctca    180 tttgagtcac cggagatgat gattaaggaa gaaattcaaa acggcgacgt ttctaactcc     240
gaagaagaag aaaaggttgg aattgatgaa gaaagatcat acagaggagt gaggaaaagg     300
ccgtggggga aatttgcagc ggagataaga gattcaacga ggaatggaat tagggtttgg     360
ctcgggacat tgacaaagcc gaggaagcc gctcttgctt atgatcaagc ggctttcgcc      420
acaaaaggat ctcttgcaac acttaatttc ccggtggaag tggttagaga gtcgctaaag     480
aaaatggaga atgtgaatct tcatgatgga ggatctccgg ttatggcctt gaagagaaaa     540
cattctcttc gaaaccggcc tagagggaaa aagcgatcct cttcttcttc ttcttcttct     600
tctaattctt cttcttgctc ttcttcttcg tctacttctt caacatcaag aagtagtagt     660
aagcagagtg ttgtgaagca agaaagtggt acacttgtgg tttttgaaga tttaggtgct     720
gagtatttag acaacttcct tatgagctca tgttgatctt gtaattgatt tcagcaaaag     780
ccactattaa actttaattt tgtgataatt aatcttgaaa tttgttttgt tcattctgca     840
atttctttgg ttctccttatt ttttgtttgt tgtatccaaa tgaaattatt ggaagagatg     900
gtgatgttaa agtgtatata tataaaaaaa aaa                                  933
```

```
<210> SEQ ID NO 42
<211> LENGTH: 243
<212> TYPE: PRT
<213> ORGANISM: Arabidopsis thaliana
<220> FEATURE:
<223> OTHER INFORMATION: G1752 polypeptide

<400> SEQUENCE: 42

Met Glu Tyr Ser Gln Ser Ser Met Tyr Ser Ser Pro Ser Ser Trp Ser
 1               5                  10                  15

Ser Ser Gln Glu Ser Leu Leu Trp Asn Glu Ser Cys Phe Leu Asp Gln
            20                  25                  30

Ser Ser Glu Pro Gln Ala Phe Phe Cys Pro Asn Tyr Asp Tyr Ser Asp
        35                  40                  45

Asp Phe Phe Ser Phe Glu Ser Pro Glu Met Met Ile Lys Glu Glu Ile
50                  55                  60

Gln Asn Gly Asp Val Ser Asn Ser Glu Glu Glu Lys Val Gly Ile
65                  70                  75                  80

Asp Glu Glu Arg Ser Tyr Arg Gly Val Arg Lys Arg Pro Trp Gly Lys
                85                  90                  95

Phe Ala Ala Glu Ile Arg Asp Ser Thr Arg Asn Gly Ile Arg Val Trp
            100                 105                 110

Leu Gly Thr Phe Asp Lys Ala Glu Glu Ala Ala Leu Ala Tyr Asp Gln
        115                 120                 125

Ala Ala Phe Ala Thr Lys Gly Ser Leu Ala Thr Leu Asn Phe Pro Val
    130                 135                 140

Glu Val Val Arg Glu Ser Leu Lys Lys Met Glu Asn Val Asn Leu His
145                 150                 155                 160

Asp Gly Gly Ser Pro Val Met Ala Leu Lys Arg Lys His Ser Leu Arg
                165                 170                 175

Asn Arg Pro Arg Gly Lys Lys Arg Ser Ser Ser Ser Ser Ser Ser Ser
            180                 185                 190

Ser Asn Ser Ser Ser Cys Ser Ser Ser Ser Thr Ser Ser Thr Ser
        195                 200                 205

Arg Ser Ser Ser Lys Gln Ser Val Val Lys Gln Glu Ser Gly Thr Leu
    210                 215                 220

Val Val Phe Glu Asp Leu Gly Ala Glu Tyr Leu Glu Gln Leu Leu Met
225                 230                 235                 240

Ser Ser Cys

<210> SEQ ID NO 43
<211> LENGTH: 832
<212> TYPE: DNA
<213> ORGANISM: Arabidopsis thaliana
<220> FEATURE:
<223> OTHER INFORMATION: G2512

<400> SEQUENCE: 43
aacttagtgc cacttagaca caataagaaa accgttaaca agaagaaaaa aaaaagatcg      60
aaaatggaat atcaaactaa cttcttaagt ggagagtttt ccccggagaa ctcttcttca     120
agctcatgga gctcacaaga atcattcttg tgggaagaga gtttcttaca tcaatcattt     180
gaccaatcct tcctttatc tagccctact gataactact gtgatgactt ctttgcattt      240
gaatcatcaa tcataaaaga agaaggaaaa gaagccaccg tggcggccga ggaggaggag     300
aagtcataca gaggagtgag gaaacggccg tgggggaaat tcgcggccga gataagagac     360
```

```
tcaacgagga aagggataag agtgtggctt gggacattcg acaccgcgga ggcggcggct    420
ctcgcttatg atcaggcggc tttcgctttg aaaggcagcc tcgcagtact caatttcccc    480
gcggatgtcg ttgaagaatc tctccggaag atggagaatg tgaatctcaa tgatggagag    540
tctccggtga tagccttgaa gagaaaacac tccatgagaa accgtcctag aggaaagaag    600
aaatcttctt cttcttcgac gttgacatct tctccttctt cctcctcctc ctattcatct    660
tcttcgtctt cttcttcttt gtcgtcaaga agtagaaaac agagtgttgt tatgacgcaa    720
gaaagtaata caacacttgt ggttcttgag gatttaggtg ctgaatactt agaagagctt    780
atgagatcat gttcttgata atctctgctt ctacaattt tatgtaattt ga             832
```

<210> SEQ ID NO 44
<211> LENGTH: 244
<212> TYPE: PRT
<213> ORGANISM: Arabidopsis thaliana
<220> FEATURE:
<223> OTHER INFORMATION: G2512 polypeptide

<400> SEQUENCE: 44

```
Met Glu Tyr Gln Thr Asn Phe Leu Ser Gly Glu Phe Ser Pro Glu Asn
1               5                   10                  15

Ser Ser Ser Ser Ser Trp Ser Ser Gln Glu Ser Phe Leu Trp Glu Glu
            20                  25                  30

Ser Phe Leu His Gln Ser Phe Asp Gln Ser Phe Leu Leu Ser Ser Pro
        35                  40                  45

Thr Asp Asn Tyr Cys Asp Asp Phe Phe Ala Phe Glu Ser Ser Ile Ile
    50                  55                  60

Lys Glu Glu Gly Lys Glu Ala Thr Val Ala Ala Glu Glu Glu Glu Lys
65                  70                  75                  80

Ser Tyr Arg Gly Val Arg Lys Arg Pro Trp Gly Lys Phe Ala Ala Glu
                85                  90                  95

Ile Arg Asp Ser Thr Arg Lys Gly Ile Arg Val Trp Leu Gly Thr Phe
            100                 105                 110

Asp Thr Ala Glu Ala Ala Ala Leu Ala Tyr Asp Gln Ala Ala Phe Ala
        115                 120                 125

Leu Lys Gly Ser Leu Ala Val Leu Asn Phe Pro Ala Asp Val Val Glu
    130                 135                 140

Glu Ser Leu Arg Lys Met Glu Asn Val Asn Leu Asn Asp Gly Glu Ser
145                 150                 155                 160

Pro Val Ile Ala Leu Lys Arg Lys His Ser Met Arg Asn Arg Pro Arg
                165                 170                 175

Gly Lys Lys Lys Ser Ser Ser Ser Ser Thr Leu Thr Ser Ser Pro Ser
            180                 185                 190

Ser Ser Ser Ser Tyr Ser Ser Ser Ser Ser Ser Ser Leu Ser Ser
        195                 200                 205

Arg Ser Arg Lys Gln Ser Val Val Met Thr Gln Glu Ser Asn Thr Thr
    210                 215                 220

Leu Val Val Leu Glu Asp Leu Gly Ala Glu Tyr Leu Glu Glu Leu Met
225                 230                 235                 240

Arg Ser Cys Ser
```

<210> SEQ ID NO 45
<211> LENGTH: 913
<212> TYPE: DNA
<213> ORGANISM: Arabidopsis thaliana

```
<220> FEATURE:
<223> OTHER INFORMATION: G1006

<400> SEQUENCE: 45
gataaatcaa tcaacaaaac aaaaaaaact ctatagttag tttctctgaa aatgtacgga        60
cagtgcaata tagaatccga ctacgctttg ttggagtcga taacacgtca cttgctagga       120
ggaggaggag agaacgagct gcgactcaat gagtcaacac cgagttcgtg tttcacagag       180
agttggggag gtttgccatt gaaagagaat gattcagagg acatgttggt gtacggactc       240
ctcaaagatg ccttccattt tgacacgtca tcatcggact tgagctgtct ttttgatttt       300
ccggcggtta aagtcgagcc aactgagaac tttacggcga tggaggagaa accaaagaaa       360
gcgataccgg ttacggagac ggcagtgaag gcgaagcatt acagaggagt gaggcagaga       420
ccgtggggga aattcgcggc ggagatacgt gatccggcga agaatggagc tagggtttgg       480
ttagggacgt ttgagacggc ggaagatgcg gctttagctt acgatatagc tgcttttagg       540
atgcgtggtt cccgcgcttt attgaatttt ccgttgaggg ttaattccgg tgaacctgac       600
ccggttcgga tcacgtctaa gagatcttct tcgtcgtcgt cgtcgtcgtc ctcttctacg       660
tcgtcgtctg aaaacgggaa gttgaaacga aggagaaaag cagagaatct gacgtcggag       720
gtggtgcagg tgaagtgtga ggttggtgat gagacacgtg ttgatgagtt attggtttca       780
taagtttgat cttgtgtgtt ttgtagttga atagttttgc tataaatgtt gaggcaccaa       840
gtaaaagtgt tcccgtgatg taaattagtt actaaacaga gccatatatc ttcaatcaaa       900
aaaaaaaaaa aaa                                                          913

<210> SEQ ID NO 46
<211> LENGTH: 243
<212> TYPE: PRT
<213> ORGANISM: Arabidopsis thaliana
<220> FEATURE:
<223> OTHER INFORMATION: G1006 polypeptide

<400> SEQUENCE: 46

Met Tyr Gly Gln Cys Asn Ile Glu Ser Asp Tyr Ala Leu Leu Glu Ser
1               5                   10                  15

Ile Thr Arg His Leu Gly Gly Gly Glu Asn Glu Leu Arg Leu
            20                  25                  30

Asn Glu Ser Thr Pro Ser Ser Cys Phe Thr Glu Ser Trp Gly Gly Leu
            35                  40                  45

Pro Leu Lys Glu Asn Asp Ser Glu Asp Met Leu Val Tyr Gly Leu Leu
        50                  55                  60

Lys Asp Ala Phe His Phe Asp Thr Ser Ser Ser Asp Leu Ser Cys Leu
65                  70                  75                  80

Phe Asp Phe Pro Ala Val Lys Val Glu Pro Thr Glu Asn Phe Thr Ala
                85                  90                  95

Met Glu Glu Lys Pro Lys Lys Ala Ile Pro Val Thr Glu Thr Ala Val
            100                 105                 110

Lys Ala Lys His Tyr Arg Gly Val Arg Gln Arg Pro Trp Gly Lys Phe
        115                 120                 125

Ala Ala Glu Ile Arg Asp Pro Ala Lys Asn Gly Ala Arg Val Trp Leu
    130                 135                 140

Gly Thr Phe Glu Thr Ala Glu Asp Ala Ala Leu Ala Tyr Asp Ile Ala
145                 150                 155                 160

Ala Phe Arg Met Arg Gly Ser Arg Ala Leu Leu Asn Phe Pro Leu Arg
                165                 170                 175
```

Val Asn Ser Gly Glu Pro Asp Pro Val Arg Ile Thr Ser Lys Arg Ser
            180                 185                 190

Ser Ser Ser Ser Ser Ser Ser Ser Thr Ser Ser Ser Glu Asn
        195                 200                 205

Gly Lys Leu Lys Arg Arg Arg Lys Ala Glu Asn Leu Thr Ser Glu Val
210                 215                 220

Val Gln Val Lys Cys Glu Val Gly Asp Glu Thr Arg Val Asp Glu Leu
225                 230                 235                 240

Leu Val Ser

<210> SEQ ID NO 47
<211> LENGTH: 964
<212> TYPE: DNA
<213> ORGANISM: Arabidopsis thaliana
<220> FEATURE:
<223> OTHER INFORMATION: G28

<400> SEQUENCE: 47
gaaatctcaa caagaaccaa accaaacaac aaaaaaacat tcttaataat tatctttctg      60
ttatgtcgat gacggcggat tctcaatctg attatgcttt tcttgagtcc atacgacgac     120
acttactagg agaatcggag ccgatactca gtgagtcgac agcgagttcg gttactcaat     180
cttgtgtaac cggtcagagc attaaaccgg tgtacgacg aaaccctagc tttagcaaac      240
tgtatccttg cttcaccgag agctggggag atttgccgtt gaagaaaac gattctgagg      300
atatgttagt ttacggtatc ctcaacgacg cctttcacgg cggttgggag ccgtcttctt     360
cgtcttccga cgaagatcgt agctctttcc cgagtgttaa gatcgagact ccggagagtt     420
tcgcggcggt ggattctgtt ccggtcaaga aggagaagac gagtcctgtt tcggcggcgg     480
tgacggcggc gaagggaaag cattatagag gagtgagaca aaggccgtgg gggaaatttg     540
cggcggagat tagagatccg gcgaagaacg gagctagggt ttggttagga acgtttgaga     600
cggcggagga cgcggcgttg gcttacgaca gagctgcttt caggatgcgt ggttcccgcg     660
ctttgttgaa ttttccgttg agagttaatt caggagaacc cgacccggtt cgaatcaagt     720
ccaagagatc ttcttttcct tcttctaacg agaacggagc tccgaagaag aggagaacgg     780
tggccgccgg tggtggaatg gataagggat tgacggtgaa gtgcgaggtt gttgaagtgg     840
cacgtgtgcga tcgtttattg gttttataat tttgatttt ctttgttgga tgattatatg     900
attcttcaaa aagaagaac gttaataaaa aaattcgttt attattaaaa aaaaaaaaa       960
aaaa                                                                  964

<210> SEQ ID NO 48
<211> LENGTH: 268
<212> TYPE: PRT
<213> ORGANISM: Arabidopsis thaliana
<220> FEATURE:
<223> OTHER INFORMATION: G28 polypeptide

<400> SEQUENCE: 48

Met Ser Met Thr Ala Asp Ser Gln Ser Asp Tyr Ala Phe Leu Glu Ser
1               5                   10                  15

Ile Arg Arg His Leu Leu Gly Glu Ser Glu Pro Ile Leu Ser Glu Ser
            20                  25                  30

Thr Ala Ser Ser Val Thr Gln Ser Cys Val Thr Gly Gln Ser Ile Lys
        35                  40                  45

Pro Val Tyr Gly Arg Asn Pro Ser Phe Ser Lys Leu Tyr Pro Cys Phe

```
              50                  55                  60
Thr Glu Ser Trp Gly Asp Leu Pro Leu Lys Glu Asn Asp Ser Glu Asp
 65                  70                  75                  80

Met Leu Val Tyr Gly Ile Leu Asn Asp Ala Phe His Gly Gly Trp Glu
                 85                  90                  95

Pro Ser Ser Ser Ser Asp Glu Asp Arg Ser Ser Phe Pro Ser Val
            100                 105                 110

Lys Ile Glu Thr Pro Glu Ser Phe Ala Ala Val Asp Ser Val Pro Val
            115                 120                 125

Lys Lys Glu Lys Thr Ser Pro Val Ser Ala Ala Val Thr Ala Ala Lys
            130                 135                 140

Gly Lys His Tyr Arg Gly Val Arg Gln Arg Pro Trp Gly Lys Phe Ala
145                 150                 155                 160

Ala Glu Ile Arg Asp Pro Ala Lys Asn Gly Ala Arg Val Trp Leu Gly
                165                 170                 175

Thr Phe Glu Thr Ala Glu Asp Ala Ala Leu Ala Tyr Asp Arg Ala Ala
            180                 185                 190

Phe Arg Met Arg Gly Ser Arg Ala Leu Leu Asn Phe Pro Leu Arg Val
            195                 200                 205

Asn Ser Gly Glu Pro Asp Pro Val Arg Ile Lys Ser Lys Arg Ser Ser
            210                 215                 220

Phe Ser Ser Ser Asn Glu Asn Gly Ala Pro Lys Lys Arg Arg Thr Val
225                 230                 235                 240

Ala Ala Gly Gly Gly Met Asp Lys Gly Leu Thr Val Lys Cys Glu Val
                245                 250                 255

Val Glu Val Ala Arg Gly Asp Arg Leu Leu Val Leu
            260                 265
```

<210> SEQ ID NO 49
<211> LENGTH: 913
<212> TYPE: DNA
<213> ORGANISM: Arabidopsis thaliana
<220> FEATURE:
<223> OTHER INFORMATION: G22

<400> SEQUENCE: 49

```
agaaaacatc tctcactctc taaaatacac actctcatca aaaaccttct cttcggttca    60
gaagcattca agaatccatt atgagctcat ctgattccgt taataacggc gttaactcac   120
ggatgtactt ccgtaacccg agtttcagca acgttatctt aaacgataac tggagcgact   180
tgccgttaag tgtcgacgat tctcaagaca tggctattta caacactctc cgtgatgccg   240
ttagctccgg ctggacaccc tccgttcctc ccgttacctc tccggcggag gaaaataagc   300
ctccggcgac gaaggcgagt ggctcacacg cgccgaggca gaaggggatg cagtacagag   360
gagtgaggag gaggccgtgg gggaaattcg cggcggagat tagggatccg aagaagaacg   420
gagctagggt ttggctcggg acttacgaga cgccggagga cgcggcggtg gcgtacgacc   480
gagcggcgtt tcagctcaga ggatcgaaag ctaagctgaa ttttccgcat ttgattggtt   540
cttgtaagta tgagccggtt aggattaggc ctcgccgtcg ctcgccggaa ccgtcagtct   600
ccgatcagtt aacgtcggag cagaagaggg aaagccacgt ggatgacggc gagtctagtt   660
tggttgtacc ggagttggat ttcacggtgg atcagtttta cttcgatggt agtttattaa   720
tggaccaatc agaatgttct tattctgata atcggatata attagtttta agattaagca   780
aaatttgtcc aacgagtttt gctgtatgaa atatctatcg atgactcaac aggttttgat   840
```

```
catgatcata tgtaatgtga tggaaattaa atattgacgt ttgttttttt gttgtaaaaa      900
aaaaaaaaaa aaa                                                         913
```

<210> SEQ ID NO 50
<211> LENGTH: 226
<212> TYPE: PRT
<213> ORGANISM: Arabidopsis thaliana
<220> FEATURE:
<223> OTHER INFORMATION: G22 polypeptide

<400> SEQUENCE: 50

```
Met Ser Ser Ser Asp Ser Val Asn Asn Gly Val Asn Ser Arg Met Tyr
1               5                   10                  15

Phe Arg Asn Pro Ser Phe Ser Asn Val Ile Leu Asn Asp Asn Trp Ser
                20                  25                  30

Asp Leu Pro Leu Ser Val Asp Asp Ser Gln Asp Met Ala Ile Tyr Asn
            35                  40                  45

Thr Leu Arg Asp Ala Val Ser Ser Gly Trp Thr Pro Ser Val Pro Pro
        50                  55                  60

Val Thr Ser Pro Ala Glu Glu Asn Lys Pro Pro Ala Thr Lys Ala Ser
65                  70                  75                  80

Gly Ser His Ala Pro Arg Gln Lys Gly Met Gln Tyr Arg Gly Val Arg
                85                  90                  95

Arg Arg Pro Trp Gly Lys Phe Ala Ala Glu Ile Arg Asp Pro Lys Lys
                100                 105                 110

Asn Gly Ala Arg Val Trp Leu Gly Thr Tyr Glu Thr Pro Glu Asp Ala
            115                 120                 125

Ala Val Ala Tyr Asp Arg Ala Ala Phe Gln Leu Arg Gly Ser Lys Ala
        130                 135                 140

Lys Leu Asn Phe Pro His Leu Ile Gly Ser Cys Lys Tyr Glu Pro Val
145                 150                 155                 160

Arg Ile Arg Pro Arg Arg Ser Pro Glu Pro Ser Val Ser Asp Gln
                165                 170                 175

Leu Thr Ser Glu Gln Lys Arg Glu Ser His Val Asp Asp Gly Glu Ser
            180                 185                 190

Ser Leu Val Val Pro Glu Leu Asp Phe Thr Val Asp Gln Phe Tyr Phe
        195                 200                 205

Asp Gly Ser Leu Leu Met Asp Gln Ser Glu Cys Ser Tyr Ser Asp Asn
    210                 215                 220

Arg Ile
225
```

<210> SEQ ID NO 51
<211> LENGTH: 1084
<212> TYPE: DNA
<213> ORGANISM: Arabidopsis thaliana
<220> FEATURE:
<223> OTHER INFORMATION: G26

<400> SEQUENCE: 51

```
ttggcttgta cccaaaccca tctttgactt caaaaataaa ataaaaataa tcataattga      60
catcatcgga taatgcatag cgggaagaga cctctatcac cagaatcaat ggccggaaat     120
agagaagaga aaaaagagtt gtgttgttgc tcaactttgt cggaatctga tgtgtctgat     180
tttgtctctg aactcactgg tcaacccatc ccatcatcca tgatgatca atcttcgtcg     240 cttactcttc aagaaaaaag taactcgagg caacgaaact acagaggcgt gaggcaagaa     300
```

-continued

```
ccgtggggaa aatgggcggc tgagattcgt gacccgaaca aggcagctcg tgtgtggctt    360
gggacgttcg acactgcaga agaagccgcc ttagcgtatg ataaagctgc atttgagttt    420
agaggtcaca aggccaagct taacttcccc gagcatattc gtgtcaaccc tactcaactc    480
tatccatcgc ccgctacttc ccatgatcgc attatcgtga caccacctag tccacctcca    540
ccaattgctc ctgacatact tcttgatcaa tatggccact tcaatctcg aagtagtgat     600
tccagtgcca acttgtccat gaatatgctg tcttcttcgt cttcatcttt gaatcatcaa    660
gggctaagac caaatttgga ggatggtgaa aacgtgaaga acattagtat ccacaaacga    720
cgaaaataac atgttaatgg cataaatatc tcttcgtcca agttatcaaa cgcattgacc    780
tccggctttg atcattttag gcgcttaatc tctttacgac ttcattttgg tagtctttaa    840
agagtctatg gagtggattt agctaggaat caggccttat ggatgaaaaa tatataaatt    900
ttgaacatga ctatgcaaga atgggatgaa gactacttag cttggaaaac gtcctgatag    960
gtcatgacga ctatatccac agaagatgac cgacggagac aacaacatgc ctcacctgat   1020
cgaccgatca aatgagataa tgtgttgacc ggaccggtcg atcaggttg ggtcgagtat    1080
atca                                                                 1084
```

<210> SEQ ID NO 52
<211> LENGTH: 218
<212> TYPE: PRT
<213> ORGANISM: Arabidopsis thaliana
<220> FEATURE:
<223> OTHER INFORMATION: G26 polypeptide

<400> SEQUENCE: 52

```
Met His Ser Gly Lys Arg Pro Leu Ser Pro Glu Ser Met Ala Gly Asn
1               5                   10                  15

Arg Glu Glu Lys Lys Glu Leu Cys Cys Cys Ser Thr Leu Ser Glu Ser
            20                  25                  30

Asp Val Ser Asp Phe Val Ser Glu Leu Thr Gly Gln Pro Ile Pro Ser
        35                  40                  45

Ser Ile Asp Asp Gln Ser Ser Ser Leu Thr Leu Gln Glu Lys Ser Asn
    50                  55                  60

Ser Arg Gln Arg Asn Tyr Arg Gly Val Arg Gln Arg Pro Trp Gly Lys
65                  70                  75                  80

Trp Ala Ala Glu Ile Arg Asp Pro Asn Lys Ala Ala Arg Val Trp Leu
                85                  90                  95

Gly Thr Phe Asp Thr Ala Glu Glu Ala Ala Leu Ala Tyr Asp Lys Ala
            100                 105                 110

Ala Phe Glu Phe Arg Gly His Lys Ala Lys Leu Asn Phe Pro Glu His
        115                 120                 125

Ile Arg Val Asn Pro Thr Gln Leu Tyr Pro Ser Pro Ala Thr Ser His
    130                 135                 140

Asp Arg Ile Ile Val Thr Pro Pro Ser Pro Pro Pro Ile Ala Pro
145                 150                 155                 160

Asp Ile Leu Leu Asp Gln Tyr Gly His Phe Gln Ser Arg Ser Ser Asp
                165                 170                 175

Ser Ser Ala Asn Leu Ser Met Asn Met Leu Ser Ser Ser Ser Ser Ser
            180                 185                 190

Leu Asn His Gln Gly Leu Arg Pro Asn Leu Glu Asp Gly Glu Asn Val
        195                 200                 205

Lys Asn Ile Ser Ile His Lys Arg Arg Lys
    210                 215
```

<210> SEQ ID NO 53
<211> LENGTH: 1123
<212> TYPE: DNA
<213> ORGANISM: Arabidopsis thaliana
<220> FEATURE:
<223> OTHER INFORMATION: G1751

<400> SEQUENCE: 53

```
aaacacaaac aaaactcata ttttcaatct ccaggtgctt tacaccaaca gagtcgcaag      60
aaaacaaaaa ccaaactcgg atttagtttg acagaagaag gaatcgagag tcgggtatgc     120
attatcctaa aacagaacc gaattcgtcg gagctccagc cccaacccgg tatcaaaagg      180
agcagttgtc accggagcaa gagctttcag ttattgtctc tgctttgcaa cacgtgatct     240
caggggaaaa cgaaacggcg ccgtgtcagg gttttccag tgacagcaca gtgataagcg      300
cgggaatgcc tcggttggat tcagacactt gtcaagtctg taggatcgaa ggatgtctcg     360
gctgtaacta cttttcgcg ccaaatcaga gaattgaaaa gaatcatcaa caagaagaag      420
agattactag tagtagtaac agaagaagag agagctctcc cgtggcgaag aaagcggaag     480
gtggcgggaa aatcaggaag aggaagaaca agaagaatgg ttacagagga gttaggcaaa    540
gaccttgggg aaaatttgca gctgagatca gagatcctaa aagagccaca cgtgtttggc   600
ttggtacttt cgaaaccgcc gaagatgcgg ctcgagctta tgatcgagcc gcgattggat   660
tccgtgggcc aagggctaaa ctcaacttcc cctttgtgga ttacacgtct tcagtttcat   720
ctcctgttgc tgctgatgat ataggagcaa aggcaagtgc aagcgccagt gtgagcgcca   780
cagattcagt tgaagcagag caatggaacg gaggaggagg ggattgcaat atggaggagt   840
ggatgaatat gatgatgatg atggattttg ggaatggaga ttcttcagat tcaggaaata   900
caattgctga tatgttccag tgataaatga gctctttctt gttggcgttt tttggagtta   960
agtgcaagaa gagattgaca ctgtggcttg tttaaagtga acaagaacaa gaaagcatgt  1020
aattagtagt ctcattcttt tgtttgtggt caattctatg tttatctcat ataaaatctg   1080
agttaaaccct atctgaggag agagtaaata aagaggttaa gaa                    1123
```

<210> SEQ ID NO 54
<211> LENGTH: 268
<212> TYPE: PRT
<213> ORGANISM: Arabidopsis thaliana
<220> FEATURE:
<223> OTHER INFORMATION: G1751 polypeptide

<400> SEQUENCE: 54

```
Met His Tyr Pro Asn Asn Arg Thr Glu Phe Val Gly Ala Pro Ala Pro
1               5                   10                  15

Thr Arg Tyr Gln Lys Glu Gln Leu Ser Pro Glu Gln Glu Leu Ser Val
            20                  25                  30

Ile Val Ser Ala Leu Gln His Val Ile Ser Gly Glu Asn Glu Thr Ala
        35                  40                  45

Pro Cys Gln Gly Phe Ser Ser Asp Ser Thr Val Ile Ser Ala Gly Met
    50                  55                  60

Pro Arg Leu Asp Ser Asp Thr Cys Gln Val Cys Arg Ile Glu Gly Cys
65                  70                  75                  80

Leu Gly Cys Asn Tyr Phe Phe Ala Pro Asn Gln Arg Ile Glu Lys Asn
                85                  90                  95

His Gln Gln Glu Glu Glu Ile Thr Ser Ser Ser Asn Arg Arg Arg Glu
            100                 105                 110
```

```
Ser Ser Pro Val Ala Lys Lys Ala Glu Gly Gly Lys Ile Arg Lys
        115                 120                 125

Arg Lys Asn Lys Lys Asn Gly Tyr Arg Gly Val Arg Gln Arg Pro Trp
    130                 135                 140

Gly Lys Phe Ala Ala Glu Ile Arg Asp Pro Lys Arg Ala Thr Arg Val
145                 150                 155                 160

Trp Leu Gly Thr Phe Glu Thr Ala Glu Asp Ala Ala Arg Ala Tyr Asp
                165                 170                 175

Arg Ala Ala Ile Gly Phe Arg Gly Pro Arg Ala Lys Leu Asn Phe Pro
            180                 185                 190

Phe Val Asp Tyr Thr Ser Ser Val Ser Ser Pro Val Ala Ala Asp Asp
        195                 200                 205

Ile Gly Ala Lys Ala Ser Ala Ser Ala Ser Val Ser Ala Thr Asp Ser
        210                 215                 220

Val Glu Ala Glu Gln Trp Asn Gly Gly Gly Asp Cys Asn Met Glu
225                 230                 235                 240

Glu Trp Met Asn Met Met Met Met Met Asp Phe Gly Asn Gly Asp Ser
                245                 250                 255

Ser Asp Ser Gly Asn Thr Ile Ala Asp Met Phe Gln
            260                 265

<210> SEQ ID NO 55
<211> LENGTH: 16
<212> TYPE: PRT
<213> ORGANISM: Arabidopsis thaliana
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(7)
<223> OTHER INFORMATION: Xaa can be any naturally occurring amino acid
<220> FEATURE:
<221> NAME/KEY: misc_feature
<222> LOCATION: (9)..(11)
<223> OTHER INFORMATION: Xaa can be any naturally occurring amino acid
<220> FEATURE:
<221> NAME/KEY: misc_feature
<222> LOCATION: (13)..(15)
<223> OTHER INFORMATION: Xaa can be any naturally occurring amino acid
<220> FEATURE:
<223> OTHER INFORMATION: EDLL Domain

<400> SEQUENCE: 55

Xaa Xaa Glu Xaa Xaa Xaa Xaa Asp Xaa Xaa Xaa Leu Xaa Xaa Xaa Leu
1               5                   10                  15

<210> SEQ ID NO 56
<211> LENGTH: 16
<212> TYPE: PRT
<213> ORGANISM: Arabidopsis thaliana
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<223> OTHER INFORMATION: conserved consecutive amino acid residues from
      CBF protein alignment
```

```
<400> SEQUENCE: 56

Pro Lys Lys Pro Ala Gly Arg Xaa Lys Phe Xaa Glu Thr Arg His Pro
1               5                   10                  15

<210> SEQ ID NO 57
<211> LENGTH: 16
<212> TYPE: PRT
<213> ORGANISM: Arabidopsis thaliana
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<223> OTHER INFORMATION: conserved consecutive amino acid residues from
      CBF protein alignment

<400> SEQUENCE: 57

Pro Lys Arg Pro Ala Gly Arg Xaa Lys Phe Xaa Glu Thr Arg His Pro
1               5                   10                  15

<210> SEQ ID NO 58
<211> LENGTH: 5
<212> TYPE: PRT
<213> ORGANISM: Arabidopsis thaliana
<220> FEATURE:
<223> OTHER INFORMATION: conserved consecutive amino acid residues from
      CBF protein alignment

<400> SEQUENCE: 58

Asp Ser Ala Trp Arg
1               5

<210> SEQ ID NO 59
<211> LENGTH: 20
<212> TYPE: DNA
<213> ORGANISM: artificial sequence
<220> FEATURE:
<223> OTHER INFORMATION: artificial sequence
<220> FEATURE:
<221> NAME/KEY: misc_feature
<222> LOCATION: (3)..(3)
<223> OTHER INFORMATION: y is c or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: h is a, c, or t
<220> FEATURE:
<221> NAME/KEY: misc_feature
<222> LOCATION: (12)..(12)
<223> OTHER INFORMATION: y is c or t
<220> FEATURE:
<221> NAME/KEY: misc_feature
<222> LOCATION: (13)..(13)
<223> OTHER INFORMATION: m is a or c
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<223> OTHER INFORMATION: Mol 368 (reverse) degenerate primer
```

<400> SEQUENCE: 59
cayccnatht aymgnggngt                                                      20

<210> SEQ ID NO 60
<211> LENGTH: 21
<212> TYPE: DNA
<213> ORGANISM: artificial sequence
<220> FEATURE:
<223> OTHER INFORMATION: artificial sequence
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (5)..(5)
<223> OTHER INFORMATION: r is a or g
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (8)..(8)
<223> OTHER INFORMATION: r is a or g
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: y is c or t
<220> FEATURE:
<221> NAME/KEY: misc_feature
<222> LOCATION: (18)..(18)
<223> OTHER INFORMATION: n is a, c, g, or t
<220> FEATURE:
<223> OTHER INFORMATION: Mol 378 (forward) degenerate primer

<400> SEQUENCE: 60
ggnarnarca tnccytcngc c                                                    21

<210> SEQ ID NO 61
<211> LENGTH: 7
<212> TYPE: PRT
<213> ORGANISM: Arabidopsis thaliana
<220> FEATURE:
<223> OTHER INFORMATION: amino acid sequence in the AP2 binding domain
      of CBF1

<400> SEQUENCE: 61

His Pro Ile Tyr Arg Gly Val
1               5

<210> SEQ ID NO 62
<211> LENGTH: 8
<212> TYPE: PRT
<213> ORGANISM: Arabidopsis thaliana
<220> FEATURE:
<223> OTHER INFORMATION: carboxyl terminal domain outside the AP2 domain
      of CBF1

<400> SEQUENCE: 62

Met Ala Glu Gly Met Leu Leu Pro
1               5